United States Patent
Timmer et al.

(10) Patent No.: US 10,844,129 B2
(45) Date of Patent: *Nov. 24, 2020

(54) MULTIVALENT AND MULTISPECIFIC GLUCOCORTICOID-INDUCED TNFR-RELATED PROTEIN (GITR)-BINDING SINGLE-DOMAIN ANTIBODY FUSION PROTEINS AND ENCODING NUCLEIC ACIDS

(71) Applicant: Inhibrx, Inc., La Jolla, CA (US)

(72) Inventors: John C. Timmer, La Jolla, CA (US); Kyle S. Jones, La Jolla, CA (US); Amir Razai, La Jolla, CA (US); Abraham Hussain, La Jolla, CA (US); Katelyn M. Willis, La Jolla, CA (US); Quinn Deveraux, La Jolla, CA (US); Brendan P. Eckelman, La Jolla, CA (US)

(73) Assignee: Inhibrx, Inc., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/119,950

(22) Filed: Aug. 31, 2018

(65) Prior Publication Data

US 2019/0100594 A1  Apr. 4, 2019

Related U.S. Application Data

(63) Continuation of application No. 15/217,754, filed on Jul. 22, 2016, now Pat. No. 10,093,742.

(60) Provisional application No. 62/195,822, filed on Jul. 23, 2015.

(51) Int. Cl.
*C07K 16/28* (2006.01)
*A61K 39/00* (2006.01)

(52) U.S. Cl.
CPC .... *C07K 16/2878* (2013.01); *A61K 2039/505* (2013.01); *C07K 2317/21* (2013.01); *C07K 2317/22* (2013.01); *C07K 2317/24* (2013.01); *C07K 2317/31* (2013.01); *C07K 2317/33* (2013.01); *C07K 2317/35* (2013.01); *C07K 2317/52* (2013.01); *C07K 2317/53* (2013.01); *C07K 2317/56* (2013.01); *C07K 2317/565* (2013.01); *C07K 2317/569* (2013.01); *C07K 2317/64* (2013.01); *C07K 2317/73* (2013.01); *C07K 2317/76* (2013.01); *C07K 2317/92* (2013.01)

(58) Field of Classification Search
CPC .......... C07K 16/2878; C07K 2317/21; C07K 2317/22; C07K 2317/24; C07K 2317/31; C07K 2317/33; C07K 2317/35; C07K 2317/52; C07K 2317/53; C07K 2317/56; C07K 2317/565; C07K 2317/569; C07K 2317/64; C07K 2317/73; C07K 2317/76; C07K 2317/92; A61K 2039/505

See application file for complete search history.

(56) References Cited

U.S. PATENT DOCUMENTS

| | | |
|---|---|---|
| 7,025,962 B1 | 4/2006 | Gorman et al. |
| 7,812,135 B2 | 10/2010 | Smith et al. |
| 8,388,967 B2 | 3/2013 | Smith et al. |
| 8,409,577 B2 | 4/2013 | Thompson et al. |
| 8,586,023 B2 | 11/2013 | Shiku et al. |
| 8,591,886 B2 | 11/2013 | Ponath et al. |
| 8,669,350 B2 | 3/2014 | Chou et al. |
| 8,709,424 B2 | 4/2014 | Schebye et al. |
| 9,005,619 B2 | 4/2015 | Kohrt et al. |
| 9,028,823 B2 | 5/2015 | Smith et al. |
| 9,228,016 B2 | 1/2016 | Wang et al. |
| 9,309,321 B2 | 4/2016 | Kwon |
| 9,464,139 B2 | 10/2016 | Beers et al. |
| 10,093,742 B2 | 10/2018 | Timmer et al. |
| 2003/0233675 A1 | 12/2003 | Cao et al. |
| 2004/0220388 A1 | 11/2004 | Mertens et al. |
| 2007/0004909 A1 | 1/2007 | Johnson et al. |
| 2007/0009523 A1 | 1/2007 | Presta |
| 2011/0189203 A1 | 8/2011 | Hermans et al. |
| 2011/0212086 A1 | 9/2011 | Shankara et al. |
| 2012/0196339 A1 | 8/2012 | Koppisch et al. |
| 2013/0108641 A1 | 5/2013 | Baurin et al. |
| 2013/0224224 A1 | 8/2013 | Singh et al. |
| 2013/0330335 A1 | 12/2013 | Bremel et al. |
| 2014/0065152 A1 | 3/2014 | Kwon |
| 2014/0120090 A1 | 5/2014 | Willemsen et al. |
| 2014/0377253 A1 | 12/2014 | Harding et al. |
| 2015/0064204 A1 | 3/2015 | Beers et al. |
| 2015/0322119 A1 | 11/2015 | Engelhardt et al. |
| 2015/0368349 A1 | 12/2015 | Gonzalez et al. |

(Continued)

FOREIGN PATENT DOCUMENTS

| | | |
|---|---|---|
| CN | 108650886 A | 10/2018 |
| EP | 3325512 A2 | 5/2018 |

(Continued)

OTHER PUBLICATIONS

Agnew, Chem Intl. Ed. Engl., 33: 183-186 (1994)).

(Continued)

*Primary Examiner* — Robert S Landsman
(74) *Attorney, Agent, or Firm* — Cooley LLP; Ivor R. Elrifi; Cynthia A. Kozakiewicz

(57) ABSTRACT

This disclosure generally provides molecules that specifically engage glucocorticoid-induced TNFR-related protein (GITR), a member of the TNF receptor superfamily (TNFRSF). More specifically, the disclosure relates to multivalent and/or multispecific molecules that bind at least GITR.

34 Claims, 15 Drawing Sheets

Specification includes a Sequence Listing.

(56) References Cited

U.S. PATENT DOCUMENTS

| | | | |
|---|---|---|---|
| 2016/0129095 A1 | 5/2016 | Noelle et al. |
| 2016/0199487 A1 | 7/2016 | Gu |
| 2017/0145104 A1 | 5/2017 | Wang et al. |
| 2017/0320958 A1 | 11/2017 | Timmer et al. |

FOREIGN PATENT DOCUMENTS

| | | |
|---|---|---|
| RU | 2487888 C2 | 7/2013 |
| WO | WO 2001/77342 | 10/2001 |
| WO | WO 2003/068257 | 8/2003 |
| WO | WO 2006/105021 | 10/2006 |
| WO | WO 2008/071447 | 6/2008 |
| WO | WO 2009/032782 | 3/2009 |
| WO | WO 2009/068649 | 6/2009 |
| WO | WO 2010/115156 | 10/2010 |
| WO | WO 2011/028683 | 3/2011 |
| WO | WO 2012/162583 | 11/2012 |
| WO | WO 2013/039954 | 3/2013 |
| WO | WO 2014/089113 | 6/2014 |
| WO | WO 2014/140376 | 9/2014 |
| WO | WO 2014/144960 | 9/2014 |
| WO | WO 2015/006337 | 1/2015 |
| WO | WO 2015/022420 | 2/2015 |
| WO | WO 2015/031667 A2 | 3/2015 |
| WO | WO 2015/184099 | 12/2015 |
| WO | WO 2015/187835 | 12/2015 |
| WO | WO 2016/040892 | 3/2016 |
| WO | WO 2016/054555 | 4/2016 |
| WO | WO 2016/054638 | 4/2016 |
| WO | WO 2016/057841 | 4/2016 |
| WO | WO 2016/057846 | 4/2016 |
| WO | WO 2016/100882 | 6/2016 |
| WO | WO 2016/196792 | 12/2016 |
| WO | WO 2016/196912 | 12/2016 |
| WO | WO 2017/015623 A2 | 1/2017 |
| WO | WO 2017/068186 | 4/2017 |
| WO | WO 2018/005950 A1 | 1/2018 |

OTHER PUBLICATIONS

Alegre et al, 1992, Effect of a single amino acid mutation on the activating and immunosuppressive properties of a "humanized" OKT3 monoclonal antibody. J Immunol, 148: 3461-3468.

Bianchini et al., "CD4+ CD25$^{low}$GITR+ cells: A novel human CD4+ T-cell population with regulatory activity," Eur. J. Immunol., vol. 41: 2269-78 (2011).

Bulliard et al., 2013, Activating Fcγ receptors contribute to the antitumor activities of immunoregulatory receptor-targeting antibodies. J. Exp. Med., 210(9): 1685.

Bulliard et al., 2014, OX40 engagement depletes intratumoral Tregs via activating FcγRs, leading to antitumor efficacy. Immunol and Cell Biol 92: 475-480.

Carter, 2001, Bispecific human IgG by design. Journal of Immunological Methods, 248: 7-15.

Cohen et al., "Agonist Anti-GITR Monoclonal Antibody Induces Melanoma Tumor Immunity in Micy by Altering Regulatory T Cell Stability and Intra-Tumor Accumulation," PLoS One, vol. 5(5): e10436 (2010).

Colman, PM. Research in Immunology, Elsevier, NY (1994) 145(1):33-36.

Croft et al., "Clinical targeting of the TNF and TNFR superfamilies," Nature Reviews, vol. 12: 147-168 (2013).

Ephrem et al., "Modulation of Treg cells/T effector function by GITR signaling is context-depedent," Eur. J. Immunol., vol. 43: 2421-49 (2013).

Ferrara & Alitalo, 1999, Clinical applications of angiogenic growth factors and their inhibitors. Nature Medicine 5(12):1359-1364.

Graves et al., 2014, Apo2L/TRAIL and the death receptor 5 agonist antibody AMG 655 cooperate to promote receptor clustering and antitumor activity. Cancer Cell 26: 177-189.

Ichikawa et al., 2001, Tumoricidal activity of a novel anti-human DR5 monoclonal antibody without hepatocyte cytotoxicity. Nat. Med. 7: 954-960.

Idusogie et al., 2001, Engineered antibodies with increased activity to recruit complement. J. Immunol, 166(4): 2571-5.

Kaneko and Niwa, 2011, Optimizing therapeutic antibody function: progress with Fc domain engineering. Biodrugs, 25(1):1-11.

Klagsbrun and D' Amore, 1991, Regulators of angiogenesis. Annu. Rev. Physiol. 53:217-39.

Lazar et al., 2006, Engineered antibody Fc variants with enhanced effector function. PNAS, 103(11): 4005-4010.

Li et al., 2008, LBY135, a novel anti-DR5 agonistic antibody induces tumor cell-specific cytotoxic activity in human colon tumor cell lines and xenografts. Drug Dev. Res. 69: 69-82.

Mahoney et al., "Combination cancer immunotherapy and new immunomodulatory targets," Cancer Immunotherapy, vol. 14: 561-84 (2015).

Moore et al., 2010, Engineered Fc variant antibodies with enhanced ability to recruit complement and mediate effector functions. mAbs, 2(2): 181-189.

Natsume et al., 2008, Engineered antibodies of IgG I/IgG3 mixed isotype with enhanced cytotoxic activities. Cancer Res, 68(10): 3863-72.

Nishioka et al., "In vivo expansion of CD4+Foxp3+ regulatory T cells mediated by GITR molecules," Immunology Letters, vol. 121: 97-104 (2008).

Nocentini, et al., "Pharmacological modulation of GITRL/GITR system: therapeutic perspectives," British Journal of Pharmacology, vol. 165:2089-99 (2012).

Paul, WE. Fundamental Immunology, $3^{rd}$ ed. Raven Press, NY, Chap 9, p. 292-295.

Pedroza, et al., "GITR engagement in combination with CTLA-4 blockade completely abrogates immunosuppression mediated by human liver tumor-derived regulatory T cells ex vivo," OncoImmunology, 4(12): e1051297-1-e1051297-11 (2015).

Pukac et al., 2005, HGS-ETRI, a fully human TRAIL-receptor 1 monoclonal antibody, induces cell death in multiple tumour types in vitro and in vivo. Br. J. Cancer 92, 1430-1441.

Rudikoff et al., "Single amino acid substitution altering antigen-binding specificity," Proc Natl. Acad. Sci. USA (1982) 79:1979-1983.

Sato, 2003, Molecular diagnosis of tumor angiogenesis and anti-angiogenic cancer therapy. Int. J. Clin. Oncol. 8:200-206.

Schaer, et al., "GITR Pathway Activation Abrogates Tumor Immune Suppression Through Loss of Regulatory T-cell Lineage Stability," Cancer Immunology Research, vol. 1(5): 320-331 (2013).

Shields et al., 2001, High resolution mapping of the binding site on human IgG1 for Fc gamma RI, Fc gamma RII, Fc gamma RIII, and FcRn and design of IgG1 variants with improved binding to the Fc gamma R. J. Biol. Chem, 276(9): 6591-6604.

Stavenhagen et al., 2007, Fc optimization of therapeutic antibodies enhances their ability to kill tumor cells in vitro and controls tumor expansion in vivo via low-affinity activating Fc gamma receptors. Cancer Res, 67(18): 8882-8890.

Stavenhagen et al., 2008, Enhancing the potency of therapeutic monoclonal antibodies via Fc optimization. Advan. Enzyme Regul., 48: 152-164.

Streit and Detmar, 2003, Angiogenesis, lymphangiogenesis, and melanoma metastasis. Oncogene 22:3172-31479.

Tonini et al., 2003, Molecular basis of angiogenesis and cancer. Oncogene 22:6549-6556.

Yada et al., 2008, A novel humanized anti-human death receptor 5 antibody CS-1008 induces apoptosis in tumor cells without toxicity in hepatocytes. Ann. Oncol. 19, 1060-1067.

Yao, et al. "Advances in targeting cell surface signalling molecules for immune modulation," Nature Reviews, vol. 12: 130-146 (2013).

Zalevsky et al., 2010, Enhanced antibody half-life improves in vivo activity. Nature Biotech, vol. 28(2) 157-159.

Zhang et al., 2007, Lexatumumab (TRAIL-receptor 2 mAb) induces expression of DR5 and promotes apoptosis in primary and metastatic renal cell carcinoma in a mouse orthotopic model. Cancer Lett. 251:146-157.

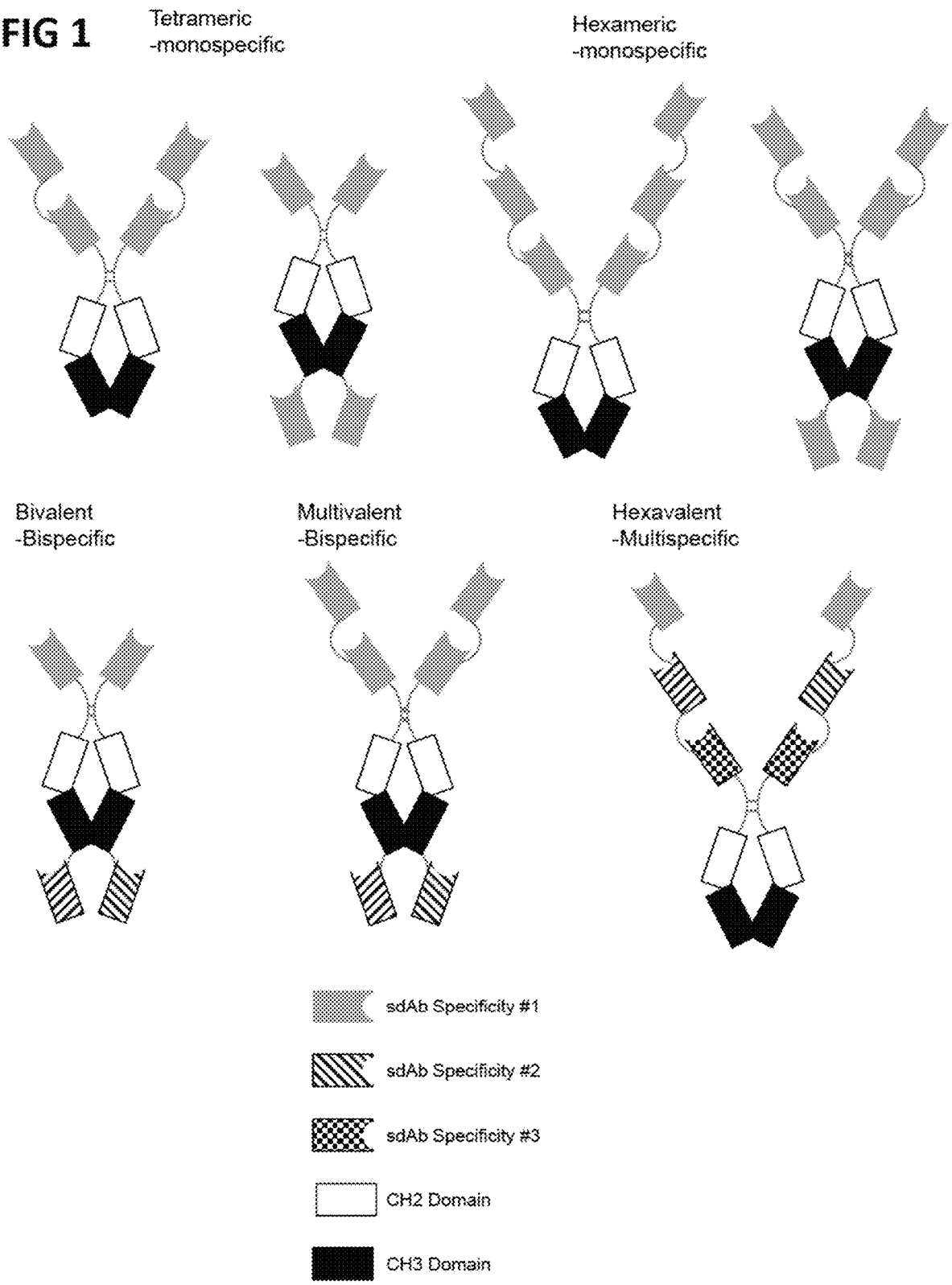

Closed symbols, solid lines: activated CD4 T cells
Open symbols, dashed lines: activated $T_{reg}$

- mIgG2a
- Tetravalent C06-mIgG2a
- Tetravalent C06-mIgG2a-silent

MULTIVALENT AND MULTISPECIFIC GLUCOCORTICOID-INDUCED TNFR-RELATED PROTEIN (GITR)-BINDING SINGLE-DOMAIN ANTIBODY FUSION PROTEINS AND ENCODING NUCLEIC ACIDS

RELATED APPLICATIONS

This application is a continuation of U.S. patent application Ser. No. 15/217,754, filed Jul. 22, 2016, issued as U.S. Pat. No. 10,093,742, on Oct. 9, 2018, entitled "MULTISPECIFIC GITR-BINDING FUSION PROTEINS AND METHODS OF USE THEREOF," which claims the benefit of U.S. Provisional Application No. 62/195,822, filed Jul. 23, 2015, the contents of which are incorporated herein by reference in their entirety.

INCORPORATION OF SEQUENCE LISTING

The present application is being filed along with a Sequence Listing in electronic format. The Sequence Listing is provided as a file entitled 744952000302SeqList.TXT, created Aug. 29, 2018, which is 214,721 bytes in size. The information in the electronic format of the Sequence Listing is incorporated by reference in its entirety.

FIELD OF THE INVENTION

This disclosure generally provides molecules that specifically engage glucocorticoid-induced TNFR-related protein (GITR), a member of the TNF receptor superfamily (TNFRSF). More specifically, the disclosure relates to multivalent and/or multispecific molecules that bind at least GITR.

BACKGROUND OF THE INVENTION

The tumor necrosis factor receptor superfamily consists of several structurally related cell surface receptors. Activation by multimeric ligands is a common feature of many of these receptors. Many members of the TNFRSF have therapeutic utility in numerous pathologies, if activated properly. Importantly, to properly agonize this receptor family often requires higher order clustering, and conventional bivalent antibodies are not ideal for this. Therefore, there exists a therapeutic need for more potent agonist molecules of the TNFRSF.

SUMMARY OF THE INVENTION

The disclosure provides multivalent TNF receptor superfamily (TNFRSF) binding fusion polypeptides that bind at least glucocorticoid-induced TNFR-related protein (GITR, also known as tumor necrosis factor receptor superfamily member 18 (TNFRSF18) and/or activation-inducible TNFR family receptor (AITR)). These molecules that bind at least GITR are referred to herein as "GITR-targeting molecules" or "GITR-targeting fusions" or "GITR-targeting proteins" or "GITR-targeting fusion polypeptides" or "GITR-targeting fusion proteins." In some embodiments, the GITR-targeting molecule is a multivalent molecule, for example, a multivalent GITR-targeting fusion protein. In some embodiments, the GITR-targeting molecule is a multispecific molecule, for example, a multispecific GITR-targeting fusion protein. In some embodiments, the GITR-targeting molecule is a multivalent and multispecific molecule, for example, a multivalent and multispecific GITR-targeting fusion protein.

As used herein, the term "fusion protein" or "fusion polypeptide" or "GITR-targeting fusion protein" or "GITR-targeting fusion polypeptide," unless otherwise specifically denoted, refers to any fusion protein embodiment of the disclosure, including, but not limited to, multivalent fusion proteins, multispecific fusion proteins, or multivalent and multispecific fusion proteins.

These GITR-targeting molecules include at least one domain that binds GITR, referred to herein as a "GITR-binding domain" (GITR-BD). These GITR-BDs include a polypeptide sequence that specifically binds to GITR. In some embodiments, the GITR-BD includes a polypeptide sequence that is or is derived from an antibody or antibody fragment including, for example, scFv, Fabs, single domain antibodies (sdAb), $V_{NAR}$, or VHHs. In some embodiments, the GITR-BD includes a human or humanized sdAb.

The GITR-targeting molecules of the disclosure overcome problems and limitations from convention antibodies that target members of the TNF receptor superfamily (TNFRSF), including GITR. Conventional antibodies targeting members of the TNFRSF have been shown to require an exogenous crosslinking to achieve sufficient agonist activity, as evidenced by the necessity for Fc-gamma Receptor (FcγRs) for the activity antibodies to DR4, DR5, GITR and OX40 (Ichikawa et al 2001 al Nat. Med. 7, 954-960, Li et al 2008 Drug Dev. Res. 69, 69-82; Pukac et al 2005 Br. J. Cancer 92, 1430-1441; Yanda et al 2008 Ann. Oncol. 19, 1060-1067; Yang et al 2007 Cancer Lett. 251:146-157; Bulliard et al 2013 JEM 210(9): 1685; Bulliard et al 2014 Immunol and Cell Biol 92: 475-480). In addition to crosslinking via FcγRs other exogenous agents including addition of the oligomeric ligand or antibody binding entities (e.g. protein A and secondary antibodies) have be demonstrated to enhance anti-TNFRSF antibody clustering and downstream signaling. For example, the addition of the DR5 ligand TRAIL enhanced the apoptosis inducing ability of an anti-DR5 antibody (Graves et al 2014 Cancer Cell 26: 177-189). These findings suggest the need for clustering of TNFRSFs beyond a dimer.

The present disclosure provides isolated polypeptides that specifically bind GITR. In some embodiments, the isolated polypeptide is derived from antibodies or antibody fragments including scFv, Fabs, single domain antibodies (sdAb), $V_{NAR}$, or VHHs. In some embodiments, the isolated polypeptide is human or humanized sdAb. The sdAb fragments can be derived from VHH, $V_{NAR}$, engineered VH or VK domains. VHHs can be generated from camelid heavy chain only antibodies. $V_{NAR}$s can be generated from cartilaginous fish heavy chain only antibodies. Various methods have been implemented to generate monomeric sdAbs from conventionally heterodimeric VH and VK domains, including interface engineering and selection of specific germline families. In other embodiments, the isolated polypeptides are derived from non-antibody scaffold proteins for example but not limited to designed ankyrin repeat proteins (darpins), avimers, anticalin/lipocalins, centyrins and fynomers.

In some embodiments, the isolated polypeptide includes an amino acid sequence selected from the group consisting of SEQ ID NO: 19-80. In some embodiments, the isolated polypeptide includes an amino acid sequence selected from the group consisting of SEQ ID NO: 42-62. In some embodiments, the isolated polypeptide includes an amino acid sequence selected from the group consisting of SEQ ID NO: 63-80.

In some embodiments, the isolated polypeptide includes an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 19-80. In some embodiments, the isolated polypeptide includes an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 42-62. In some embodiments, the isolated polypeptide includes an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 63-80.

In some embodiments, the isolated polypeptide comprises a complementarity determining region 1 (CDR1) comprising an amino acid sequence selected from the group consisting of SEQ ID NO: 106, 109, 112, 117, 120, 125, 131, 138, 143, 148, and 149; a complementarity determining region 2 (CDR2) comprising an amino acid sequence selected from the group consisting of SEQ ID NO: 107, 110, 113, 115, 118, 121, 123, 128, 130, 132, 134, 136, 137, 139, 141, 144, and 147; and a complementarity determining region 3 (CDR3) comprising an amino acid sequence selected from the group consisting of SEQ ID NO: 108, 111, 114, 116, 119, 122, 124, 126, 127, 129, 133, 135, 140, 142, 145, 146, and 150.

The present disclosure also provides multivalent TNFRSF binding fusion proteins, which comprise two or more TNFRSF binding domains (TBDs), where at least one TBD binds GITR, referred to herein as a GITR-binding domain (GITR-BD). In some embodiments, the fusion proteins of the present disclosure have utility in treating neoplasms. In some embodiments, the fusion proteins of the present disclosure bind TNFRSF member expressed on a tumor cell, for example, at least GITR.

In some embodiments, GITR-BDs of the present disclosure are derived from antibodies or antibody fragments including scFv, Fabs, single domain antibodies (sdAb), $V_{NAR}$, or VHHs. In some embodiments, the GITR-BDs are human or humanized sdAb. The sdAb fragments can be derived from VHH, $V_{NAR}$, engineered VH or VK domains. VHHs can be generated from camelid heavy chain only antibodies. $V_{NAR}$s can be generated from cartilaginous fish heavy chain only antibodies. Various methods have been implemented to generate monomeric sdAbs from conventionally heterodimeric VH and VK domains, including interface engineering and selection of specific germline families. In other embodiments, the GITR-BDs are derived from non-antibody scaffold proteins for example but not limited to designed ankyrin repeat proteins (darpins), avimers, anticalin/lipocalins, centyrins and fynomers.

Generally, the multivalent fusion proteins of the present disclosure include at least two or more GITR-BDs operably linked via a linker polypeptide. The utilization of sdAb fragments as the specific GITR-BD sequences within the multivalent fusion proteins of the present disclosure has the benefit of avoiding the heavy chain: light chain mis-pairing problem common to many bi/multispecific antibody approaches. In addition, the multivalent fusion proteins of the present disclosure avoid the use of long linkers necessitated by many bispecific antibodies.

In some embodiments, the multivalent fusion protein contains two or more different GITR-BDs. In some embodiments, the multivalent fusion protein contains three or more different GITR-BDs. In some embodiments, the multivalent fusion protein contains four or more different GITR-BDs. In some embodiments, the multivalent fusion protein contains five or more different GITR-BDs. In some embodiments, the multivalent fusion protein contains six or more different GITR-BDs.

In some embodiments, the multivalent fusion protein contains multiple copies of a GITR-BD. For example, in some embodiments, the multivalent fusion protein contains at least two copies of a GITR-BD. In some embodiments, the multivalent fusion protein contains at least three copies of a GITR-BD. In some embodiments, the multivalent fusion protein contains at least four copies of a GITR-BD. In some embodiments, the multivalent fusion protein contains at least five copies of a GITR-BD. In some embodiments, the multivalent fusion protein contains at least six copies of a GITR-BD. In some embodiments, the multivalent fusion protein contains six or more copies of a GITR-BD.

In some embodiments, the multivalent fusion protein contains at least one GITR-BD that comprises an amino acid sequence selected from the group consisting of SEQ ID NO: 19-80. In some embodiments, the multivalent fusion protein contains two or more copies of a GITR-BD that comprises an amino acid sequence selected from the group consisting of SEQ ID NO: 19-80. In some embodiments, the multivalent fusion protein contains three or more copies of a GITR-BD that comprises an amino acid sequence selected from the group consisting of SEQ ID NO: 19-80. In some embodiments, the multivalent fusion protein contains four or more copies of a GITR-BD that comprises an amino acid sequence selected from the group consisting of SEQ ID NO: 19-80. In some embodiments, the multivalent fusion protein contains five or more copies of a GITR-BD that comprises an amino acid sequence selected from the group consisting of SEQ ID NO: 19-80. In some embodiments, the multivalent fusion protein contains six or more copies of a GITR-BD that comprises an amino acid sequence selected from the group consisting of SEQ ID NO: 19-80.

In some embodiments, the multivalent fusion protein contains at least one GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 19-80. In some embodiments, the multivalent fusion protein contains two or more copies of a GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 19-80. In some embodiments, the multivalent fusion protein contains three or more copies of a GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 19-80. In some embodiments, the multivalent fusion protein contains four or more copies of a GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 19-80. In some embodiments, the multivalent fusion protein contains five or more copies of a GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 19-80. In some embodiments, the multivalent fusion protein contains six or more copies of a GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 19-80.

In some embodiments, the multivalent fusion protein contains at least one GITR-BD that comprises an amino acid sequence selected from the group consisting of SEQ ID NO: 42-62. In some embodiments, the multivalent fusion protein contains two or more copies of a GITR-BD that comprises an amino acid sequence selected from the group consisting of SEQ ID NO: 42-62. In some embodiments, the multivalent fusion protein contains three or more copies of a GITR-BD that comprises an amino acid sequence selected from the group consisting of SEQ ID NO: 42-62. In some embodiments, the multivalent fusion protein contains four or more copies of a GITR-BD that comprises an amino acid sequence selected from the group consisting of SEQ ID NO: 42-62. In some embodiments, the multivalent fusion protein contains five or more copies of a GITR-BD that comprises an amino acid sequence selected from the group consisting of SEQ ID NO: 42-62. In some embodiments, the multivalent fusion protein contains six or more copies of a GITR-BD that comprises an amino acid sequence selected from the group consisting of SEQ ID NO: 42-62.

In some embodiments, the multivalent fusion protein contains at least one GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 42-62. In some embodiments, the multivalent fusion protein contains two or more copies of a GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 42-62. In some embodiments, the multivalent fusion protein contains three or more copies of a GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 42-62. In some embodiments, the multivalent fusion protein contains four or more copies of a GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 42-62. In some embodiments, the multivalent fusion protein contains five or more copies of a GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 42-62. In some embodiments, the multivalent fusion protein contains six or more copies of a GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 42-62.

In some embodiments, the multivalent fusion protein contains at least one GITR-BD that comprises an amino acid sequence selected from the group consisting of SEQ ID NO: 63-80. In some embodiments, the multivalent fusion protein contains two or more copies of a GITR-BD that comprises an amino acid sequence selected from the group consisting of SEQ ID NO: 63-80. In some embodiments, the multivalent fusion protein contains three or more copies of a GITR-BD that comprises an amino acid sequence selected from the group consisting of SEQ ID NO: 63-80. In some embodiments, the multivalent fusion protein contains four or more copies of a GITR-BD that comprises an amino acid sequence selected from the group consisting of SEQ ID NO: 63-80. In some embodiments, the multivalent fusion protein contains five or more copies of a GITR-BD that comprises an amino acid sequence selected from the group consisting of SEQ ID NO: 63-80. In some embodiments, the multivalent fusion protein contains six or more copies of a GITR-BD that comprises an amino acid sequence selected from the group consisting of SEQ ID NO: 63-80.

In some embodiments, the multivalent fusion protein contains at least one GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 63-80. In some embodiments, the multivalent fusion protein contains two or more copies of a GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 63-80. In some embodiments, the multivalent fusion protein contains three or more copies of a GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 63-80. In some embodiments, the multivalent fusion protein contains four or more copies of a GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 63-80. In some embodiments, the multivalent fusion protein contains five or more copies of a GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 63-80. In some embodiments, the multivalent fusion protein contains six or more copies of a GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 63-80.

In some embodiments, the multivalent fusion protein contains at least one GITR-BD that comprises a complementarity determining region 1 (CDR1) comprising an amino acid sequence selected from the group consisting of SEQ ID NO: 106, 109, 112, 117, 120, 125, 131, 138, 143, 148, and 149; a complementarity determining region 2 (CDR2) comprising an amino acid sequence selected from the group consisting of SEQ ID NO: 107, 110, 113, 115, 118, 121, 123, 128, 130, 132, 134, 136, 137, 139, 141, 144, and 147; and a complementarity determining region 3 (CDR3) comprising an amino acid sequence selected from the group consisting of SEQ ID NO: 108, 111, 114, 116, 119, 122, 124, 126, 127, 129, 133, 135, 140, 142, 145, 146, and 150. In some embodiments, the multivalent fusion protein contains two or more copies of a GITR-BD that comprises a CDR1 comprising an amino acid sequence selected from the group consisting of SEQ ID NO: 106, 109, 112, 117, 120, 125, 131, 138, 143, 148, and 149; a CDR2 comprising an amino acid sequence selected from the group consisting of SEQ ID NO: 107, 110, 113, 115, 118, 121, 123, 128, 130, 132, 134, 136, 137, 139, 141, 144, and 147; and a CDR3 comprising an amino acid sequence selected from the group consisting of SEQ ID NO: 108, 111, 114, 116, 119, 122, 124, 126, 127, 129, 133, 135, 140, 142, 145, 146, and 150. In some embodiments, the multivalent fusion protein contains three or more copies of a GITR-BD that comprises a CDR1 comprising an amino acid sequence selected from the group consisting of SEQ ID NO: 106, 109, 112, 117, 120, 125, 131, 138, 143, 148, and 149; a CDR2 comprising an amino acid sequence selected from the group consisting of SEQ ID NO: 107, 110, 113, 115, 118, 121, 123, 128, 130, 132, 134, 136, 137, 139, 141, 144, and 147; and a CDR3 comprising an amino acid sequence selected from the group consisting of SEQ ID NO: 108, 111, 114, 116, 119, 122, 124, 126, 127, 129, 133, 135, 140, 142, 145, 146, and 150. In some embodiments, the multivalent fusion protein contains four or more copies of a GITR-BD that comprises a CDR1 comprising an amino acid sequence selected from the group consisting of SEQ ID NO: 106, 109, 112, 117, 120, 125, 131, 138, 143, 148, and 149; a CDR2 comprising an amino acid sequence selected from the group consisting of SEQ ID NO: 107, 110, 113, 115, 118, 121, 123, 128, 130, 132, 134, 136, 137, 139, 141, 144, and 147; and a CDR3 comprising an amino acid sequence selected from the group consisting of SEQ ID NO: 108, 111, 114, 116, 119, 122, 124, 126, 127, 129, 133, 135, 140, 142, 145, 146, and 150. In some embodiments, the multivalent fusion protein contains five or more copies of a GITR-BD that comprises a CDR1 comprising an amino acid sequence selected from the group consisting of SEQ ID NO: 106, 109, 112, 117, 120, 125, 131, 138, 143, 148, and 149; a CDR2 comprising an amino acid sequence selected from the group consisting of SEQ ID NO: 107, 110, 113, 115, 118, 121, 123, 128, 130, 132, 134, 136, 137, 139, 141, 144, and 147; and a CDR3 comprising an amino acid sequence selected from the group consisting of SEQ ID NO: 108, 111, 114, 116, 119, 122, 124, 126, 127, 129, 133, 135, 140, 142, 145, 146, and 150. In some embodiments, the multivalent fusion protein contains six or more copies of a GITR-BD that comprises a CDR1 comprising an amino acid sequence selected from the group consisting of SEQ ID NO: 106, 109, 112, 117, 120, 125, 131, 138, 143, 148, and 149; a CDR2 comprising an amino acid sequence selected from the group consisting of SEQ ID NO: 107, 110, 113, 115, 118, 121, 123, 128, 130, 132, 134, 136, 137, 139, 141, 144, and 147; and a CDR3 comprising an amino acid sequence selected from the group consisting of SEQ ID NO: 108, 111, 114, 116, 119, 122, 124, 126, 127, 129, 133, 135, 140, 142, 145, 146, and 150.

In some embodiments, the multivalent fusion protein contains at least one GITR-BD that comprises an amino acid sequence selected from the group consisting of SEQ ID NO: 19-80 and at least one immunoglobulin Fc region polypeptide comprising an amino acid sequence selected from the group consisting of SEQ ID NOs: 1-6. In some embodiments, the multivalent fusion protein contains two or more copies of a GITR-BD that comprises an amino acid sequence selected from the group consisting of SEQ ID NO: 19-80 and at least one immunoglobulin Fc region polypeptide comprising an amino acid sequence selected from the group consisting of SEQ ID NOs: 1-6. In some embodiments, the multivalent fusion protein contains three or more copies of a GITR-BD that comprises an amino acid sequence selected from the group consisting of SEQ ID NO: 19-80 and at least one immunoglobulin Fc region polypeptide comprising an amino acid sequence selected from the group consisting of SEQ ID NOs: 1-6. In some embodiments, the multivalent fusion protein contains four or more copies of a GITR-BD that comprises an amino acid sequence selected from the group consisting of SEQ ID NO: 19-80 and at least one immunoglobulin Fc region polypeptide comprising an amino acid sequence selected from the group consisting of SEQ ID NOs: 1-6. In some embodiments, the multivalent fusion protein contains five or more copies of a GITR-BD that comprises an amino acid sequence selected from the group consisting of SEQ ID NO: 19-80 and at least one immunoglobulin Fc region polypeptide comprising an amino acid sequence selected from the group consisting of SEQ ID NOs: 1-6. In some embodiments, the multivalent fusion protein contains six or more copies of a GITR-BD that comprises an amino acid sequence selected from the group consisting of SEQ ID NO: 19-80 and at least one immunoglobulin Fc region polypeptide comprising an amino acid sequence selected from the group consisting of SEQ ID NOs: 1-6.

In some embodiments, the multivalent fusion protein contains at least one GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 19-80 and at least one immunoglobulin Fc region polypeptide comprising an amino acid sequence selected from the group consisting of SEQ ID NOs: 1-6. In some embodiments, the multivalent fusion protein contains two or more copies of a GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 19-80 and at least one immunoglobulin Fc region polypeptide comprising an amino acid sequence selected from the group consisting of SEQ ID NOs: 1-6. In some embodiments, the multivalent fusion protein contains three or more copies of a GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 19-80 and at least one immunoglobulin Fc region polypeptide comprising an amino acid sequence selected from the group consisting of SEQ ID NOs: 1-6. In some embodiments, the multivalent fusion protein contains four or more copies of a GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 19-80 and at least one immunoglobulin Fc region polypeptide comprising an amino acid sequence selected from the group consisting of SEQ ID NOs: 1-6. In some embodiments, the multivalent fusion protein contains five or more copies of a GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 19-80 and at least one immunoglobulin Fc region polypeptide comprising an amino acid sequence selected from the group consisting of SEQ ID NOs: 1-6. In some embodiments, the multivalent fusion protein contains six or more copies of a GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 19-80 and at least one immunoglobulin Fc region polypeptide comprising an amino acid sequence selected from the group consisting of SEQ ID NOs: 1-6.

In some embodiments, the multivalent fusion protein contains at least one GITR-BD that comprises an amino acid sequence selected from the group consisting of SEQ ID NO: 42-62 and at least one immunoglobulin Fc region polypeptide comprising an amino acid sequence selected from the group consisting of SEQ ID NOs: 1-6. In some embodiments, the multivalent fusion protein contains two or more copies of a GITR-BD that comprises an amino acid sequence selected from the group consisting of SEQ ID NO: 42-62 and at least one immunoglobulin Fc region polypeptide comprising an amino acid sequence selected from the group consisting of SEQ ID NOs: 1-6. In some embodiments, the multivalent fusion protein contains three or more copies of a GITR-BD that comprises an amino acid sequence selected from the group consisting of SEQ ID NO: 42-62 and at least one immunoglobulin Fc region polypeptide comprising an amino acid sequence selected from the group consisting of SEQ ID NOs: 1-6. In some embodiments, the multivalent fusion protein contains four or more copies of a GITR-BD that comprises an amino acid sequence selected from the group consisting of SEQ ID NO: 42-62 and at least one immunoglobulin Fc region polypeptide comprising an amino acid sequence selected from the group consisting of SEQ ID NOs: 1-6. In some embodiments, the multivalent fusion protein contains five or more copies of a GITR-BD that comprises an amino acid sequence selected from the group consisting of SEQ ID NO: 42-62 and at least one immunoglobulin Fc region polypeptide comprising an amino acid sequence selected from the group consisting of SEQ ID NOs: 1-6. In some embodiments, the multivalent fusion protein contains six or more copies of a GITR-BD that comprises an amino acid sequence selected from the group consisting of SEQ ID NO: 42-62 and at least one immunoglobulin Fc region polypeptide comprising an amino acid sequence selected from the group consisting of SEQ ID NOs: 1-6.

In some embodiments, the multivalent fusion protein contains at least one GITR-BD that comprises an amino acid sequence selected from the group consisting of SEQ ID NO: 42-62 and at least one immunoglobulin Fc region polypeptide comprising the amino acid sequence of SEQ ID NO: 1. In some embodiments, the multivalent fusion protein contains two or more copies of a GITR-BD that comprises an amino acid sequence selected from the group consisting of SEQ ID NO: 42-62 and at least one immunoglobulin Fc region polypeptide comprising the amino acid sequence of SEQ ID NO: 1. In some embodiments, the multivalent fusion protein contains three or more copies of a GITR-BD that comprises an amino acid sequence selected from the group consisting of SEQ ID NO: 42-62 and at least one immunoglobulin Fc region polypeptide comprising the amino acid sequence of SEQ ID NO: 1. In some embodiments, the multivalent fusion protein contains four or more copies of a GITR-BD that comprises an amino acid sequence selected from the group consisting of SEQ ID NO: 42-62 and at least one immunoglobulin Fc region polypeptide comprising the amino acid sequence of SEQ ID NO: 1. In some embodiments, the multivalent fusion protein contains five or more copies of a GITR-BD that comprises an amino acid sequence selected from the group consisting of SEQ ID NO: 42-62 and at least one immunoglobulin Fc region polypeptide comprising the amino acid sequence of SEQ ID NO: 1. In some embodiments, the multivalent fusion protein contains six or more copies of a GITR-BD that comprises an amino acid sequence selected from the group consisting of SEQ ID NO: 42-62 and at least one immunoglobulin Fc region polypeptide comprising the amino acid sequence of SEQ ID NO: 1.

In some embodiments, the multivalent fusion protein contains at least one GITR-BD that comprises an amino acid sequence selected from the group consisting of SEQ ID NO: 42-62 and at least one immunoglobulin Fc region polypeptide comprising the amino acid sequence of SEQ ID NO: 2. In some embodiments, the multivalent fusion protein contains two or more copies of a GITR-BD that comprises an amino acid sequence selected from the group consisting of SEQ ID NO: 42-62 and at least one immunoglobulin Fc region polypeptide comprising the amino acid sequence of SEQ ID NO: 2. In some embodiments, the multivalent fusion protein contains three or more copies of a GITR-BD that comprises an amino acid sequence selected from the group consisting of SEQ ID NO: 42-62 and at least one immunoglobulin Fc region polypeptide comprising the amino acid sequence of SEQ ID NO: 2. In some embodiments, the multivalent fusion protein contains four or more copies of a GITR-BD that comprises an amino acid sequence selected from the group consisting of SEQ ID NO: 42-62 and at least one immunoglobulin Fc region polypeptide comprising the amino acid sequence of SEQ ID NO: 2. In some embodiments, the multivalent fusion protein contains five or more copies of a GITR-BD that comprises an amino acid sequence selected from the group consisting of SEQ ID NO: 42-62 and at least one immunoglobulin Fc region polypeptide comprising the amino acid sequence of SEQ ID NO: 2. In some embodiments, the multivalent fusion protein contains six or more copies of a GITR-BD that comprises an amino acid sequence selected from the group consisting of SEQ ID NO: 42-62 and at least one immunoglobulin Fc region polypeptide comprising the amino acid sequence of SEQ ID NO: 2.

In some embodiments, the multivalent fusion protein contains at least one GITR-BD that comprises an amino acid sequence selected from the group consisting of SEQ ID NO: 42-62 and at least one immunoglobulin Fc region polypeptide comprising the amino acid sequence of SEQ ID NO: 3. In some embodiments, the multivalent fusion protein contains two or more copies of a GITR-BD that comprises an amino acid sequence selected from the group consisting of SEQ ID NO: 42-62 and at least one immunoglobulin Fc region polypeptide comprising the amino acid sequence of SEQ ID NO: 3. In some embodiments, the multivalent fusion protein contains three or more copies of a GITR-BD that comprises an amino acid sequence selected from the group consisting of SEQ ID NO: 42-62 and at least one immunoglobulin Fc region polypeptide comprising the amino acid sequence of SEQ ID NO: 3. In some embodiments, the multivalent fusion protein contains four or more copies of a GITR-BD that comprises an amino acid sequence selected from the group consisting of SEQ ID NO: 42-62 and at least one immunoglobulin Fc region polypeptide comprising the amino acid sequence of SEQ ID NO: 3. In some embodiments, the multivalent fusion protein contains five or more copies of a GITR-BD that comprises an amino acid sequence selected from the group consisting of SEQ ID NO: 42-62 and at least one immunoglobulin Fc region polypeptide comprising the amino acid sequence of SEQ ID NO: 3. In some embodiments, the multivalent fusion protein contains six or more copies of a GITR-BD that comprises an amino acid sequence selected from the group consisting of SEQ ID NO: 42-62 and at least one immunoglobulin Fc region polypeptide comprising the amino acid sequence of SEQ ID NO: 3.

In some embodiments, the multivalent fusion protein contains at least one GITR-BD that comprises an amino acid sequence selected from the group consisting of SEQ ID NO: 42-62 and at least one immunoglobulin Fc region polypeptide comprising the amino acid sequence of SEQ ID NO: 4. In some embodiments, the multivalent fusion protein contains two or more copies of a GITR-BD that comprises an amino acid sequence selected from the group consisting of SEQ ID NO: 42-62 and at least one immunoglobulin Fc region polypeptide comprising the amino acid sequence of SEQ ID NO: 4. In some embodiments, the multivalent fusion protein contains three or more copies of a GITR-BD that comprises an amino acid sequence selected from the group consisting of SEQ ID NO: 42-62 and at least one immunoglobulin Fc region polypeptide comprising the amino acid sequence of SEQ ID NO: 4. In some embodiments, the multivalent fusion protein contains four or more copies of a GITR-BD that comprises an amino acid sequence selected from the group consisting of SEQ ID NO: 42-62 and at least one immunoglobulin Fc region polypeptide comprising the amino acid sequence of SEQ ID NO: 4. In some embodiments, the multivalent fusion protein contains five or more copies of a GITR-BD that comprises an amino acid sequence selected from the group consisting of SEQ ID NO: 42-62 and at least one immunoglobulin Fc region polypeptide comprising the amino acid sequence of SEQ ID NO: 4. In some embodiments, the multivalent fusion protein contains six or more copies of a GITR-BD that comprises an amino acid sequence selected from the group consisting of SEQ ID NO: 42-62 and at least one immunoglobulin Fc region polypeptide comprising the amino acid sequence of SEQ ID NO: 4.

In some embodiments, the multivalent fusion protein contains at least one GITR-BD that comprises an amino acid sequence selected from the group consisting of SEQ ID NO: 42-62 and at least one immunoglobulin Fc region polypeptide comprising the amino acid sequence of SEQ ID NO: 5. In some embodiments, the multivalent fusion protein contains two or more copies of a GITR-BD that comprises an amino acid sequence selected from the group consisting of SEQ ID NO: 42-62 and at least one immunoglobulin Fc region polypeptide comprising the amino acid sequence of SEQ ID NO: 5. In some embodiments, the multivalent fusion protein contains three or more copies of a GITR-BD that comprises an amino acid sequence selected from the group consisting of SEQ ID NO: 42-62 and at least one immunoglobulin Fc region polypeptide comprising the amino acid sequence of SEQ ID NO: 5. In some embodiments, the multivalent fusion protein contains four or more copies of a GITR-BD that comprises an amino acid sequence selected from the group consisting of SEQ ID NO: 42-62 and at least one immunoglobulin Fc region polypeptide comprising the amino acid sequence of SEQ ID NO: 5. In some embodiments, the multivalent fusion protein contains five or more copies of a GITR-BD that comprises an amino acid sequence selected from the group consisting of SEQ ID NO: 42-62 and at least one immunoglobulin Fc region polypeptide comprising the amino acid sequence of SEQ ID NO: 5. In some embodiments, the multivalent fusion protein contains six or more copies of a GITR-BD that comprises an amino acid sequence selected from the group consisting of SEQ ID NO: 42-62 and at least one immunoglobulin Fc region polypeptide comprising the amino acid sequence of SEQ ID NO: 5.

In some embodiments, the multivalent fusion protein contains at least one GITR-BD that comprises an amino acid sequence selected from the group consisting of SEQ ID NO: 42-62 and at least one immunoglobulin Fc region polypeptide comprising the amino acid sequence of SEQ ID NO: 6. In some embodiments, the multivalent fusion protein contains two or more copies of a GITR-BD that comprises an amino acid sequence selected from the group consisting of SEQ ID NO: 42-62 and at least one immunoglobulin Fc region polypeptide comprising the amino acid sequence of SEQ ID NO: 6. In some embodiments, the multivalent fusion protein contains three or more copies of a GITR-BD that comprises an amino acid sequence selected from the group consisting of SEQ ID NO: 42-62 and at least one immunoglobulin Fc region polypeptide comprising the amino acid sequence of SEQ ID NO: 6. In some embodiments, the multivalent fusion protein contains four or more copies of a GITR-BD that comprises an amino acid sequence selected from the group consisting of SEQ ID NO: 42-62 and at least one immunoglobulin Fc region polypeptide comprising the amino acid sequence of SEQ ID NO: 6. In some embodiments, the multivalent fusion protein contains five or more copies of a GITR-BD that comprises an amino acid sequence selected from the group consisting of SEQ ID NO: 42-62 and at least one immunoglobulin Fc region polypeptide comprising the amino acid sequence of SEQ ID NO: 6. In some embodiments, the multivalent fusion protein contains six or more copies of a GITR-BD that comprises an amino acid sequence selected from the group consisting of SEQ ID NO: 42-62 and at least one immunoglobulin Fc region polypeptide comprising the amino acid sequence of SEQ ID NO: 6.

In some embodiments, the multivalent fusion protein contains at least one GITR-BD that comprises an amino acid sequence selected from the group consisting of SEQ ID NO: 63-80 and at least one immunoglobulin Fc region polypeptide comprising an amino acid sequence selected from the group consisting of SEQ ID NOs: 1-6. In some embodiments, the multivalent fusion protein contains two or more copies of a GITR-BD that comprises an amino acid sequence selected from the group consisting of SEQ ID NO: 63-80 and at least one immunoglobulin Fc region polypeptide comprising an amino acid sequence selected from the group consisting of SEQ ID NOs: 1-6. In some embodiments, the multivalent fusion protein contains three or more copies of a GITR-BD that comprises an amino acid sequence selected from the group consisting of SEQ ID NO: 63-80 and at least one immunoglobulin Fc region polypeptide comprising an amino acid sequence selected from the group consisting of SEQ ID NOs: 1-6. In some embodiments, the multivalent fusion protein contains four or more copies of a GITR-BD that comprises an amino acid sequence selected from the group consisting of SEQ ID NO: 63-80 and at least one immunoglobulin Fc region polypeptide comprising an amino acid sequence selected from the group consisting of SEQ ID NOs: 1-6. In some embodiments, the multivalent fusion protein contains five or more copies of a GITR-BD that comprises an amino acid sequence selected from the group consisting of SEQ ID NO: 63-80 and at least one immunoglobulin Fc region polypeptide comprising an amino acid sequence selected from the group consisting of SEQ ID NOs: 1-6. In some embodiments, the multivalent fusion protein contains six or more copies of a GITR-BD that comprises an amino acid sequence selected from the group consisting of SEQ ID NO: 63-80 and at least one immunoglobulin Fc region polypeptide comprising an amino acid sequence selected from the group consisting of SEQ ID NOs: 1-6.

In some embodiments, the multivalent fusion protein contains at least one GITR-BD that comprises an amino acid sequence selected from the group consisting of SEQ ID NO: 63-80 and at least one immunoglobulin Fc region polypeptide comprising the amino acid sequence of SEQ ID NO: 1. In some embodiments, the multivalent fusion protein contains two or more copies of a GITR-BD that comprises an amino acid sequence selected from the group consisting of SEQ ID NO: 63-80 and at least one immunoglobulin Fc region polypeptide comprising the amino acid sequence of SEQ ID NO: 1. In some embodiments, the multivalent fusion protein contains three or more copies of a GITR-BD that comprises an amino acid sequence selected from the group consisting of SEQ ID NO: 63-80 and at least one immunoglobulin Fc region polypeptide comprising the amino acid sequence of SEQ ID NO: 1. In some embodiments, the multivalent fusion protein contains four or more copies of a GITR-BD that comprises an amino acid sequence selected from the group consisting of SEQ ID NO: 63-80 and at least one immunoglobulin Fc region polypeptide comprising the amino acid sequence of SEQ ID NO: 1. In some embodiments, the multivalent fusion protein contains five or more copies of a GITR-BD that comprises an amino acid sequence selected from the group consisting of SEQ ID NO: 63-80 and at least one immunoglobulin Fc region polypeptide comprising the amino acid sequence of SEQ ID NO: 1. In some embodiments, the multivalent fusion protein contains six or more copies of a GITR-BD that comprises an amino acid sequence selected from the group consisting of SEQ ID NO: 63-80 and at least one immunoglobulin Fc region polypeptide comprising the amino acid sequence of SEQ ID NO: 1.

In some embodiments, the multivalent fusion protein contains at least one GITR-BD that comprises an amino acid sequence selected from the group consisting of SEQ ID NO: 63-80 and at least one immunoglobulin Fc region polypeptide comprising the amino acid sequence of SEQ ID NO: 2. In some embodiments, the multivalent fusion protein contains two or more copies of a GITR-BD that comprises an amino acid sequence selected from the group consisting of SEQ ID NO: 63-80 and at least one immunoglobulin Fc region polypeptide comprising the amino acid sequence of SEQ ID NO: 2. In some embodiments, the multivalent fusion protein contains three or more copies of a GITR-BD that comprises an amino acid sequence selected from the group consisting of SEQ ID NO: 63-80 and at least one immunoglobulin Fc region polypeptide comprising the amino acid sequence of SEQ ID NO: 2. In some embodiments, the multivalent fusion protein contains four or more copies of a GITR-BD that comprises an amino acid sequence selected from the group consisting of SEQ ID NO: 63-80 and at least one immunoglobulin Fc region polypeptide comprising the amino acid sequence of SEQ ID NO: 2. In some embodiments, the multivalent fusion protein contains five or more copies of a GITR-BD that comprises an amino acid sequence selected from the group consisting of SEQ ID NO: 63-80 and at least one immunoglobulin Fc region polypeptide comprising the amino acid sequence of SEQ ID NO: 2. In some embodiments, the multivalent fusion protein contains six or more copies of a GITR-BD that comprises an amino acid sequence selected from the group consisting of SEQ ID NO: 63-80 and at least one immunoglobulin Fc region polypeptide comprising the amino acid sequence of SEQ ID NO: 2.

In some embodiments, the multivalent fusion protein contains at least one GITR-BD that comprises an amino acid sequence selected from the group consisting of SEQ ID NO: 63-80 and at least one immunoglobulin Fc region polypeptide comprising the amino acid sequence of SEQ ID NO: 3. In some embodiments, the multivalent fusion protein contains two or more copies of a GITR-BD that comprises an amino acid sequence selected from the group consisting of SEQ ID NO: 63-80 and at least one immunoglobulin Fc region polypeptide comprising the amino acid sequence of SEQ ID NO: 3. In some embodiments, the multivalent fusion protein contains three or more copies of a GITR-BD that comprises an amino acid sequence selected from the group consisting of SEQ ID NO: 63-80 and at least one immunoglobulin Fc region polypeptide comprising the amino acid sequence of SEQ ID NO: 3. In some embodiments, the multivalent fusion protein contains four or more copies of a GITR-BD that comprises an amino acid sequence selected from the group consisting of SEQ ID NO: 63-80 and at least one immunoglobulin Fc region polypeptide comprising the amino acid sequence of SEQ ID NO: 3. In some embodiments, the multivalent fusion protein contains five or more copies of a GITR-BD that comprises an amino acid sequence selected from the group consisting of SEQ ID NO: 63-80 and at least one immunoglobulin Fc region polypeptide comprising the amino acid sequence of SEQ ID NO: 3. In some embodiments, the multivalent fusion protein contains six or more copies of a GITR-BD that comprises an amino acid sequence selected from the group consisting of SEQ ID NO: 63-80 and at least one immunoglobulin Fc region polypeptide comprising the amino acid sequence of SEQ ID NO: 3.

In some embodiments, the multivalent fusion protein contains at least one GITR-BD that comprises an amino acid sequence selected from the group consisting of SEQ ID NO: 63-80 and at least one immunoglobulin Fc region polypeptide comprising the amino acid sequence of SEQ ID NO: 4. In some embodiments, the multivalent fusion protein contains two or more copies of a GITR-BD that comprises an amino acid sequence selected from the group consisting of SEQ ID NO: 63-80 and at least one immunoglobulin Fc region polypeptide comprising the amino acid sequence of SEQ ID NO: 4. In some embodiments, the multivalent fusion protein contains three or more copies of a GITR-BD that comprises an amino acid sequence selected from the group consisting of SEQ ID NO: 63-80 and at least one immunoglobulin Fc region polypeptide comprising the amino acid sequence of SEQ ID NO: 4. In some embodiments, the multivalent fusion protein contains four or more copies of a GITR-BD that comprises an amino acid sequence selected from the group consisting of SEQ ID NO: 63-80 and at least one immunoglobulin Fc region polypeptide comprising the amino acid sequence of SEQ ID NO: 4. In some embodiments, the multivalent fusion protein contains five or more copies of a GITR-BD that comprises an amino acid sequence selected from the group consisting of SEQ ID NO: 63-80 and at least one immunoglobulin Fc region polypeptide comprising the amino acid sequence of SEQ ID NO: 4. In some embodiments, the multivalent fusion protein contains six or more copies of a GITR-BD that comprises an amino acid sequence selected from the group consisting of SEQ ID NO: 63-80 and at least one immunoglobulin Fc region polypeptide comprising the amino acid sequence of SEQ ID NO: 4.

In some embodiments, the multivalent fusion protein contains at least one GITR-BD that comprises an amino acid sequence selected from the group consisting of SEQ ID NO:

63-80 and at least one immunoglobulin Fc region polypeptide comprising the amino acid sequence of SEQ ID NO: 5. In some embodiments, the multivalent fusion protein contains two or more copies of a GITR-BD that comprises an amino acid sequence selected from the group consisting of SEQ ID NO: 63-80 and at least one immunoglobulin Fc region polypeptide comprising the amino acid sequence of SEQ ID NO: 5. In some embodiments, the multivalent fusion protein contains three or more copies of a GITR-BD that comprises an amino acid sequence selected from the group consisting of SEQ ID NO: 63-80 and at least one immunoglobulin Fc region polypeptide comprising the amino acid sequence of SEQ ID NO: 5. In some embodiments, the multivalent fusion protein contains four or more copies of a GITR-BD that comprises an amino acid sequence selected from the group consisting of SEQ ID NO: 63-80 and at least one immunoglobulin Fc region polypeptide comprising the amino acid sequence of SEQ ID NO: 5. In some embodiments, the multivalent fusion protein contains five or more copies of a GITR-BD that comprises an amino acid sequence selected from the group consisting of SEQ ID NO: 63-80 and at least one immunoglobulin Fc region polypeptide comprising the amino acid sequence of SEQ ID NO: 5. In some embodiments, the multivalent fusion protein contains six or more copies of a GITR-BD that comprises an amino acid sequence selected from the group consisting of SEQ ID NO: 63-80 and at least one immunoglobulin Fc region polypeptide comprising the amino acid sequence of SEQ ID NO: 5.

In some embodiments, the multivalent fusion protein contains at least one GITR-BD that comprises an amino acid sequence selected from the group consisting of SEQ ID NO: 63-80 and at least one immunoglobulin Fc region polypeptide comprising the amino acid sequence of SEQ ID NO: 6. In some embodiments, the multivalent fusion protein contains two or more copies of a GITR-BD that comprises an amino acid sequence selected from the group consisting of SEQ ID NO: 63-80 and at least one immunoglobulin Fc region polypeptide comprising the amino acid sequence of SEQ ID NO: 6. In some embodiments, the multivalent fusion protein contains three or more copies of a GITR-BD that comprises an amino acid sequence selected from the group consisting of SEQ ID NO: 63-80 and at least one immunoglobulin Fc region polypeptide comprising the amino acid sequence of SEQ ID NO: 6. In some embodiments, the multivalent fusion protein contains four or more copies of a GITR-BD that comprises an amino acid sequence selected from the group consisting of SEQ ID NO: 63-80 and at least one immunoglobulin Fc region polypeptide comprising the amino acid sequence of SEQ ID NO: 6. In some embodiments, the multivalent fusion protein contains five or more copies of a GITR-BD that comprises an amino acid sequence selected from the group consisting of SEQ ID NO: 63-80 and at least one immunoglobulin Fc region polypeptide comprising the amino acid sequence of SEQ ID NO: 6. In some embodiments, the multivalent fusion protein contains six or more copies of a GITR-BD that comprises an amino acid sequence selected from the group consisting of SEQ ID NO: 63-80 and at least one immunoglobulin Fc region polypeptide comprising the amino acid sequence of SEQ ID NO: 6.

In some embodiments, the multivalent fusion protein contains at least one GITR-BD that comprises a complementarity determining region 1 (CDR1) comprising an amino acid sequence selected from the group consisting of SEQ ID NO: 106, 109, 112, 117, 120, 125, 131, 138, 143, 148, and 149; a complementarity determining region 2 (CDR2) comprising an amino acid sequence selected from the group consisting of SEQ ID NO: 107, 110, 113, 115, 118, 121, 123, 128, 130, 132, 134, 136, 137, 139, 141, 144, and 147; and a complementarity determining region 3 (CDR3) comprising an amino acid sequence selected from the group consisting of SEQ ID NO: 108, 111, 114, 116, 119, 122, 124, 126, 127, 129, 133, 135, 140, 142, 145, 146, and 150 and at least one immunoglobulin Fc region polypeptide comprising an amino acid sequence selected from the group consisting of SEQ ID NOs: 1-6. In some embodiments, the multivalent fusion protein contains two or more copies of a GITR-BD that comprises a CDR1 comprising an amino acid sequence selected from the group consisting of SEQ ID NO: 106, 109, 112, 117, 120, 125, 131, 138, 143, 148, and 149; a CDR2 comprising an amino acid sequence selected from the group consisting of SEQ ID NO: 107, 110, 113, 115, 118, 121, 123, 128, 130, 132, 134, 136, 137, 139, 141, 144, and 147; and a CDR3 comprising an amino acid sequence selected from the group consisting of SEQ ID NO: 108, 111, 114, 116, 119, 122, 124, 126, 127, 129, 133, 135, 140, 142, 145, 146, and 150 and at least one immunoglobulin Fc region polypeptide comprising an amino acid sequence selected from the group consisting of SEQ ID NOs: 1-6. In some embodiments, the multivalent fusion protein contains three or more copies of a GITR-BD that comprises a CDR1 comprising an amino acid sequence selected from the group consisting of SEQ ID NO: 106, 109, 112, 117, 120, 125, 131, 138, 143, 148, and 149; a CDR2 comprising an amino acid sequence selected from the group consisting of SEQ ID NO: 107, 110, 113, 115, 118, 121, 123, 128, 130, 132, 134, 136, 137, 139, 141, 144, and 147; and a CDR3 comprising an amino acid sequence selected from the group consisting of SEQ ID NO: 108, 111, 114, 116, 119, 122, 124, 126, 127, 129, 133, 135, 140, 142, 145, 146, and 150 and at least one immunoglobulin Fc region polypeptide comprising an amino acid sequence selected from the group consisting of SEQ ID NOs: 1-6. In some embodiments, the multivalent fusion protein contains four or more copies of a GITR-BD that comprises a CDR1 comprising an amino acid sequence selected from the group consisting of SEQ ID NO: 106, 109, 112, 117, 120, 125, 131, 138, 143, 148, and 149; a CDR2 comprising an amino acid sequence selected from the group consisting of SEQ ID NO: 107, 110, 113, 115, 118, 121, 123, 128, 130, 132, 134, 136, 137, 139, 141, 144, and 147; and a CDR3 comprising an amino acid sequence selected from the group consisting of SEQ ID NO: 108, 111, 114, 116, 119, 122, 124, 126, 127, 129, 133, 135, 140, 142, 145, 146, and 150 and at least one immunoglobulin Fc region polypeptide comprising an amino acid sequence selected from the group consisting of SEQ ID NOs: 1-6. In some embodiments, the multivalent fusion protein contains five or more copies of a GITR-BD that comprises a CDR1 comprising an amino acid sequence selected from the group consisting of SEQ ID NO: 106, 109, 112, 117, 120, 125, 131, 138, 143, 148, and 149; a CDR2 comprising an amino acid sequence selected from the group consisting of SEQ ID NO: 107, 110, 113, 115, 118, 121, 123, 128, 130, 132, 134, 136, 137, 139, 141, 144, and 147; and a CDR3 comprising an amino acid sequence selected from the group consisting of SEQ ID NO: 108, 111, 114, 116, 119, 122, 124, 126, 127, 129, 133, 135, 140, 142, 145, 146, and 150 and at least one immunoglobulin Fc region polypeptide comprising an amino acid sequence selected from the group consisting of SEQ ID NOs: 1-6. In some embodiments, the multivalent fusion protein contains six or more copies of a GITR-BD that comprises a CDR1 comprising an amino acid sequence selected from the group consisting of SEQ ID NO: 106, 109, 112, 117, 120, 125, 131, 138, 143, 148, and 149; a CDR2 comprising an amino acid sequence selected from the group consisting of SEQ ID NO: 107, 110, 113, 115, 118, 121, 123, 128, 130, 132, 134, 136, 137, 139, 141, 144, and 147; and a CDR3 comprising an amino acid sequence selected from the group consisting of SEQ ID NO: 108, 111, 114, 116, 119, 122, 124, 126, 127, 129, 133, 135, 140, 142, 145, 146, and 150 and at least one immunoglobulin Fc region polypeptide comprising an amino acid sequence selected from the group consisting of SEQ ID NOs: 1-6.

In some embodiments, the multivalent fusion protein comprises an amino acid sequence selected from the group consisting of SEQ ID NO: 81-105. In some embodiments, the multivalent fusion protein comprises an amino acid sequence selected from the group consisting of SEQ ID NO: 81-93. In some embodiments, the multivalent fusion protein comprises an amino acid sequence selected from the group consisting of SEQ ID NO: 94-105.

In some embodiments, the multivalent fusion protein comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 81-105. In some embodiments, the multivalent fusion protein comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 81-93. In some embodiments, the multivalent fusion protein comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 94-105.

In some embodiments, the multivalent fusion protein comprises the amino acid sequence of SEQ ID NO: 81. In some embodiments, the multivalent fusion protein comprises the amino acid sequence of SEQ ID NO: 82. In some embodiments, the multivalent fusion protein comprises the amino acid sequence of SEQ ID NO: 83. In some embodiments, the multivalent fusion protein comprises the amino acid sequence of SEQ ID NO: 84. In some embodiments, the multivalent fusion protein comprises the amino acid sequence of SEQ ID NO: 85. In some embodiments, the multivalent fusion protein comprises the amino acid sequence of SEQ ID NO: 86. In some embodiments, the multivalent fusion protein comprises the amino acid sequence of SEQ ID NO: 87. In some embodiments, the multivalent fusion protein comprises the amino acid sequence of SEQ ID NO: 88. In some embodiments, the multivalent fusion protein comprises the amino acid sequence of SEQ ID NO: 89. In some embodiments, the multivalent fusion protein comprises the amino acid sequence of SEQ ID NO: 90. In some embodiments, the multivalent fusion protein comprises the amino acid sequence of SEQ ID NO: 91. In some embodiments, the multivalent fusion protein comprises the amino acid sequence of SEQ ID NO: 92. In some embodiments, the multivalent fusion protein comprises the amino acid sequence of SEQ ID NO: 93. In some embodiments, the multivalent fusion protein comprises the amino acid sequence of SEQ ID NO: 94. In some embodiments, the multivalent fusion protein comprises the amino acid sequence of SEQ ID NO: 95. In some embodiments, the multivalent fusion protein comprises the amino acid sequence of SEQ ID NO: 96. In some embodiments, the multivalent fusion protein comprises the amino acid sequence of SEQ ID NO: 97. In some embodiments, the multivalent fusion protein comprises the amino acid sequence of SEQ ID NO: 98. In some embodiments, the multivalent fusion protein comprises the amino acid sequence of SEQ ID NO: 99. In some embodiments, the multivalent fusion protein comprises the amino acid sequence of SEQ ID NO: 100. In some embodiments, the multivalent fusion protein comprises the amino acid sequence of SEQ ID NO: 101. In some embodiments, the multivalent fusion protein comprises the amino acid sequence of SEQ ID NO: 102. In some embodiments, the multivalent fusion protein comprises the amino acid sequence of SEQ ID NO: 103. In some embodiments, the multivalent fusion protein comprises the amino acid sequence of SEQ ID NO: 104. In some embodiments, the multivalent fusion protein comprises the amino acid sequence of SEQ ID NO: 105.

In some embodiments, the multivalent GITR-targeting fusion protein is tetravalent. As used herein, a tetravalent GITR-targeting molecule refers to two copies of a GITR-targeting fusion protein that includes two GITR-BDs. For example, in some embodiments, a tetravalent GITR-targeting molecule of the disclosure includes two copies of a GITR-targeting fusion protein having the following structure: (GITR-BD)-Linker-(GITR-BD)-Linker-Hinge-Fc. In some embodiments, the tetravalent GITR-targeting molecule of the disclosure includes two copies of a GITR-binding fusion protein having the following structure: (GITR-BD)-Linker-(GITR-BD)-Linker-Hinge-Fc, where the GITR-BD is an isolated polypeptide sequence that binds GITR. In some embodiments, the tetravalent GITR-targeting molecule of the disclosure includes two copies of a GITR-binding fusion protein having the following structure: (GITR-BD)-Linker-(GITR-BD)-Linker-Hinge-Fc, where the GITR-BD is an sdAb sequence that binds GITR. In some embodiments, the tetravalent GITR-targeting molecule of the disclosure includes two copies of a GITR-binding fusion protein having the following structure: (GITR-BD)-Linker-(GITR-BD)-Linker-Hinge-Fc, where the GITR-BD is a humanized or fully human sdAb sequence that binds GITR. In some embodiments, the GITR-BD comprises a complementarity determining region 1 (CDR1) comprising an amino acid sequence selected from the group consisting of SEQ ID NO: 106, 109, 112, 117, 120, 125, 131, 138, 143, 148, and 149; a complementarity determining region 2 (CDR2) comprising an amino acid sequence selected from the group consisting of SEQ ID NO: 107, 110, 113, 115, 118, 121, 123, 128, 130, 132, 134, 136, 137, 139, 141, 144, and 147; and a complementarity determining region 3 (CDR3) comprising an amino acid sequence selected from the group consisting of SEQ ID NO: 108, 111, 114, 116, 119, 122, 124, 126, 127, 129, 133, 135, 140, 142, 145, 146, and 150. In some embodiments, the tetravalent GITR-targeting molecule contains at least one GITR-BD that comprises an amino acid sequence selected from the group consisting of SEQ ID NO: 19-80. In some embodiments, the tetravalent GITR-targeting molecule contains at least one GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 19-80. In some embodiments, the tetravalent GITR-targeting molecule contains at least one GITR-BD that comprises an amino acid sequence selected from the group consisting of SEQ ID NO: 42-62. In some embodiments, the tetravalent GITR-targeting molecule contains at least one GITR-BD that comprises an amino acid sequence selected from the group consisting of SEQ ID NO: 63-80. In some embodiments, the tetravalent GITR-targeting molecule comprises two copies of an amino acid sequence selected from the group consisting of SEQ ID NO: 81-93.

In some embodiments, the multivalent GITR-targeting fusion protein is hexavalent. As used herein, a hexavalent GITR-targeting molecule refers to two copies of a GITR-targeting fusion protein that includes three GITR-BDs. For example, in some embodiments, a hexavalent GITR-targeting molecule of the disclosure includes two copies of a GITR-targeting fusion protein having the following structure: (GITR-BD)-Linker-(GITR-BD)-Linker-(GITR-BD)-Linker-Hinge-Fc. In some embodiments, the hexavalent GITR-targeting molecule of the disclosure includes two copies of a GITR-targeting fusion protein has the following structure: (GITR-BD)-Linker-(GITR-BD)-Linker-(GITR-BD)-Linker-Hinge-Fc, where the GITR-BD is an isolated polypeptide sequence that binds GITR. In some embodiments, the hexavalent GITR-targeting molecule of the disclosure includes two copies of a GITR-targeting fusion protein has the following structure: (GITR-BD)-Linker-(GITR-BD)-Linker-(GITR-BD)-Linker-Hinge-Fc, where the GITR-BD is an sdAb sequence that binds GITR. In some embodiments, the hexavalent GITR-targeting molecule of the disclosure includes two copies of a GITR-targeting fusion protein has the following structure: (GITR-BD)-Linker-(GITR-BD)-Linker-(GITR-BD)-Linker-Hinge-Fc, where the GITR-BD is a humanized or fully human sdAb sequence. In some embodiments, the tetravalent GITR-targeting molecule contains at least one GITR-BD that comprises an amino acid sequence selected from the group consisting of SEQ ID NO: 19-80. In some embodiments, the tetravalent GITR-targeting molecule contains at least one GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 19-80. In some embodiments, the tetravalent GITR-targeting molecule contains at least one GITR-BD that comprises an amino acid sequence selected from the group consisting of SEQ ID NO: 42-62. In some embodiments, the tetravalent GITR-targeting molecule contains at least one GITR-BD that comprises an amino acid sequence selected from the group consisting of SEQ ID NO: 63-80. In some embodiments, the tetravalent GITR-targeting molecule comprises an amino acid sequence selected from the group consisting of SEQ ID NO: 94-105.

The multivalent fusion proteins of the present disclosure are capable of enhanced clustering of TNFRSF members compared to non-cross-linked bivalent antibodies. The enhanced clustered of TNFRSF members mediated by the multivalent fusion proteins of the present disclosure induce enhanced TNFRSF-dependent signaling compared to non-cross-linked bivalent antibodies. In most embodiments, the multivalent fusion protein will incorporate more than two GITR-BDs, for example, three, four, five, or six. In these embodiments, the interaction of the non-TNFRSF antigen is capable of providing the additional crosslinking function and TNFRSF activation is achieved with only one or two TBDs.

In some embodiments, the multivalent fusion protein also includes one or more GITR-BDs and one or more additional binding domain(s) that bind to a target other than GITR. In some embodiments, the multivalent, multispecific fusion protein also includes one or more GITR-BDs and one or more additional binding domain(s) directed toward non-TNFRSF member antigen. In any of these embodiments, the multivalent, multispecific fusion protein can also include one or more additional binding domain(s) directed to a TNFRSF member, referred to herein as a TNFRSF-binding domain (TBD). In any of these embodiments, the interaction of the non-TNFRSF antigen is capable of providing the additional crosslinking function and TNFRSF activation is achieved with only one or two GITR-BDs or only one or two GITR-BDs and TBDs.

In some embodiments, the multivalent, multispecific fusion protein also includes one or more additional binding domain(s) directed to a TNFRSF member, referred to herein as a TNFRSF-binding domain (TBD). In these embodiments, the multivalent, multispecific fusion protein is binds at least two distinct antigens. In some embodiments, all of the TBDs of the multivalent, multispecific fusion protein recognize the same epitope on the given TNFRSF member. For example, the multivalent, multispecific fusion proteins of present disclosure may incorporate 2, 3, 4, 5, or 6 TBDs with identical specificity to a given TNFRSF member. In other embodiments, the multivalent, multispecific fusion protein incorporates TBDs that recognize distinct epitopes on the given TNFRSF member. For example, the multivalent, multispecific fusion proteins of present disclosure may incorporate 2, 3, 4, 5, or 6 TBDs with distinct recognition specificities toward various epitopes on GITR, CD40 or CD137. In these embodiments, the multivalent, multispecific fusion proteins of the present disclosure with contain multiple TBDs that target distinct regions of the particular TNFRSF member. In some embodiments, the TBDs may recognize different epitopes on the same TNFRSF member or recognize epitopes on distinct TNFRSF members. For example, the present disclosure provides multivalent, multispecific fusion proteins incorporating TBDs that bind GITR and OX40.

In other embodiments, the fusion proteins of the present disclosure is a multispecific fusion protein that binds GITR and a second TNFRSF member expressed on a non-tumor cell such as, by way of non-limiting example, OX40, CD27, HVEM, CD40, lymphotoxin beta receptor (LTBR), ectodysplasin A2 receptor (ED2R), ectodysplasin A receptor (EDAR), TweakR, BCMA, BAFFR, DR3, DR6 or CD137. In some embodiments, the multispecific fusion protein is also multivalent. In some embodiments, the multispecific fusion protein is bispecific. In these embodiments, the multispecific fusion proteins of the present disclosure modulate immune cells leading to enhanced tumor destruction. In other embodiments, the multispecific fusion proteins of the present disclosure have utility in treating inflammatory conditions. In these embodiments, the multispecific fusion proteins of the present disclosure modulate immune cells leading to dampening of the inflammatory insult. For example, specifically agonizing TNFR2 can enhance Treg proliferation leading to immune suppression.

In some embodiments, the multispecific fusion protein contains at least one GITR-BD that comprises an amino acid sequence selected from the group consisting of SEQ ID NO: 19-80. In some embodiments, the multispecific fusion protein contains at least one GITR-BD that comprises an amino acid sequence selected from the group consisting of SEQ ID NO: 42-62. In some embodiments, the multispecific fusion protein contains at least one GITR-BD that comprises an amino acid sequence selected from the group consisting of SEQ ID NO: 63-80.

In some embodiments, the multispecific fusion protein contains at least one GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 19-80. In some embodiments, the multispecific fusion protein contains at least one GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 42-62. In some embodiments, the multispecific fusion protein contains at least one GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 63-80.

In some embodiments, the multispecific fusion protein contains at least one GITR-BD that comprises a complementarity determining region 1 (CDR1) comprising an amino acid sequence selected from the group consisting of SEQ ID NO: 106, 109, 112, 117, 120, 125, 131, 138, 143, 148, and 149; a complementarity determining region 2 (CDR2) comprising an amino acid sequence selected from the group consisting of SEQ ID NO: 107, 110, 113, 115, 118, 121, 123, 128, 130, 132, 134, 136, 137, 139, 141, 144, and 147; and a complementarity determining region 3 (CDR3) comprising an amino acid sequence selected from the group consisting of SEQ ID NO: 108, 111, 114, 116, 119, 122, 124, 126, 127, 129, 133, 135, 140, 142, 145, 146, and 150.

In some embodiments, the multispecific fusion protein contains at least one GITR-BD that comprises an amino acid sequence selected from the group consisting of SEQ ID NO: 19-80 and at least one immunoglobulin Fc region polypeptide comprising an amino acid sequence selected from the group consisting of SEQ ID NOs: 1-6. In some embodiments, the multispecific fusion protein contains at least one GITR-BD that comprises an amino acid sequence selected from the group consisting of SEQ ID NO: 42-62 and at least one immunoglobulin Fc region polypeptide comprising an amino acid sequence selected from the group consisting of SEQ ID NOs: 1-6. In some embodiments, the multispecific fusion protein contains at least one GITR-BD that comprises an amino acid sequence selected from the group consisting of SEQ ID NO: 63-80 and at least one immunoglobulin Fc region polypeptide comprising an amino acid sequence selected from the group consisting of SEQ ID NOs: 1-6.

In some embodiments, the multispecific fusion protein contains at least one GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 19-80 and at least one immunoglobulin Fc region polypeptide comprising an amino acid sequence selected from the group consisting of SEQ ID NOs: 1-6. In some embodiments, the multispecific fusion protein contains at least one GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 42-62 and at least one immunoglobulin Fc region polypeptide comprising an amino acid sequence selected from the group consisting of SEQ ID NOs: 1-6. In some embodiments, the multispecific fusion protein contains at least one GITR-BD that comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 63-80 and at least one immunoglobulin Fc region polypeptide comprising an amino acid sequence selected from the group consisting of SEQ ID NOs: 1-6.

In some embodiments, the multispecific fusion protein contains at least one GITR-BD that comprises a complementarity determining region 1 (CDR1) comprising an amino acid sequence selected from the group consisting of SEQ ID NO: 106, 109, 112, 117, 120, 125, 131, 138, 143, 148, and 149; a complementarity determining region 2 (CDR2) comprising an amino acid sequence selected from the group consisting of SEQ ID NO: 107, 110, 113, 115, 118, 121, 123, 128, 130, 132, 134, 136, 137, 139, 141, 144, and 147; and a complementarity determining region 3 (CDR3) comprising an amino acid sequence selected from the group consisting of SEQ ID NO: 108, 111, 114, 116, 119, 122, 124, 126, 127, 129, 133, 135, 140, 142, 145, 146, and 150 and at least one immunoglobulin Fc region polypeptide comprising an amino acid sequence selected from the group consisting of SEQ ID NOs: 1-6.

The multispecific fusion proteins of the present disclosure are capable of enhanced clustering of TNFRSF members compared to non-cross-linked bivalent antibodies. The enhanced clustered of TNFRSF members mediated by the multispecific fusion proteins of the present disclosure induce enhanced TNFRSF-dependent signaling compared to non-cross-linked bivalent antibodies. In most embodiments, the multispecific fusion protein will incorporate more than 2 TBDs, for example, three, four, five, or six. In some embodiments, the multispecific fusion protein will incorporate TBDs and a binding domain directed toward non-TNFRSF member antigen. In these embodiments, the interaction of the non-TNFRSF antigen is capable of providing the additional crosslinking function and TNFRSF activation is achieved with only one or two TBDs. In these embodiments, the multispecific fusion protein is multispecific, binding two distinct antigens.

In some embodiments, TBDs of the present disclosure are derived from antibodies or antibody fragments including scFv, Fabs, single domain antibodies (sdAb), $V_{NAR}$, or VHHs. In some embodiments, the TBDs are human or humanized sdAb. The sdAb fragments can be derived from VHH, $V_{NAR}$, engineered VH or VK domains. VHHs can be generated from camelid heavy chain only antibodies. $V_{NAR}$s can be generated from cartilaginous fish heavy chain only antibodies. Various methods have been implemented to generate monomeric sdAbs from conventionally heterodimeric VH and VK domains, including interface engineering and selection of specific germline families. In other embodiments, the TDBs are derived from non-antibody scaffold proteins for example but not limited to designed ankyrin repeat proteins (darpins), avimers, anticalin/lipocalins, centyrins and fynomers.

Generally the multispecific fusion proteins of the present disclosure consist of at least two or more TBDs operably linked via a linker polypeptide. The utilization of sdAb fragments as the specific TBD within the multispecific fusion the present disclosure has the benefit of avoiding the heavy chain:light chain mis-pairing problem common to many bi/multispecific antibody approaches. In addition, the multispecific fusion proteins of the present disclosure avoid the use of long linkers necessitated by many bispecific antibodies.

In some embodiments, all of the TBDs of the multispecific fusion protein recognize the same epitope on the given TNFRSF member. For example, the multispecific fusion proteins of present disclosure may incorporate 2, 3, 4, 5, or 6 TBDs with identical specificity to GITR. In other embodiments, the multispecific fusion protein incorporates TBDs that recognize distinct epitopes on the given TNFRSF member. For example, the multispecific fusion proteins of present disclosure may incorporate 2, 3, 4, 5, or 6 TBDs with distinct recognition specificities toward various epitopes on GITR, CD40 or CD137. In these embodiments, the multispecific fusion proteins of the present disclosure with contain multiple TBDs that target distinct regions of the particular TNFRSF member. In some embodiments, the TBDs may recognize different epitopes on the same TNFRSF member or recognize epitopes on distinct TNFRSF members. For example, the present disclosure provides multispecific fusion proteins incorporating TBDs that bind GITR and OX40.

In some embodiments, the fusion protein of the present disclosure, e.g. multivalent and/or multispecific fusion proteins, is composed of a single polypeptide. In other embodiments, the fusion protein of the present disclosure is composed of more than one polypeptide. For example, a heterodimerization domain is incorporated into the fusion protein such that the construct is an asymmetric fusion protein. For example, if an immunoglobulin Fc region is incorporated into the fusion protein, the CH3 domain can be used as homodimerization domain, or the CH3 dimer interface region can be mutated so as to enable heterodimerization.

In some embodiments, the fusion protein contains the TBDs and/or GITR-BDs at opposite ends of the fusion protein. For example, in some embodiments, the TBDs and/or GITR-BDs are located on both the amino-terminal (N-terminal) portion of the fusion protein and the carboxy-terminal (C-terminal) portion of the fusion protein. In other embodiments, all the TBDs and/or GITR-BDs reside on the same end of the fusion protein. For example, TBDs and/or GITR-BDs reside on either the amino or carboxyl terminal portions of the fusion protein.

In some embodiments, the fusion protein contains an immunoglobulin Fc region. In some embodiments, the immunoglobulin Fc region is an IgG isotype selected from the group consisting of IgG1 isotype, IgG2 isotype, IgG3 isotype, and IgG4 subclass.

In some embodiments, the immunoglobulin Fc region or immunologically active fragment thereof is an IgG isotype. For example, the immunoglobulin Fc region of the fusion protein is of human IgG1 isotype, having an amino acid sequence:

```
                                          (SEQ ID NO: 1)
PAPELLGGPS VFLFPPKPKD TLMISRTPEV TCVVVDVSHE

DPEVKFNWYV DGVEVHNAKT KPREEQYNST YRVVSVLTVL

HQDWLNGKEY KCKVSNKALP APIEKTISKA KGQPREPQVY

TLPPSRDELT KNQVSLTCLV KGFYPSDIAV EWESNGQPEN

NYKTTPPVLD SDGSFFLYSK LTVDKSRWQQ GNVFSCSVMH

EALHNHYTQK SLSLSPGK
```

In some embodiments, the immunoglobulin Fc region or immunologically active fragment thereof comprises a human IgG1 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 1.

In some embodiments, the human IgG1 Fc region is modified at amino acid Asn297 (Boxed, Kabat Numbering) to prevent to glycosylation of the fusion protein, e.g., Asn297Ala (N297A) or Asn297Asp (N297D). In some embodiments, the Fc region of the fusion protein is modified at amino acid Leu235 (Boxed, Kabat Numbering) to alter Fc receptor interactions, e.g., Leu235Glu (L235E) or Leu235Ala (L235A). In some embodiments, the Fc region of the fusion protein is modified at amino acid Leu234 (Boxed, Kabat Numbering) to alter Fc receptor interactions, e.g., Leu234Ala (L234A). In some embodiments, the Fc region of the fusion protein is modified at amino acid Leu234 (Boxed, Kabat Numbering) to alter Fc receptor interactions, e.g., Leu235Glu (L235E). In some embodiments, the Fc region of the fusion protein is altered at both amino acids 234 and 235, e.g., Leu234Ala and Leu235Ala (L234A/L235A) or Leu234Val and Leu235Ala (L234V/L235A). In some embodiments, the Fc region of the fusion protein is altered at Gly235 to reduce Fc receptor binding. For example, wherein Gly235 is deleted from the fusion protein. In some embodiments, the human IgG1 Fc region is modified at amino acid Gly236 to enhance the interaction with CD32A, e.g., Gly236Ala (G236A). In some embodiments, the human IgG1 Fc region is lacks Lys447 (EU index of Kabat et al 1991 *Sequences of Proteins of Immunological Interest*).

In some embodiments, the Fc region of the fusion protein is altered at one or more of the following positions to reduce Fc receptor binding: Leu 234 (L234), Leu235 (L235), Asp265 (D265), Asp270 (D270), Ser298 (S298), Asn297 (N297), Asn325 (N325) or Ala327 (A327). For example, Leu 234Ala (L234A), Leu235Ala (L235A), Asp265Asn (D265N), Asp270Asn (D270N), Ser298Asn (S298N), Asn297Ala (N297A), Asn325Glu (N325E) or Ala327Ser (A327S). In preferred embodiments, modifications within the Fc region reduce binding to Fc-receptor-gamma receptors while have minimal impact on binding to the neonatal Fc receptor (FcRn).

In some embodiments, the Fc region of the fusion protein is lacking an amino acid at one or more of the following positions to reduce Fc receptor binding: Glu233 (E233), Leu234 (L234), or Leu235 (L235). In these embodiments, Fc deletion of these three amino acids reduces the complement protein C1q binding. These modified Fc region polypeptides are referred to herein as "Fc deletion" polypeptides.

```
                                          (SEQ ID NO: 2)
PAPGGPSVFL FPPKPKDTLM ISRTPEVTCV VVDVSHEDPE

VKFNWYVDGV EVHNAKTKPR EEQYNSTYRV VSVLTVLHQD

WLNGKEYKCK VSNKALPAPI EKTISKAKGQ PREPQVYTLP

PSRDELTKNQ VSLTCLVKGF YPSDIAVEWE SNGQPENNYK

TTPPVLDSDG SFFLYSKLTV DKSRWQQGNV FSCSVMHEAL

HNHYTQKSLS LSPGK
```

In some embodiments, the immunoglobulin Fc region or immunologically active fragment thereof comprises a human IgG1 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 2.

In some embodiments, the immunoglobulin Fc region or immunologically active fragment of the fusion protein is of human IgG2 isotype, having an amino acid sequence:

```
                                              (SEQ ID NO: 3)
PAPPVAGPSV  FLFPPKPKDT  LMISRTPEVT  CVVVDVSHED

PEVQFNWYVD  GVEVHNAKTK  PREEQF[N]STF  RVVSVLTVVH

QDWLNGKEYK  CKVSNKGLPA  PIEKTISKTK  GQPREPQVYT

LPPSREEMTK  NQVSLTCLVK  GFYPSDISVE  WESNGQPENN

YKTTPPMLDS  DGSFFLYSKL  TVDKSRWQQG  NVFSCSVMHE

ALHNHYTQKS  LSLSPGK
```

In some embodiments, the fusion or immunologically active fragment thereof comprises a human IgG2 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 3.

In some embodiments, the human IgG2 Fc region is modified at amino acid Asn297 (Boxed, to prevent to glycosylation of the antibody, e.g., Asn297Ala (N297A) or Asn297Asp (N297D). In some embodiments, the human IgG2 Fc region is lacks Lys447 (EU index of Kabat et al 1991 *Sequences of Proteins of Immunological Interest*).

In some embodiments, the immunoglobulin Fc region or immunologically active fragment of the fusion protein is of human IgG3 isotype, having an amino acid sequence:

```
                                              (SEQ ID NO: 4)
PAPELLGGPS  VFLFPPKPKD  TLMISRTPEV  TCVVVDVSHE

DPEVQFKWYV  DGVEVHNAKT  KPREEQY[N]ST  FRVVSVLTVL

HQDWLNGKEY  KCKVSNKALP  APIEKTISKT  KGQPREPQVY

TLPPSREEMT  KNQVSLTCLV  KGFYPSDIAV  EWESSGQPEN

NYNTTPPMLD  SDGSFFLYSK  LTVDKSRWQQ  GNIFSCSVMH

EALHN[R]FTQK  SLSLSPGK
```

In some embodiments, the antibody or immunologically active fragment thereof comprises a human IgG3 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 4.

In some embodiments, the human IgG3 Fc region is modified at amino acid Asn297 (Boxed, Kabat Numbering) to prevent to glycosylation of the antibody, e.g., Asn297Ala (N297A) or Asn297Asp (N297D). In some embodiments, the human IgG3 Fc region is modified at amino acid 435 to extend the half-life, e.g., Arg435His (R435H). In some embodiments, the human IgG3 Fc region is lacks Lys447 (EU index of Kabat et al 1991 *Sequences of Proteins of Immunological Interest*).

In some embodiments, the immunoglobulin Fc region or immunologically active fragment of the fusion protein is of human IgG4 isotype, having an amino acid sequence:

```
                                              (SEQ ID NO: 5)
PAPEF[L]GGPS  VFLFPPKPKD  TLMISRTPEV  TCVVVDVSQE

DPEVQFNWYV  DGVEVHNAKT  KPREEQF[N]ST  YRVVSVLTVL

HQDWLNGKEY  KCKVSNKGLP  SSIEKTISKA  KGQPREPQVY

TLPPSQEEMT  KNQVSLTCLV  KGFYPSDIAV  EWESNGQPEN

NYKTTPPVLD  SDGSFFLYSR  LTVDKSRWQE  GNVFSCSVMH

EALHNHYTQK  SLSLSLGK
```

In some embodiments, the antibody or immunologically active fragment thereof comprises a human IgG4 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 5.

In some embodiments, the immunoglobulin Fc region or immunologically active fragment of the fusion protein is of human IgG4 isotype, having an amino acid sequence:

```
                                              (SEQ ID NO: 6)
PAPELLGGPS  VFLFPPKPKD  TLMISRTPEV  TCVVVDVSQE

DPEVQFNWYV  DGVEVHNAKT  KPREEQF[N]ST  YRVVSVLTVL

HQDWLNGKEY  KCKVSNKGLP  SSIEKTISKA  KGQPREPQVY

TLPPSQEEMT  KNQVSLTCLV  KGFYPSDIAV  EWESNGQPEN

NYKTTPPVLD  SDGSFFLYSR  LTVDKSRWQE  GNVFSCSVMH

EALHNHYTQK  SLSLSLGK
```

In some embodiments, the antibody or immunologically active fragment thereof comprises a human IgG4 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 6.

In other embodiments, the human IgG4 Fc region is modified at amino acid 235 to alter Fc receptor interactions, e.g., Leu235Glu (L235E). In some embodiments, the human IgG4 Fc region is modified at amino acid Asn297 (Kabat Numbering) to prevent to glycosylation of the antibody, e.g., Asn297Ala (N297A) or Asn297Asp (N297D). In some embodiments, the human IgG4 Fc region is lacks Lys447 (EU index of Kabat et al 1991 *Sequences of Proteins of Immunological Interest*).

In some embodiments, the human IgG Fc region is modified to enhance FcRn binding. Examples of Fc mutations that enhance binding to FcRn are Met252Tyr, Ser254Thr, Thr256Glu (M252Y, S254T, T256E, respectively) (Kabat numbering, Dall'Acqua et al 2006, *J Biol Chem* Vol. 281(33) 23514-23524), Met428Leu and Asn434Ser (M428L, N434S) (Zalevsky et al 2010 *Nature Biotech*, Vol. 28(2) 157-159), or Met252Ile, Thr256Asp, Met428Leu (M252I, T256D, M428L, respectively), (EU index of Kabat et al 1991 *Sequences of Proteins of Immunological Interest*).

In some embodiments where the fusion protein of the disclosure includes an Fc polypeptide, the Fc polypeptide is mutated or modified. In these embodiments, the mutated or modified Fc polypeptide includes the following mutations: Met252Tyr and Met428Leu (M252Y, M428L) using the Kabat numbering system.

In some embodiments, the human IgG Fc region is modified to alter antibody-dependent cellular cytotoxicity (ADCC) and/or complement-dependent cytotoxicity (CDC), e.g., the amino acid modifications described in Natsume et al., 2008 Cancer Res, 68(10): 3863-72; Idusogie et al., 2001 J Immunol, 166(4): 2571-5; Moore et al., 2010 mAbs, 2(2): 181-189; Lazar et al., 2006 PNAS, 103(11): 4005-4010, Shields et al., 2001 JBC, 276(9): 6591-6604; Stavenhagen et al., 2007 Cancer Res, 67(18): 8882-8890; Stavenhagen et al., 2008 Advan. Enzyme Regul., 48: 152-164; Alegre et al, 1992 J Immunol, 148: 3461-3468; Reviewed in Kaneko and Niwa, 2011 Biodrugs, 25(1):1-11. Examples of mutations that enhance ADCC include modification at Ser239 and Ile332, for example Ser239Asp and Ile332Glu (S239D, I332E). Examples of mutations that enhance CDC include modifications at Lys326 and Glu333. In some embodiments, the Fc region is modified at one or both of these positions, for example Lys326Ala and/or Glu333Ala (K326A and E333A) using the Kabat numbering system.

In some embodiments, the human IgG Fc region is modified to induce heterodimerization. For example, having an amino acid modification within the CH3 domain at Thr366, which when replaced with a more bulky amino acid, e.g., Try (T366W), is able to preferentially pair with a second CH3 domain having amino acid modifications to less bulky amino acids at positions Thr366, Leu368, and Tyr407, e.g., Ser, Ala and Val, respectively (T366S/L368A/Y407V). Heterodimerization via CH3 modifications can be further stabilized by the introduction of a disulfide bond, for example by changing Ser354 to Cys (S354C) and Y349 to Cys (Y349C) on opposite CH3 domains (Reviewed in Carter, 2001 Journal of Immunological Methods, 248: 7-15).

In some embodiments, the human IgG Fc region is modified to prevent dimerization. In these embodiments, the fusion proteins of the present disclosure are monomeric. For example modification at residue Thr366 to a charged residue, e.g. Thr366Lys, Thr366Arg, Thr366Asp, or Thr366Glu (T366K, T366R, T366D, or T366E, respectively), prevents CH3-CH3 dimerization.

In some embodiments, the Fc region of the fusion protein is altered at one or more of the following positions to reduce Fc receptor binding: Leu 234 (L234), Leu235 (L235), Asp265 (D265), Asp270 (D270), Ser298 (S298), Asn297 (N297), Asn325 (N325) orAla327 (A327). For example, Leu 234Ala (L234A), Leu235Ala (L235A), Asp265Asn (D265N), Asp270Asn (D270N), Ser298Asn (S298N), Asn297Ala (N297A), Asn325Glu (N325E) orAla327Ser (A327S). In preferred embodiments, modifications within the Fc region reduce binding to Fc-receptor-gamma receptors while have minimal impact on binding to the neonatal Fc receptor (FcRn).

In some embodiments, the fusion protein contains a polypeptide derived from an immunoglobulin hinge region. The hinge region can be selected from any of the human IgG subclasses. For example, the fusion protein may contain a modified IgG1 hinge having the sequence of EPKSSDK-THTCPPC (SEQ ID NO: 7), where in the Cys220 that forms a disulfide with the C-terminal cysteine of the light chain is mutated to serine, e.g., Cys220Ser (C220S). In other embodiments, the fusion protein contains a truncated hinge having a sequence DKTHTCPPC (SEQ ID NO: 8).

In some embodiments, the fusion protein has a modified hinge from IgG4, which is modified to prevent or reduce strand exchange, e.g., Ser228Pro (S228P), having the sequence ESKYGPPCPPC (SEQ ID NO: 9). In some embodiments, the fusion protein contains linker polypeptides. In other embodiments, the fusion protein contains linker and hinge polypeptides.

In some embodiments, the fusion proteins of the present disclosure lack or have reduced Fucose attached to the N-linked glycan-chain at N297. There are numerous ways to prevent fucosylation, including but not limited to production in a FUT8 deficient cell line; addition inhibitors to the mammalian cell culture media, for example Castanospermine; and metabolic engineering of the production cell line.

In some embodiments, the TBD is engineered to eliminate recognition by pre-existing antibodies found in humans. In some embodiments, single domain antibodies of the present disclosure are modified by mutation of position Leu11, for example Leu11Glu (L11E) or Leu11Lys (L11K). In other embodiments, single domain antibodies of the present disclosure are modified by changes in carboxy-terminal region, for example the terminal sequence consists of GQGTLVT-VKPGG (SEQ ID NO: 10) or GQGTLVTVEPGG (SEQ ID NO: 11) or modification thereof. In some embodiments, the single domain antibodies of the present disclosure are modified by mutation of position 11 and by changes in carboxy-terminal region.

In some embodiments, the TBDs and/or GITR-BDs of the fusion proteins of the present disclosure are operably linked via amino acid linkers. In some embodiments, these linkers are composed predominately of the amino acids Glycine and Serine, denoted as GS-linkers herein. The GS-linkers of the fusion proteins of the present disclosure can be of various lengths, for example, 5, 6, 7, 8, 9, 10, 11, 12, 13, 14, 15, 16, 17, 18, 19, 20 amino acids in length.

In some embodiments, the GS-linker comprises an amino acid sequence selected from the group consisting of GGSGGS, i.e., $(GGS)_2$ (SEQ ID NO: 12); GGSGGSGGS, i.e., $(GGS)_3$ (SEQ ID NO: 13); GGSGGSGGSGGS, i.e., $(GGS)_4$ (SEQ ID NO: 14); and GGSGGSGGSGGSGGS, i.e., $(GGS)_5$ (SEQ ID NO: 15).

In some embodiments, the linker is a flexible linker comprising Glycine residues, such as, by way of non-limiting example, GG, GGG, GGGG (SEQ ID NO: 16), GGGGG (SEQ ID NO: 17), and GGGGGG (SEQ ID NO: 18).

In some embodiments, the GITR-targeting fusion protein includes a combination of a GS-linker and a Glycine linker.

BRIEF DESCRIPTION OF FIGURES

FIG. 1 is schematic representation of exemplary multivalent fusion proteins of the present disclosure.

FIG. 6 is a schematic representation of tetravalent anti-GITR molecules of the disclosure, which are constructed with two tandem copies of a single-domain variable region (sdAb) fused to a human IgG1 Fc domain. Surrogate molecules are constructed with Fc domains derived from mouse IgG2a.

DETAILED DESCRIPTION

Figure 2A:
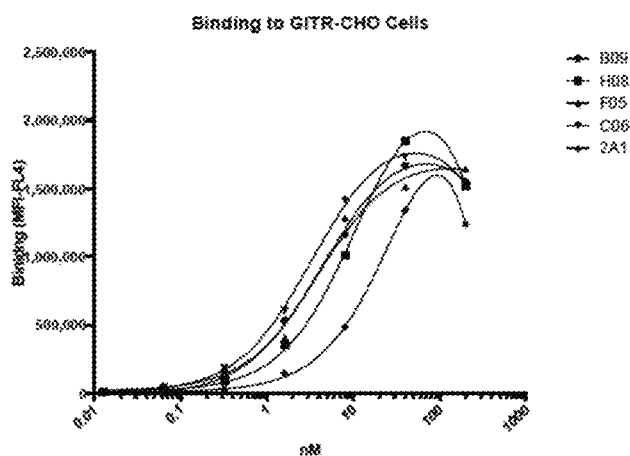
FIGS. 2A, 2B, and 2C are a series of graphs demonstrating the binding of GITR-targeting fusion proteins to GITR expressed on CHO cells as assessed by flow cytometry. The GITR antibody, TRX-518, was used as a control for these studies.

The disclosure provides molecules that specifically engage glucocorticoid-induced TNFR-related protein (GITR), a member of the TNF receptor superfamily (TNFRSF). More specifically this disclosure relates to multivalent molecules that bind at least GITR. These multivalent TNFRSF binding fusion proteins comprise two or more TNFRSF binding domains (TBDs), where at least one TBD binds GITR, referred to herein as a "GITR-binding domain" (GITR-BD).

GITR is a member of the TNFRSF and is constitutively expressed on CD4+/CD25+/Foxop3+ regulatory T-cells (Treg) in a tumor and upregulated on other T-cell populations following activation. It is hypothesized to have a dominant role in Treg-mediated immunological self-tolerance. GITR agonists dampen the suppressive activities of Tregs and in mouse models have been shown to enhance effector T-cell killing of tumors. Therefore a functional GITR agonist has great potential tumor immunotherapy.

In some embodiments, the fusion proteins of the present disclosure incorporate at least one GITR-BD. In some embodiments, the fusion protein is a multivalent fusion protein. In some embodiments, the fusion protein is a multispecific fusion protein that binds GITR and a second antigen, such as, for example, any other TNFRSF member. In some embodiments, the fusion protein is a multispecific and multivalent fusion protein.

In some embodiments, the GITR-BD binds human and cynomolgus monkey GITR. In some embodiments, the GITR-BD blocks, inhibits or otherwise modulates the interaction of GITR and its ligand GITR-Ligand (GITR-L). In other embodiments, the GITR-BD does not block, inhibit or otherwise modulate the interaction of GITR and GITR-L. In some embodiments, the fusion protein of the present disclosure incorporates multiple copies of the same GITR-BD. In some embodiments, the fusion protein of the present disclosure incorporates multiple GITR-BDs that recognize the same epitope on GITR. In some embodiments, the fusion protein of the present disclosure incorporates multiple GITR-BDs that recognize distinct epitopes on GITR. In some embodiments, the fusion protein of the present disclosure incorporates multiple GITR-BDs, wherein some GITR-BDs block the GITR-GITR-L interaction and other do not block the GITR-GITR-L interaction. In preferred embodiments, GITR-targeting fusion proteins of the present disclosure induce direct cell death of tumor cells.

In some embodiments, the GITR-targeting molecule includes at least one copy of a single-domain antibody (sdAb) sequence that specifically binds GITR. In some embodiments, the GITR-targeting molecules include two or more copies of an sdAb that specifically binds GITR, for example, three or more, four or more, five or more, or six or more copies of an sdAb that specifically binds GITR.

A single-domain antibody (sdAb) is an antibody fragment consisting of a single monomeric variable antibody domain that is able to bind selectively to a specific antigen. With a molecular weight of only 12-15 kDa, single-domain antibodies are much smaller than common antibodies (150-160 kDa) which are composed of two heavy protein chains and two light chains, and even smaller than Fab fragments (~50 kDa, one light chain and half a heavy chain) and single-chain variable fragments (~25 kDa, two variable domains, one from a light and one from a heavy chain).

Single domain antibodies are antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be derived from any species including, but not limited to mouse, human, camel, llama, goat, rabbit, and/or bovine. In some embodiments, a single domain antibody as used herein is a naturally occurring single domain antibody known as heavy chain antibody devoid of light chains. For clarity reasons, this variable domain derived from a heavy chain antibody naturally devoid of light chain is known herein as a VHH to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the disclosure.

GITR VHH (llama-derived) and humanized sequences are shown below, and the CDR sequences are shown in the sequences presented below. In some embodiments, the GITR-binding sdAb is fused to an IgG Fc region and in these embodiments, the fusion protein is bivalent having two GITR-binding domains per molecule. In some embodiments, two GITR-binding sdAbs (2×) are fused to an IgG Fc region and in these embodiments, the fusion protein is tetravalent having four GITR-binding domains per molecule. In some embodiments, three GITR-binding sdAbs (3×) are fused to an IgG Fc region and in these embodiments, the fusion protein is hexavalent having six GITR-binding domains per molecule.

| Exemplary GITR-Binding sdAbs |
| --- |
| B09<br>QVQLQESGGXLVQSGGSLRLSCAASGSVFSIDAMGWYRLAPGKQRELVAVMSSGSPKYADS<br>VKGRFTISRGSARGTVYLQMDSLKPEDTAVYYCYADVATGWGRDASAYWGQGTQVTVSS<br>(SEQ ID NO: 19)<br>CDR1: GSVFSIDAM (SEQ ID NO: 106)<br>CDR2: VMSSGSPK (SEQ ID NO: 107)<br>CDR3: YADVATGWGRDASAYW (SEQ ID NO: 108)<br><br>H09<br>QVQLQQSGGGLVRAGGSLRLSCVAAGSTFSVNSMAWYRQAPGKERELVAAFTGGSTMNYAS<br>SVKGRFTISRGNAAHTVLLQMINLKPEDTAVYYCNAEVNEGWNADYHDYWGQGTQVIVSS<br>(SEQ ID NO: 20)<br>CDR1: AGSTFSVNSM (SEQ ID NO: 109)<br>CDR2: FTGGSTMN (SEQ ID NO: 110)<br>CDR3: NAEVNEGWNADYHDYW (SEQ ID NO: 111)<br><br>F05<br>QVQLVQSGGGLVQAGGSLRLSCIASGSIFSINHMAWYRQAPGKQREMVAHITGGASTKYAD<br>SVKGRFTISRDSALNIVSLRMNSLKPEDTAVYYCNAEVNEGWNADYYDVWGQGTQVIVSS<br>(SEQ ID NO: 21)<br>CDR1: SGSIFSINHM (SEQ ID NO: 112)<br>CDR2: HITGGASTK (SEQ ID NO: 113)<br>CDR3: NAEVNEGWNADYYDVW (SEQ ID NO: 114)<br><br>C06<br>QVQLQESGGGLVQAGGSLRLSCAASGSVFSIDAMGWYRLAPGQQRELVAVLNGISSAKYAD<br>SVKGRFTISGDSAKNAVYLQMDGLKPEDTAVYYCYADVSTGWGRDAHGYWGQGTQVIVSS<br>(SEQ ID NO: 22)<br>CDR1: GSVFSIDAM (SEQ ID NO: 106)<br>CDR2: VLNGISSAK (SEQ ID NO: 115)<br>CDR3: YADVSTGWGRDAHGYW (SEQ ID NO: 116)<br><br>2A1<br>EVQLVQSGGGLVQPGGSLRLSCAASGNIFSIDAMGWYRQAPGRQRELVAQIPGGPTDSVKG<br>RFTVSGNSAKNIGYLQMNILKPEDTAVYYCNIVASTSWGSPSKVYWGQGTQATVSS (SEQ<br>ID NO: 23)<br>CDR1: SGNIFSIDAM (SEQ ID NO: 117)<br>CDR2: QIPGG (SEQ ID NO: 118)<br>CDR3: NIVASTSWGSPSKVYW (SEQ ID NO: 119)<br><br>E2<br>QVQLQESGGGLVQPGGSLRLSCAASGSVFSIDSMSWFRQAPGNERELVALITGGRITTYAD<br>SVKGRFTISRASAPNIVYLQMNSLKPEDTAVYYCNAVVSTGWGRNADDYWGQGTQVIVS<br>(SEQ ID NO: 24)<br>CDR1: SGSVFSIDSM (SEQ ID NO: 120)<br>CDR2: LITGGRITT (SEQ ID NO: 121)<br>CDR3: NAVVSTGWGRNADDYW (SEQ ID NO: 122)<br><br>B12<br>QVQLQQSGGGLVQAGGSLRLSCAASGSIFSIDAMGWYRLAPGKQRELVAVIDGVSPNYADS<br>VKGRFTISSDIAKNIVYLQMHSPKPEDTAVYYCNADVSTGWGRPADHYWGQGTQVIVS<br>(SEQ ID NO: 25)<br>CDR1: SGSIFSIDAM (SEQ ID NO: 149)<br>CDR2: VIDGVSPN (SEQ ID NO: 123)<br>CDR3: NADVSTGWGRPADHYW (SEQ ID NO: 150)<br><br>B2<br>QVQLQESGGGLVQPGGSLRLSCAASGSVFSIDSMSWFRQAPGNERELVALITGGHTITYGD<br>SVKGRFTISRASAPNIVHLQMNSLQPEDTAVYYCNAVSTGWGRNADDYWGQGTQVIVS<br>(SEQ ID NO: 26)<br>CDR1: SGSVFSIDSM (SEQ ID NO: 120)<br>CDR2: LITGGHTTT (SEQ ID NO: 123)<br>CDR3: NAAVSTGWGRNADDYW (SEQ ID NO: 124)<br><br>F2<br>QLVQSGGGLVQPGESLRLSCAASGSVFSIDSVSWFRQGPGNERELVALITGGRITTYADSV<br>KGRFTISRANAPNIVHLRMNSLKPEDTAVYYCNAVSTGWGRNADDYWGQGTQVIVS |

Exemplary GITR-Binding sdAbs (SEQ ID NO: 27)
CDR1: SGSVFSIDSV (SEQ ID NO: 125)
CDR2: LITGGRITT (SEQ ID NO: 121)
CDR3: NAAVSTGWGRNADDYW (SEQ ID NO: 124)

B3
QVQLVQSGGGLVQPGGSLRLICAASGSVFSIDSMSWFRQRPGNERELVALITGGRITTYSD
SVKGRFTISRASALNIVHLQMNSLKPEDTAVYYCNAALSTGWGRDASAYWGQGTQVIVS
(SEQ ID NO: 28)
CDR1: SGSVFSIDSM (SEQ ID NO: 120)
CDR2: LITGGRITT (SEQ ID NO: 121)
CDR3: NAALSTGWGRDASAYW (SEQ ID NO: 126)

E3
QVQLQESGGGLVQAGGSLRLSCIASGSIFSINHMAWYRQAPGKQREMVAHITGGASTKYAD
SVKGRFTISRDSALNIVSLRMNSLKPEDTAVYYCNAEVNEGWNADYYDVWGQGTQVIVS
(SEQ ID NO: 29)
CDR1: SGSIFSINHM (SEQ ID NO: 112)
CDR2: HITGGASTK (SEQ ID NO: 113)
CDR3: AEVNEGWNADYYDVW (SEQ ID NO: 127)

B4
QLQLQESGGGIVQAGGSLRLSCAASRSIASINVMGWYRQAPGNQHELVAAITSGGSPNYAG
SVRGRFIISRDNAKNIVYLQMNDLKPEDTAVYYCAGELRDDSNGYLHYWGQGTQVIVS
(SEQ ID NO: 30)
CDR1: SRSIASINVM (SEQ ID NO: 148)
CDR2: ITSGGSPN (SEQ ID NO: 128)
CDR3: AGELRDDSNGYLHYW (SEQ ID NO: 129)

B7
QVQLQESGGGLVQPGGSLRLSCAASGSVFSIDSMSWFRQTPGNERELVAHITGGRITTYAD
SVKGRFTISRASAPNIVHLQMNNLKPEDTAVYYCNAAVSTGWGRNADDYWGQGTQVIVS
(SEQ ID NO: 31)
CDR1: SGSVFSIDSM (SEQ ID NO: 120)
CDR2: HITGGRITT (SEQ ID NO: 130)
CDR3: NAAVSTGWGRNADDYW (SEQ ID NO: 124)

C7
QVQLQESGGGLVQAGGSLRLSCTASGSIFSIDDMGWYRLAPGKQRELVAVHSGSSTNYGDS
VKGRFTISGDSAKNTVYLQMHRLEPEDTAVYYCYAAISSGWGRDAEDYWGQGTQVTVS
(SEQ ID NO: 32)
CDR1: SGSIFSIDDM (SEQ ID NO: 131)
CDR2: VHSGSSTN (SEQ ID NO: 132)
CDR3: YAAISSGWGRDAEDYW (SEQ ID NO: 133)

C4
QVQLVQSGGGLVQPGESLRLSCAASGSVFSIDSMSWFRQGPGNERELVALITGGRTTTYAD
SVKGRFTISRANAPNIVHLQMNSLKPEDTAVYYCNAAVSTGWGRSADDYWGQGTQVIVS
(SEQ ID NO: 33)
CDR1: SGSVFSIDSM (SEQ ID NO: 120)
CDR2: ITGGRTTT (SEQ ID NO: 134)
CDR3: NAAVSTGWGRSADDYW (SEQ ID NO: 135)

B5
QVQLVQSGGGLVQPGESLRLSCAASGSVFSIDSMSWFRQGPGNERELVALITGGRTTTYAD
SVKGRFTISRANAPNIVHLQMNSLEPEDTAVYYCNAAVSTGWGRNADDYWGQGTQVIVS
(SEQ ID NO: 34)
CDR1: SGSVFSIDSM (SEQ ID NO: 120)
CDR2: LITGGRTTT (SEQ ID NO: 121)
CDR3: NAAVSTGWGRNADDYW (SEQ ID NO: 124)

H11
QVQLVQSGGGLVQPGGSLRLSCAASGSVFSIDSMSWFRQAPGNERELVALITGGRTTTYAD
SVKGRFTISRASAPNIVHLQMNSLKPEDTAVYYCNAVVSTGWGRNADDYWGQGTQVIVS
(SEQ ID NO: 35)
CDR1: SGSVFSIDSM (SEQ ID NO: 120)
CDR2: LITGGRTTT (SEQ ID NO: 121)
CDR3: NAVVSTGWGRNADDYW (SEQ ID NO: 122)

H11v420
EVQLLESGGGEVQPGGSLRLSCAASGSVFSIDAMSWFRQAPGKGLELVSAITGGRITYYAE
SVKGRFTISRDNAKNTLYLQMSSLRAEDTAVYYCNAVVSTGWGRNADDYWGQGTLVIVKP
(SEQ ID NO: 36)
CDR1: GSVFSIDAM (SEQ ID NO: 106)
CDR2: ITGGRTTY (SEQ ID NO: 136)
CDR3: NAVVSTGWGRNADDYW (SEQ ID NO: 122)

Exemplary GITR-Binding sdAbs

H11v420.1
EVQLLESGGGEVQPGGSLRLSCAASGSVFSIDAMSWFRQAPGKGLELVCAITGGRITYYAE
SVKGRFICSRDNAKNTLYLQMSSLRAEDTAVYYCNAVVSTGWGRNADDYWGQGTLVIVKP
(SEQ ID NO: 37)
CDR1: GSVFSIDAM (SEQ ID NO: 106)
CDR2: AITGGRTTY (SEQ ID NO: 137)
CDR3: NAVVSTGWGRNADDYW (SEQ ID NO: 122)

H11v401
EVQLLESGGGEVQPGGSLRLSCAASGSVFSIDSMSWFRQAPGKGLELVSLITGGRITYYAE
SVKGRFTISRDNAKNTLYLQMSSLRAEDTAVYYCNAVVSTGWGRNADDYWGQGTLVIVKP
(SEQ ID NO: 38)
CDR1: SGSVFSIDSM (SEQ ID NO: 120)
CDR2: LITGGRTTY (SEQ ID NO: 137)
CDR3: NAVVSTGWGRNADDYW (SEQ ID NO: 122)

H11v401.1
EVQLLESGGGEVQPGGSLRLSCAASGSVFSIDSMSWFRQAPGKGLELVCLITGGRITYYAE
SVKGRFICSRDNAKNTLYLQMSSLRAEDTAVYYCNAVVSTGWGRNADDYWGQGTLVIVKP
(SEQ ID NO: 39)
CDR1: SGSVFSIDSM (SEQ ID NO: 120)
CDR2: LITGGRTTY (SEQ ID NO: 137)
CDR3: NAVVSTGWGRNADDYW (SEQ ID NO: 122)

H11v421
EVQLLESGGGEVQPGGSLRLSCAASGSVFSIDAMSWFRQAPGKGLELVSLITGGRITYYAE
SVKGRFTISRDNAKNTLYLQMSSLRAEDTAVYYCNAVVSTGWGRNADDYWGQGTLVIVKP
(SEQ ID NO: 40)
CDR1: SGSVFSIDAM (SEQ ID NO: 138)
CDR2: LITGGRTTY (SEQ ID NO: 137)
CDR3: NAVVSTGWGRNADDYW (SEQ ID NO: 122)

H11v421.1
EVQLLESGGGEVQPGGSLRLSCAASGSVFSIDAMSWFRQAPGKGLELVCLITGGRITYYAE
SVKGRFICSRDNAKNTLYLQMSSLRAEDTAVYYCNAVVSTGWGRNADDYWGQGTLVIVKP
(SEQ ID NO: 41)
CDR1: SGSVFSIDAM (SEQ ID NO: 138)
CDR2: LITGGRTTY (SEQ ID NO: 137)
CDR3: NAVVSTGWGRNADDYW (SEQ ID NO: 122)

hzC06v1.1
EVQLLESGGGEVQPGGSLRLSCAASGSVFSIDAMGWYRQAPGKGLELVSALSGISSATYAE
SVKGRFTISRDNAKNTLYLQMSSLRAEDTAVYYCYADVSTGWGRDAHGYWGQGTLVTV
(SEQ ID NO: 42)
CDR1: SGSVFSIDAM (SEQ ID NO: 138)
CDR2: LSGISSAT (SEQ ID NO: 139)
CDR3: YADVSTGWGRDAHGYW (SEQ ID NO: 116)

hzC06v1.2
EVQLLESGGGEVQPGGSLRLSCAASGSVFSIDAMGWYRQAPGKGRELVSALSGISSATYAE
SVKGRFTISRDNAKNTLYLQMSSLRAEDTAVYYCYADVSTGWGRDAHGYWGQGTLVTV
(SEQ ID NO: 43)
CDR1: GSVFSIDAM (SEQ ID NO: 106)
CDR2: LSGISSAT (SEQ ID NO: 139)
CDR3: YADVSTGWGRDAHGYW (SEQ ID NO: 116)

hzC06v1.3
EVQLLESGGGEVQPGGSLRLSCAASGSVFSIDAMGWYRQAPGKQRELVSALSGISSATYAE
SVKGRFTISRDNAKNTLYLQMSSLRAEDTAVYYCYADVSTGWGRDAHGYWGQGTLVTV
(SEQ ID NO: 44)
CDR1: GSVFSIDAM (SEQ ID NO: 106)
CDR2: LSGISSAT (SEQ ID NO: 139)
CDR3: YADVSTGWGRDAHGYW (SEQ ID NO: 116)

hzC06v1.4
EVQLLESGGGEVQPGGSLRLSCAASGSVFSIDAMGWYRQAPGQQRELVSALSGISSATYAE
SVKGRFTISRDNAKNTLYLQMSSLRAEDTAVYYCYADVSTGWGRDAHGYWGQGTLVTV
(SEQ ID NO: 45)
CDR1: SGSVFSIDAM (SEQ ID NO: 138)
CDR2: LSGISSAT (SEQ ID NO: 139)
CDR3: ADVSTGWGRDAHGYW (SEQ ID NO: 140)

| Exemplary GITR-Binding sdAbs |
| --- | hzC06v2.1
EVQLLESGGGEVQPGGSLRLSCAASGSVFSIDAMGWYRQAPGKGLELVAVLSGISSATYAE
SVKGRFTISRDNAKNTLYLQMSSLRAEDTAVYYCYADVSTGWGRDAHGYWGQGTLVTV
(SEQ ID NO: 46)
CDR1: SGSVFSIDAM (SEQ ID NO: 138)
CDR2: LSGISSAT (SEQ ID NO: 139)
CDR3: YADVSTGWGRDAHGYW (SEQ ID NO: 116)

hzC06v2.2
EVQLLESGGGEVQPGGSLRLSCAASGSVFSIDAMGWYRQAPGKGRELVAVLSGISSATYAE
SVKGRFTISRDNAKNTLYLQMSSLRAEDTAVYYCYADVSTGWGRDAHGYWGQGTLVTV
(SEQ ID NO: 47)
CDR1: SGSVFSIDAM (SEQ ID NO: 138)
CDR2: LSGISSAT (SEQ ID NO: 139)
CDR3: YADVSTGWGRDAHGYW (SEQ ID NO: 116)

hzC06v2.3
EVQLLESGGGEVQPGGSLRLSCAASGSVFSIDAMGWYRQAPGKQRELVAVLSGISSATYAE
SVKGRFTISRDNAKNTLYLQMSSLRAEDTAVYYCYADVSTGWGRDAHGYWGQGTLVTV
(SEQ ID NO: 48)
CDR1: SGSVFSIDAM (SEQ ID NO: 138)
CDR2: LSGISSAT (SEQ ID NO: 139)
CDR3: YADVSTGWGRDAHGYW (SEQ ID NO: 116)

hzC06v2.4
EVQLLESGGGEVQPGGSLRLSCAASGSVFSIDAMGWYRQAPGQQRELVAVLSGISSATYAE
SVKGRFTISRDNAKNTLYLQMSSLRAEDTAVYYCYADVSTGWGRDAHGYWGQGTLVTV
(SEQ ID NO: 49)
CDR1: SGSVFSIDAM (SEQ ID NO: 138)
CDR2: LSGISSAT (SEQ ID NO: 139)
CDR3: YADVSTGWGRDAHGYW (SEQ ID NO: 116)

hzC06v3
EVQLLESGGGEVQPGGSLRLSCAASGSVFSIDAMGWYRQAPGKQRELVAVLSGISSAKYAE
SVKGRFTISRDNAKNTLYLQMSSLRAEDTAVYYCYADVSTGWGRDAHGYWGQGTLVTV
(SEQ ID NO: 50)
CDR1: SGSVFSIDAM (SEQ ID NO: 138)
CDR2: LSGISSAK (SEQ ID NO: 141)
CDR3: YADVSTGWGRDAHGYW (SEQ ID NO: 116)

hzC06v3.1
EVQLLESGGGEVQPGGSLRLSCAASGSVFSIDAMGWYRLAPGQQRELVAVLSGISSAKYAE
SVKGRFTISRDNAKNTLYLQMSSLRAEDTAVYYCYADVSTGWGRDAHGYWGQGTLVTV
(SEQ ID NO: 51)
CDR1: SGSVFSIDAM (SEQ ID NO: 138)
CDR2: LSGISSAK (SEQ ID NO: 141)
CDR3: YADVSTGWGRDAHGYW (SEQ ID NO: 116)

hzC06v3.2
EVQLLESGGGEVQPGGSLRLSCAASGSVFSIDAMGWYRQAPGKQRELVAVLSGISSAKYAD
SVKGRFTISGDNAKNTLYLQMSSLRAEDTAVYYCYADVSTGWGRDAHGYWGQGTLVTV
(SEQ ID NO: 52)
CDR1: SGSVFSIDAM (SEQ ID NO: 138)
CDR2: LSGISSAK (SEQ ID NO: 141)
CDR3: YADVSTGWGRDAHGYW (SEQ ID NO: 116)

hzC06v3.3
EVQLLESGGGEVQPGGSLRLSCAASGSVFSIDAMGWYRQAPGKQRELVAVLSGISSAKYAE
SVKGRFTISRDSAKNAVYLQMDGLKPEDTAVYYCYADVSTGWGRDAHGYWGQGTLVTV
(SEQ ID NO: 53)
CDR1: SGSVFSIDAM (SEQ ID NO: 138)
CDR2: LSGISSAK (SEQ ID NO: 141)
CDR3: YADVSTGWGRDAHGYW (SEQ ID NO: 116)

hzC06v3.4
EVQLLESGGGEVQPGGSLRLSCAASGSVFSIDAMGWYRQAPGKQRELVAVLSGISSAKYAE
SVKGRFTISRDNAKNIVYLQMSSLRAEDTAVYYCYADVSTGWGRDAHGYWGQGTLVTV
(SEQ ID NO: 54)
CDR1: SGSVFSIDAM (SEQ ID NO: 138)
CDR2: LSGISSAK (SEQ ID NO: 141)
CDR3: YADVSTGWGRDAHGYW (SEQ ID NO: 116)

Exemplary GITR-Binding sdAbs hzC06v3.5
EVQLLESGGGEVQPGGSLRLSCAASGSVFSIDAMGWYRQAPGKQRELVAVLSGISSAKYAE
SVKGRFTISRASAPNTLYLQMSSLRAEDTAVYYCYADVSTGWGRDAHGYWGQGTLVTV
(SEQ ID NO: 55)
CDR1: SGSVFSIDAM (SEQ ID NO: 138)
CDR2: LSGISSAK (SEQ ID NO: 141)
CDR3: YADVSTGWGRDAHGYW (SEQ ID NO: 116)

hzC06v3.6
EVQLLESGGGEVQPGGSLRLSCAASGSVFSIDAMGWYRQAPGKQRELVAVLSGISSAKYAE
SVKGRFTISRASAPNIVYLQMSSLRAEDTAVYYCYADVSTGWGRDAHGYWGQGTLVTV
(SEQ ID NO: 56)
CDR1: SGSVFSIDAM (SEQ ID NO: 138)
CDR2: LSGISSAK (SEQ ID NO: 141)
CDR3: YADVSTGWGRDAHGYW (SEQ ID NO: 116)

hzC06v3.7
EVQLLESGGGEVQPGGSLRLSCAASGSVFSIDAMGWYRQAPGKQRELVAVLSGISSAKYAA
SAPGRFTISRDAVKNIVYLQMSSLRAEDTAVYYCYADVSTGWGRDAHGYWGQGTLVTV
(SEQ ID NO: 57)
CDR1: SGSVFSIDAM (SEQ ID NO: 138)
CDR2: LSGISSAK (SEQ ID NO: 141)
CDR3: YADVSTGWGRDAHGYW (SEQ ID NO: 116)

hzC06v3.8
EVQLLESGGGEVQPGGSLRLSCAASGSVFSIDAMGWYRQAPGKQRELVAVLSGISSAKYAA
SAPGRFTISRDAVENTVYLQMSSLRAEDTAVYYCYADVSTGWGRDAHGYWGQGTLVTV
(SEQ ID NO: 58)
CDR1: SGSVFSIDAM (SEQ ID NO: 138)
CDR2: LSGISSAK (SEQ ID NO: 141)
CDR3: YADVSTGWGRDAHGYW (SEQ ID NO: 116)

hzC06v3.9
EVQLLESGGGEVQPGGSLRLSCAASGSVFSIDAMGWYRQAPGKQRELVAVLSGISSAKYAA
SAPGRFTISRDNAKNIVYLQMSSLRAEDTAVYYCYADVSTGWGRDAHGYWGQGTLVTV
(SEQ ID NO: 59)
CDR1: SGSVFSIDAM (SEQ ID NO: 138)
CDR2: LSGISSAK (SEQ ID NO: 141)
CDR3: YADVSTGWGRDAHGYW (SEQ ID NO: 116)

hzC06v3.10
EVQLLESGGGEVQPGGSLRLSCAASGSVFSIDAMGWYRQAPGKQRELVAVLSGISSAKYAD
AVKGRFTISRASAPNIVYLQMSSLRAEDTAVYYCYADVSTGWGRDAHGYWGQGTLVTV
(SEQ ID NO: 60)
CDR1: SGSVFSIDAM (SEQ ID NO: 138)
CDR2: LSGISSAK (SEQ ID NO: 141)
CDR3: ADVSTGWGRDAHGYW (SEQ ID NO: 142)

hzC06v3.11
EVQLLESGGGEVQPGGSLRLSCAASGSVFSIDAMGWYRQAPGKQRELVAVLSGISSAKYAD
AVEGRFTISRASAPNIVYLQMSSLRAEDTAVYYCYADVSTGWGRDAHGYWGQGTLVTV
(SEQ ID NO: 61)
CDR1: SGSVFSIDAM (SEQ ID NO: 138)
CDR2: LSGISSAK (SEQ ID NO: 141)
CDR3: YADVSTGWGRDAHGYW (SEQ ID NO: 116)

hzC06v3.12
EVQLLESGGGEVQPGGSLRLSCAASGSVFSIDAMGWYRQAPGKQRELVAVLSGISSAKYAA
SAPGRFTISRASAPNIVYLQMSSLRAEDTAVYYCYADVSTGWGRDAHGYWGQGTLVTV
(SEQ ID NO: 62)
CDR1: SGSVFSIDAM (SEQ ID NO: 138)
CDR2: LSGISSAK (SEQ ID NO: 141)
CDR3: YADVSTGWGRDAHGYW (SEQ ID NO: 116)

hzC04v1
EVQLLESGGGEVQPGGSLRLSCAASGFIFSTHGMDWFRQAPGKDLEWVSAINNGGSWISYA
SSVKGRFTISRDNAKNTLYLQMSSLRAEDTAVYWCQNRVIRGQGTLVTV (SEQ ID
NO: 63)
CDR1: SGFTFSTHGM (SEQ ID NO: 143)
CDR2: AINNGGSWTS (SEQ ID NO: 144)
CDR3: CQNRVTR (SEQ ID NO: 145)

TABLE-continued

Exemplary GITR-Binding sdAbs hzC04v1.2
EVQLLESGGGEVQPGGSLRLSCAASGFTFSTHGMDWFRQAPGKDLEWVSAINNGGSWTSYA
SSVKGRFTISRDNAKNTLYLQMSSLRAEDTAVYYCQNRVTRGQGTLVTV (SEQ ID
NO: 64)
CDR1: SGFTFSTHGM (SEQ ID NO: 143)
CDR2: AINNGGSWTS (SEQ ID NO: 144)
CDR3: QNRVTR (SEQ ID NO: 146)

hzC04v1.2.1
EVQLLESGGGEVQPGGSLRLSCAASGFTFSTHGMDWFRQAPGKDLEWVSAINQGGSWTSYA
SSVKGRFTISRDNAKNTLYLQMSSLRAEDTAVYYCQNRVTRGQGTLVTV (SEQ ID
NO: 65)
CDR1: SGFTFSTHGM (SEQ ID NO: 143)
CDR2: INQGGSWTS (SEQ ID NO: 147)
CDR3: QNRVTR (SEQ ID NO: 146)

hzC04v2
EVQLLESGGGEVQPGGSLRLSCAASGFTFSTHGMDWFRQAPGKGLEWVSAINNGGSWTSYA
SSVKGRFTISRDNAKNTLYLQMSSLRAEDTAVYWCQNRVTRGQGTLVTV (SEQ ID
NO: 66)
CDR1: SGFTFSTHGM (SEQ ID NO: 143)
CDR2: AINNGGSWTS (SEQ ID NO: 144)
CDR3: QNRVTR (SEQ ID NO: 146)

hzC04v2.2
EVQLLESGGGEVQPGGSLRLSCAASGFTFSTHGMDWFRQAPGKGLEWVSAINNGGSWTSYA
SSVKGRFTISRDNAKNTLYLQMSSLRAEDTAVYYCQNRVTRGQGTLVTV (SEQ ID
NO: 67)
CDR1: SGFTFSTHGM (SEQ ID NO: 143)
CDR2: AINNGGSWTS (SEQ ID NO: 144)
CDR3: QNRVTR (SEQ ID NO: 146)

hzC04v5
EVQLLESGGGEVQPGGSLRLSCAASGFTFSTHGMDWFRQAPGKDLEWVSAIQSGGSWTSYA
SSVKGRFTISRDNAKNTLYLQMSSLRAEDTAVYWCQNRVTRGQGTLVTV (SEQ ID
NO: 68)
CDR1: SGFTFSTHGM (SEQ ID NO: 143)
CDR2: AIQSGGSWTS (SEQ ID NO: 147)
CDR3: QNRVTR (SEQ ID NO: 146)

hzC04v5.1
EVQLLESGGGEVQPGGSLRLSCAASGFTFSTHGMDWFRQAPGKDLEWVSAIQSGGSWTSYA
SSVKGRFTISRDNAKNTLYLEMNNLKPEDTAVYWCQNRVTRGQGTLVTV (SEQ ID
NO: 69)
CDR1: SGFTFSTHGM (SEQ ID NO: 143)
CDR2: AIQSGGSWTS (SEQ ID NO: 147)
CDR3: QNRVTR (SEQ ID NO: 146)

hzC04v5.2
EVQLLESGGGEVQPGGSLRLSCAASGFTFSTHGMDWFRQAPGKDLEWVSAIQSGGSWTSYA
SSVKGRFTISRDNAKNTLYLQMNNLRAEDTAVYWCQNRVTRGQGTLVTV (SEQ ID
NO: 70)
CDR1: SGFTFSTHGM (SEQ ID NO: 143)
CDR2: AIQSGGSWTS (SEQ ID NO: 147)
CDR3: QNRVTR (SEQ ID NO: 146)

hzC04v5.3
EVQLLESGGGEVQPGGSLRLSCAASGFTFSTHGMDWFRQAPGKDLEWVSAIQSGGSWTSYA
SSVKGRFTISRDNAKNTLYLEMSSLRAEDTAVYWCQNRVTRGQGTLVTV (SEQ ID
NO: 71)
CDR1: SGFTFSTHGM (SEQ ID NO: 143)
CDR2: AIQSGGSWTS (SEQ ID NO: 147)
CDR3: QNRVTR (SEQ ID NO: 146)

hzC04v5.4
EVQLLESGGGEVQPGGSLRLSCAASGFTFSTHGMDWFRQAPGKDLEWVSAIQSGGSWTSYA
SSVKGRFTISRDNAKNTLYLQMSSLRPEDTAVYWCQNRVTRGQGTLVTV (SEQ ID
NO: 72)
CDR1: SGFTFSTHGM (SEQ ID NO: 143)
CDR2: AIQSGGSWTS (SEQ ID NO: 147)
CDR3: QNRVTR (SEQ ID NO: 146)

Exemplary GITR-Binding sdAbs hzC04v5.5
EVQLLESGGGEVQPGGSLRLSCAASGFTFSTHGMDWFRQAPGKDLEWVSAIQSGGSWTSYA
SSVKGRFTISRDNAKNTLYLQMQQLRAEDTAVYWCQNRVTRGQGTLVTV (SEQ ID
NO: 73)
CDR1: SGFTFSTHGM (SEQ ID NO: 143)
CDR2: AIQSGGSWTS (SEQ ID NO: 147)
CDR3: QNRVTR (SEQ ID NO: 146)

hzC04v5.6
EVQLLESGGGEVQPGGSLRLSCAASGFTFSTHGMDWFRQAPGKDLEWVSAIQSGGSWTSYA
SSVKGRFTISRDNAKNTLYLQMQNLRAEDTAVYWCQNRVTRGQGTLVTV (SEQ ID
NO: 74)
CDR1: SGFTFSTHGM (SEQ ID NO: 143)
CDR2: AIQSGGSWTS (SEQ ID NO: 147)
CDR3: QNRVTR (SEQ ID NO: 146)

hzC04v5.7
EVQLLESGGGEVQPGGSLRLSCAASGFTFSTHGMDWFRQAPGKDLEWVSAIQSGGSWTSYA
SSVKGRFTISRDNAKNTLYLQMDNLRAEDTAVYWCQNRVTRGQGTLVTV (SEQ ID
NO: 75)
CDR1: SGFTFSTHGM (SEQ ID NO: 143)
CDR2: AIQSGGSWTS (SEQ ID NO: 147)
CDR3: QNRVTR (SEQ ID NO: 146)

hzC04v5.8
EVQLLESGGGEVQPGGSLRLSCAASGFTFSTHGMDWFRQAPGKDLEWVSAIQSGGSWTSYA
SSVKGRFTISRDNAKNTLYLQMNDLRAEDTAVYWCQNRVTRGQGTLVTV (SEQ ID
NO: 76)
CDR1: SGFTFSTHGM (SEQ ID NO: 143)
CDR2: AIQSGGSWTS (SEQ ID NO: 147)
CDR3: QNRVTR (SEQ ID NO: 146)

hzC04v5.9
EVQLLESGGGEVQPGGSLRLSCAASGFTFSTHGMDWFRQAPGKDLEWVSAIQSGGSWTSYA
SSVKGRFTISRDNAKNTLYLQMDDLRAEDTAVYWCQNRVTRGQGTLVTV (SEQ ID
NO: 77)
CDR1: SGFTFSTHGM (SEQ ID NO: 143)
CDR2: AIQSGGSWTS (SEQ ID NO: 147)
CDR3: QNRVTR (SEQ ID NO: 146)

hzC04v5.10
EVQLLESGGGEVQPGGSLRLSCAASGFTFSTHGMDWFRQAPGKDLEWVSAIQSGGSWTSYA
SSVKGRFTISRDNAKNTLYLQMQDLRAEDTAVYWCQNRVTRGQGTLVTV (SEQ ID
NO: 78)
CDR1: SGFTFSTHGM (SEQ ID NO: 143)
CDR2: AIQSGGSWTS (SEQ ID NO: 147)
CDR3: QNRVTR (SEQ ID NO: 146)

hzC04v5.11
EVQLLESGGGEVQPGGSLRLSCAASGFTFSTHGMDWFRQAPGKDLEWVSAIQSGGSWTSYA
SSVKGRFTISRDNAKNTLYLQMNQLRAEDTAVYWCQNRVTRGQGTLVTV (SEQ ID
NO: 79)
CDR1: SGFTFSTHGM (SEQ ID NO: 143)
CDR2: AIQSGGSWTS (SEQ ID NO: 147)
CDR3: QNRVTR (SEQ ID NO: 146)

hzC04v5.12
EVQLLESGGGEVQPGGSLRLSCAASGFTFSTHGMDWFRQAPGKDLEWVSAIQSGGSWTSYA
SSVKGRFTISRDNAKNTLYLQMSNLRAEDTAVYWCQNRVTRGQGTLVTV (SEQ ID
NO: 80)
CDR1: SGFTFSTHGM (SEQ ID NO: 143)
CDR2: AIQSGGSWTS (SEQ ID NO: 147)
CDR3: QNRVTR (SEQ ID NO: 146)

2x H11v420 + Fc deletion polypeptide
MKWVTFISLLFLFSSAYSEVQLLESGGGEVQPGGSLRLSCAASGSVFSIDAMSWFRQAPGK
GLELVSAITGGRTTYYAESVKGRFTISRDNAKNTLYLQMSSLRAEDTAVYYCNAVVSTGWG
RNADDYWGQGTLVTVKPGGSGGSEVQLLESGGGEVQPGGSLRLSCAASGSVFSIDAMSWFR
QAPGKGLELVSAITGGRITYYAESVKGRFTISRDNAKNTLYLQMSSLRAEDTAVYYCNAVV
STGWGRNADDYWGQGTLVTVKPGGGDKTHTCPPCPAPGGPSVFLFPPKPKDTLMISRTPE
VTCVVVDVSHEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLICLVKGFYPSDIAVE
WESNGQPENNYKTTPPVLDSDGSFFLYSKLTVDKSRWQQGNVFSCSVMHEALHNHYTQKSL
SLSPGK (SEQ ID NO: 81)

| Exemplary GITR-Binding sdAbs |
| --- |

2x H11v420.1 + Fc deletion polypeptide
MKWVTFISLLFLFSSAYSEVQLLESGGGEVQPGGSLRLSCAASGSVFSIDAMSWFRQAPGK
GLELVCAITGGRTTYYAESVKGRFTCSRDNAKNTLYLQMSSLRAEDTAVYYCNAVVSTGWG
RNADDYWGQGTLVTVKPGGSGGSEVQLLESGGGEVQPGGSLRLSCAASGSVFSIDAMSWFR
QAPGKGLELVCAITGGRITYYAESVKGRFICSRDNAKNTLYLQMSSLRAEDTAVYYCNAVV
STGWGRNADDYWGQGTLVTVKPGGGGDKTHTCPPCPAPGGPSVFLFPPKPKDTLMISRTPE
VTCVVVDVSHEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLICLVKGFYPSDIAVE
WESNGQPENNYKTTPPVLDSDGSFFLYSKLTVDKSRWQQGNVFSCSVMHEALHNHYTQKSL
SLSPGK (SEQ ID NO: 82)

2x H11v420 IgG1-Fc
MKWVTFISLLFLFSSAYSEVQLLESGGGEVQPGGSLRLSCAASGSVFSIDAMSWFRQAPGK
GLELVSAITGGRTTYYAESVKGRFTISRDNAKNTLYLQMSSLRAEDTAVYYCNAVVSTGWG
RNADDYWGQGTLVTVKPGGSGGSEVQLLESGGGEVQPGGSLRLSCAASGSVFSIDAMSWFR
QAPGKGLELVSAITGGRITYYAESVKGRFTISRDNAKNTLYLQMSSLRAEDTAVYYCNAVV
STGWGRNADDYWGQGTLVTVKPGGGGDKTHTCPPCPAPELLGGPSVFLFPPKPKDTLMISR
TPEVTCVVVDVSHEDPEVKFNWYVDGVEVHNAKTKPREEQYNSTYRVVSVLTVLHQDWLNG
KEYKCKVSNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMHEALHNHYTQ
KSLSLSPGK (SEQ ID NO: 83)

2x H11v420.1 IgG1-Fc
MKWVTFISLLFLFSSAYSEVQLLESGGGEVQPGGSLRLSCAASGSVFSIDAMSWFRQAPGK
GLELVCAITGGRTTYYAESVKGRFTCSRDNAKNTLYLQMSSLRAEDTAVYYCNAVVSTGWG
RNADDYWGQGTLVTVKPGGSGGSEVQLLESGGGEVQPGGSLRLSCAASGSVFSIDAMSWFR
QAPGKGLELVCAITGGRITYYAESVKGRFICSRDNAKNTLYLQMSSLRAEDTAVYYCNAVV
STGWGRNADDYWGQGTLVTVKPGGGGDKTHTCPPCPAPELLGGPSVFLFPPKPKDTLMISR
TPEVTCVVVDVSHEDPEVKFNWYVDGVEVHNAKTKPREEQYNSTYRVVSVLTVLHQDWLNG
KEYKCKVSNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMHEALHNHYTQ
KSLSLSPGK (SEQ ID NO: 84)

2x H11v401 + Fc deletion polypeptide
MKWVTFISLLFLFSSAYSEVQLLESGGGEVQPGGSLRLSCAASGSVFSIDSMSWFRQAPGK
GLELVSLITGGRTTYYAESVKGRFTISRDNAKNTLYLQMSSLRAEDTAVYYCNAVVSTGWG
RNADDYWGQGTLVTVKPGGSGGSEVQLLESGGGEVQPGGSLRLSCAASGSVFSIDSMSWFR
QAPGKGLELVSLITGGRITYYAESVKGRFTISRDNAKNTLYLQMSSLRAEDTAVYYCNAVV
STGWGRNADDYWGQGTLVTVKPGGGGDKTHTCPPCPAPGGPSVFLFPPKPKDTLMISRTPE
VTCVVVDVSHEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVMHEALHNHYTQKSL
SLSPGK (SEQ ID NO: 85)

2x H11v401.1 + Fc deletion polypeptide
MKWVTFISLLFLFSSAYSEVQLLESGGGEVQPGGSLRLSCAASGSVFSIDSMSWFRQAPGK
GLELVCLITGGRTTYYAESVKGRFTCSRDNAKNTLYLQMSSLRAEDTAVYYCNAVVSTGWG
RNADDYWGQGTLVTVKPGGSGGSEVQLLESGGGEVQPGGSLRLSCAASGSVFSIDSMSWFR
QAPGKGLELVCLITGGRITYYAESVKGRFICSRDNAKNTLYLQMSSLRAEDTAVYYCNAVV
STGWGRNADDYWGQGTLVTVKPGGGGDKTHTCPPCPAPGGPSVFLFPPKPKDTLMISRTPE
VTCVVVDVSHEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVMHEALHNHYTQKSL
SLSPGK (SEQ ID NO: 86)

2x H11v401 IgG1-Fc
MKWVTFISLLFLFSSAYSEVQLLESGGGEVQPGGSLRLSCAASGSVFSIDSMSWFRQAPGK
GLELVSLITGGRTTYYAESVKGRFTISRDNAKNTLYLQMSSLRAEDTAVYYCNAVVSTGWG
RNADDYWGQGTLVTVKPGGSGGSEVQLLESGGGEVQPGGSLRLSCAASGSVFSIDSMSWFR
QAPGKGLELVSLITGGRITYYAESVKGRFTISRDNAKNTLYLQMSSLRAEDTAVYYCNAVV
STGWGRNADDYWGQGTLVTVKPGGGGDKTHTCPPCPAPELLGGPSVFLFPPKPKDTLMISR
TPEVTCVVVDVSHEDPEVKFNWYVDGVEVHNAKTKPREEQYNSTYRVVSVLTVLHQDWLNG
KEYKCKVSNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMHEALHNHYTQ
KSLSLSPGK (SEQ ID NO: 87)

2x H11v401.1 IgG1-Fc
MKWVTFISLLFLFSSAYSEVQLLESGGGEVQPGGSLRLSCAASGSVFSIDSMSWFRQAPGK
GLELVCLITGGRTTYYAESVKGRFTCSRDNAKNTLYLQMSSLRAEDTAVYYCNAVVSTGWG
RNADDYWGQGTLVTVKPGGSGGSEVQLLESGGGEVQPGGSLRLSCAASGSVFSIDSMSWFR
QAPGKGLELVCLITGGRITYYAESVKGRFICSRDNAKNTLYLQMSSLRAEDTAVYYCNAVV
STGWGRNADDYWGQGTLVTVKPGGGGDKTHTCPPCPAPELLGGPSVFLFPPKPKDTLMISR
TPEVTCVVVDVSHEDPEVKFNWYVDGVEVHNAKTKPREEQYNSTYRVVSVLTVLHQDWLNG
KEYKCKVSNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMHEALHNHYTQ
KSLSLSPGK (SEQ ID NO: 88)

Exemplary GITR-Binding sdAbs

2x H11v421 + Fc deletion polypeptide
MKWVTFISLLFLFSSAYSEVQLLESGGGEVQPGGSLRLSCAASGSVFSIDAMSWFRQAPGK
GLELVSLITGGRTTYYAESVKGRFTISRDNAKNTLYLQMSSLRAEDTAVYYCNAVVSTGWG
RNADDYWGQGTLVTVKPGGSGGSEVQLLESGGGEVQPGGSLRLSCAASGSVFSIDAMSWFR
QAPGKGLELVSLITGGRITYYAESVKGRFTISRDNAKNTLYLQMSSLRAEDTAVYYCNAVV
STGWGRNADDYWGQGTLVTVKPGGGGDKTHTCPPCPAPGGPSVFLFPPKPKDTLMISRTPE
VTCVVVDVSHEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLICLVKGFYPSDIAVE
WESNGQPENNYKTTPPVLDSDGSFFLYSKLTVDKSRWQQGNVFSCSVMHEALHNHYTQKSL
SLSPGK (SEQ ID NO: 89)

2x H11v421.1 + Fc deletion polypeptide
MKWVTFISLLFLFSSAYSEVQLLESGGGEVQPGGSLRLSCAASGSVFSIDAMSWFRQAPGK
GLELVCLITGGRTTYYAESVKGRFTCSRDNAKNTLYLQMSSLRAEDTAVYYCNAVVSTGWG
RNADDYWGQGTLVTVKPGGSGGSEVQLLESGGGEVQPGGSLRLSCAASGSVFSIDAMSWFR
QAPGKGLELVCLITGGRITYYAESVKGRFICSRDNAKNTLYLQMSSLRAEDTAVYYCNAVV
STGWGRNADDYWGQGTLVTVKPGGGGDKTHTCPPCPAPGGPSVFLFPPKPKDTLMISRTPE
VTCVVVDVSHEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLICLVKGFYPSDIAVE
WESNGQPENNYKTTPPVLDSDGSFFLYSKLTVDKSRWQQGNVFSCSVMHEALHNHYTQKSL
SLSPGK (SEQ ID NO: 90)

2x H11v421 IgG1-Fc
MKWVTFISLLFLFSSAYSEVQLLESGGGEVQPGGSLRLSCAASGSVFSIDAMSWFRQAPGK
GLELVSLITGGRTTYYAESVKGRFTISRDNAKNTLYLQMSSLRAEDTAVYYCNAVVSTGWG
RNADDYWGQGTLVTVKPGGSGGSEVQLLESGGGEVQPGGSLRLSCAASGSVFSIDAMSWFR
QAPGKGLELVSLITGGRITYYAESVKGRFTISRDNAKNTLYLQMSSLRAEDTAVYYCNAVV
STGWGRNADDYWGQGTLVTVKPGGGGDKTHTCPPCPAPELLGGPSVFLFPPKPKDTLMISR
TPEVTCVVVDVSHEDPEVKFNWYVDGVEVHNAKTKPREEQYNSTYRVVSVLTVLHQDWLNG
KEYKCKVSNKALPAPIEKTISKAKGQPREPQVYTLPPSRDELTKNQVSLICLVKGFYPSDI
AVEWESNGQPENNYKTTPPVLDSDGSFFLYSKLTVDKSRWQQGNVFSCSVMHEALHNHYTQ
KSLSLSPGK (SEQ ID NO: 91)

2x H11v421.1 IgG1-Fc
MKWVTFISLLFLFSSAYSEVQLLESGGGEVQPGGSLRLSCAASGSVFSIDAMSWFRQAPGK
GLELVCLITGGRTTYYAESVKGRFTCSRDNAKNTLYLQMSSLRAEDTAVYYCNAVVSTGWG
RNADDYWGQGTLVTVKPGGSGGSEVQLLESGGGEVQPGGSLRLSCAASGSVFSIDAMSWFR
QAPGKGLELVCLITGGRITYYAESVKGRFICSRDNAKNTLYLQMSSLRAEDTAVYYCNAVV
STGWGRNADDYWGQGTLVTVKPGGGGDKTHTCPPCPAPELLGGPSVFLFPPKPKDTLMISR
TPEVTCVVVDVSHEDPEVKFNWYVDGVEVHNAKTKPREEQYNSTYRVVSVLTVLHQDWLNG
KEYKCKVSNKALPAPIEKTISKAKGQPREPQVYTLPPSRDELTKNQVSLICLVKGFYPSDI
AVEWESNGQPENNYKTTPPVLDSDGSFFLYSKLTVDKSRWQQGNVFSCSVMHEALHNHYTQ
KSLSLSPGK (SEQ ID NO: 92)

2x hzC06 IgG1-Fc
EVQLLESGGGEVQPGGSLRLSCAASGSVFSIDAMGWYRQAPGKQRELVAVLSGISSAKYAA
SAPGRFTISRDNAKNIVYLQMSSLRAEDTAVYYCYADVSTGWGRDAHGYWGQGTLVIVKPG
GSGGSEVQLLESGGGEVQPGGSLRLSCAASGSVFSIDAMGWYRQAPGKQRELVAVLSGISS
AKYAASAPGRFTISRDNAKNTVYLQMSSLRAEDTAVYYCYADVSTGWGRDAHGYWGQGTLV
TVKPGGGGDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIEK
TISKAKGQPREPQVYTLPPSRDELTKNQVSLICLVKGFYPSDIAVEWESNGQPENNYKTIP
PVLDSDGSFFLYSKLIVDKSRWQQGNVFSCSVMHEALHNHYTQKSLSLSPGK (SEQ ID
NO: 93)

3x H11v420 + Fc deletion polypeptide
MKWVTFISLLFLFSSAYSEVQLLESGGGEVQPGGSLRLSCAASGSVFSIDAMSWFRQAPGK
GLELVSAITGGRTTYYAESVKGRFTISRDNAKNTLYLQMSSLRAEDTAVYYCNAVVSTGWG
RNADDYWGQGTLVTVKPGGSGGSEVQLLESGGGEVQPGGSLRLSCAASGSVFSIDAMSWFR
QAPGKGLELVSAITGGRITYYAESVKGRFTISRDNAKNTLYLQMSSLRAEDTAVYYCNAVV
STGWGRNADDYWGQGTLVTVKPGGSGGSEVQLLESGGGEVQPGGSLRLSCAASGSVFSIDA
MSWFRQAPGKGLELVSAITGGRTTYYAESVKGRFTISRDNAKNTLYLQMSSLRAEDTAVYY
CNAVVSTGWGRNADDYWGQGTLVTVKPGGGGDKTHTCPPCPAPGGPSVFLFPPKPKDTLMI
SRTPEVTCVVVDVSHEDPEVKFNWYVDGVEVHNAKTKPREEQYNSTYRVVSVLTVLHQDWL
NGKEYKCKVSNKALPAPIEKTISKAKGQPREPQVYTLPPSRDELTKNQVSLICLVKGFYPS
DIAVEWESNGQPENNYKTTPPVLDSDGSFFLYSKLTVDKSRWQQGNVFSCSVMHEALHNHY
TQKSLSLSPGK (SEQ ID NO: 94)

3x H11v420.1 + Fc deletion polypeptide
MKWVTFISLLFLFSSAYSEVQLLESGGGEVQPGGSLRLSCAASGSVFSIDAMSWFRQAPGK
GLELVCAITGGRTTYYAESVKGRFTCSRDNAKNTLYLQMSSLRAEDTAVYYCNAVVSTGWG
RNADDYWGQGTLVTVKPGGSGGSEVQLLESGGGEVQPGGSLRLSCAASGSVFSIDAMSWFR
QAPGKGLELVCAITGGRITYYAESVKGRFICSRDNAKNTLYLQMSSLRAEDTAVYYCNAVV
STGWGRNADDYWGQGTLVTVKPGGSGGSEVQLLESGGGEVQPGGSLRLSCAASGSVFSIDA
MSWFRQAPGKGLELVCAITGGRTTYYAESVKGRFTCSRDNAKNTLYLQMSSLRAEDTAVYY
CNAVVSTGWGRNADDYWGQGTLVTVKPGGGGDKTHTCPPCPAPGGPSVFLFPPKPKDTLMI

| Exemplary GITR-Binding sdAbs |
|---|
| SRTPEVTCVVVDVSHEDPEVKFNWYVDGVEVHNAKTKPREEQYNSTYRVVSVLTVLHQDWL<br>NGKEYKCKVSNKALPAPIEKTISKAKGQPREPQVYTLPPSRDELTKNQVSLICLVKGFYPS<br>DIAVEWESNGQPENNYKTTPPVLDSDGSFFLYSKLTVDKSRWQQGNVFSCSVMHEALHNHY<br>TQKSLSLSPGK (SEQ ID NO: 95) |
| 3x H11v420 IgG1-Fc<br>MKWVTFISLLFLFSSAYSEVQLLESGGGEVQPGGSLRLSCAASGSVFSIDAMSWFRQAPGK<br>GLELVSAITGGRTTYYAESVKGRFTISRDNAKNTLYLQMSSLRAEDTAVYYCNAVVSTGWG<br>RNADDYWGQGTLVTVKPGGSGGSEVQLLESGGGEVQPGGSLRLSCAASGSVFSIDAMSWFR<br>QAPGKGLELVSAITGGRITYYAESVKGRFTISRDNAKNTLYLQMSSLRAEDTAVYYCNAVV<br>STGWGRNADDYWGQGTLVTVKPGGSGGSEVQLLESGGGEVQPGGSLRLSCAASGSVFSIDA<br>MSWFRQAPGKGLELVSAITGGRTTYYAESVKGRFTISRDNAKNTLYLQMSSLRAEDTAVYY<br>CNAVVSTGWGRNADDYWGQGTLVTVKPGGGDKTHTCPPCPAPELLGGPSVFLFPPKPKDT<br>LMISRTPEVTCVVVDVSHEDPEVKFNWYVDGVEVHNAKTKPREEQYNSTYRVVSVLTVLHQ<br>DWLNGKEYKCKVSNKALPAPIEKTISKAKGQPREPQVYTLPPSRDELTKNQVSLICLVKGF<br>YPSDIAVEWESNGQPENNYKTTPPVLDSDGSFFLYSKLTVDKSRWQQGNVFSCSVMHEALH<br>NHYTQKSLSLSPGK (SEQ ID NO: 96) |
| 3x H11v420.1 IgG1-Fc<br>MKWVTFISLLFLFSSAYSEVQLLESGGGEVQPGGSLRLSCAASGSVFSIDAMSWFRQAPGK<br>GLELVCAITGGRTTYYAESVKGRFTCSRDNAKNTLYLQMSSLRAEDTAVYYCNAVVSTGWG<br>RNADDYWGQGTLVTVKPGGSGGSEVQLLESGGGEVQPGGSLRLSCAASGSVFSIDAMSWFR<br>QAPGKGLELVCAITGGRITYYAESVKGRFICSRDNAKNTLYLQMSSLRAEDTAVYYCNAVV<br>STGWGRNADDYWGQGTLVTVKPGGSGGSEVQLLESGGGEVQPGGSLRLSCAASGSVFSIDA<br>MSWFRQAPGKGLELVCAITGGRTTYYAESVKGRFTCSRDNAKNTLYLQMSSLRAEDTAVYY<br>CNAVVSTGWGRNADDYWGQGTLVTVKPGGGDKTHTCPPCPAPELLGGPSVFLFPPKPKDT<br>LMISRTPEVTCVVVDVSHEDPEVKFNWYVDGVEVHNAKTKPREEQYNSTYRVVSVLTVLHQ<br>DWLNGKEYKCKVSNKALPAPIEKTISKAKGQPREPQVYTLPPSRDELTKNQVSLICLVKGF<br>YPSDIAVEWESNGQPENNYKTTPPVLDSDGSFFLYSKLTVDKSRWQQGNVFSCSVMHEALH<br>NHYTQKSLSLSPGK (SEQ ID NO: 97) |
| 3x H11v401 + Fc deletion polypeptide<br>MKWVTFISLLFLFSSAYSEVQLLESGGGEVQPGGSLRLSCAASGSVFSIDSMSWFRQAPGK<br>GLELVSLITGGRTTYYAESVKGRFTISRDNAKNTLYLQMSSLRAEDTAVYYCNAVVSTGWG<br>RNADDYWGQGTLVTVKPGGSGGSEVQLLESGGGEVQPGGSLRLSCAASGSVFSIDSMSWFR<br>QAPGKGLELVSLITGGRITYYAESVKGRFTISRDNAKNTLYLQMSSLRAEDTAVYYCNAVV<br>STGWGRNADDYWGQGTLVTVKPGGSGGSEVQLLESGGGEVQPGGSLRLSCAASGSVFSIDS<br>MSWFRQAPGKGLELVSLITGGRTTYYAESVKGRFTISRDNAKNTLYLQMSSLRAEDTAVYY<br>CNAVVSTGWGRNADDYWGQGTLVTVKPGGGDKTHTCPPCPAPGGPSVFLFPPKPKDTLMI<br>SRTPEVTCVVVDVSHEDPEVKFNWYVDGVEVHNAKTKPREEQYNSTYRVVSVLTVLHQDWL<br>NGKEYKCKVSNKALPAPIEKTISKAKGQPREPQVYTLPPSRDELTKNQVSLICLVKGFYPS<br>DIAVEWESNGQPENNYKTTPPVLDSDGSFFLYSKLTVDKSRWQQGNVFSCSVMHEALHNHY<br>TQKSLSLSPGK (SEQ ID NO: 98) |
| 3x H11v401.1 + Fc deletion polypeptide<br>MKWVTFISLLFLFSSAYSEVQLLESGGGEVQPGGSLRLSCAASGSVFSIDSMSWFRQAPGK<br>GLELVCLITGGRTTYYAESVKGRFTCSRDNAKNTLYLQMSSLRAEDTAVYYCNAVVSTGWG<br>RNADDYWGQGTLVTVKPGGSGGSEVQLLESGGGEVQPGGSLRLSCAASGSVFSIDSMSWFR<br>QAPGKGLELVCLITGGRITYYAESVKGRFICSRDNAKNTLYLQMSSLRAEDTAVYYCNAVV<br>STGWGRNADDYWGQGTLVTVKPGGSGGSEVQLLESGGGEVQPGGSLRLSCAASGSVFSIDS<br>MSWFRQAPGKGLELVCLITGGRTTYYAESVKGRFTCSRDNAKNTLYLQMSSLRAEDTAVYY<br>CNAVVSTGWGRNADDYWGQGTLVTVKPGGGDKTHTCPPCPAPGGPSVFLFPPKPKDTLMI<br>SRTPEVTCVVVDVSHEDPEVKFNWYVDGVEVHNAKTKPREEQYNSTYRVVSVLTVLHQDWL<br>NGKEYKCKVSNKALPAPIEKTISKAKGQPREPQVYTLPPSRDELTKNQVSLICLVKGFYPS<br>DIAVEWESNGQPENNYKTTPPVLDSDGSFFLYSKLTVDKSRWQQGNVFSCSVMHEALHNHY<br>TQKSLSLSPGK (SEQ ID NO: 99) |
| 3x H11v401 IgG1-Fc<br>MKWVTFISLLFLFSSAYSEVQLLESGGGEVQPGGSLRLSCAASGSVFSIDSMSWFRQAPGK<br>GLELVSLITGGRTTYYAESVKGRFTISRDNAKNTLYLQMSSLRAEDTAVYYCNAVVSTGWG<br>RNADDYWGQGTLVTVKPGGSGGSEVQLLESGGGEVQPGGSLRLSCAASGSVFSIDSMSWFR<br>QAPGKGLELVSLITGGRITYYAESVKGRFTISRDNAKNTLYLQMSSLRAEDTAVYYCNAVV<br>STGWGRNADDYWGQGTLVTVKPGGSGGSEVQLLESGGGEVQPGGSLRLSCAASGSVFSIDS<br>MSWFRQAPGKGLELVSLITGGRTTYYAESVKGRFTISRDNAKNTLYLQMSSLRAEDTAVYY<br>CNAVVSTGWGRNADDYWGQGTLVTVKPGGGDKTHTCPPCPAPELLGGPSVFLFPPKPKDT<br>LMISRTPEVTCVVVDVSHEDPEVKFNWYVDGVEVHNAKTKPREEQYNSTYRVVSVLTVLHQ<br>DWLNGKEYKCKVSNKALPAPIEKTISKAKGQPREPQVYTLPPSRDELTKNQVSLICLVKGF<br>YPSDIAVEWESNGQPENNYKTTPPVLDSDGSFFLYSKLTVDKSRWQQGNVFSCSVMHEALH<br>NHYTQKSLSLSPGK (SEQ ID NO: 100) |
| 3x H11v401.1 IgG1-Fc<br>MKWVTFISLLFLFSSAYSEVQLLESGGGEVQPGGSLRLSCAASGSVFSIDSMSWFRQAPGK<br>GLELVCLITGGRTTYYAESVKGRFTCSRDNAKNTLYLQMSSLRAEDTAVYYCNAVVSTGWG<br>RNADDYWGQGTLVTVKPGGSGGSEVQLLESGGGEVQPGGSLRLSCAASGSVFSIDSMSWFR<br>QAPGKGLELVCLITGGRITYYAESVKGRFICSRDNAKNTLYLQMSSLRAEDTAVYYCNAVV<br>STGWGRNADDYWGQGTLVTVKPGGSGGSEVQLLESGGGEVQPGGSLRLSCAASGSVFSIDS<br>MSWFRQAPGKGLELVCLITGGRTTYYAESVKGRFTCSRDNAKNTLYLQMSSLRAEDTAVYY |

Exemplary GITR-Binding sdAbs

```
CNAVVSTGWGRNADDYWGQGTLVTVKPGGGGDKTHTCPPCPAPELLGGPSVFLFPPKPKDT
LMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTKNQVSLICLVKGF
YPSDIAVEWESNGQPENNYKTTPPVLDSDGSFFLYSKLTVDKSRWQQGNVFSCSVMHEALH
NHYTQKSLSLSPGK (SEQ ID NO: 101)

3x H11v421 + Fc deletion polypeptide
MKWVTFISLLFLFSSAYSEVQLLESGGGEVQPGGSLRLSCAASGSVFSIDAMSWFRQAPGK
GLELVSLITGGRTTYYAESVKGRFTISRDNAKNTLYLQMSSLRAEDTAVYYCNAVVSTGWG
RNADDYWGQGTLVTVKPGGSGGSEVQLLESGGGEVQPGGSLRLSCAASGSVFSIDAMSWFR
QAPGKGLELVSLITGGRITYYAESVKGRFTISRDNAKNTLYLQMSSLRAEDTAVYYCNAVV
STGWGRNADDYWGQGTLVTVKPGGSGGSEVQLLESGGGEVQPGGSLRLSCAASGSVFSIDA
MSWFRQAPGKGLELVSLITGGRTTYYAESVKGRFTISRDNAKNTLYLQMSSLRAEDTAVYY
CNAVVSTGWGRNADDYWGQGTLVTVKPGGGGDKTHTCPPCPAPGGPSVFLFPPKPKDTLMI
SRTPEVTCVVVDVSHEDPEVKFNWYVDGVEVHNAKTKPREEQYNSTYRVVSVLTVLHQDWL
NGKEYKCKVSNKALPAPIEKTISKAKGQPREPQVYTLPPSRDELTKNQVSLICLVKGFYPS
DIAVEWESNGQPENNYKTTPPVLDSDGSFFLYSKLTVDKSRWQQGNVFSCSVMHEALHNHY
TQKSLSLSPGK (SEQ ID NO: 102)

3x H11v421.1 + Fc deletion polypeptide
MKWVTFISLLFLFSSAYSEVQLLESGGGEVQPGGSLRLSCAASGSVFSIDAMSWFRQAPGK
GLELVCLITGGRTTYYAESVKGRFTCSRDNAKNTLYLQMSSLRAEDTAVYYCNAVVSTGWG
RNADDYWGQGTLVTVKPGGSGGSEVQLLESGGGEVQPGGSLRLSCAASGSVFSIDAMSWFR
QAPGKGLELVCLITGGRITYYAESVKGRFICSRDNAKNTLYLQMSSLRAEDTAVYYCNAVV
STGWGRNADDYWGQGTLVTVKPGGSGGSEVQLLESGGGEVQPGGSLRLSCAASGSVFSIDA
MSWFRQAPGKGLELVCLITGGRTTYYAESVKGRFTCSRDNAKNTLYLQMSSLRAEDTAVYY
CNAVVSTGWGRNADDYWGQGTLVTVKPGGGGDKTHTCPPCPAPGGPSVFLFPPKPKDTLMI
SRTPEVTCVVVDVSHEDPEVKFNWYVDGVEVHNAKTKPREEQYNSTYRVVSVLTVLHQDWL
NGKEYKCKVSNKALPAPIEKTISKAKGQPREPQVYTLPPSRDELTKNQVSLICLVKGFYPS
DIAVEWESNGQPENNYKTTPPVLDSDGSFFLYSKLTVDKSRWQQGNVFSCSVMHEALHNHY
TQKSLSLSPGK (SEQ ID NO: 103)

3x H11v421 IgG1-Fc
MKWVTFISLLFLFSSAYSEVQLLESGGGEVQPGGSLRLSCAASGSVFSIDAMSWFRQAPGK
GLELVSLITGGRTTYYAESVKGRFTISRDNAKNTLYLQMSSLRAEDTAVYYCNAVVSTGWG
RNADDYWGQGTLVTVKPGGSGGSEVQLLESGGGEVQPGGSLRLSCAASGSVFSIDAMSWFR
QAPGKGLELVSLITGGRITYYAESVKGRFTISRDNAKNTLYLQMSSLRAEDTAVYYCNAVV
STGWGRNADDYWGQGTLVTVKPGGSGGSEVQLLESGGGEVQPGGSLRLSCAASGSVFSIDA
MSWFRQAPGKGLELVSLITGGRTTYYAESVKGRFTISRDNAKNTLYLQMSSLRAEDTAVYY
CNAVVSTGWGRNADDYWGQGTLVTVKPGGGGDKTHTCPPCPAPELLGGPSVFLFPPKPKDT
LMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTKNQVSLICLVKGF
YPSDIAVEWESNGQPENNYKTTPPVLDSDGSFFLYSKLTVDKSRWQQGNVFSCSVMHEALH
NHYTQKSLSLSPGK (SEQ ID NO: 104)

3x H11v421.1 IgG1-Fc
MKWVTFISLLFLFSSAYSEVQLLESGGGEVQPGGSLRLSCAASGSVFSIDAMSWFRQAPGK
GLELVCLITGGRTTYYAESVKGRFTCSRDNAKNTLYLQMSSLRAEDTAVYYCNAVVSTGWG
RNADDYWGQGTLVTVKPGGSGGSEVQLLESGGGEVQPGGSLRLSCAASGSVFSIDAMSWFR
QAPGKGLELVCLITGGRITYYAESVKGRFICSRDNAKNTLYLQMSSLRAEDTAVYYCNAVV
STGWGRNADDYWGQGTLVTVKPGGSGGSEVQLLESGGGEVQPGGSLRLSCAASGSVFSIDA
MSWFRQAPGKGLELVCLITGGRTTYYAESVKGRFTCSRDNAKNTLYLQMSSLRAEDTAVYY
CNAVVSTGWGRNADDYWGQGTLVTVKPGGGGDKTHTCPPCPAPELLGGPSVFLFPPKPKDT
LMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTKNQVSLICLVKGF
YPSDIAVEWESNGQPENNYKTTPPVLDSDGSFFLYSKLTVDKSRWQQGNVFSCSVMHEALH
NHYTQKSLSLSPGK (SEQ ID NO: 105)
```

In some embodiments, the fusion proteins targeting GITR of the present disclosure include two or more polypeptide sequences that are operably linked via amino acid linkers. In some embodiments, these linkers are composed predominately of the amino acids Glycine and Serine, denoted as GS-linkers herein. The GS-linkers of the fusion proteins of the present disclosure can be of various lengths, for example, 5, 6, 7, 8, 9, 10, 11, 12, 13, 14, 15, 16, 17, 18, 19, 20 amino acids in length.

In some embodiments, the GS-linker comprises an amino acid sequence selected from the group consisting of GGSGGS, i.e., (GGS)$_2$ (SEQ ID NO: 12); GGSGGSGGS, i.e., (GGS)$_3$ (SEQ ID NO: 13); GGSGGSGGSGGS, i.e., (GGS)$_4$ (SEQ ID NO: 14); and GGSGGSGGSGGSGGS, i.e., (GGS)$_5$ (SEQ ID NO: 15).

In some embodiments, the linker is a flexible linker comprising Glycine residues, such as, by way of non-limiting example, GG, GGG, GGGG (SEQ ID NO: 16), GGGGG (SEQ ID NO: 17), and GGGGGG (SEQ ID NO: 18).

In some embodiments, the GITR-binding fusion protein includes a combination of a GS-linker and a Glycine linker.

In some embodiments, the multivalent GITR-targeting fusion protein is tetravalent. In some embodiments, the tetravalent GITR-targeting molecule of the disclosure includes two copies of a GITR-targeting fusion protein having the following structure: (GITR-BD)-Linker-(GITR-BD)-Linker-Hinge-Fc. In some embodiments, the tetravalent GITR-targeting molecule of the disclosure includes two copies of a GITR-binding fusion protein having the following structure: (GITR-BD)-Linker-(GITR-BD)-Linker-Hinge-Fc, where the GITR-BD is an isolated polypeptide sequence that binds GITR. In some embodiments, the tetravalent GITR-targeting molecule of the disclosure includes two copies of a GITR-binding fusion protein having the following structure: (GITR-BD)-Linker-(GITR-BD)-Linker-Hinge-Fc, where the GITR-BD is an sdAb sequence that binds GITR. In some embodiments, the tetravalent GITR-targeting molecule of the disclosure includes two copies of a GITR-binding fusion protein having the following structure: (GITR-BD)-Linker-(GITR-BD)-Linker-Hinge-Fc, where the GITR-BD is a humanized or fully human sdAb sequence that binds GITR. In some embodiments, the tetravalent GITR-targeting molecule comprises a complementarity determining region 1 (CDR1) comprising an amino acid sequence selected from the group consisting of SEQ ID NO: 106, 109, 112, 117, 120, 125, 131, 138, 143, 148, and 149; a complementarity determining region 2 (CDR2) comprising an amino acid sequence selected from the group consisting of SEQ ID NO: 107, 110, 113, 115, 118, 121, 123, 128, 130, 132, 134, 136, 137, 139, 141, 144, and 147; and a complementarity determining region 3 (CDR3) comprising an amino acid sequence selected from the group consisting of SEQ ID NO: 108, 111, 114, 116, 119, 122, 124, 126, 127, 129, 133, 135, 140, 142, 145, 146, and 150. In some embodiments, the tetravalent GITR-targeting molecule contains at least one GITR-BD that comprises an amino acid sequence selected from the group consisting of SEQ ID NO: 19-80. In some embodiments, the tetravalent GITR-targeting molecule contains at least one GITR-BD that comprises an amino acid sequence selected from the group consisting of SEQ ID NO: 42-62. In some embodiments, the tetravalent GITR-targeting molecule at least one GITR-BD that comprises an amino acid sequence selected from the group consisting of SEQ ID NO: 63-80. In some embodiments, the tetravalent GITR-targeting molecule comprises an amino acid sequence selected from the group consisting of SEQ ID NO: 81-93.

In some embodiments, the multivalent GITR-targeting fusion protein is hexavalent. In some embodiments, the hexavalent GITR-targeting molecule of the disclosure includes two copies of a GITR-targeting fusion protein having the following structure: (GITR-BD)-Linker-(GITR-BD)-Linker-(GITR-BD)-Linker-Hinge-Fc. In some embodiments, the hexavalent GITR-targeting molecule of the disclosure includes two copies of a GITR-targeting fusion protein having the following structure: (GITR-BD)-Linker-(GITR-BD)-Linker-(GITR-BD)-Linker-Hinge-Fc, where the GITR-BD is a humanized or an isolated polypeptide sequence that binds GITR. In some embodiments, the hexavalent GITR-targeting molecule of the disclosure includes two copies of a GITR-targeting fusion protein having the following structure: (GITR-BD)-Linker-(GITR-BD)-Linker-(GITR-BD)-Linker-Hinge-Fc, where the GITR-BD is an sdAb sequence that binds GITR. In some embodiments, the hexavalent GITR-targeting molecule of the disclosure includes two copies of a GITR-targeting fusion protein having the following structure: (GITR-BD)-Linker-(GITR-BD)-Linker-(GITR-BD)-Linker-Hinge-Fc, where the GITR-BD is a humanized or fully human sdAb sequence that binds GITR. In some embodiments, the hexavalent GITR-targeting molecule comprises a complementarity determining region 1 (CDR1) comprising an amino acid sequence selected from the group consisting of SEQ ID NO: 106, 109, 112, 117, 120, 125, 131, 138, 143, 148, and 149; a complementarity determining region 2 (CDR2) comprising an amino acid sequence selected from the group consisting of SEQ ID NO: 107, 110, 113, 115, 118, 121, 123, 128, 130, 132, 134, 136, 137, 139, 141, 144, and 147; and a complementarity determining region 3 (CDR3) comprising an amino acid sequence selected from the group consisting of SEQ ID NO: 108, 111, 114, 116, 119, 122, 124, 126, 127, 129, 133, 135, 140, 142, 145, 146, and 150. In some embodiments, the hexavalent GITR-targeting molecule contains at least one GITR-BD that comprises an amino acid sequence selected from the group consisting of SEQ ID NO: 19-80. In some embodiments, the hexavalent GITR-targeting molecule contains at least one GITR-BD that comprises an amino acid sequence selected from the group consisting of SEQ ID NO: 42-62. In some embodiments, the hexavalent GITR-targeting molecule contains at least one GITR-BD that comprises an amino acid sequence selected from the group consisting of SEQ ID NO: 63-80. In some embodiments, the hexavalent GITR-targeting molecule comprises an amino acid sequence selected from the group consisting of SEQ ID NO: 94-105.

The GITR-targeting proteins described herein are useful in a variety of therapeutic, diagnostic and prophylactic indications. For example, the GITR-targeting proteins are useful in treating a variety of diseases and disorders in a subject. In some embodiments, the GITR-targeting proteins are useful in treating, alleviating a symptom of, ameliorating and/or delaying the progression of a disease or disorder in a subject suffering from or identified as being at risk for an inflammatory disease or disorder. In some embodiments, the GITR-targeting proteins are useful in treating, alleviating a symptom of, ameliorating and/or delaying the progression of a cancer or other neoplastic condition. In some embodiments, the cancer is bladder cancer, breast cancer, uterine/cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, and virus-related cancer. In certain embodiments, the cancer is a metastatic cancer, refractory cancer, or recurrent cancer. In some embodiments, the GITR-targeting proteins are useful in reducing or depleting the number of T regulatory cells in a tumor of a subject in need thereof. In some embodiments, the GITR-targeting proteins are useful in stimulating an immune response in a subject. In some embodiments, the GITR-targeting proteins are useful in treating, alleviating a symptom of, ameliorating and/or delaying the progression of an autoimmune disease or disorder. In some embodiments, the GITR-targeting proteins are useful in treating, alleviating a symptom of, ameliorating and/or delaying the progression of viral, bacterial and parasitic infections.

Therapeutic formulations of the disclosure, which include a GITR-targeting molecule of the disclosure, are used to treat or alleviate a symptom associated with a disease or disorder associated with aberrant activity and/or expression of GITR in a subject. A therapeutic regimen is carried out by identifying a subject, e.g., a human patient suffering from (or at risk of developing) a disease or disorder associated with aberrant activity and/or expression of GITR using standard methods, including any of a variety of clinical and/or laboratory procedures. The term patient includes human and veterinary subjects. The term subject includes humans and other mammals.

Efficaciousness of treatment is determined in association with any known method for diagnosing or treating the particular disease or disorder associated with aberrant activity and/or expression of GITR. Alleviation of one or more symptoms of the disease or disorder associated with aberrant activity and/or expression of GITR indicates that the GITR-targeting molecule confers a clinical benefit.

Therapeutic uses of the GITR-targeting molecules of the disclosure can also include the administration of one or more additional agents. In some embodiments, the one or more additional agents is an anti-GITR antibody or fusion protein, an anti-PD1 antibody or fusion protein, a LAG-3 antibody or fusion protein, a CTLA-4 antibody or fusion protein, and/or a PD-L1 antibody or fusion protein.

The GITR-targeting molecules of the present invention may be administered alone or with other modes of treatment. They may be provided before, substantially contemporaneous with, or after other modes of treatment, for example, surgery, chemotherapy, radiation therapy, or the administration of a biologic, such as another therapeutic polypeptide/antibody.

In some embodiments, the GITR-targeting molecules of the present invention may be used in combination with a chemotherapeutic agent. Examples of chemotherapeutic agents include, but are not limited to, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., *Agnew, Chem Intl. Ed. Engl.*, 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluorometlhylornithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras, EGFR (e.g., erlotinib (TARCEVA®)) and VEGF-A that reduce cell proliferation and pharmaceutically acceptable salts, acids or derivatives of any of the above.

Further nonlimiting exemplary chemotherapeutic agents include anti-hormonal agents that act to regulate or inhibit hormone action on cancers such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® (aldesleukin) rIL-2; LURTOTECAN® topoisomerase 1 inhibitor; ABARELIX® GnRH agoninst; and pharmaceutically acceptable salts, acids or derivatives of any of the above.

In some embodiments, the GITR-targeting molecule of the present invention can be used together with an anti-angiogenesis agent. The angiogenesis agent refers to a small molecular weight substance, a polynucleotide (including, e.g., an inhibitory RNA (RNAi or siRNA)), a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent, e.g., antibodies to VEGF-A (e.g., bevacizumab (AVASTIN®)) or to the VEGF-A receptor (e.g., KDR receptor or Flt-1 receptor), anti-PDGFR inhibitors such as GLEEVEC® (Imatinib Mesylate), small molecules that block VEGF receptor signaling (e.g., PTK787/ZK2284, SU6668, SUTENT®/SU11248 (sunitinib malate), AMG706, or those described in, e.g., international patent application WO 2004/113304). Anti-angiogensis agents also include native angiogenesis inhibitors, e.g., angiostatin, endostatin, etc. See, e.g., Klagsbrun and D'Amore (1991) *Annu. Rev. Physiol.* 53:217-39; Streit and Detmar (2003) *Oncogene* 22:3172-3179 (e.g., Table 3 listing anti-angiogenic therapy in malignant melanoma); Ferrara & Alitalo (1999) *Nature Medicine* 5(12): 1359-1364; Tonini et al. (2003) *Oncogene* 22:6549-6556 (e.g., Table 2 listing known anti-angiogenic factors); and, Sato (2003) *Int. J. Clin. Oncol.* 8:200-206 (e.g., Table 1 listing anti-angiogenic agents used in clinical trials).

In some embodiments, the GITR-targeting molecule is used in combination with other anti-tumor agents, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (TARCEVA®), platelet derived growth factor inhibitors (e.g., GLEEVEC® (Imatinib Mesylate)), a COX-2 inhibitor (e.g., celecoxib), interferons, CTLA4 inhibitors (e.g., anti-CTLA antibody ipilimumab (YERVOY®)). PD-1 inhibitors (e.g., anti-PD1 antibodies, BMS-936558), PDL1 inhibitors (e.g., anti-PDL1 antibodies, MPDL3280A), PDL2 inhibitors (e.g., anti-PDL2 antibodies), cytokines, antagonists (e.g., neutralizing antibodies) that bind to one or more of the following targets ErbB2, ErbB3, ErbB4, PDGFR-beta, BlyS, APRIL, BCMA, PD-1, PDL1, PDL2, CTLA4, or VEGF receptor(s), TRAIL/Apo2, and other bioactive and organic chemical agents, etc.

In some embodiments, the GITR-targeting molecule is administered during and/or after treatment in combination with one or more additional agents. In some embodiments, the GITR-targeting molecule and the additional agent are formulated into a single therapeutic composition, and the GITR-targeting molecule and additional agent are administered simultaneously. Alternatively, the GITR-targeting molecule and additional agent are separate from each other, e.g., each is formulated into a separate therapeutic composition, and the GITR-targeting molecule and the additional agent are administered simultaneously, or the GITR-targeting molecule and the additional agent are administered at different times during a treatment regimen. For example, the GITR-targeting molecule is administered prior to the administration of the additional agent, the GITR-targeting molecule is administered subsequent to the administration of the additional agent, or the GITR-targeting molecule and the additional agent are administered in an alternating fashion. As described herein, the GITR-targeting molecule and additional agent are administered in single doses or in multiple doses.

In some embodiments, the GITR-targeting molecule and the additional agent(s) are administered simultaneously. For example, the GITR-targeting molecule and the additional agent(s) can be formulated in a single composition or administered as two or more separate compositions. In some embodiments, the GITR-targeting molecule and the additional agent(s) are administered sequentially, or the GITR-targeting molecule and the additional agent are administered at different times during a treatment regimen.

Methods for the screening of GITR-targeting molecules that possess the desired specificity include, but are not limited to, enzyme linked immunosorbent assay (ELISA), enzymatic assays, flow cytometry, and other immunologically mediated techniques known within the art.

The disclosure further provides nucleic acid sequences and particularly DNA sequences that encode the present fusion proteins. Preferably, the DNA sequence is carried by a vector suited for extrachromosomal replication such as a phage, virus, plasmid, phagemid, cosmid, YAC, or episome. In particular, a DNA vector that encodes a desired fusion protein can be used to facilitate the methods of preparing the GITR-targeting molecules described herein and to obtain significant quantities of the fusion protein. The DNA sequence can be inserted into an appropriate expression vector, i.e., a vector which contains the necessary elements for the transcription and translation of the inserted protein-coding sequence. A variety of host-vector systems may be utilized to express the protein-coding sequence. These include mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA or cosmid DNA. Depending on the host-vector system utilized, any one of a number of suitable transcription and translation elements may be used.

The disclosure also provides methods of producing a GITR-targeting molecule by culturing a cell under conditions that lead to expression of the polypeptide, wherein the cell comprises an isolated nucleic acid molecule encoding a GITR-targeting molecule described herein, and/or vectors that include these isolated nucleic acid sequences. The disclosure provides methods of producing a GITR-targeting molecule by culturing a cell under conditions that lead to expression of the GITR-targeting molecule, wherein the cell comprises an isolated nucleic acid molecule encoding a GITR-targeting molecule described herein, and/or vectors that include these isolated nucleic acid sequences.

The fusion proteins of the disclosure (also referred to herein as "active compounds"), and derivatives, fragments, analogs and homologs thereof, can be incorporated into pharmaceutical compositions suitable for administration. Such compositions typically comprise the fusion protein and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Suitable examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, subcutaneous, intratumoral, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

The pharmaceutical compositions can be included in a kit, container, pack, or dispenser together with instructions for administration. These pharmaceutical compositions can be included in diagnostic kits with instructions for use.

Pharmaceutical compositions are administered in an amount effective for treatment or prophylaxis of the specific indication. The therapeutically effective amount is typically dependent on the weight of the subject being treated, his or her physical or health condition, the extensiveness of the condition to be treated, or the age of the subject being treated. In some embodiments, the pharmaceutical composition may be administered in an amount in the range of about 50 μg/kg body weight to about 50 mg/kg body weight per dose. In some embodiments, the pharmaceutical composition may be administered in an amount in the range of about 100 μg/kg body weight to about 50 mg/kg body weight per dose. In some embodiments, the pharmaceutical composition may be administered in an amount in the range of about 100 μg/kg body weight to about 20 mg/kg body weight per dose. In some embodiments, the pharmaceutical composition may be administered in an amount in the range of about 0.5 mg/kg body weight to about 20 mg/kg body weight per dose.

In some embodiments, the pharmaceutical composition may be administered in an amount in the range of about 10 mg to about 1,000 mg per dose. In some embodiments, the pharmaceutical composition may be administered in an amount in the range of about 20 mg to about 500 mg per dose. In some embodiments, the pharmaceutical composition may be administered in an amount in the range of about 20 mg to about 300 mg per dose. In some embodiments, the pharmaceutical composition may be administered in an amount in the range of about 20 mg to about 200 mg per dose.

The pharmaceutical composition may be administered as needed to subjects. In some embodiments, an effective dose of the pharmaceutical composition is administered to a subject one or more times. In various embodiments, an effective dose of the pharmaceutical composition is administered to the subject once a month, less than once a month, such as, for example, every two months, every three months, or every six months. In other embodiments, an effective dose of the pharmaceutical composition is administered more than once a month, such as, for example, every two weeks, every week, twice per week, three times per week, daily, or multiple times per day. An effective dose of the pharmaceutical composition is administered to the subject at least once. In some embodiments, the effective dose of the pharmaceutical composition may be administered multiple times, including for periods of at least a month, at least six months, or at least a year. In some embodiments, the pharmaceutical composition is administered to a subject as-needed to alleviate one or more symptoms of a condition.

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients. The term patient includes human and veterinary subjects.

As utilized in accordance with the present disclosure, the following terms, unless otherwise indicated, shall be understood to have the following meanings:

As used herein, the terms "targeting fusion protein" and "antibody" can be synonyms. As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" "or directed against" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, dAb (domain antibody), single chain, Fab, Fab, and F(ab')$_2$ fragments, $F_v$, scFvs, an Fab expression library, and single domain antibody (sdAb) fragments, for example $V_HH$, $V_{NAR}$, engineered $V_H$ or $V_K$.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses (also known as isotypes) as well, such as IgG$_1$, IgG$_2$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three-dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

The single domain antibody (sdAb) fragments portions of the fusion proteins of the present disclosure are referred to interchangeably herein as targeting polypeptides herein.

As used herein, the term "epitope" includes any protein determinant capable of specific binding to/by an immunoglobulin or fragment thereof, or a T-cell receptor. The term "epitope" includes any protein determinant capable of specific binding to/by an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is ≤1 µM; e.g., ≤100 nM, preferably ≤10 nM and more preferably ≤1 nM.

As used herein, the terms "immunological binding" and "immunological binding properties" and "specific binding" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($k_{on}$) and the "off rate constant" ($k_{off}$) can be determined by calculation of the concentrations and the actual rates of association and dissociation. (See Nature 361:186-87 (1993)). The ratio of $k_{off}/k_{on}$ enables the cancellation of all parameters not related to affinity, and is equal to the dissociation constant $K_d$. (See, generally, Davies et al. (1990) Annual Rev Biochem 59:439-473). An antibody of the present disclosure is said to specifically bind to an antigen, when the equilibrium binding constant ($K_d$) is ≤1 µM, preferably ≤100 nM, more preferably ≤10 nM, and most preferably ≤100 pM to about 1 pM, as measured by assays such as radioligand binding assays, surface plasmon resonance (SPR), flow cytometry binding assay, or similar assays known to those skilled in the art.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Suitable conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present disclosure, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Suitable amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the disclosure.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991).

The term "polypeptide fragment" as used herein refers to a polypeptide that has an amino terminal and/or carboxy-terminal deletion, but where the remaining amino acid sequence is identical to the corresponding positions in the naturally-occurring sequence deduced, for example, from a full length cDNA sequence. Fragments typically are at least 5, 6, 8 or 10 amino acids long, preferably at least 14 amino acids long' more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has specific binding to GITR, under suitable binding conditions. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, J. Adv. Drug Res. 15:29 (1986), Veber and Freidinger TINS p. 392 (1985); and Evans et al. J. Med. Chem. 30:1229 (1987). Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —$CH_2NH$—, —$CH_2S$—, —$CH_2$—$CH_2$—, —CH=CH— (cis and trans), —$COCH_2$—, $CH(OH)CH_2$—, and —$CH_2SO$—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992)); for example, by adding internal cysteine residues capable of forming intramolecular disulfide bridges which cyclize the peptide.

The term "agent" is used herein to denote a chemical compound, a mixture of chemical compounds, a biological macromolecule, and/or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

As used herein, the terms "treat," treating," "treatment," and the like refer to reducing and/or ameliorating a disorder and/or symptoms associated therewith. By "alleviate" and/or "alleviating" is meant decrease, suppress, attenuate, diminish, arrest, and/or stabilize the development or progression of a disease such as, for example, a cancer. It will be appreciated that, although not precluded, treating a disorder or condition does not require that the disorder, condition or symptoms associated therewith be completely eliminated.

In this disclosure, "comprises," "comprising," "containing," "having," and the like can have the meaning ascribed to them in U.S. Patent law and can mean "includes," "including," and the like; the terms "consisting essentially of" or "consists essentially" likewise have the meaning ascribed in U.S. Patent law and these terms are open-ended, allowing for the presence of more than that which is recited so long as basic or novel characteristics of that which is recited are not changed by the presence of more than that which is recited, but excludes prior art embodiments.

By "effective amount" is meant the amount required to ameliorate the symptoms of a disease relative to an untreated patient. The effective amount of active compound(s) used to practice the present disclosure for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "subject" is meant a mammal, including, but not limited to, a human or non-human mammal, such as a bovine, equine, canine, rodent, ovine, primate, camelid, or feline.

The term "administering," as used herein, refers to any mode of transferring, delivering, introducing, or transporting a therapeutic agent to a subject in need of treatment with such an agent. Such modes include, but are not limited to, oral, topical, intravenous, intraperitoneal, intramuscular, intradermal, intranasal, and subcutaneous administration.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the terms "a," "an," and "the" are understood to be singular or plural. Unless specifically stated or obvious from context, as used herein, the term "or" is understood to be inclusive.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

The disclosure will be further described in the following examples, which do not limit the scope of the disclosure described in the claims.

EXAMPLES

Example 1. GITR-Targeting Molecules Bind GITR

Figure 2B:
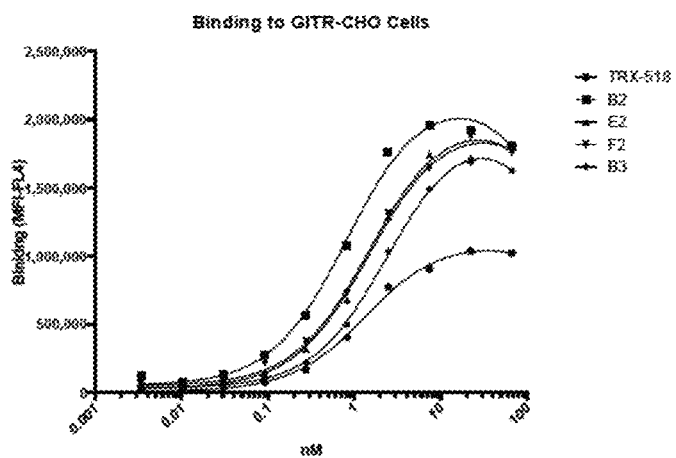
Figure 2C:
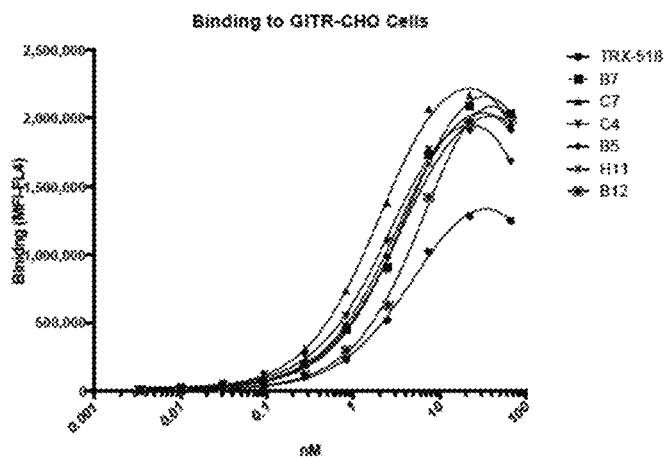

As shown in FIGS. 2A, 2B, and 2C, various GITR-targeting fusion proteins of the disclosure bind to GITR expressed on CHO cells as assessed by flow cytometry. The GITR antibody, TRX-518, was used as a control for these studies.

The binding affinities of the GITR-targeting molecules referred to herein as hzC06v1.1 (SEQ ID NO: 42), hzC06v1.2 (SEQ ID NO: 43), hzC06v1.3 (SEQ ID NO: 44), hzC06v1.4 (SEQ ID NO: 45), hzC06v2.1 (SEQ ID NO: 46), hzC06v2.2 (SEQ ID NO: 47), hzC06v2.3 (SEQ ID NO: 48), hzC06v2.4 (SEQ ID NO: 49), hzC06v3 (SEQ ID NO: 50), hzC06v3.1 (SEQ ID NO: 51), hzC06v3.2 (SEQ ID NO: 52), hzC06v3.3 (SEQ ID NO: 53), hzC06v3.4 (SEQ ID NO: 54), hzC06v3.5 (SEQ ID NO: 55), hzC06v3.6 (SEQ ID NO: 56), hzC06v3.7 (SEQ ID NO: 57), hzC06v3.8 (SEQ ID NO: 58), hzC06v3.9 (SEQ ID NO: 59), hzC06v3.10 (SEQ ID NO: 60), hzC06v3.11 (SEQ ID NO: 61), hzC06v3.12 (SEQ ID NO: 62), hzC04v4.1 (SEQ ID NO: 63), hzC04v4.1.2 (SEQ ID NO: 64), hzC04v4.2 (SEQ ID NO: 65), hzC04v4.2.2 (SEQ ID NO: 66), hzC04v5 (SEQ ID NO: 67), hzC04v1.2.1 (SEQ ID NO: 68), hzC04v5.1 (SEQ ID NO: 69), hzC04v5.2 (SEQ ID NO: 70), hzC04v5.3 (SEQ ID NO: 71), hzC04v5.4 (SEQ ID NO: 72), hzC04v5.5 (SEQ ID NO: 73), hzC04v5.6 (SEQ ID NO: 74), hzC04v5.7 (SEQ ID NO: 75), hzC04v5.8 (SEQ ID NO: 76), hzC04v5.9 (SEQ ID NO: 77), hzC04v5.10 (SEQ ID NO: 78), hzC04v5.11 (SEQ ID NO: 79), and hzC04v5.12 (SEQ ID NO: 80) for human and cynomolgus GITR expressed on the surface of CHO cells were determined by flow cytometry. The results are shown in FIGS. 4A-4F and 5A-5E.

Figure 3A:
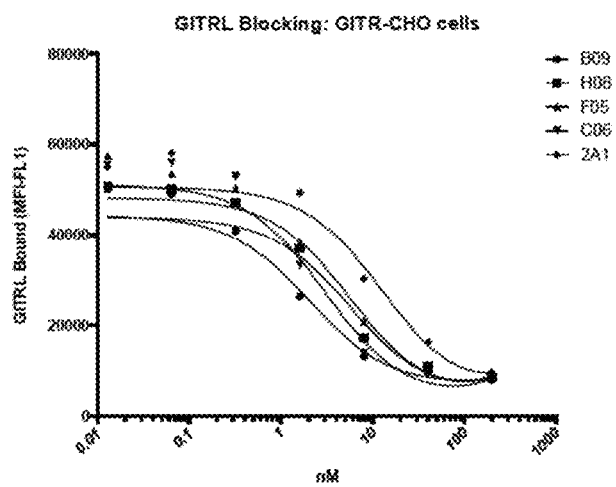
FIGS. 3A, 3B, and 3C are a series of graphs demonstrating the ability of GITR-targeting fusion proteins to block the interaction between GITRL and GITR. Herein, a flow cytometry assay using GITR expressing CHO cells and recombinant GITRL was used to assess blocking capacity. The GITR antibody, TRX-518, was used as a control for these studies.
Figure 3B:
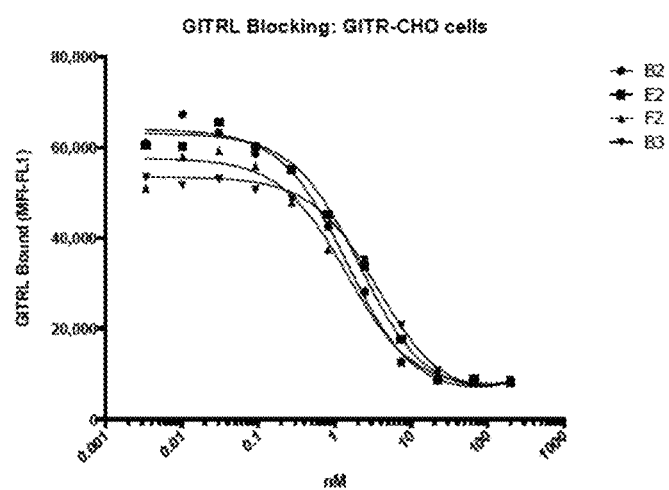
Figure 3C:
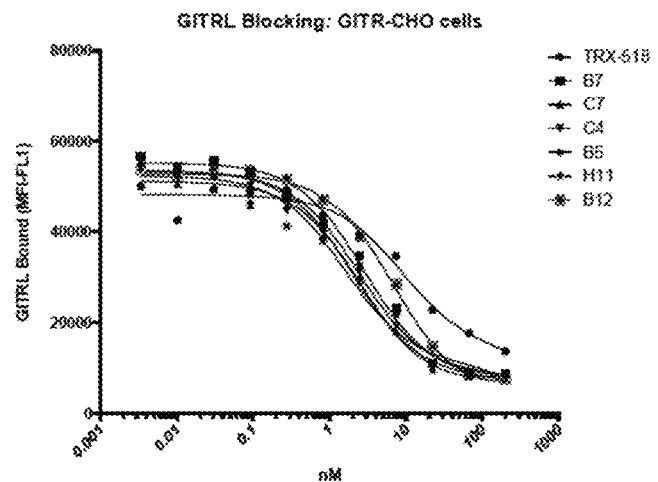
Figure 4A:
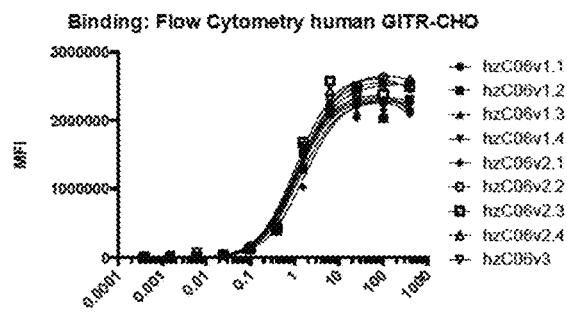
FIGS. 4A, 4B, 4C, 4D, 4E and 4F are a series of graphs depicting the binding of the GITR-targeting molecules of the disclosure referred to as hzC06v1.1, hzC06v1.2, hzC06v1.3, hzC06v1.4, hzC06v2.1, hzC06v2.2, hzC06v2.3, hzC06v2.4, hzC06v3, hzC06v3.1, hzC06v3.2, hzC06v3.3, hzC06v3.4, hzC06v3.5, hzC06v3.6, hzC06v3.7, hzC06v3.8, hzC06v3.9, hzC06v3.10, hzC06v3.11, and hzC06v3.12 for human GITR and cynomolgus GITR ("cyno GITR") expressed on the surface of CHO cells, as measured by flow cytometry.
Figure 4B:
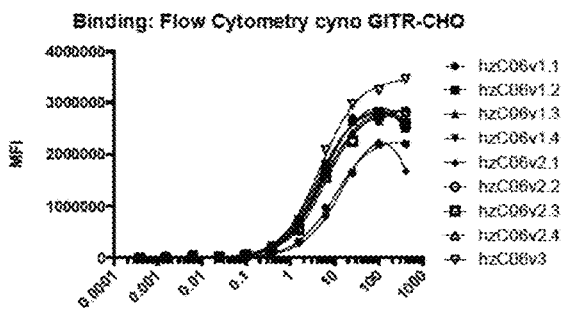
Figure 4C:
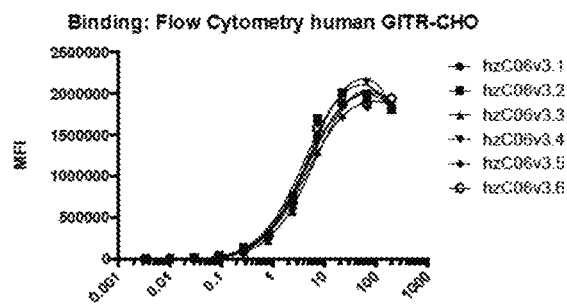
Figure 4D:
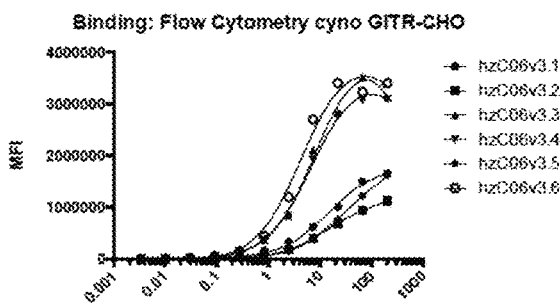
Figure 4E:
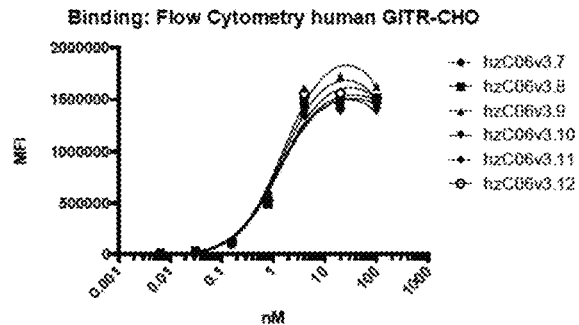
Figure 4F:
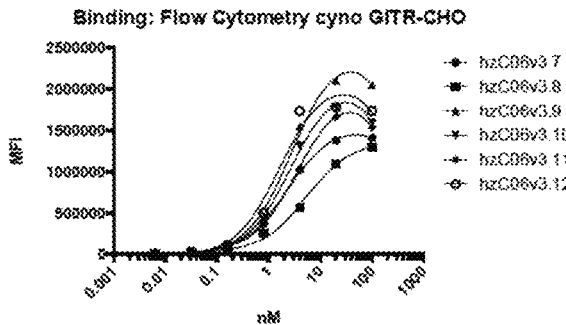
Figure 5A:
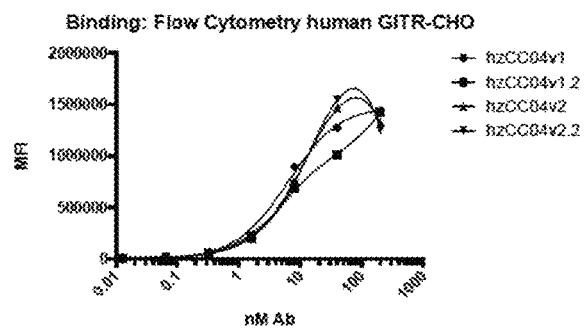
FIGS. 5A, 5B, 5C, 5D, 5E, 5F and 5G are a series of graphs depicting the binding of the GITR-targeting molecules of the disclosure referred to as hzC04v4.1, hzC04v4.1.2, hzC04v4.2, hzC04v4.2.2, hzC04v5, hzC04v1.2.1, hzC04v5.1, hzC04v5.2, hzC04v5.3, hzC04v5.4, hzC04v5.5, hzC04v5.6, hzC04v5.7, hzC04v5.8, hzC04v5.9, hzC04v5.10, hzC04v5.11, and hzC04v5.12 for human GITR and cynomolgus GITR ("cyno GITR") expressed on the surface of CHO cells, as measured by flow cytometry.
Figure 5B:
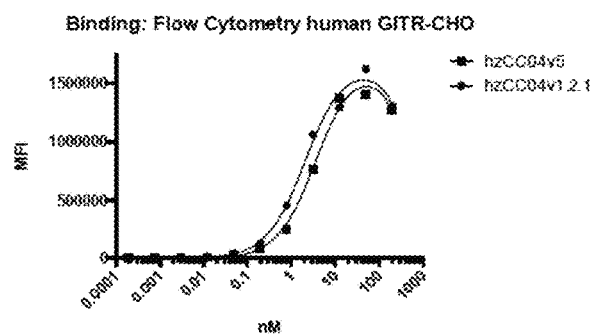
Figure 5C:
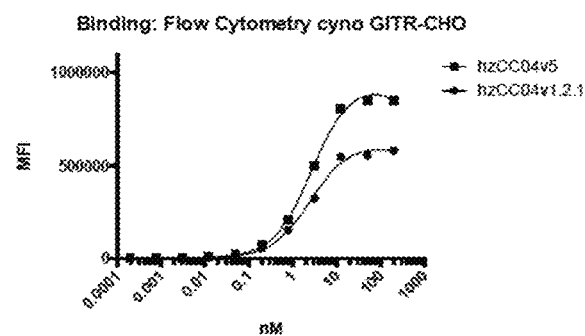
Figure 5D:
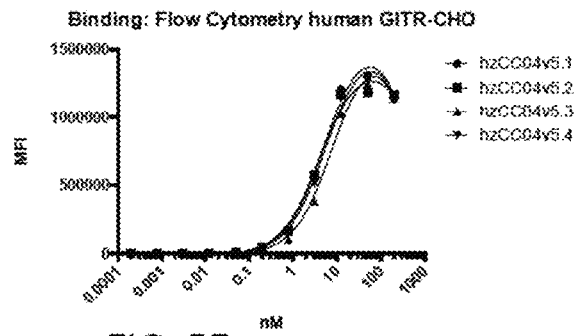
Figure 5E:
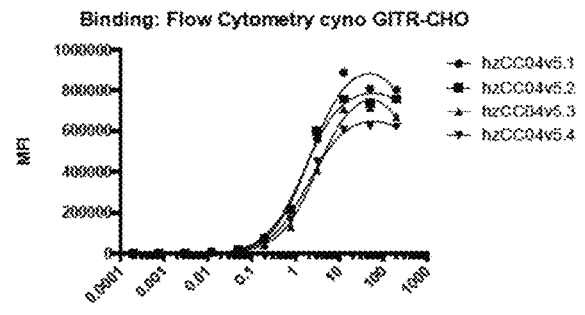
Figure 5F:
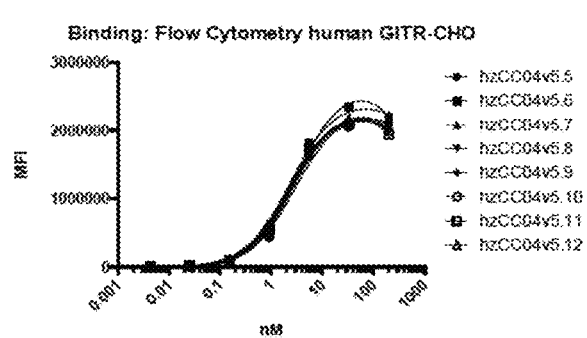
Figure 5G:
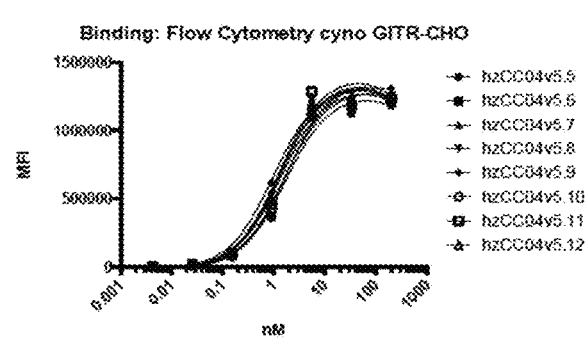
Figure 6:
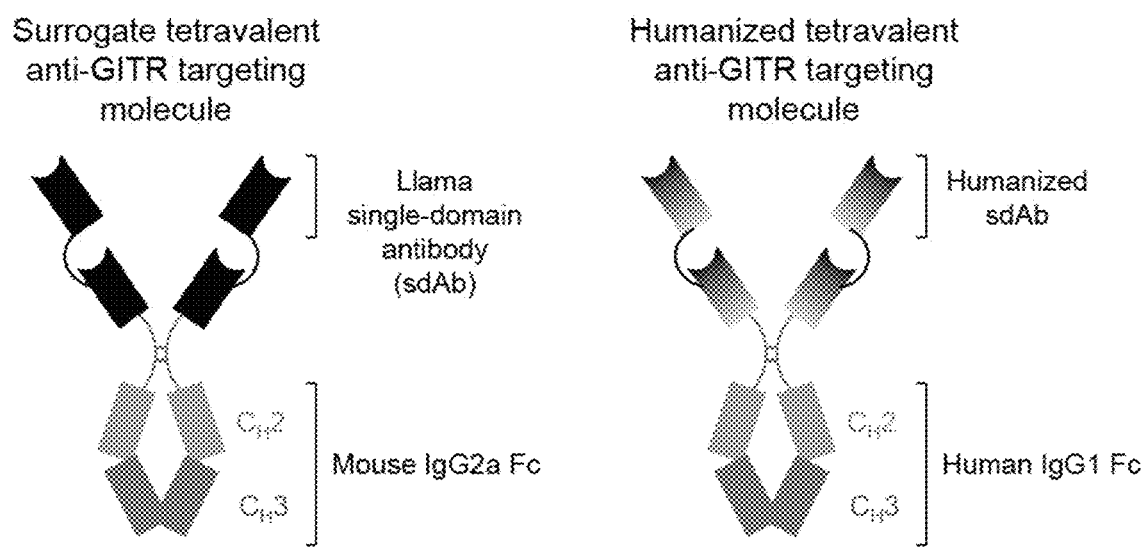

Example 2. GITR-Targeting Molecules Block the Interaction Between GITR and GITR-L As shown in FIGS. 3A, 3B, and 3C, various GITR-targeting fusion proteins of the disclosure were able to block the interaction between GITRL and GITR. Briefly, in these studies, a flow cytometry assay using GITR expressing CHO cells and recombinant GITRL was used to implement to assess blocking capacity. The GITR antibody, TRX-518, was used as a control for these studies.

Example 3. Binding Affinities of GITR-Targeting Molecules for Human and Cynomolgus GITR The binding affinities of the GITR-targeting molecule referred to herein as bivalent hzC06v3.9-hIgG1 or 2×hzC06v3.9-IgG1 Fc (SEQ ID NO: 93) for human and cynomolgus GITR extracellular domain human IgG1 fusion protein (GITR-Fc) were determined by surface plasmon resonance. Briefly, biotinylated human and cynomolgus GITR-Fc were captured on the chip surface and then bivalent hzC06v3.9-hIgG1 was injected at 10 concentrations (0 nM-600 nM) at 40 ul/min for 120 seconds. Dissociation was followed for 240 seconds. ka1, kd1, and KD1 are reported in the table below.

| GITR-Fc | ka1 (1/Ms) | kd1 (1/s) | KD(nM) |
| --- | --- | --- | --- |
| Cyno | 1.22E+05 | 1.06E−02 | 87.1 |
| Human | 6.40E+05 | 4.12E−03 | 6.4 |

Example 4. Binding of GITR-Targeting Molecules for Primary Human T Cells

The ability of an anti-GITR molecule of the disclosure, referred to herein as tetravalent hzC06-hIgG1, to primary human T cells was evaluated herein. Tetravalent hzC06-hIgG1 is constructed with two copies of the GITR-binding molecule of SEQ ID NO: 93, which, in turn, is constructed with two tandem copies of a single-domain variable region (sdAb) of SEQ ID NO: 59 fused to a human IgG1 Fc domain of SEQ ID NO: 1.

Figure 7:
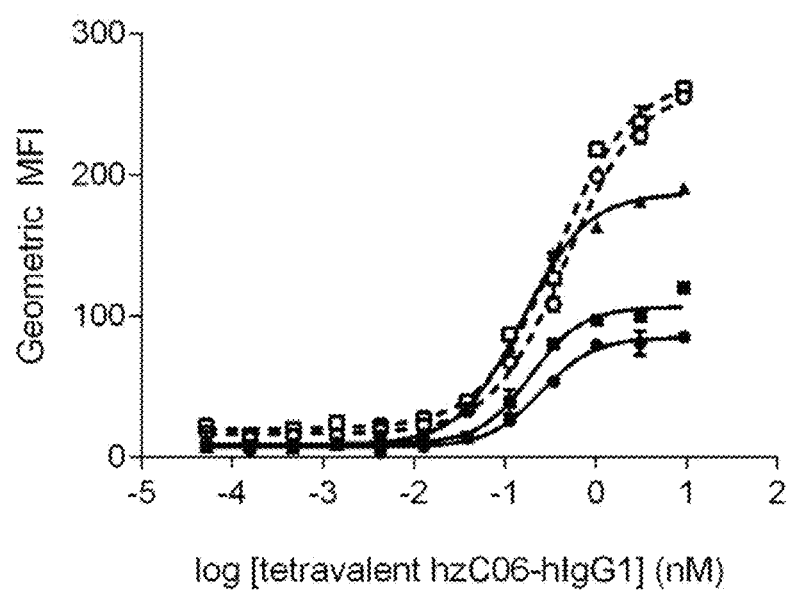
FIG. 7 is a graph depicting the binding an anti-GITR molecule of the disclosure, referred to herein as tetravalent hzC06-hIgG1, to primary human T cells. Tetravalent hzC06-hIgG1 is constructed with two copies of the GITR-binding molecule of SEQ ID NO: 93, which, in turn, is constructed with two tandem copies of a single-domain variable region (sdAb) of SEQ ID NO: 59 fused to a human IgG1 Fc domain of SEQ ID NO: 1.

Total PBMC or purified Treg isolated by fluorescence-activated cell sorting were prepared from healthy human donors. The cells were activated in vitro with anti-CD3 and anti-CD28 supplemented with recombinant human IL2. The cells were incubated with varying concentrations of tetravalent hzC06-hIgG1 and a surface phenotyping antibody cocktail. Samples were then washed and stained with a fluorescently-labeled anti-hIgG secondary antibody and then assessed by flow cytometry. Activated CD4 T cells were identified by staining with CD3, CD4, and CD25. Results of these studies are shown in FIG. 7 for activated CD4 T cells from three donors (closed symbols, solid lines) and activated Treg from two donors (open symbols, dashed lines).

Example 5. GITR-Targeting Molecules Activate NF-kB Signaling

Tetravalent anti-GITR-targeting molecules activated NF-kB signaling in reporter cell lines expressing GITR. The studies described herein used two tetravalent GITR-targeting molecules of the disclosure. The first tetravalent GITR-targeting molecule includes two copies of the GITR-binding fusion protein referred to herein as 2×hzC06v3.9 IgG1-Fc (SEQ ID NO: 93), which, in turn, includes two copies of the hzC06v3.9 GITR-BD (SEQ ID NO: 59) and the IgG1 Fc polypeptide of SEQ ID NO: 1. The second tetravalent GITR-targeting molecule includes two copies of the GITR-binding fusion protein is referred to herein as 2×C06 IgG1-Fc, which, in turn, includes two copies of the C06 GITR-BD (SEQ ID NO: 22) and the IgG1 Fc polypeptide of SEQ ID NO: 1.

Figure 8A:
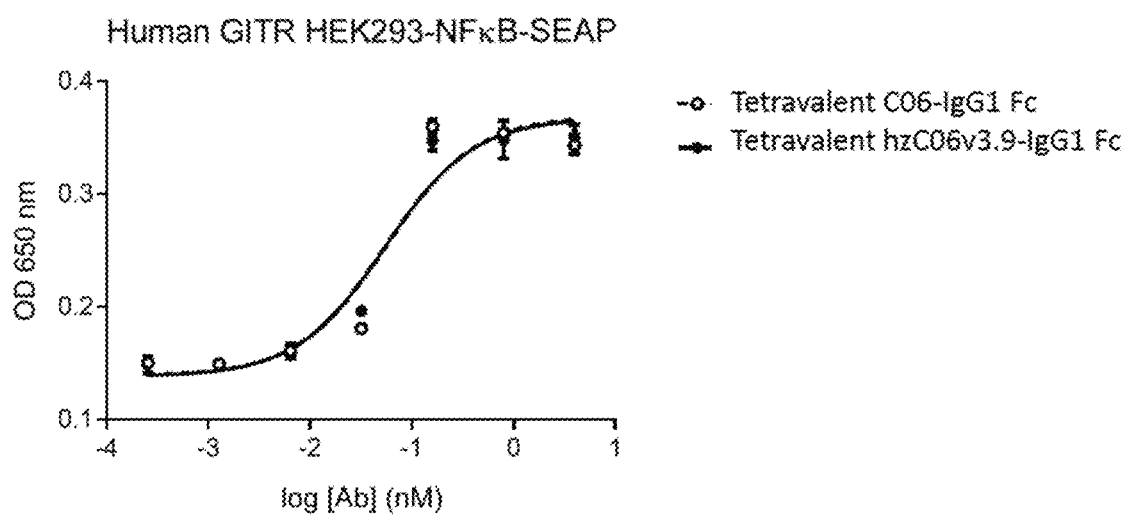
FIGS. 8A and 8B are a series of graphs depicting the ability of tetravalent GITR-targeting molecules of the disclosure to activate NF-kB signaling in reporter cell lines expressing GITR.
Figure 8B:
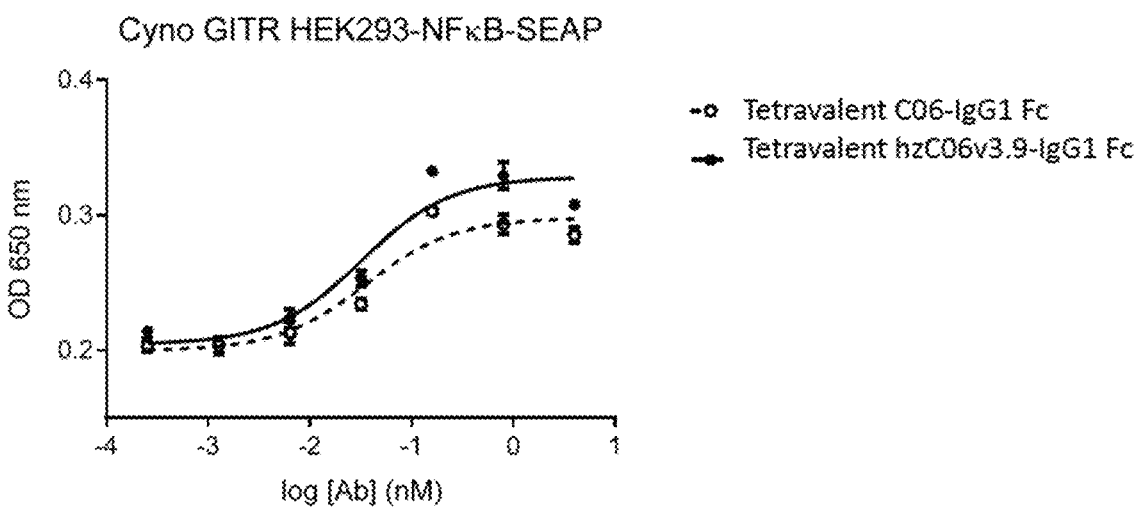

HEK293 cell lines containing a NF-kB-driven secreted alkaline phosphatase (SEAP) reporter gene were stably transfected with human GITR (FIG. 8A) or cynomolgus monkey GITR (FIG. 8B). The cell lines were incubated with titrating doses of tetravalent GITR antibodies overnight at 37° C. SEAP reporter gene expression was quantified by the hydrolysis of a substrate that is measured by optical density at 650 nM.

Example 6. GITR-Targeting Molecules in Tumor Models

Figure 9A:
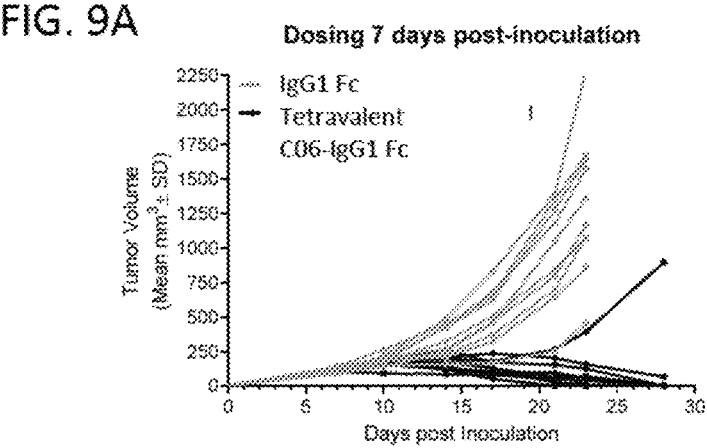
FIGS. 9A, 9B, and 9C are a series of graphs depicting that treatment with a tetravalent GITR-targeting molecule of the disclosure significantly reduced CT26 tumor growth irrespective of day of administration.
Figure 9B:
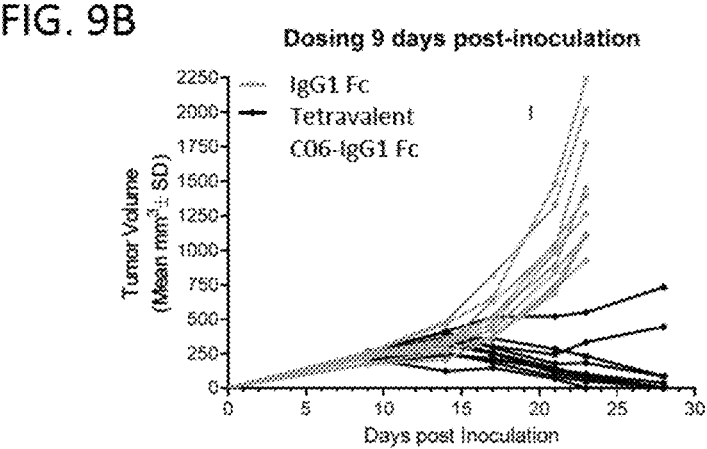
Figure 9C:
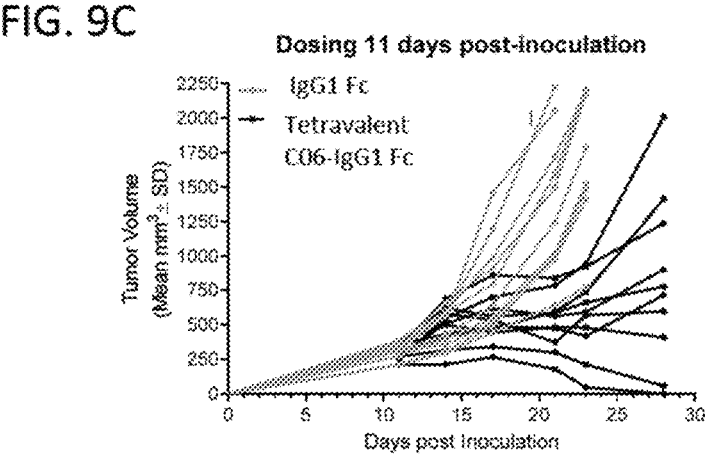

As shown in FIGS. 9A-9C, treatment with a GITR-targeting molecule of the disclosure significantly reduced CT26 tumor growth irrespective of day of administration. BALB/c mice were inoculated subcutaneously with CT26 colorectal carcinoma cells and were administered tetravalent C06-hIgG1, which includes two copies of the GITR-binding fusion protein referred to herein as 2×C06-IgG1 Fc, which, in turn, includes two copies of the GITR-BD of SEQ ID NO: 22 and the human IgG1 Fc polypeptide sequence of SEQ ID NO: 1) or Human IgG1-Fc as a control on Day 7 (FIG. 9A), Day 9 (FIG. 9B), or Day 11 (FIG. 9C), at which points the mean tumor volumes were 125, 230, or 310 mm$^3$. Tetravalent C06-IgG1 Fc treatment resulted in significant reduction in tumor growth compared to Human Fc beginning 6-8 days after administration regardless of the day of treatment ($p<0.05$, determined via two-tailed, unpaired t-test).

Figure 10:
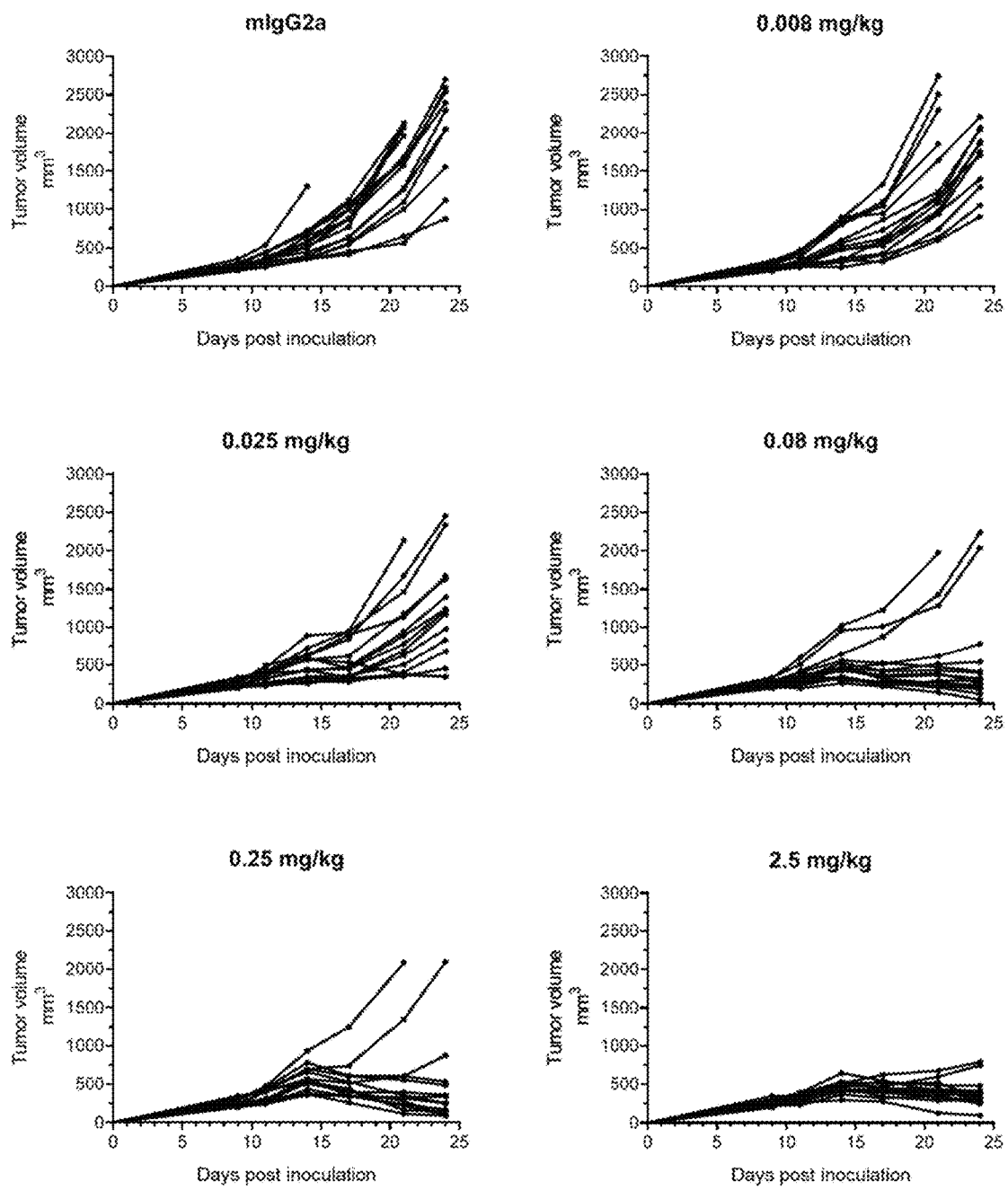
FIG. 10 is a series of graphs depicting the dose-dependent suppression of CT26 tumor growth by a tetravalent GITR-targeting molecule of the disclosure.

As shown in FIG. 10, treatment with a GITR-targeting molecule of the disclosure produced dose-dependent suppression of CT26 tumor growth. BALB/c mice were inoculated subcutaneously with CT26 colorectal carcinoma cells and were administered tetravalent C06-mIgG2a, which includes two copies of the GITR-binding fusion protein referred to herein as 2×C06-mIgG1 2a Fc, which, in turn, includes two copies of the GITR-BD of SEQ ID NO: 22 and a murine IgG2a sequence or non-specific mIgG2a as a control on Day 9 (approximate tumor volume 260 mm$^3$). Tetravalent C06-mIgG2a treatment resulted in significant reduction in tumor volume compared to control when administered at 2.5, 0.25, 0.08, or 0.025 mg/kg ($p<0.05$). Tetravalent C06-mIgG2a dosed at 0.008 mg/kg did not significantly suppress CT26 tumor growth. Statistical significance was determined via one-way ANOVA with multiple comparisons of the Tetravalent C06-mIgG2a groups to mIgG2a.

Figure 11A:
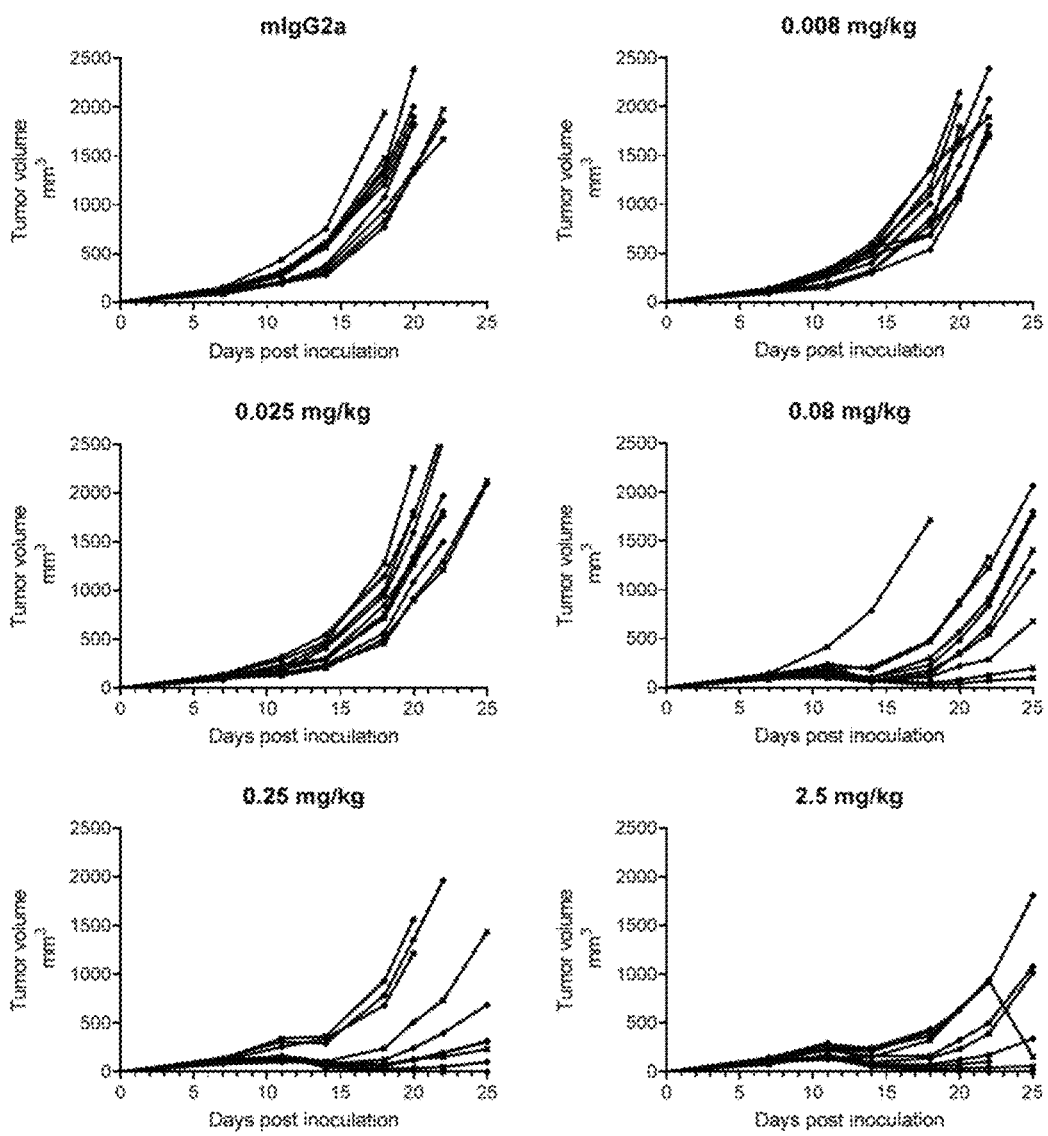
FIG. 11A is a series of graphs depicting the dose-dependent suppression of MC38 tumor growth by a tetravalent GITR-targeting molecule of the disclosure.
Figure 11B:
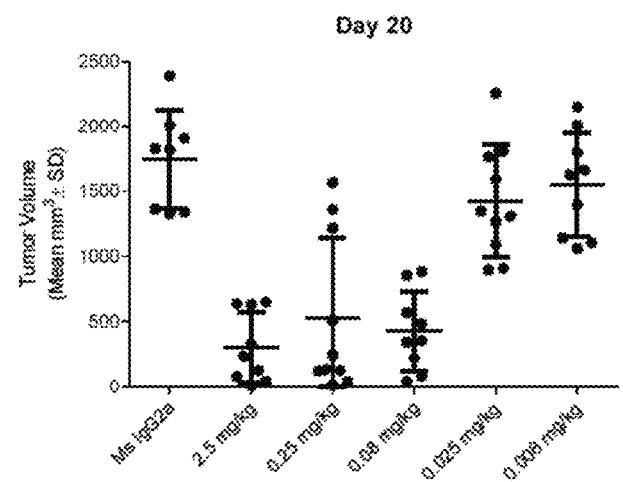
FIG. 11B depicts individual tumor volumes at Day 20 of treated mice after MC38 inoculation.

As shown in FIGS. 11A-11B, treatment with a GITR-targeting molecule of the disclosure produced dose-dependent suppression of MC38 tumor growth. C57BL/6 mice were inoculated subcutaneously with MC38 colorectal carcinoma cells and were administered tetravalent C06-mIgG2a or non-specific mIgG2a as a control on Day 7 (mean tumor volume 110-115 mm$^3$). Administration of tetravalent C06-mIgG2a at doses of 0.08 or above resulted in significant tumor growth reduction compared to mIgG2a control beginning on Day 14 ($p<0.05$) (FIG. 11A). Tetravalent C06-mIgG2a treatment at 0.025 significantly reduced tumor growth compared to mIgG2a control beginning on Day 18 ($p<0.05$). Tetravalent C06-mIgG2a dosed at 0.008 mg/kg did not significantly suppress MC38 tumor growth. Statistical significance was determined via one-way ANOVA with multiple comparisons of the C06 groups to IgG2a. Individual tumor volumes on Day 20 after MC38 inoculation are shown in FIG. 11B. There is a similar reduction in tumor growth at this timepoint in the 2.5, 0.25, and 0.08 mg/kg treatment groups.

Example 7. Impact of Fc Function on Inhibition of CT26 Tumor Growth

Figure 12A:
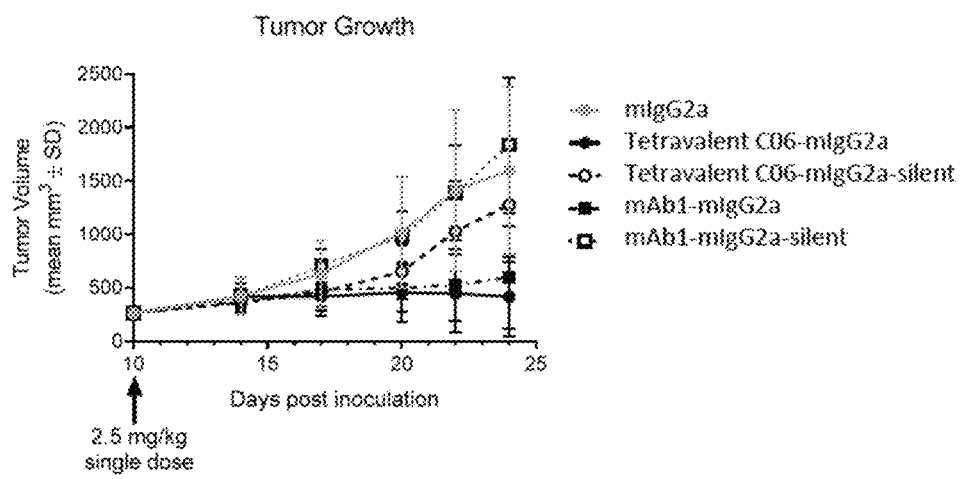
FIGS. 12A, 12B, and 12C are a series of graphs depicting the impact of Fc function on inhibition of CT26 tumor growth.
Figure 12B:
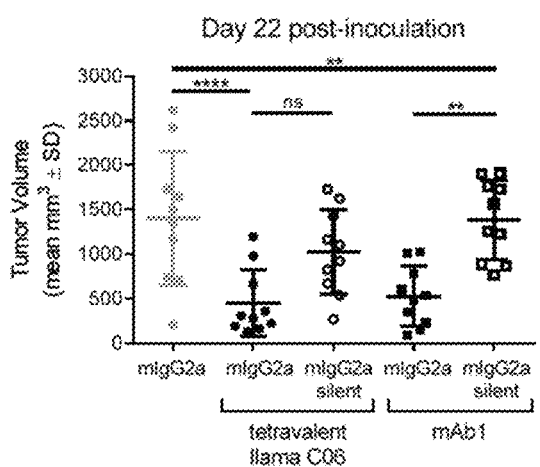
Figure 12C:
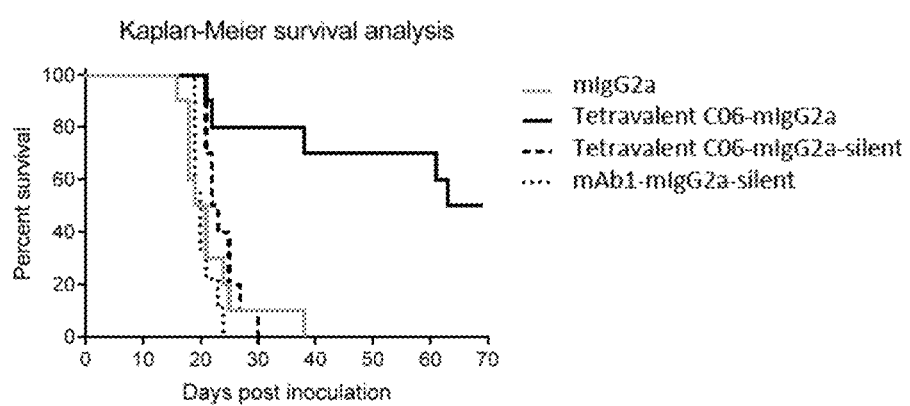

BALB/c mice were inoculated subcutaneously with CT26 colorectal carcinoma cells and were administered tetravalent C06-mIgG2a with either wild-type Fc or N297G mutation to block binding to Fc receptors (mIgG2a-silent) on Day 9 (mean tumor volume 260 mm$^3$). Non-specific mIgG2a, anti-GITR mAb1-mIgG2a, and anti-GITR control mAb1-mIgG2a-silent were used as controls. As shown in FIG. 12A, although tetravalent C06 was most potent with wild-type Fc, both wild-type and silent formats significantly reduced tumor growth compared to control ($p<0.05$). mAb1 only inhibited CT26 growth when administered in the wild-type Fc format. Statistical significance was determined via one-way ANOVA with multiple comparisons of the treatment groups to mIgG2a. Individual tumor volumes on Day 22 after CT26 inoculation are shown in FIG. 12B. The difference in tumor growth between Fc wild-type and silent formats of tetravalent C06 is not significant, while format was significant for the ability of mAb1 to suppress tumor growth. Kaplan-Meier analysis shows that treatment with tetravalent C06 with wild-type Fc can significantly enhance the survival of CT26-bearing mice (FIG. 12C). A single administration of tetravalent C06-mIgG2a on Day 10 extends median survival to 66 days, compared to 20 days for the mIgG2a control group.

Figure 13A:
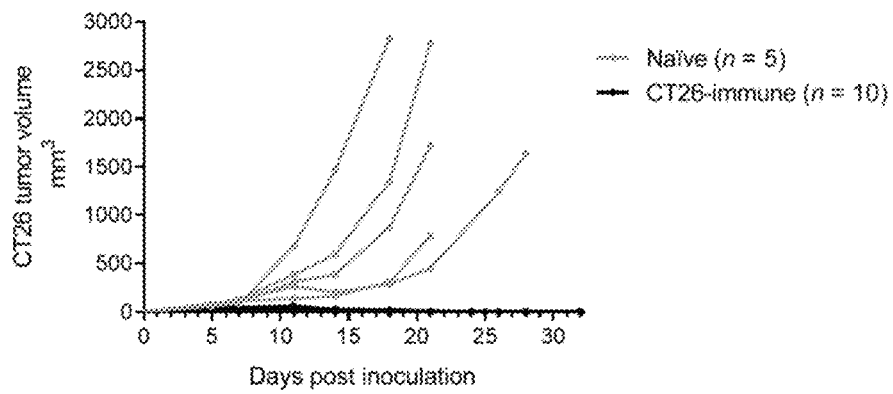
FIGS. 13A, 13B, and 13C are a series of graphs depicting that treatment with a tetravalent GITR-targeting molecule had subsequence resistance to re-challenge with CT26 tumors.
Figure 13B:
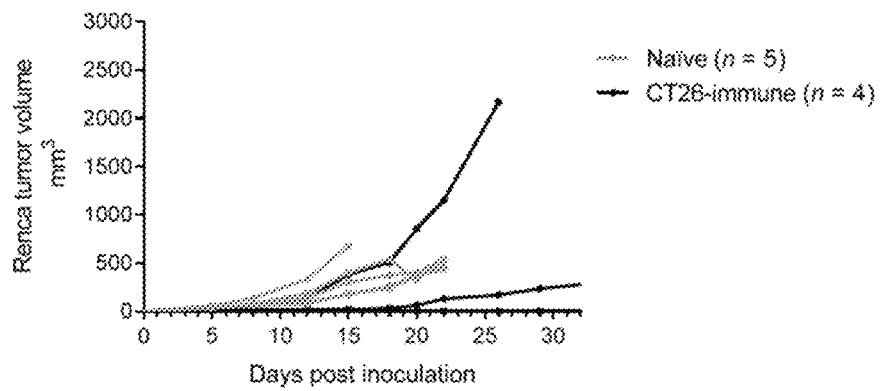
Figure 13C:
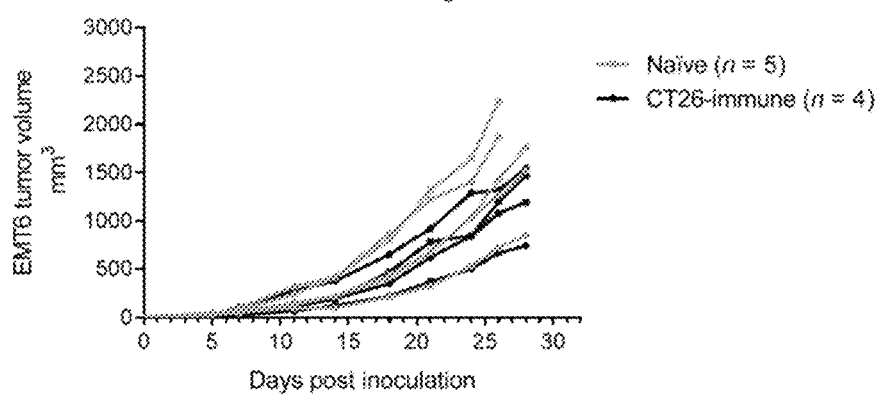

Example 8. Treatment with GITR-Targeting Molecules Results in Resistance to Re-Challenge Mice that had received tetravalent C06-mIgG2a-induced CT26 rejection were resistant to re-challenge. BALB/c mice that had rejected CT26 tumors upon treatment with tetravalent C06-mIgG2a were re-inoculated with CT26, Renca, or EMT6 murine tumor cell lines. As shown in FIG. 13A, mice that have previously rejected CT26 were completely resistant to tumor growth upon subsequent re-inoculation of this model. Importantly, naïve, age-matched mice demonstrated CT26 tumor growth. As shown in FIG. 13B, Renca tumors did not grow well in mice that had previously rejected CT26. Indeed, two of four mice were completely resistant, and one mouse had marked reduction in Renca growth compared to naïve, age-matched controls. Renca shares T cell epitopes with CT26, suggesting that T cell-mediated immunity is induced. As shown in FIG. 13C, EMT6 tumors grow well in BALB/c mice whether they previously eliminated CT26 upon C06 treatment or were naïve. EMT6 does not share T cell epitopes with CT26.

Example 9. Effect of Treatment with GITR-Targeting Molecules on T Cells

Figure 14A:
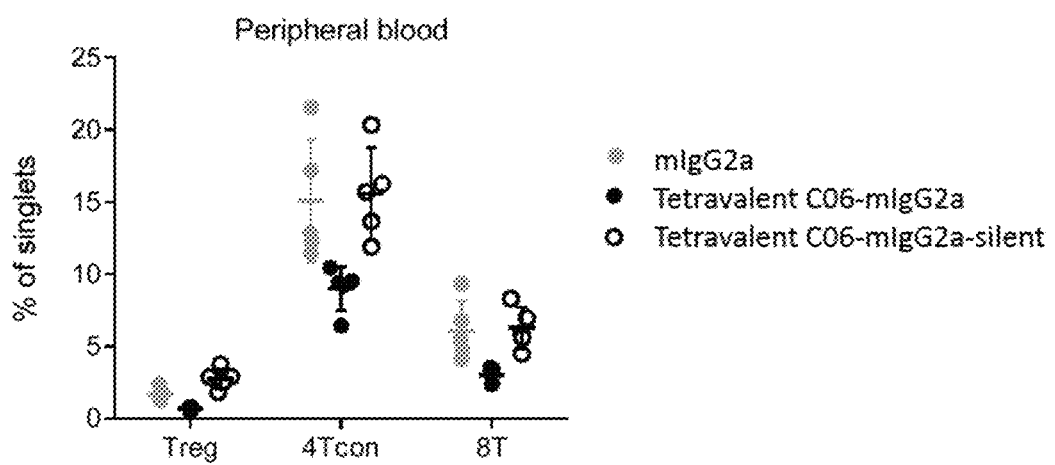
FIGS. 14A, 14B, and 14C are a series of graphs depicting that treatment with a tetravalent GITR-targeting molecule of the disclosure significantly reduced $T_{reg}$ frequency and altered the ratio of $T_{reg}$ to $T_{effector}$ cells within the tumor microenvironment.
Figure 14B:
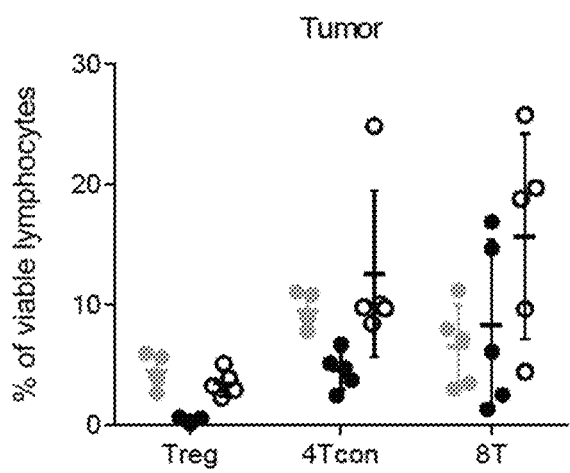
Figure 14C:
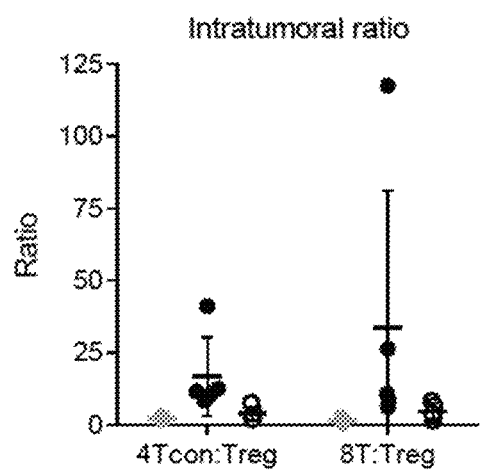

Treatment significantly reduced $T_{reg}$ frequency and altered the ratio to $T_{effector}$ cells within the tumor microenvironment. BALB/c mice were inoculated subcutaneously with CT26 colorectal carcinoma cells and were administered 2.5 mg/kg tetravalent C06-mIgG2a with either wild-type Fc or N297G mutation to block binding to Fc receptors (mIgG2a-silent) on Day 9. Non-specific mIgG2a was used as a control. Peripheral blood and tumors were collected and analyzed by flow cytometry 3 days after treatment. As shown in FIG. 14A, treatment with tetravalent C06-mIgG2a significantly reduced the frequency of circulating $T_{reg}$, conventional CD4 T cells (4Tcon), and CD8 T cells (8T) (p<0.05). No effect was observed with the mIgG2a-silent format. As shown in FIG. 14B, treatment with tetravalent C06-mIgG2a significantly reduced the frequency of intratumoral $T_{reg}$ and conventional CD4 T cells (p<0.001), but CD8 T cells were not changed. No effect was observed with the mIgG2a-silent format. As shown in FIG. 14C, as a consequence of the potent reduction of $T_{reg}$ by tetravalent C06-mIgG2a, the ratios of effector T cells to $T_{reg}$ were significantly increased in the tumor (p<0.05). Statistical significance was determined via two-tailed, unpaired t-test.

Figure 15A:
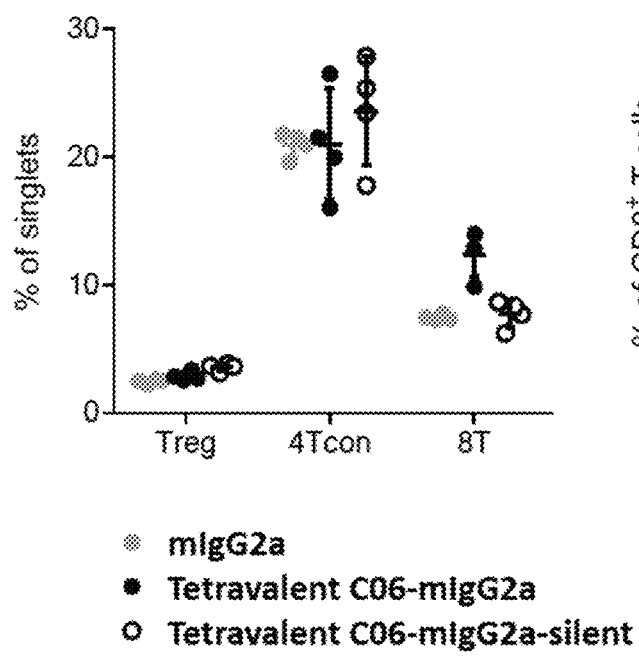
FIGS. 15A and 15B are a series of graphs depicting that treatment with a tetravalent GITR-targeting molecule of the disclosure significantly induced CD8 T cell activation and proliferation.
Figure 15B:
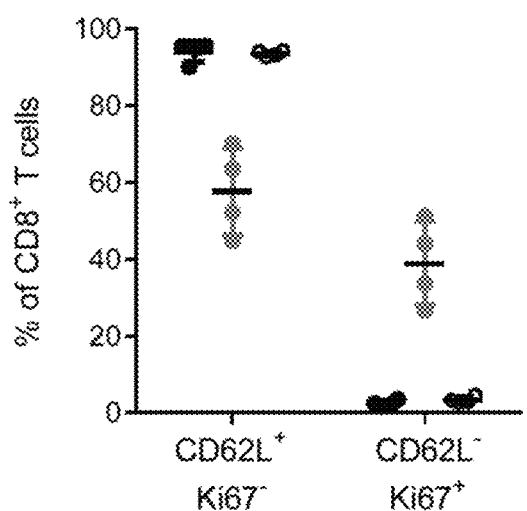

Example 10. Effect of GITR-Targeting Molecules on T Cell Activation and Proliferation Treatment significantly induced CD8 T cell activation and proliferation. BALB/c mice were inoculated subcutaneously with CT26 colorectal carcinoma cells and were administered 2.5 mg/kg tetravalent C06-mIgG2a with either wild-type Fc or N297G mutation to block binding to Fc receptors (mIgG2a-silent) on Day 9. Non-specific mIgG2a was used as a control. Peripheral blood was analyzed by flow cytometry 12 days after treatment. As shown in FIG. 15A, treatment with tetravalent C06-mIgG2a significantly induced the frequency of circulating CD8 T cells (p<0.005), but $T_{reg}$ and conventional CD4 T cells were not changed. This effect was not observed with the mIgG2a-silent format. As shown in FIG. 15B, CD8 T cells also adopted an activated, proliferating phenotype (CD62L$^-$ Ki67$^+$) following treatment with tetravalent C06-mIgG2a. Statistical significance was determined via two-tailed, unpaired t-test.

---

What is claimed is:

1. A fusion protein that binds glucocorticoid-induced TNFR-related protein (GITR), comprising at least one GITR-binding domain (GITR-BD), wherein the GITR-BD comprises a single-domain antibody (sdAb), wherein the GITR-BD comprises a CDR1, CDR2, and CDR3 comprising:

the amino acid sequences set forth in SEQ ID NOS: 106, 107 and 108, respectively;
the amino acid sequences set forth in SEQ ID NOS: 109, 110 and 111, respectively;
the amino acid sequences set forth in SEQ ID NOS: 112, 113 and 114, respectively;
the amino acid sequences set forth in SEQ ID NOS: 106, 115 and 116, respectively;
the amino acid sequences set forth in SEQ ID NOS: 117, 118 and 119, respectively;
the amino acid sequences set forth in SEQ ID NOS: 120, 121 and 122, respectively;
the amino acid sequences set forth in SEQ ID NOS: 149, 123 and 150, respectively;
the amino acid sequences set forth in SEQ ID NOS: 120, 123 and 124, respectively;
the amino acid sequences set forth in SEQ ID NOS: 125, 121 and 124, respectively;
the amino acid sequences set forth in SEQ ID NOS: 120, 121 and 126, respectively;
the amino acid sequences set forth in SEQ ID NOS: 112, 113 and 127, respectively;
the amino acid sequences set forth in SEQ ID NOS: 148, 128 and 129, respectively;
the amino acid sequences set forth in SEQ ID NOS: 120, 130 and 124, respectively;
the amino acid sequences set forth in SEQ ID NOS: 131, 132 and 133, respectively;
the amino acid sequences set forth in SEQ ID NOS: 120, 134 and 135, respectively;
the amino acid sequences set forth in SEQ ID NOS: 120, 121 and 122, respectively;
the amino acid sequences set forth in SEQ ID NOS: 106, 136 and 122, respectively;
the amino acid sequences set forth in SEQ ID NOS: 106, 137 and 122, respectively;
the amino acid sequences set forth in SEQ ID NOS: 120, 137 and 122, respectively;
the amino acid sequences set forth in SEQ ID NOS: 138, 137 and 122, respectively;
the amino acid sequences set forth in SEQ ID NOS: 138, 139 and 116, respectively;
the amino acid sequences set forth in SEQ ID NOS: 106, 139 and 116, respectively;
the amino acid sequences set forth in SEQ ID NOS: 138, 139 and 140, respectively;
the amino acid sequences set forth in SEQ ID NOS: 109, 110 and 111, respectively;
the amino acid sequences set forth in SEQ ID NOS: 138, 141 and 116, respectively;
the amino acid sequences set forth in SEQ ID NOS: 138, 141 and 142, respectively;
the amino acid sequences set forth in SEQ ID NOS: 143, 144 and 145, respectively;
the amino acid sequences set forth in SEQ ID NOS: 143, 144 and 146, respectively; or
the amino acid sequences set forth in SEQ ID NOS: 143, 147 and 146, respectively.

2. The fusion protein of claim 1, wherein the GITR-BD comprises a CDR1, CDR2, and CDR3 comprising:

a) the amino acid sequences set forth in SEQ ID NOS: 106, 107 and 108, respectively;
the amino acid sequences set forth in SEQ ID NOS: 109, 110 and 111, respectively;
the amino acid sequences set forth in SEQ ID NOS: 112, 113 and 114, respectively;
the amino acid sequences set forth in SEQ ID NOS: 106, 115 and 116, respectively;
the amino acid sequences set forth in SEQ ID NOS: 117, 118 and 119, respectively;
the amino acid sequences set forth in SEQ ID NOS: 120, 121 and 122, respectively;
the amino acid sequences set forth in SEQ ID NOS: 149, 123 and 150, respectively;
the amino acid sequences set forth in SEQ ID NOS: 120, 123 and 124, respectively;
the amino acid sequences set forth in SEQ ID NOS: 125, 121 and 124, respectively;
the amino acid sequences set forth in SEQ ID NOS: 120, 121 and 126, respectively;
the amino acid sequences set forth in SEQ ID NOS: 112, 113 and 127, respectively;
the amino acid sequences set forth in SEQ ID NOS: 148, 128 and 129, respectively;
the amino acid sequences set forth in SEQ ID NOS: 120, 130 and 124, respectively;
the amino acid sequences set forth in SEQ ID NOS: 131, 132 and 133, respectively;
the amino acid sequences set forth in SEQ ID NOS: 120, 134 and 135, respectively; or
the amino acid sequences set forth in SEQ ID NOS: 120, 121 and 122, respectively; wherein the GITR-BD comprises an amino acid sequence selected from the group consisting of any one of SEQ ID NOs: 19-35, or a sequence that is at least 95% identical to an amino acid sequence selected from the group consisting of any one of SEQ ID NOs: 19-35;

b) the amino acid sequences set forth in SEQ ID NOS: 106, 136 and 122, respectively;
the amino acid sequences set forth in SEQ ID NOS: 106, 137 and 122, respectively;
the amino acid sequences set forth in SEQ ID NOS: 120, 137 and 122, respectively; or
the amino acid sequences set forth in SEQ ID NOS: 138, 137 and 122, respectively; wherein the GITR-BD comprises an amino acid sequence selected from the group consisting of any one of SEQ ID NOs: 36-41, or a sequence that is at least 95% identical to an amino acid sequence selected from the group consisting of any one of SEQ ID NOs: 36-41;
c) the amino acid sequences set forth in SEQ ID NOS: 138, 139 and 116, respectively;
the amino acid sequences set forth in SEQ ID NOS: 106, 139 and 116, respectively;
the amino acid sequences set forth in SEQ ID NOS: 138, 139 and 140, respectively;
the amino acid sequences set forth in SEQ ID NOS: 109, 110 and 111, respectively; or
the amino acid sequences set forth in SEQ ID NOS: 138, 141 and 116, respectively; wherein the GITR-BD comprises an amino acid sequence selected from the group consisting of any one of SEQ ID NOs: 42-62, or a sequence that is at least 95% identical to an amino acid sequence selected from the group consisting of any one of SEQ ID NOs: 42-62;
d) the amino acid sequences set forth in SEQ ID NOS: 138, 141 and 142, respectively;
the amino acid sequences set forth in SEQ ID NOS: 143, 144 and 145, respectively;
the amino acid sequences set forth in SEQ ID NOS: 143, 144 and 146, respectively; or
the amino acid sequences set forth in SEQ ID NOS: 143, 147 and 146, respectively; wherein the GITR-BD comprises an amino acid sequence selected from the group consisting of any one of SEQ ID NOs: 63-80, or a sequence that is at least 95% identical to an amino acid sequence selected from the group consisting of any one of SEQ ID NOs: 63-80.

3. The fusion protein of claim 1, wherein the fusion protein comprises an immunoglobulin Fc-region polypeptide.

4. The fusion protein of claim 3, wherein the fusion protein comprises at least two GITR-BDs, wherein each GITR-BD comprises a CDR1, CDR2, and CDR3 comprising an amino acid sequence selected from the group consisting of:
a) the amino acid sequences set forth in SEQ ID NOS: 106, 136 and 122, respectively;
the amino acid sequences set forth in SEQ ID NOS: 106, 137 and 122, respectively;
the amino acid sequences set forth in SEQ ID NOS: 120, 137 and 122, respectively; or
the amino acid sequences set forth in SEQ ID NOS: 138, 137 and 122, respectively; wherein the polypeptide comprises an amino acid sequence according to SEQ ID NO: 81-92, or an amino acid sequence that is at least 95% identical to an amino acid sequence selected from the group consisting of SEQ ID NOs: 81-92 and 94-105; or
b) the amino acid sequences set forth in SEQ ID NO: 138, 141 and 116; wherein the polypeptide comprises an amino acid sequence according to SEQ ID NO: 93.

5. The fusion protein of claim 3, wherein the fusion protein is tetravalent for binding GITR.

6. The fusion protein of claim 5, wherein the fusion protein comprises two copies of a fusion protein that comprises the structure: (GITR-BD)-Linker-(GITR-BD)-Linker-Hinge-Fc.

7. The fusion protein of claim 3, wherein the fusion protein is hexavalent for binding GITR.

8. The fusion protein of claim 7, wherein the fusion protein comprises two copies of a fusion protein that comprises the structure: (GITR-BD)-Linker-(GITR-BD)-Linker-(GITR-BD)-Linker-Hinge-Fc.

9. The fusion protein of claim 8, wherein each GITR-BD comprises a complementarity determining region 1 (CDR1) comprising the amino acid sequence of SEQ ID NO: 138; a complementarity determining region 2 (CDR2) comprising the amino acid sequence of SEQ ID NO: 141; and a complementarity determining region 3 (CDR3) comprising the amino acid sequence of SEQ ID NO: 116.

10. The fusion protein of claim 8, wherein each GITR-BD comprises the amino acid sequence selected from any one of SEQ ID NOs: 50-59 and 61-62.

11. The fusion protein of claim 8, wherein each GITR-BD comprises the amino acid sequence set forth in SEQ ID NO:59.

12. The fusion protein of claim 8, wherein the fusion protein comprises the amino acid sequence set forth in SEQ ID NO:93.

13. A pharmaceutical composition comprising the fusion protein of claim 1.

14. The fusion protein of claim 1, wherein the polypeptide comprises two or more GITR-binding domains (GITR-BDs) that specifically bind GITR.

15. The fusion protein of claim 14, wherein said two or more GITR-binding domains are operably linked via a linker polypeptide.

16. The fusion protein of claim 14, wherein the polypeptide comprises at least two copies of the same GITR-BD.

17. The fusion protein of claim 14, wherein the polypeptide comprises at least three copies of the same GITR-BD.

18. A fusion protein that binds at least glucocorticoid-induced TNFR-related protein (GITR), comprising at least one GITR-binding domain (GITR-BD) that specifically binds GITR, wherein the GITR-BD comprises a single-domain antibody (sdAb) and one or more additional binding domains that binds a target other than GITR, wherein the GITR-BD comprises a CDR1, CDR2, and CDR3 comprising:
the amino acid sequences set forth in SEQ ID NOS: 106, 107 and 108, respectively;
the amino acid sequences set forth in SEQ ID NOS: 109, 110 and 111, respectively;
the amino acid sequences set forth in SEQ ID NOS: 112, 113 and 114, respectively;
the amino acid sequences set forth in SEQ ID NOS: 106, 115 and 116, respectively;
the amino acid sequences set forth in SEQ ID NOS: 117, 118 and 119, respectively;
the amino acid sequences set forth in SEQ ID NOS: 120, 121 and 122, respectively;
the amino acid sequences set forth in SEQ ID NOS: 149, 123 and 150, respectively;
the amino acid sequences set forth in SEQ ID NOS: 120, 123 and 124, respectively;
the amino acid sequences set forth in SEQ ID NOS: 125, 121 and 124, respectively;
the amino acid sequences set forth in SEQ ID NOS: 120, 121 and 126, respectively;
the amino acid sequences set forth in SEQ ID NOS: 112, 113 and 127, respectively;
the amino acid sequences set forth in SEQ ID NOS: 148, 128 and 129, respectively;
the amino acid sequences set forth in SEQ ID NOS: 120, 130 and 124, respectively;
the amino acid sequences set forth in SEQ ID NOS: 131, 132 and 133, respectively;
the amino acid sequences set forth in SEQ ID NOS: 120, 134 and 135, respectively;

the amino acid sequences set forth in SEQ ID NOS: 120, 121 and 122, respectively;
the amino acid sequences set forth in SEQ ID NOS: 106, 136 and 122, respectively;
the amino acid sequences set forth in SEQ ID NOS: 106, 137 and 122, respectively;
the amino acid sequences set forth in SEQ ID NOS: 120, 137 and 122, respectively;
the amino acid sequences set forth in SEQ ID NOS: 138, 137 and 122, respectively;
the amino acid sequences set forth in SEQ ID NOS: 138, 139 and 116, respectively;
the amino acid sequences set forth in SEQ ID NOS: 106, 139 and 116, respectively;
the amino acid sequences set forth in SEQ ID NOS: 138, 139 and 140, respectively;
the amino acid sequences set forth in SEQ ID NOS: 109, 110 and 111, respectively;
the amino acid sequences set forth in SEQ ID NOS: 138, 141 and 116, respectively;
the amino acid sequences set forth in SEQ ID NOS: 138, 141 and 142, respectively;
the amino acid sequences set forth in SEQ ID NOS: 143, 144 and 145, respectively;
the amino acid sequences set forth in SEQ ID NOS: 143, 144 and 146, respectively; or
the amino acid sequences set forth in SEQ ID NOS: 143, 147 and 146, respectively.

19. The fusion protein of claim 18, wherein the at least one GITR-BD comprises an antibody or antigen-binding fragment thereof.

20. The fusion protein of claim 18, wherein the one or more additional binding domains bind a Tumor Necrosis Factor receptor superfamily (TNFRSF).

21. The fusion protein of claim 20, wherein the TNFRSF member is selected from the group consisting of OX40, CD27, herpesvirus entry mediator (HVEM), CD40, lymphotoxin beta receptor (LTBR), ectodysplasin A2 receptor (ED2R), ectodysplasin A receptor (EDAR), TweakR, B cell maturation antigen (BCMA), B cell-activating factor receptor (BAFFR), death receptor 3 (DR3), death receptor 6 (DR6), and CD137.

22. The fusion protein of claim 18, wherein the one or more additional binding domains bind a non-TNFRSF-member.

23. The fusion protein of claim 18, wherein the one or more additional binding domains comprise an antibody or antigen-binding fragment thereof.

24. A pharmaceutical composition comprising the fusion protein of claim 18.

25. A nucleic acid encoding the fusion protein of claim 1.

26. A nucleic acid encoding the fusion protein of claim 18.

27. An isolated host cell comprising the nucleic acid of claim 25.

28. A method of treating cancer in a subject in need thereof, the method comprising administering to the subject a therapeutically effective amount of the pharmaceutical composition of claim 13.

29. A method of treating cancer in a subject in need thereof, the method comprising administering to the subject a therapeutically effective amount of the pharmaceutical composition of claim 24.

30. The method of claim 28, wherein the cancer is a metastatic cancer, refractory cancer, or recurrent cancer.

31. The method of claim 30, wherein the cancer is selected from the group consisting of bladder cancer, breast cancer, uterine cancer, cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, and virus-related cancer.

32. The method of claim 28 further comprising administration of an anti-PD1 or anti-PDL1 antibody.

33. A method for inhibiting tumor growth, for reducing the frequency of intratumoral regulatory T cells ($T_{reg}$), for inducing activation and proliferation of CD8+ T cells, or for reducing the frequency of $T_{reg}$ cells and inducing activation and proliferation of CD8+ T cells, in a subject, the method comprising administering to said subject the fusion protein of claim 1.

34. A method for inhibiting tumor growth, for reducing the frequency of intratumoral regulatory T cells ($T_{reg}$), for inducing activation and proliferation of CD8+ T cells, or for reducing the frequency of $T_{reg}$ cells and inducing activation and proliferation of CD8+ T cells, in a subject, the method comprising administering to said subject the fusion protein of claim 18.

* * * * *

SEQUENCE LISTING

<160> NUMBER OF SEQ ID NOS: 150

<210> SEQ ID NO 1
<211> LENGTH: 218
<212> TYPE: PRT
<213> ORGANISM: Artificial Sequence
<220> FEATURE:
<223> OTHER INFORMATION: chemically synthesized

<400> SEQUENCE: 1

```
Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Asp Glu
        115                 120                 125

Leu Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215
```

<210> SEQ ID NO 2
<211> LENGTH: 215
<212> TYPE: PRT
<213> ORGANISM: Artificial Sequence
<220> FEATURE:
<223> OTHER INFORMATION: chemically synthesized

<400> SEQUENCE: 2

```
Pro Ala Pro Gly Gly Pro Ser Val Phe Leu Phe Pro Pro Lys Pro Lys
1               5                   10                  15

Asp Thr Leu Met Ile Ser Arg Thr Pro Glu Val Thr Cys Val Val Val
            20                  25                  30

Asp Val Ser His Glu Asp Pro Glu Val Lys Phe Asn Trp Tyr Val Asp
        35                  40                  45

Gly Val Glu Val His Asn Ala Lys Thr Lys Pro Arg Glu Glu Gln Tyr
    50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Ala Leu
                85                  90                  95

Pro Ala Pro Ile Glu Lys Thr Ile Ser Lys Ala Lys Gly Gln Pro Arg
            100                 105                 110

Glu Pro Gln Val Tyr Thr Leu Pro Pro Ser Arg Asp Glu Leu Thr Lys
        115                 120                 125

Asn Gln Val Ser Leu Thr Cys Leu Val Lys Gly Phe Tyr Pro Ser Asp
130                 135                 140

Ile Ala Val Glu Trp Glu Ser Asn Gly Gln Pro Glu Asn Asn Tyr Lys
145                 150                 155                 160

Thr Thr Pro Pro Val Leu Asp Ser Asp Gly Ser Phe Phe Leu Tyr Ser
                165                 170                 175

Lys Leu Thr Val Asp Lys Ser Arg Trp Gln Gln Gly Asn Val Phe Ser
            180                 185                 190

Cys Ser Val Met His Glu Ala Leu His Asn His Tyr Thr Gln Lys Ser
        195                 200                 205

Leu Ser Leu Ser Pro Gly Lys
    210                 215
```

<210> SEQ ID NO 3
<211> LENGTH: 217
<212> TYPE: PRT
<213> ORGANISM: Artificial Sequence
<220> FEATURE:
<223> OTHER INFORMATION: chemically synthesized

<400> SEQUENCE: 3

```
Pro Ala Pro Pro Val Ala Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Phe Arg Val Val Ser Val Leu Thr Val Val His
65                  70                  75                  80

Gln Asp Trp Leu Asn Gly Lys Glu Tyr Lys Cys Lys Val Ser Asn Lys
                85                  90                  95
```

Gly Leu Pro Ala Pro Ile Glu Lys Thr Ile Ser Lys Thr Lys Gly Gln
              100                 105                 110

Pro Arg Glu Pro Gln Val Tyr Thr Leu Pro Pro Ser Arg Glu Glu Met
          115                 120                 125

Thr Lys Asn Gln Val Ser Leu Thr Cys Leu Val Lys Gly Phe Tyr Pro
      130                 135                 140

Ser Asp Ile Ser Val Glu Trp Glu Ser Asn Gly Gln Pro Glu Asn Asn
145                 150                 155                 160

Tyr Lys Thr Thr Pro Pro Met Leu Asp Ser Asp Gly Ser Phe Phe Leu
              165                 170                 175

Tyr Ser Lys Leu Thr Val Asp Lys Ser Arg Trp Gln Gln Gly Asn Val
          180                 185                 190

Phe Ser Cys Ser Val Met His Glu Ala Leu His Asn His Tyr Thr Gln
      195                 200                 205

Lys Ser Leu Ser Leu Ser Pro Gly Lys
          210                 215

<210> SEQ ID NO 4
<211> LENGTH: 218
<212> TYPE: PRT
<213> ORGANISM: Artificial Sequence
<220> FEATURE:
<223> OTHER INFORMATION: chemically synthesized

<400> SEQUENCE: 4

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
              20                  25                  30

Val Val Val Asp Val Ser His Glu Asp Pro Glu Val Gln Phe Lys Trp
          35                  40                  45

Tyr Val Asp Gly Val Glu Val His Asn Ala Lys Thr Lys Pro Arg Glu
      50                  55                  60

Glu Gln Tyr Asn Ser Thr Phe Arg Val Val Ser Val Leu Thr Val Leu
65                  70                  75                  80

His Gln Asp Trp Leu Asn Gly Lys Glu Tyr Lys Cys Lys Val Ser Asn
              85                  90                  95

Lys Ala Leu Pro Ala Pro Ile Glu Lys Thr Ile Ser Lys Thr Lys Gly
          100                 105                 110

Gln Pro Arg Glu Pro Gln Val Tyr Thr Leu Pro Pro Ser Arg Glu Glu
      115                 120                 125

Met Thr Lys Asn Gln Val Ser Leu Thr Cys Leu Val Lys Gly Phe Tyr
  130                 135                 140

Pro Ser Asp Ile Ala Val Glu Trp Glu Ser Gly Gln Pro Glu Asn
145                 150                 155                 160

Asn Tyr Asn Thr Thr Pro Pro Met Leu Asp Ser Asp Gly Ser Phe Phe
              165                 170                 175

Leu Tyr Ser Lys Leu Thr Val Asp Lys Ser Arg Trp Gln Gln Gly Asn
          180                 185                 190

Ile Phe Ser Cys Ser Val Met His Glu Ala Leu His Asn Arg Phe Thr
      195                 200                 205

Gln Lys Ser Leu Ser Leu Ser Pro Gly Lys
  210                 215

<210> SEQ ID NO 5

<211> LENGTH: 218
<212> TYPE: PRT
<213> ORGANISM: Artificial Sequence
<220> FEATURE:
<223> OTHER INFORMATION: chemically synthesized

<400> SEQUENCE: 5

Pro Ala Pro Glu Phe Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser Gln Glu Asp Pro Glu Val Gln Phe Asn Trp
        35                  40                  45

Tyr Val Asp Gly Val Glu Val His Asn Ala Lys Thr Lys Pro Arg Glu
    50                  55                  60

Glu Gln Phe Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Gly Leu Pro Ser Ser Ile Glu Lys Thr Ile Ser Lys Ala Lys Gly
            100                 105                 110

Gln Pro Arg Glu Pro Gln Val Tyr Thr Leu Pro Pro Ser Gln Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
            180                 185                 190

Val Phe Ser Cys Ser Val Met His Glu Ala Leu His Asn His Tyr Thr
        195                 200                 205

Gln Lys Ser Leu Ser Leu Ser Leu Gly Lys
    210                 215

<210> SEQ ID NO 6
<211> LENGTH: 218
<212> TYPE: PRT
<213> ORGANISM: Artificial Sequence
<220> FEATURE:
<223> OTHER INFORMATION: chemically synthesized

<400> SEQUENCE: 6

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser Gln Glu Asp Pro Glu Val Gln Phe Asn Trp
        35                  40                  45

Tyr Val Asp Gly Val Glu Val His Asn Ala Lys Thr Lys Pro Arg Glu
    50                  55                  60

Glu Gln Phe Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Gly Leu Pro Ser Ser Ile Glu Lys Thr Ile Ser Lys Ala Lys Gly

```
                100             105             110
Gln Pro Arg Glu Pro Gln Val Tyr Thr Leu Pro Pro Ser Gln Glu Glu
            115                 120                 125

Met Thr Lys Asn Gln Val Ser Leu Thr Cys Leu Val Lys Gly Phe Tyr
        130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
            180                 185                 190

Val Phe Ser Cys Ser Val Met His Glu Ala Leu His Asn His Tyr Thr
                195                 200                 205

Gln Lys Ser Leu Ser Leu Ser Leu Gly Lys
        210                 215

<210> SEQ ID NO 7
<211> LENGTH: 14
<212> TYPE: PRT
<213> ORGANISM: Artificial Sequence
<220> FEATURE:
<223> OTHER INFORMATION: chemically synthesized

<400> SEQUENCE: 7

Glu Pro Lys Ser Ser Asp Lys Thr His Thr Cys Pro Pro Cys
1               5                   10

<210> SEQ ID NO 8
<211> LENGTH: 9
<212> TYPE: PRT
<213> ORGANISM: Artificial Sequence
<220> FEATURE:
<223> OTHER INFORMATION: chemically synthesized

<400> SEQUENCE: 8

Asp Lys Thr His Thr Cys Pro Pro Cys
1               5

<210> SEQ ID NO 9
<211> LENGTH: 11
<212> TYPE: PRT
<213> ORGANISM: Artificial Sequence
<220> FEATURE:
<223> OTHER INFORMATION: chemically synthesized

<400> SEQUENCE: 9

Glu Ser Lys Tyr Gly Pro Pro Cys Pro Pro Cys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: chemically synthesized

<400> SEQUENCE: 10

Gly Gln Gly Thr Leu Val Thr Val Lys Pro Gly Gly
1               5                   10

<210> SEQ ID NO 11
<211> LENGTH: 12
<212> TYPE: PRT
```

<213> ORGANISM: Artificial Sequence
<220> FEATURE:
<223> OTHER INFORMATION: chemically synthesized

<400> SEQUENCE: 11

Gly Gln Gly Thr Leu Val Thr Val Glu Pro Gly Gly
1               5                   10

<210> SEQ ID NO 12
<211> LENGTH: 6
<212> TYPE: PRT
<213> ORGANISM: Artificial Sequence
<220> FEATURE:
<223> OTHER INFORMATION: chemically synthesized

<400> SEQUENCE: 12

Gly Gly Ser Gly Gly Ser
1               5

<210> SEQ ID NO 13
<211> LENGTH: 9
<212> TYPE: PRT
<213> ORGANISM: Artificial Sequence
<220> FEATURE:
<223> OTHER INFORMATION: chemically synthesized

<400> SEQUENCE: 13

Gly Gly Ser Gly Gly Ser Gly Gly Ser
1               5

<210> SEQ ID NO 14
<211> LENGTH: 12
<212> TYPE: PRT
<213> ORGANISM: Artificial Sequence
<220> FEATURE:
<223> OTHER INFORMATION: chemically synthesized

<400> SEQUENCE: 14

Gly Gly Ser Gly Gly Ser Gly Gly Ser Gly Gly Ser
1               5                   10

<210> SEQ ID NO 15
<211> LENGTH: 15
<212> TYPE: PRT
<213> ORGANISM: Artificial Sequence
<220> FEATURE:
<223> OTHER INFORMATION: chemically synthesized

<400> SEQUENCE: 15

Gly Gly Ser Gly Gly Ser Gly Gly Ser Gly Gly Ser Gly Gly Ser
1               5                   10                  15

<210> SEQ ID NO 16
<211> LENGTH: 4
<212> TYPE: PRT
<213> ORGANISM: Artificial Sequence
<220> FEATURE:
<223> OTHER INFORMATION: chemically synthesized

<400> SEQUENCE: 16

Gly Gly Gly Gly
1

<210> SEQ ID NO 17
<211> LENGTH: 5
<212> TYPE: PRT
<213> ORGANISM: Artificial Sequence

```
<220> FEATURE:
<223> OTHER INFORMATION: chemically synthesized

<400> SEQUENCE: 17

Gly Gly Gly Gly Gly
1               5

<210> SEQ ID NO 18
<211> LENGTH: 6
<212> TYPE: PRT
<213> ORGANISM: Artificial Sequence
<220> FEATURE:
<223> OTHER INFORMATION: chemically synthesized

<400> SEQUENCE: 18

Gly Gly Gly Gly Gly Gly
1               5

<210> SEQ ID NO 19
<211> LENGTH: 120
<212> TYPE: PRT
<213> ORGANISM: Artificial Sequence
<220> FEATURE:
<223> OTHER INFORMATION: chemically synthesized
<220> FEATURE:
<221> NAME/KEY: misc_feature
<222> LOCATION: (10)..(10)
<223> OTHER INFORMATION: Xaa can be any naturally occurring amino acid

<400> SEQUENCE: 19

Gln Val Gln Leu Gln Glu Ser Gly Gly Xaa Leu Val Gln Ser Gly Gly
1               5                   10                  15

Ser Leu Arg Leu Ser Cys Ala Ala Ser Gly Ser Val Phe Ser Ile Asp
            20                  25                  30

Ala Met Gly Trp Tyr Arg Leu Ala Pro Gly Lys Gln Arg Glu Leu Val
        35                  40                  45

Ala Val Met Ser Ser Gly Ser Pro Lys Tyr Ala Asp Ser Val Lys Gly
    50                  55                  60

Arg Phe Thr Ile Ser Arg Gly Ser Ala Arg Gly Thr Val Tyr Leu Gln
65                  70                  75                  80

Met Asp Ser Leu Lys Pro Glu Asp Thr Ala Val Tyr Tyr Cys Tyr Ala
                85                  90                  95

Asp Val Ala Thr Gly Trp Gly Arg Asp Ala Ser Ala Tyr Trp Gly Gln
            100                 105                 110

Gly Thr Gln Val Thr Val Ser Ser
        115                 120

<210> SEQ ID NO 20
<211> LENGTH: 121
<212> TYPE: PRT
<213> ORGANISM: Artificial Sequence
<220> FEATURE:
<223> OTHER INFORMATION: chemically synthesized

<400> SEQUENCE: 20

Gln Val Gln Leu Gln Gln Ser Gly Gly Gly Leu Val Arg Ala Gly Gly
1               5                   10                  15

Ser Leu Arg Leu Ser Cys Val Ala Gly Ser Thr Phe Ser Val Asn
            20                  25                  30

Ser Met Ala Trp Tyr Arg Gln Ala Pro Gly Lys Glu Arg Glu Leu Val
        35                  40                  45

Ala Ala Phe Thr Gly Gly Ser Thr Met Asn Tyr Ala Ser Ser Val Lys
```

```
                    50                  55                  60
Gly Arg Phe Thr Ile Ser Arg Gly Asn Ala Ala His Thr Val Leu Leu
 65                  70                  75                  80

Gln Met Thr Asn Leu Lys Pro Glu Asp Thr Ala Val Tyr Tyr Cys Asn
                     85                  90                  95

Ala Glu Val Asn Glu Gly Trp Asn Ala Asp Tyr His Asp Tyr Trp Gly
                    100                 105                 110

Gln Gly Thr Gln Val Thr Val Ser Ser
            115                 120

<210> SEQ ID NO 21
<211> LENGTH: 121
<212> TYPE: PRT
<213> ORGANISM: Artificial Sequence
<220> FEATURE:
<223> OTHER INFORMATION: chemically synthesized

<400> SEQUENCE: 21

Gln Val Gln Leu Val Gln Ser Gly Gly Gly Leu Val Gln Ala Gly Gly
 1                   5                  10                  15

Ser Leu Arg Leu Ser Cys Thr Ala Ser Gly Ser Ile Phe Ser Ile Asn
                    20                  25                  30

His Met Ala Trp Tyr Arg Gln Ala Pro Gly Lys Gln Arg Glu Met Val
                35                  40                  45

Ala His Ile Thr Gly Gly Ala Ser Thr Lys Tyr Ala Asp Ser Val Lys
            50                  55                  60

Gly Arg Phe Thr Ile Ser Arg Asp Ser Ala Leu Asn Thr Val Ser Leu
 65                  70                  75                  80

Arg Met Asn Ser Leu Lys Pro Glu Asp Thr Ala Val Tyr Tyr Cys Asn
                     85                  90                  95

Ala Glu Val Asn Glu Gly Trp Asn Ala Asp Tyr Tyr Asp Val Trp Gly
                    100                 105                 110

Gln Gly Thr Gln Val Thr Val Ser Ser
            115                 120

<210> SEQ ID NO 22
<211> LENGTH: 121
<212> TYPE: PRT
<213> ORGANISM: Artificial Sequence
<220> FEATURE:
<223> OTHER INFORMATION: chemically synthesized

<400> SEQUENCE: 22

Gln Val Gln Leu Gln Glu Ser Gly Gly Gly Leu Val Gln Ala Gly Gly
 1                   5                  10                  15

Ser Leu Arg Leu Ser Cys Ala Ala Ser Gly Ser Val Phe Ser Ile Asp
                    20                  25                  30

Ala Met Gly Trp Tyr Arg Leu Ala Pro Gly Gln Gln Arg Glu Leu Val
                35                  40                  45

Ala Val Leu Asn Gly Ile Ser Ser Ala Lys Tyr Ala Asp Ser Val Lys
            50                  55                  60

Gly Arg Phe Thr Ile Ser Gly Asp Ser Ala Lys Asn Ala Val Tyr Leu
 65                  70                  75                  80

Gln Met Asp Gly Leu Lys Pro Glu Asp Thr Ala Val Tyr Tyr Cys Tyr
                     85                  90                  95

Ala Asp Val Ser Thr Gly Trp Gly Arg Asp Ala His Gly Tyr Trp Gly
                    100                 105                 110
```

```
Gln Gly Thr Gln Val Thr Val Ser Ser
        115                 120
```

<210> SEQ ID NO 23
<211> LENGTH: 117
<212> TYPE: PRT
<213> ORGANISM: Artificial Sequence
<220> FEATURE:
<223> OTHER INFORMATION: chemically synthesized

<400> SEQUENCE: 23

```
Glu Val Gln Leu Val Gln Ser Gly Gly Gly Leu Val Gln Pro Gly Gly
1               5                   10                  15

Ser Leu Arg Leu Ser Cys Ala Ala Ser Gly Asn Ile Phe Ser Ile Asp
            20                  25                  30

Ala Met Gly Trp Tyr Arg Gln Ala Pro Gly Arg Gln Arg Glu Leu Val
        35                  40                  45

Ala Gln Ile Pro Gly Gly Pro Thr Asp Ser Val Lys Gly Arg Phe Thr
    50                  55                  60

Val Ser Gly Asn Ser Ala Lys Asn Thr Gly Tyr Leu Gln Met Asn Thr
65                  70                  75                  80

Leu Lys Pro Glu Asp Thr Ala Val Tyr Tyr Cys Asn Ile Val Ala Ser
                85                  90                  95

Thr Ser Trp Gly Ser Pro Ser Lys Val Tyr Trp Gly Gln Gly Thr Gln
            100                 105                 110

Ala Thr Val Ser Ser
        115
```

<210> SEQ ID NO 24
<211> LENGTH: 120
<212> TYPE: PRT
<213> ORGANISM: Artificial Sequence
<220> FEATURE:
<223> OTHER INFORMATION: chemically synthesized

<400> SEQUENCE: 24

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Val Phe Ser Ile Asp
            20                  25                  30

Ser Met Ser Trp Phe Arg Gln Ala Pro Gly Asn Glu Arg Glu Leu Val
        35                  40                  45

Ala Leu Ile Thr Gly Gly Arg Thr Thr Tyr Ala Asp Ser Val Lys
    50                  55                  60

Gly Arg Phe Thr Ile Ser Arg Ala Ser Ala Pro Asn Thr Val Tyr Leu
65                  70                  75                  80

Gln Met Asn Ser Leu Lys Pro Glu Asp Thr Ala Val Tyr Tyr Cys Asn
                85                  90                  95

Ala Val Val Ser Thr Gly Trp Gly Arg Asn Ala Asp Asp Tyr Trp Gly
            100                 105                 110

Gln Gly Thr Gln Val Thr Val Ser
        115                 120
```

<210> SEQ ID NO 25
<211> LENGTH: 119
<212> TYPE: PRT
<213> ORGANISM: Artificial Sequence
<220> FEATURE:
<223> OTHER INFORMATION: chemically synthesized

<400> SEQUENCE: 25

Gln Val Gln Leu Gln Gln Ser Gly Gly Gly Leu Val Gln Ala Gly Gly
1               5                   10                  15

Ser Leu Arg Leu Ser Cys Ala Ala Ser Gly Ser Ile Phe Ser Ile Asp
            20                  25                  30

Ala Met Gly Trp Tyr Arg Leu Ala Pro Gly Lys Gln Arg Glu Leu Val
        35                  40                  45

Ala Val Ile Asp Gly Val Ser Pro Asn Tyr Ala Asp Ser Val Lys Gly
    50                  55                  60

Arg Phe Thr Ile Ser Ser Asp Ile Ala Lys Asn Thr Val Tyr Leu Gln
65                  70                  75                  80

Met His Ser Pro Lys Pro Glu Asp Thr Ala Val Tyr Tyr Cys Asn Ala
                85                  90                  95

Asp Val Ser Thr Gly Trp Gly Arg Pro Ala Asp His Tyr Trp Gly Gln
            100                 105                 110

Gly Thr Gln Val Thr Val Ser
        115

<210> SEQ ID NO 26
<211> LENGTH: 120
<212> TYPE: PRT
<213> ORGANISM: Artificial Sequence
<220> FEATURE:
<223> OTHER INFORMATION: chemically synthesized

<400> SEQUENCE: 26

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Val Phe Ser Ile Asp
            20                  25                  30

Ser Met Ser Trp Phe Arg Gln Ala Pro Gly Asn Glu Arg Glu Leu Val
        35                  40                  45

Ala Leu Ile Thr Gly Gly His Thr Thr Thr Tyr Gly Asp Ser Val Lys
    50                  55                  60

Gly Arg Phe Thr Ile Ser Arg Ala Ser Ala Pro Asn Thr Val His Leu
65                  70                  75                  80

Gln Met Asn Ser Leu Gln Pro Glu Asp Thr Ala Val Tyr Tyr Cys Asn
                85                  90                  95

Ala Ala Val Ser Thr Gly Trp Gly Arg Asn Ala Asp Asp Tyr Trp Gly
            100                 105                 110

Gln Gly Thr Gln Val Thr Val Ser
        115                 120

<210> SEQ ID NO 27
<211> LENGTH: 118
<212> TYPE: PRT
<213> ORGANISM: Artificial Sequence
<220> FEATURE:
<223> OTHER INFORMATION: chemically synthesized

<400> SEQUENCE: 27

Gln Leu Val Gln Ser Gly Gly Gly Leu Val Gln Pro Gly Glu Ser Leu
1               5                   10                  15

Arg Leu Ser Cys Ala Ala Ser Gly Ser Val Phe Ser Ile Asp Ser Val
            20                  25                  30

Ser Trp Phe Arg Gln Gly Pro Gly Asn Glu Arg Glu Leu Val Ala Leu
        35                  40                  45

```
Ile Thr Gly Gly Arg Thr Thr Thr Tyr Ala Asp Ser Val Lys Gly Arg
 50                  55                  60

Phe Thr Ile Ser Arg Ala Asn Ala Pro Asn Thr Val His Leu Arg Met
 65                  70                  75                  80

Asn Ser Leu Lys Pro Glu Asp Thr Ala Val Tyr Tyr Cys Asn Ala Ala
                 85                  90                  95

Val Ser Thr Gly Trp Gly Arg Asn Ala Asp Asp Tyr Trp Gly Gln Gly
            100                 105                 110

Thr Gln Val Thr Val Ser
        115
```

<210> SEQ ID NO 28
<211> LENGTH: 120
<212> TYPE: PRT
<213> ORGANISM: Artificial Sequence
<220> FEATURE:
<223> OTHER INFORMATION: chemically synthesized

<400> SEQUENCE: 28

```
Gln Val Gln Leu Val Gln Ser Gly Gly Gly Leu Val Gln Pro Gly Gly
 1               5                  10                  15

Ser Leu Arg Leu Ile Cys Ala Ala Ser Gly Ser Val Phe Ser Ile Asp
             20                  25                  30

Ser Met Ser Trp Phe Arg Gln Arg Pro Gly Asn Glu Arg Glu Leu Val
         35                  40                  45

Ala Leu Ile Thr Gly Gly Arg Thr Thr Thr Tyr Ser Asp Ser Val Lys
 50                  55                  60

Gly Arg Phe Thr Ile Ser Arg Ala Ser Ala Leu Asn Thr Val His Leu
 65                  70                  75                  80

Gln Met Asn Ser Leu Lys Pro Glu Asp Thr Ala Val Tyr Tyr Cys Asn
                 85                  90                  95

Ala Ala Leu Ser Thr Gly Trp Gly Arg Asp Ala Ser Ala Tyr Trp Gly
            100                 105                 110

Gln Gly Thr Gln Val Thr Val Ser
        115                 120
```

<210> SEQ ID NO 29
<211> LENGTH: 120
<212> TYPE: PRT
<213> ORGANISM: Artificial Sequence
<220> FEATURE:
<223> OTHER INFORMATION: chemically synthesized

<400> SEQUENCE: 29

```
Gln Val Gln Leu Gln Glu Ser Gly Gly Gly Leu Val Gln Ala Gly Gly
 1               5                  10                  15

Ser Leu Arg Leu Ser Cys Thr Ala Ser Gly Ser Ile Phe Ser Ile Asn
             20                  25                  30

His Met Ala Trp Tyr Arg Gln Ala Pro Gly Lys Gln Arg Glu Met Val
         35                  40                  45

Ala His Ile Thr Gly Gly Ala Ser Thr Lys Tyr Ala Asp Ser Val Lys
 50                  55                  60

Gly Arg Phe Thr Ile Ser Arg Asp Ser Ala Leu Asn Thr Val Ser Leu
 65                  70                  75                  80

Arg Met Asn Ser Leu Lys Pro Glu Asp Thr Ala Val Tyr Tyr Cys Asn
                 85                  90                  95

Ala Glu Val Asn Glu Gly Trp Asn Ala Asp Tyr Tyr Asp Val Trp Gly
            100                 105                 110
```

```
Gln Gly Thr Gln Val Thr Val Ser
        115                 120

<210> SEQ ID NO 30
<211> LENGTH: 119
<212> TYPE: PRT
<213> ORGANISM: Artificial Sequence
<220> FEATURE:
<223> OTHER INFORMATION: chemically synthesized

<400> SEQUENCE: 30

Gln Leu Gln Leu Gln Glu Ser Gly Gly Thr Val Gln Ala Gly Gly
1               5                   10                  15

Ser Leu Arg Leu Ser Cys Ala Ala Ser Arg Ser Ile Ala Ser Ile Asn
            20                  25                  30

Val Met Gly Trp Tyr Arg Gln Ala Pro Gly Asn Gln His Glu Leu Val
        35                  40                  45

Ala Ala Ile Thr Ser Gly Gly Ser Pro Asn Tyr Ala Gly Ser Val Arg
    50                  55                  60

Gly Arg Phe Ile Ile Ser Arg Asp Asn Ala Lys Asn Thr Val Tyr Leu
65                  70                  75                  80

Gln Met Asn Asp Leu Lys Pro Glu Asp Thr Ala Val Tyr Tyr Cys Ala
                85                  90                  95

Gly Glu Leu Arg Asp Asp Ser Asn Gly Tyr Leu His Tyr Trp Gly Gln
            100                 105                 110

Gly Thr Gln Val Thr Val Ser
        115

<210> SEQ ID NO 31
<211> LENGTH: 120
<212> TYPE: PRT
<213> ORGANISM: Artificial Sequence
<220> FEATURE:
<223> OTHER INFORMATION: chemically synthesized

<400> SEQUENCE: 31

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Val Phe Ser Ile Asp
            20                  25                  30

Ser Met Ser Trp Phe Arg Gln Thr Pro Gly Asn Glu Arg Glu Leu Val
        35                  40                  45

Ala His Ile Thr Gly Gly Arg Thr Thr Thr Tyr Ala Asp Ser Val Lys
    50                  55                  60

Gly Arg Phe Thr Ile Ser Arg Ala Ser Ala Pro Asn Thr Val His Leu
65                  70                  75                  80

Gln Met Asn Asn Leu Lys Pro Glu Asp Thr Ala Val Tyr Tyr Cys Asn
                85                  90                  95

Ala Ala Val Ser Thr Gly Trp Gly Arg Asn Ala Asp Tyr Trp Gly
            100                 105                 110

Gln Gly Thr Gln Val Thr Val Ser
        115                 120

<210> SEQ ID NO 32
<211> LENGTH: 119
<212> TYPE: PRT
<213> ORGANISM: Artificial Sequence
<220> FEATURE:
<223> OTHER INFORMATION: chemically synthesized
```

<400> SEQUENCE: 32

Gln Val Gln Leu Gln Glu Ser Gly Gly Gly Leu Val Gln Ala Gly Gly
1               5                   10                  15

Ser Leu Arg Leu Ser Cys Thr Ala Ser Gly Ser Ile Phe Ser Ile Asp
            20                  25                  30

Asp Met Gly Trp Tyr Arg Leu Ala Pro Gly Lys Gln Arg Glu Leu Val
        35                  40                  45

Ala Val His Ser Gly Ser Ser Thr Asn Tyr Gly Asp Ser Val Lys Gly
    50                  55                  60

Arg Phe Thr Ile Ser Gly Asp Ser Ala Lys Asn Thr Val Tyr Leu Gln
65                  70                  75                  80

Met His Arg Leu Glu Pro Glu Asp Thr Ala Val Tyr Tyr Cys Tyr Ala
                85                  90                  95

Ala Ile Ser Ser Gly Trp Gly Arg Asp Ala Glu Asp Tyr Trp Gly Gln
            100                 105                 110

Gly Thr Gln Val Thr Val Ser
        115

<210> SEQ ID NO 33
<211> LENGTH: 120
<212> TYPE: PRT
<213> ORGANISM: Artificial Sequence
<220> FEATURE:
<223> OTHER INFORMATION: chemically synthesized

<400> SEQUENCE: 33

Gln Val Gln Leu Val Gln Ser Gly Gly Gly Leu Val Gln Pro Gly Glu
1               5                   10                  15

Ser Leu Arg Leu Ser Cys Ala Ala Ser Gly Ser Val Phe Ser Ile Asp
            20                  25                  30

Ser Met Ser Trp Phe Arg Gln Gly Pro Gly Asn Glu Arg Glu Leu Val
        35                  40                  45

Ala Leu Ile Thr Gly Gly Arg Thr Thr Thr Tyr Ala Asp Ser Val Lys
    50                  55                  60

Gly Arg Phe Thr Ile Ser Arg Ala Asn Ala Pro Asn Thr Val His Leu
65                  70                  75                  80

Gln Met Asn Ser Leu Lys Pro Glu Asp Thr Ala Val Tyr Tyr Cys Asn
                85                  90                  95

Ala Ala Val Ser Thr Gly Trp Gly Arg Ser Ala Asp Asp Tyr Trp Gly
            100                 105                 110

Gln Gly Thr Gln Val Thr Val Ser
        115                 120

<210> SEQ ID NO 34
<211> LENGTH: 120
<212> TYPE: PRT
<213> ORGANISM: Artificial Sequence
<220> FEATURE:
<223> OTHER INFORMATION: chemically synthesized

<400> SEQUENCE: 34

Gln Val Gln Leu Val Gln Ser Gly Gly Gly Leu Val Gln Pro Gly Glu
1               5                   10                  15

Ser Leu Arg Leu Ser Cys Ala Ala Ser Gly Ser Val Phe Ser Ile Asp
            20                  25                  30

Ser Met Ser Trp Phe Arg Gln Gly Pro Gly Asn Glu Arg Glu Leu Val
        35                  40                  45

Ala Leu Ile Thr Gly Gly Arg Thr Thr Thr Tyr Ala Asp Ser Val Lys
        50                  55                  60

Gly Arg Phe Thr Ile Ser Arg Ala Asn Ala Pro Asn Thr Val His Leu
65                  70                  75                  80

Gln Met Asn Ser Leu Glu Pro Glu Asp Thr Ala Val Tyr Tyr Cys Asn
                85                  90                  95

Ala Ala Val Ser Thr Gly Trp Gly Arg Asn Ala Asp Asp Tyr Trp Gly
            100                 105                 110

Gln Gly Thr Gln Val Thr Val Ser
        115                 120

<210> SEQ ID NO 35
<211> LENGTH: 120
<212> TYPE: PRT
<213> ORGANISM: Artificial Sequence
<220> FEATURE:
<223> OTHER INFORMATION: chemically synthesized

<400> SEQUENCE: 35

Gln Val Gln Leu Val Gln Ser Gly Gly Gly Leu Val Gln Pro Gly Gly
1               5                   10                  15

Ser Leu Arg Leu Ser Cys Ala Ala Ser Gly Ser Val Phe Ser Ile Asp
            20                  25                  30

Ser Met Ser Trp Phe Arg Gln Ala Pro Gly Asn Glu Arg Glu Leu Val
        35                  40                  45

Ala Leu Ile Thr Gly Gly Arg Thr Thr Thr Tyr Ala Asp Ser Val Lys
        50                  55                  60

Gly Arg Phe Thr Ile Ser Arg Ala Ser Ala Pro Asn Thr Val His Leu
65                  70                  75                  80

Gln Met Asn Ser Leu Lys Pro Glu Asp Thr Ala Val Tyr Tyr Cys Asn
                85                  90                  95

Ala Val Val Ser Thr Gly Trp Gly Arg Asn Ala Asp Asp Tyr Trp Gly
            100                 105                 110

Gln Gly Thr Gln Val Thr Val Ser
        115                 120

<210> SEQ ID NO 36
<211> LENGTH: 121
<212> TYPE: PRT
<213> ORGANISM: Artificial Sequence
<220> FEATURE:
<223> OTHER INFORMATION: chemically synthesized

<400> SEQUENCE: 36

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Val Phe Ser Ile Asp
            20                  25                  30

Ala Met Ser Trp Phe Arg Gln Ala Pro Gly Lys Gly Leu Glu Leu Val
        35                  40                  45

Ser Ala Ile Thr Gly Gly Arg Thr Thr Tyr Tyr Ala Glu Ser Val Lys
        50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Asn
                85                  90                  95

Ala Val Val Ser Thr Gly Trp Gly Arg Asn Ala Asp Asp Tyr Trp Gly

Gln Gly Thr Leu Val Thr Val Lys Pro
            115                 120

<210> SEQ ID NO 37
<211> LENGTH: 121
<212> TYPE: PRT
<213> ORGANISM: Artificial Sequence
<220> FEATURE:
<223> OTHER INFORMATION: chemically synthesized

<400> SEQUENCE: 37

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Val Phe Ser Ile Asp
            20                  25                  30

Ala Met Ser Trp Phe Arg Gln Ala Pro Gly Lys Gly Leu Glu Leu Val
        35                  40                  45

Cys Ala Ile Thr Gly Gly Arg Thr Thr Tyr Tyr Ala Glu Ser Val Lys
    50                  55                  60

Gly Arg Phe Thr Cys Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Asn
                85                  90                  95

Ala Val Val Ser Thr Gly Trp Gly Arg Asn Ala Asp Asp Tyr Trp Gly
            100                 105                 110

Gln Gly Thr Leu Val Thr Val Lys Pro
            115                 120

<210> SEQ ID NO 38
<211> LENGTH: 121
<212> TYPE: PRT
<213> ORGANISM: Artificial Sequence
<220> FEATURE:
<223> OTHER INFORMATION: chemically synthesized

<400> SEQUENCE: 38

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Val Phe Ser Ile Asp
            20                  25                  30

Ser Met Ser Trp Phe Arg Gln Ala Pro Gly Lys Gly Leu Glu Leu Val
        35                  40                  45

Ser Leu Ile Thr Gly Gly Arg Thr Thr Tyr Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Asn
                85                  90                  95

Ala Val Val Ser Thr Gly Trp Gly Arg Asn Ala Asp Asp Tyr Trp Gly
            100                 105                 110

Gln Gly Thr Leu Val Thr Val Lys Pro
            115                 120

<210> SEQ ID NO 39
<211> LENGTH: 121
<212> TYPE: PRT
<213> ORGANISM: Artificial Sequence
<220> FEATURE:

<223> OTHER INFORMATION: chemically synthesized

<400> SEQUENCE: 39

Glu Val Gln Leu Leu Glu Ser Gly Gly Gly Glu Val Gln Pro Gly Gly
1               5                   10                  15
Ser Leu Arg Leu Ser Cys Ala Ala Ser Gly Ser Val Phe Ser Ile Asp
            20                  25                  30
Ser Met Ser Trp Phe Arg Gln Ala Pro Gly Lys Gly Leu Glu Leu Val
        35                  40                  45
Cys Leu Ile Thr Gly Gly Arg Thr Thr Tyr Tyr Ala Glu Ser Val Lys
    50                  55                  60
Gly Arg Phe Thr Cys Ser Arg Asp Asn Ala Lys Asn Thr Leu Tyr Leu
65                  70                  75                  80
Gln Met Ser Ser Leu Arg Ala Glu Asp Thr Ala Val Tyr Tyr Cys Asn
                85                  90                  95
Ala Val Val Ser Thr Gly Trp Gly Arg Asn Ala Asp Asp Tyr Trp Gly
            100                 105                 110
Gln Gly Thr Leu Val Thr Val Lys Pro
        115                 120

<210> SEQ ID NO 40
<211> LENGTH: 121
<212> TYPE: PRT
<213> ORGANISM: Artificial Sequence
<220> FEATURE:
<223> OTHER INFORMATION: chemically synthesized

<400> SEQUENCE: 40

Glu Val Gln Leu Leu Glu Ser Gly Gly Gly Glu Val Gln Pro Gly Gly
1               5                   10                  15
Ser Leu Arg Leu Ser Cys Ala Ala Ser Gly Ser Val Phe Ser Ile Asp
            20                  25                  30
Ala Met Ser Trp Phe Arg Gln Ala Pro Gly Lys Gly Leu Glu Leu Val
        35                  40                  45
Ser Leu Ile Thr Gly Gly Arg Thr Thr Tyr Tyr Ala Glu Ser Val Lys
    50                  55                  60
Gly Arg Phe Thr Ile Ser Arg Asp Asn Ala Lys Asn Thr Leu Tyr Leu
65                  70                  75                  80
Gln Met Ser Ser Leu Arg Ala Glu Asp Thr Ala Val Tyr Tyr Cys Asn
                85                  90                  95
Ala Val Val Ser Thr Gly Trp Gly Arg Asn Ala Asp Asp Tyr Trp Gly
            100                 105                 110
Gln Gly Thr Leu Val Thr Val Lys Pro
        115                 120

<210> SEQ ID NO 41
<211> LENGTH: 121
<212> TYPE: PRT
<213> ORGANISM: Artificial Sequence
<220> FEATURE:
<223> OTHER INFORMATION: chemically synthesized

<400> SEQUENCE: 41

Glu Val Gln Leu Leu Glu Ser Gly Gly Gly Glu Val Gln Pro Gly Gly
1               5                   10                  15
Ser Leu Arg Leu Ser Cys Ala Ala Ser Gly Ser Val Phe Ser Ile Asp
            20                  25                  30
Ala Met Ser Trp Phe Arg Gln Ala Pro Gly Lys Gly Leu Glu Leu Val

```
            35                  40                  45

Cys Leu Ile Thr Gly Gly Arg Thr Thr Tyr Tyr Ala Glu Ser Val Lys
         50                  55                  60

Gly Arg Phe Thr Cys Ser Arg Asp Asn Ala Lys Asn Thr Leu Tyr Leu
 65                  70                  75                  80

Gln Met Ser Ser Leu Arg Ala Glu Asp Thr Ala Val Tyr Tyr Cys Asn
                 85                  90                  95

Ala Val Val Ser Thr Gly Trp Gly Arg Asn Ala Asp Asp Tyr Trp Gly
            100                 105                 110

Gln Gly Thr Leu Val Thr Val Lys Pro
        115                 120

<210> SEQ ID NO 42
<211> LENGTH: 119
<212> TYPE: PRT
<213> ORGANISM: Artificial Sequence
<220> FEATURE:
<223> OTHER INFORMATION: chemically synthesized

<400> SEQUENCE: 42

Glu Val Gln Leu Leu Glu Ser Gly Gly Glu Val Gln Pro Gly Gly
 1               5                  10                  15

Ser Leu Arg Leu Ser Cys Ala Ala Ser Gly Ser Val Phe Ser Ile Asp
                20                  25                  30

Ala Met Gly Trp Tyr Arg Gln Ala Pro Gly Lys Gly Leu Glu Leu Val
            35                  40                  45

Ser Ala Leu Ser Gly Ile Ser Ser Ala Thr Tyr Ala Glu Ser Val Lys
         50                  55                  60

Gly Arg Phe Thr Ile Ser Arg Asp Asn Ala Lys Asn Thr Leu Tyr Leu
 65                  70                  75                  80

Gln Met Ser Ser Leu Arg Ala Glu Asp Thr Ala Val Tyr Tyr Cys Tyr
                 85                  90                  95

Ala Asp Val Ser Thr Gly Trp Gly Arg Asp Ala His Gly Tyr Trp Gly
            100                 105                 110

Gln Gly Thr Leu Val Thr Val
        115

<210> SEQ ID NO 43
<211> LENGTH: 119
<212> TYPE: PRT
<213> ORGANISM: Artificial Sequence
<220> FEATURE:
<223> OTHER INFORMATION: chemically synthesized

<400> SEQUENCE: 43

Glu Val Gln Leu Leu Glu Ser Gly Gly Glu Val Gln Pro Gly Gly
 1               5                  10                  15

Ser Leu Arg Leu Ser Cys Ala Ala Ser Gly Ser Val Phe Ser Ile Asp
                20                  25                  30

Ala Met Gly Trp Tyr Arg Gln Ala Pro Gly Lys Gly Arg Glu Leu Val
            35                  40                  45

Ser Ala Leu Ser Gly Ile Ser Ser Ala Thr Tyr Ala Glu Ser Val Lys
         50                  55                  60

Gly Arg Phe Thr Ile Ser Arg Asp Asn Ala Lys Asn Thr Leu Tyr Leu
 65                  70                  75                  80

Gln Met Ser Ser Leu Arg Ala Glu Asp Thr Ala Val Tyr Tyr Cys Tyr
                 85                  90                  95
```

Ala Asp Val Ser Thr Gly Trp Gly Arg Asp Ala His Gly Tyr Trp Gly
            100                 105                 110

Gln Gly Thr Leu Val Thr Val
        115

<210> SEQ ID NO 44
<211> LENGTH: 119
<212> TYPE: PRT
<213> ORGANISM: Artificial Sequence
<220> FEATURE:
<223> OTHER INFORMATION: chemically synthesized

<400> SEQUENCE: 44

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Val Phe Ser Ile Asp
            20                  25                  30

Ala Met Gly Trp Tyr Arg Gln Ala Pro Gly Lys Gln Arg Glu Leu Val
        35                  40                  45

Ser Ala Leu Ser Gly Ile Ser Ser Ala Thr Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Tyr
                85                  90                  95

Ala Asp Val Ser Thr Gly Trp Gly Arg Asp Ala His Gly Tyr Trp Gly
            100                 105                 110

Gln Gly Thr Leu Val Thr Val
        115

<210> SEQ ID NO 45
<211> LENGTH: 119
<212> TYPE: PRT
<213> ORGANISM: Artificial Sequence
<220> FEATURE:
<223> OTHER INFORMATION: chemically synthesized

<400> SEQUENCE: 45

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Val Phe Ser Ile Asp
            20                  25                  30

Ala Met Gly Trp Tyr Arg Gln Ala Pro Gly Gln Gln Arg Glu Leu Val
        35                  40                  45

Ser Ala Leu Ser Gly Ile Ser Ser Ala Thr Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Tyr
                85                  90                  95

Ala Asp Val Ser Thr Gly Trp Gly Arg Asp Ala His Gly Tyr Trp Gly
            100                 105                 110

Gln Gly Thr Leu Val Thr Val
        115

<210> SEQ ID NO 46
<211> LENGTH: 119
<212> TYPE: PRT
<213> ORGANISM: Artificial Sequence -continued

```
<220> FEATURE:
<223> OTHER INFORMATION: chemically synthesized

<400> SEQUENCE: 46

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Val Phe Ser Ile Asp
            20                  25                  30

Ala Met Gly Trp Tyr Arg Gln Ala Pro Gly Lys Gly Leu Glu Leu Val
        35                  40                  45

Ala Val Leu Ser Gly Ile Ser Ser Ala Thr Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Tyr
                85                  90                  95

Ala Asp Val Ser Thr Gly Trp Gly Arg Asp Ala His Gly Tyr Trp Gly
            100                 105                 110

Gln Gly Thr Leu Val Thr Val
        115

<210> SEQ ID NO 47
<211> LENGTH: 119
<212> TYPE: PRT
<213> ORGANISM: Artificial Sequence
<220> FEATURE:
<223> OTHER INFORMATION: chemically synthesized

<400> SEQUENCE: 47

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Val Phe Ser Ile Asp
            20                  25                  30

Ala Met Gly Trp Tyr Arg Gln Ala Pro Gly Lys Gly Arg Glu Leu Val
        35                  40                  45

Ala Val Leu Ser Gly Ile Ser Ser Ala Thr Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Tyr
                85                  90                  95

Ala Asp Val Ser Thr Gly Trp Gly Arg Asp Ala His Gly Tyr Trp Gly
            100                 105                 110

Gln Gly Thr Leu Val Thr Val
        115

<210> SEQ ID NO 48
<211> LENGTH: 119
<212> TYPE: PRT
<213> ORGANISM: Artificial Sequence
<220> FEATURE:
<223> OTHER INFORMATION: chemically synthesized

<400> SEQUENCE: 48

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Val Phe Ser Ile Asp
            20                  25                  30
```

Ala Met Gly Trp Tyr Arg Gln Ala Pro Gly Lys Gln Arg Glu Leu Val
                35                  40                  45

Ala Val Leu Ser Gly Ile Ser Ser Ala Thr Tyr Ala Glu Ser Val Lys
 50                  55                  60

Gly Arg Phe Thr Ile Ser Arg Asp Asn Ala Lys Asn Thr Leu Tyr Leu
 65                  70                  75                  80

Gln Met Ser Ser Leu Arg Ala Glu Asp Thr Ala Val Tyr Tyr Cys Tyr
                85                  90                  95

Ala Asp Val Ser Thr Gly Trp Gly Arg Asp Ala His Gly Tyr Trp Gly
               100                 105                 110

Gln Gly Thr Leu Val Thr Val
            115

<210> SEQ ID NO 49
<211> LENGTH: 119
<212> TYPE: PRT
<213> ORGANISM: Artificial Sequence
<220> FEATURE:
<223> OTHER INFORMATION: chemically synthesized

<400> SEQUENCE: 49

Glu Val Gln Leu Leu Glu Ser Gly Gly Gly Val Gln Pro Gly Gly
  1               5                  10                  15

Ser Leu Arg Leu Ser Cys Ala Ala Ser Gly Ser Val Phe Ser Ile Asp
                 20                  25                  30

Ala Met Gly Trp Tyr Arg Gln Ala Pro Gly Gln Gln Arg Glu Leu Val
                35                  40                  45

Ala Val Leu Ser Gly Ile Ser Ser Ala Thr Tyr Ala Glu Ser Val Lys
 50                  55                  60

Gly Arg Phe Thr Ile Ser Arg Asp Asn Ala Lys Asn Thr Leu Tyr Leu
 65                  70                  75                  80

Gln Met Ser Ser Leu Arg Ala Glu Asp Thr Ala Val Tyr Tyr Cys Tyr
                85                  90                  95

Ala Asp Val Ser Thr Gly Trp Gly Arg Asp Ala His Gly Tyr Trp Gly
               100                 105                 110

Gln Gly Thr Leu Val Thr Val
            115

<210> SEQ ID NO 50
<211> LENGTH: 119
<212> TYPE: PRT
<213> ORGANISM: Artificial Sequence
<220> FEATURE:
<223> OTHER INFORMATION: chemically synthesized

<400> SEQUENCE: 50

Glu Val Gln Leu Leu Glu Ser Gly Gly Gly Val Gln Pro Gly Gly
  1               5                  10                  15

Ser Leu Arg Leu Ser Cys Ala Ala Ser Gly Ser Val Phe Ser Ile Asp
                 20                  25                  30

Ala Met Gly Trp Tyr Arg Gln Ala Pro Gly Lys Gln Arg Glu Leu Val
                35                  40                  45

Ala Val Leu Ser Gly Ile Ser Ser Ala Lys Tyr Ala Glu Ser Val Lys
 50                  55                  60

Gly Arg Phe Thr Ile Ser Arg Asp Asn Ala Lys Asn Thr Leu Tyr Leu
 65                  70                  75                  80

Gln Met Ser Ser Leu Arg Ala Glu Asp Thr Ala Val Tyr Tyr Cys Tyr
                85                  90                  95

```
Ala Asp Val Ser Thr Gly Trp Gly Arg Asp Ala His Gly Tyr Trp Gly
            100                 105                 110

Gln Gly Thr Leu Val Thr Val
        115

<210> SEQ ID NO 51
<211> LENGTH: 119
<212> TYPE: PRT
<213> ORGANISM: Artificial Sequence
<220> FEATURE:
<223> OTHER INFORMATION: chemically synthesized

<400> SEQUENCE: 51

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Val Phe Ser Ile Asp
            20                  25                  30

Ala Met Gly Trp Tyr Arg Leu Ala Pro Gly Gln Gln Arg Glu Leu Val
        35                  40                  45

Ala Val Leu Ser Gly Ile Ser Ser Ala Lys Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Tyr
                85                  90                  95

Ala Asp Val Ser Thr Gly Trp Gly Arg Asp Ala His Gly Tyr Trp Gly
            100                 105                 110

Gln Gly Thr Leu Val Thr Val
        115

<210> SEQ ID NO 52
<211> LENGTH: 119
<212> TYPE: PRT
<213> ORGANISM: Artificial Sequence
<220> FEATURE:
<223> OTHER INFORMATION: chemically synthesized

<400> SEQUENCE: 52

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Val Phe Ser Ile Asp
            20                  25                  30

Ala Met Gly Trp Tyr Arg Gln Ala Pro Gly Lys Gln Arg Glu Leu Val
        35                  40                  45

Ala Val Leu Ser Gly Ile Ser Ser Ala Lys Tyr Ala Asp Ser Val Lys
    50                  55                  60

Gly Arg Phe Thr Ile Ser Gly Asp Asn Ala Lys Asn Thr Leu Tyr Leu
65                  70                  75                  80

Gln Met Ser Ser Leu Arg Ala Glu Asp Thr Ala Val Tyr Tyr Cys Tyr
                85                  90                  95

Ala Asp Val Ser Thr Gly Trp Gly Arg Asp Ala His Gly Tyr Trp Gly
            100                 105                 110

Gln Gly Thr Leu Val Thr Val
        115

<210> SEQ ID NO 53
<211> LENGTH: 119
<212> TYPE: PRT
```

<213> ORGANISM: Artificial Sequence
<220> FEATURE:
<223> OTHER INFORMATION: chemically synthesized

<400> SEQUENCE: 53

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Val Phe Ser Ile Asp
            20                  25                  30

Ala Met Gly Trp Tyr Arg Gln Ala Pro Gly Lys Gln Arg Glu Leu Val
        35                  40                  45

Ala Val Leu Ser Gly Ile Ser Ser Ala Lys Tyr Ala Glu Ser Val Lys
    50                  55                  60

Gly Arg Phe Thr Ile Ser Arg Asp Ser Ala Lys Asn Ala Val Tyr Leu
65                  70                  75                  80

Gln Met Asp Gly Leu Lys Pro Glu Asp Thr Ala Val Tyr Tyr Cys Tyr
                85                  90                  95

Ala Asp Val Ser Thr Gly Trp Gly Arg Asp Ala His Gly Tyr Trp Gly
            100                 105                 110

Gln Gly Thr Leu Val Thr Val
        115

<210> SEQ ID NO 54
<211> LENGTH: 119
<212> TYPE: PRT
<213> ORGANISM: Artificial Sequence
<220> FEATURE:
<223> OTHER INFORMATION: chemically synthesized

<400> SEQUENCE: 54

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Val Phe Ser Ile Asp
            20                  25                  30

Ala Met Gly Trp Tyr Arg Gln Ala Pro Gly Lys Gln Arg Glu Leu Val
        35                  40                  45

Ala Val Leu Ser Gly Ile Ser Ser Ala Lys Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Tyr
                85                  90                  95

Ala Asp Val Ser Thr Gly Trp Gly Arg Asp Ala His Gly Tyr Trp Gly
            100                 105                 110

Gln Gly Thr Leu Val Thr Val
        115

<210> SEQ ID NO 55
<211> LENGTH: 119
<212> TYPE: PRT
<213> ORGANISM: Artificial Sequence
<220> FEATURE:
<223> OTHER INFORMATION: chemically synthesized

<400> SEQUENCE: 55

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Val Phe Ser Ile Asp
            20                  25                  30

```
Ala Met Gly Trp Tyr Arg Gln Ala Pro Gly Lys Gln Arg Glu Leu Val
        35                  40                  45

Ala Val Leu Ser Gly Ile Ser Ser Ala Lys Tyr Ala Glu Ser Val Lys
    50                  55                  60

Gly Arg Phe Thr Ile Ser Arg Ala Ser Ala Pro Asn Thr Leu Tyr Leu
65                  70                  75                  80

Gln Met Ser Ser Leu Arg Ala Glu Asp Thr Ala Val Tyr Tyr Cys Tyr
                85                  90                  95

Ala Asp Val Ser Thr Gly Trp Gly Arg Asp Ala His Gly Tyr Trp Gly
            100                 105                 110

Gln Gly Thr Leu Val Thr Val
            115

<210> SEQ ID NO 56
<211> LENGTH: 119
<212> TYPE: PRT
<213> ORGANISM: Artificial Sequence
<220> FEATURE:
<223> OTHER INFORMATION: chemically synthesized

<400> SEQUENCE: 56

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Val Phe Ser Ile Asp
            20                  25                  30

Ala Met Gly Trp Tyr Arg Gln Ala Pro Gly Lys Gln Arg Glu Leu Val
        35                  40                  45

Ala Val Leu Ser Gly Ile Ser Ser Ala Lys Tyr Ala Glu Ser Val Lys
    50                  55                  60

Gly Arg Phe Thr Ile Ser Arg Ala Ser Ala Pro Asn Thr Val Tyr Leu
65                  70                  75                  80

Gln Met Ser Ser Leu Arg Ala Glu Asp Thr Ala Val Tyr Tyr Cys Tyr
                85                  90                  95

Ala Asp Val Ser Thr Gly Trp Gly Arg Asp Ala His Gly Tyr Trp Gly
            100                 105                 110

Gln Gly Thr Leu Val Thr Val
            115

<210> SEQ ID NO 57
<211> LENGTH: 119
<212> TYPE: PRT
<213> ORGANISM: Artificial Sequence
<220> FEATURE:
<223> OTHER INFORMATION: chemically synthesized

<400> SEQUENCE: 57

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Val Phe Ser Ile Asp
            20                  25                  30

Ala Met Gly Trp Tyr Arg Gln Ala Pro Gly Lys Gln Arg Glu Leu Val
        35                  40                  45

Ala Val Leu Ser Gly Ile Ser Ser Ala Lys Tyr Ala Ala Ser Ala Pro
    50                  55                  60

Gly Arg Phe Thr Ile Ser Arg Asp Ala Val Lys Asn Thr Val Tyr Leu
65                  70                  75                  80

Gln Met Ser Ser Leu Arg Ala Glu Asp Thr Ala Val Tyr Tyr Cys Tyr
```

-continued

```
                85                  90                  95
Ala Asp Val Ser Thr Gly Trp Gly Arg Asp Ala His Gly Tyr Trp Gly
            100                 105                 110

Gln Gly Thr Leu Val Thr Val
        115

<210> SEQ ID NO 58
<211> LENGTH: 119
<212> TYPE: PRT
<213> ORGANISM: Artificial Sequence
<220> FEATURE:
<223> OTHER INFORMATION: chemically synthesized

<400> SEQUENCE: 58

Glu Val Gln Leu Leu Glu Ser Gly Gly Glu Val Gln Pro Gly Gly
1               5                   10                  15

Ser Leu Arg Leu Ser Cys Ala Ala Ser Gly Ser Val Phe Ser Ile Asp
            20                  25                  30

Ala Met Gly Trp Tyr Arg Gln Ala Pro Gly Lys Gln Arg Glu Leu Val
        35                  40                  45

Ala Val Leu Ser Gly Ile Ser Ser Ala Lys Tyr Ala Ala Ser Ala Pro
    50                  55                  60

Gly Arg Phe Thr Ile Ser Arg Asp Ala Val Glu Asn Thr Val Tyr Leu
65                  70                  75                  80

Gln Met Ser Ser Leu Arg Ala Glu Asp Thr Ala Val Tyr Tyr Cys Tyr
                85                  90                  95

Ala Asp Val Ser Thr Gly Trp Gly Arg Asp Ala His Gly Tyr Trp Gly
            100                 105                 110

Gln Gly Thr Leu Val Thr Val
        115

<210> SEQ ID NO 59
<211> LENGTH: 119
<212> TYPE: PRT
<213> ORGANISM: Artificial Sequence
<220> FEATURE:
<223> OTHER INFORMATION: chemically synthesized

<400> SEQUENCE: 59

Glu Val Gln Leu Leu Glu Ser Gly Gly Glu Val Gln Pro Gly Gly
1               5                   10                  15

Ser Leu Arg Leu Ser Cys Ala Ala Ser Gly Ser Val Phe Ser Ile Asp
            20                  25                  30

Ala Met Gly Trp Tyr Arg Gln Ala Pro Gly Lys Gln Arg Glu Leu Val
        35                  40                  45

Ala Val Leu Ser Gly Ile Ser Ser Ala Lys Tyr Ala Ala Ser Ala Pro
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Tyr
                85                  90                  95

Ala Asp Val Ser Thr Gly Trp Gly Arg Asp Ala His Gly Tyr Trp Gly
            100                 105                 110

Gln Gly Thr Leu Val Thr Val
        115

<210> SEQ ID NO 60
<211> LENGTH: 119
```

```
<212> TYPE: PRT
<213> ORGANISM: Artificial Sequence
<220> FEATURE:
<223> OTHER INFORMATION: chemically synthesized

<400> SEQUENCE: 60

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Val Phe Ser Ile Asp
            20                  25                  30

Ala Met Gly Trp Tyr Arg Gln Ala Pro Gly Lys Gln Arg Glu Leu Val
        35                  40                  45

Ala Val Leu Ser Gly Ile Ser Ser Ala Lys Tyr Ala Asp Ala Val Lys
    50                  55                  60

Gly Arg Phe Thr Ile Ser Arg Ala Ser Ala Pro Asn Thr Val Tyr Leu
65                  70                  75                  80

Gln Met Ser Ser Leu Arg Ala Glu Asp Thr Ala Val Tyr Tyr Cys Tyr
                85                  90                  95

Ala Asp Val Ser Thr Gly Trp Gly Arg Asp Ala His Gly Tyr Trp Gly
            100                 105                 110

Gln Gly Thr Leu Val Thr Val
            115

<210> SEQ ID NO 61
<211> LENGTH: 119
<212> TYPE: PRT
<213> ORGANISM: Artificial Sequence
<220> FEATURE:
<223> OTHER INFORMATION: chemically synthesized

<400> SEQUENCE: 61

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Val Phe Ser Ile Asp
            20                  25                  30

Ala Met Gly Trp Tyr Arg Gln Ala Pro Gly Lys Gln Arg Glu Leu Val
        35                  40                  45

Ala Val Leu Ser Gly Ile Ser Ser Ala Lys Tyr Ala Asp Ala Val Glu
    50                  55                  60

Gly Arg Phe Thr Ile Ser Arg Ala Ser Ala Pro Asn Thr Val Tyr Leu
65                  70                  75                  80

Gln Met Ser Ser Leu Arg Ala Glu Asp Thr Ala Val Tyr Tyr Cys Tyr
                85                  90                  95

Ala Asp Val Ser Thr Gly Trp Gly Arg Asp Ala His Gly Tyr Trp Gly
            100                 105                 110

Gln Gly Thr Leu Val Thr Val
            115

<210> SEQ ID NO 62
<211> LENGTH: 119
<212> TYPE: PRT
<213> ORGANISM: Artificial Sequence
<220> FEATURE:
<223> OTHER INFORMATION: chemically synthesized

<400> SEQUENCE: 62

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Val Phe Ser Ile Asp
```

```
            20                  25                  30
Ala Met Gly Trp Tyr Arg Gln Ala Pro Gly Lys Gln Arg Glu Leu Val
                35                  40                  45

Ala Val Leu Ser Gly Ile Ser Ser Ala Lys Tyr Ala Ala Ser Ala Pro
    50                  55                  60

Gly Arg Phe Thr Ile Ser Arg Ala Ser Ala Pro Asn Thr Val Tyr Leu
65                  70                  75                  80

Gln Met Ser Ser Leu Arg Ala Glu Asp Thr Ala Val Tyr Tyr Cys Tyr
                85                  90                  95

Ala Asp Val Ser Thr Gly Trp Gly Arg Asp Ala His Gly Tyr Trp Gly
                100                 105                 110

Gln Gly Thr Leu Val Thr Val
                115

<210> SEQ ID NO 63
<211> LENGTH: 110
<212> TYPE: PRT
<213> ORGANISM: Artificial Sequence
<220> FEATURE:
<223> OTHER INFORMATION: chemically synthesized

<400> SEQUENCE: 63

Glu Val Gln Leu Leu Glu Ser Gly Gly Glu Val Gln Pro Gly Gly
1               5                   10                  15

Ser Leu Arg Leu Ser Cys Ala Ala Ser Gly Phe Thr Phe Ser Thr His
                20                  25                  30

Gly Met Asp Trp Phe Arg Gln Ala Pro Gly Lys Asp Leu Glu Trp Val
                35                  40                  45

Ser Ala Ile Asn Asn Gly Gly Ser Trp Thr Ser Tyr Ala Ser Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Trp Cys
                85                  90                  95

Gln Asn Arg Val Thr Arg Gly Gly Thr Leu Val Thr Val
                100                 105                 110

<210> SEQ ID NO 64
<211> LENGTH: 110
<212> TYPE: PRT
<213> ORGANISM: Artificial Sequence
<220> FEATURE:
<223> OTHER INFORMATION: chemically synthesized

<400> SEQUENCE: 64

Glu Val Gln Leu Leu Glu Ser Gly Gly Glu Val Gln Pro Gly Gly
1               5                   10                  15

Ser Leu Arg Leu Ser Cys Ala Ala Ser Gly Phe Thr Phe Ser Thr His
                20                  25                  30

Gly Met Asp Trp Phe Arg Gln Ala Pro Gly Lys Asp Leu Glu Trp Val
                35                  40                  45

Ser Ala Ile Asn Asn Gly Gly Ser Trp Thr Ser Tyr Ala Ser Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95
```

```
Gln Asn Arg Val Thr Arg Gly Gln Gly Thr Leu Val Thr Val
            100                 105                 110

<210> SEQ ID NO 65
<211> LENGTH: 110
<212> TYPE: PRT
<213> ORGANISM: Artificial Sequence
<220> FEATURE:
<223> OTHER INFORMATION: chemically synthesized

<400> SEQUENCE: 65

Glu Val Gln Leu Leu Glu Ser Gly Gly Gly Glu Val Gln Pro Gly Gly
1               5                   10                  15

Ser Leu Arg Leu Ser Cys Ala Ala Ser Gly Phe Thr Phe Ser Thr His
            20                  25                  30

Gly Met Asp Trp Phe Arg Gln Ala Pro Gly Lys Asp Leu Glu Trp Val
        35                  40                  45

Ser Ala Ile Asn Gln Gly Gly Ser Trp Thr Ser Tyr Ala Ser Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Gln Asn Arg Val Thr Arg Gly Gln Gly Thr Leu Val Thr Val
            100                 105                 110

<210> SEQ ID NO 66
<211> LENGTH: 110
<212> TYPE: PRT
<213> ORGANISM: Artificial Sequence
<220> FEATURE:
<223> OTHER INFORMATION: chemically synthesized

<400> SEQUENCE: 66

Glu Val Gln Leu Leu Glu Ser Gly Gly Gly Glu Val Gln Pro Gly Gly
1               5                   10                  15

Ser Leu Arg Leu Ser Cys Ala Ala Ser Gly Phe Thr Phe Ser Thr His
            20                  25                  30

Gly Met Asp Trp Phe Arg Gln Ala Pro Gly Lys Gly Leu Glu Trp Val
        35                  40                  45

Ser Ala Ile Asn Asn Gly Gly Ser Trp Thr Ser Tyr Ala Ser Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Trp Cys
                85                  90                  95

Gln Asn Arg Val Thr Arg Gly Gln Gly Thr Leu Val Thr Val
            100                 105                 110

<210> SEQ ID NO 67
<211> LENGTH: 110
<212> TYPE: PRT
<213> ORGANISM: Artificial Sequence
<220> FEATURE:
<223> OTHER INFORMATION: chemically synthesized

<400> SEQUENCE: 67

Glu Val Gln Leu Leu Glu Ser Gly Gly Gly Glu Val Gln Pro Gly Gly
1               5                   10                  15

Ser Leu Arg Leu Ser Cys Ala Ala Ser Gly Phe Thr Phe Ser Thr His
```

```
                    20                  25                  30

Gly Met Asp Trp Phe Arg Gln Ala Pro Gly Lys Gly Leu Glu Trp Val
                35                  40                  45

Ser Ala Ile Asn Asn Gly Gly Ser Trp Thr Ser Tyr Ala Ser Ser Val
            50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Tyr Cys
                85                  90                  95

Gln Asn Arg Val Thr Arg Gly Gln Gly Thr Leu Val Thr Val
                100                 105                 110

<210> SEQ ID NO 68
<211> LENGTH: 110
<212> TYPE: PRT
<213> ORGANISM: Artificial Sequence
<220> FEATURE:
<223> OTHER INFORMATION: chemically synthesized

<400> SEQUENCE: 68

Glu Val Gln Leu Leu Glu Ser Gly Gly Gly Glu Val Gln Pro Gly Gly
1               5                   10                  15

Ser Leu Arg Leu Ser Cys Ala Ala Ser Gly Phe Thr Phe Ser Thr His
                20                  25                  30

Gly Met Asp Trp Phe Arg Gln Ala Pro Gly Lys Asp Leu Glu Trp Val
                35                  40                  45

Ser Ala Ile Gln Ser Gly Gly Ser Trp Thr Ser Tyr Ala Ser Ser Val
            50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ala Glu Asp Thr Ala Val Tyr Trp Cys
                85                  90                  95

Gln Asn Arg Val Thr Arg Gly Gln Gly Thr Leu Val Thr Val
                100                 105                 110

<210> SEQ ID NO 69
<211> LENGTH: 110
<212> TYPE: PRT
<213> ORGANISM: Artificial Sequence
<220> FEATURE:
<223> OTHER INFORMATION: chemically synthesized

<400> SEQUENCE: 69

Glu Val Gln Leu Leu Glu Ser Gly Gly Gly Val Gln Pro Gly Gly
1               5                   10                  15

Ser Leu Arg Leu Ser Cys Ala Ala Ser Gly Phe Thr Phe Ser Thr His
                20                  25                  30

Gly Met Asp Trp Phe Arg Gln Ala Pro Gly Lys Asp Leu Glu Trp Val
                35                  40                  45

Ser Ala Ile Gln Ser Gly Gly Ser Trp Thr Ser Tyr Ala Ser Ser Val
            50                  55                  60

Lys Gly Arg Phe Thr Ile Ser Arg Asp Asn Ala Lys Asn Thr Leu Tyr
65                  70                  75                  80

Leu Glu Met Asn Asn Leu Lys Pro Glu Asp Thr Ala Val Tyr Trp Cys
                85                  90                  95

Gln Asn Arg Val Thr Arg Gly Gln Gly Thr Leu Val Thr Val
                100                 105                 110
```

```
<210> SEQ ID NO 70
<211> LENGTH: 110
<212> TYPE: PRT
<213> ORGANISM: Artificial Sequence
<220> FEATURE:
<223> OTHER INFORMATION: chemically synthesized

<400> SEQUENCE: 70

Glu Val Gln Leu Leu Glu Ser Gly Gly Gly Glu Val Gln Pro Gly Gly
1               5                   10                  15

Ser Leu Arg Leu Ser Cys Ala Ala Ser Gly Phe Thr Phe Ser Thr His
            20                  25                  30

Gly Met Asp Trp Phe Arg Gln Ala Pro Gly Lys Asp Leu Glu Trp Val
        35                  40                  45

Ser Ala Ile Gln Ser Gly Gly Ser Trp Thr Ser Tyr Ala Ser Ser Val
    50                  55                  60

Lys Gly Arg Phe Thr Ile Ser Arg Asp Asn Ala Lys Asn Thr Leu Tyr
65                  70                  75                  80

Leu Gln Met Asn Asn Leu Arg Ala Glu Asp Thr Ala Val Tyr Trp Cys
                85                  90                  95

Gln Asn Arg Val Thr Arg Gly Gly Gly Thr Leu Val Thr Val
            100                 105                 110

<210> SEQ ID NO 71
<211> LENGTH: 110
<212> TYPE: PRT
<213> ORGANISM: Artificial Sequence
<220> FEATURE:
<223> OTHER INFORMATION: chemically synthesized

<400> SEQUENCE: 71

Glu Val Gln Leu Leu Glu Ser Gly Gly Gly Glu Val Gln Pro Gly Gly
1               5                   10                  15

Ser Leu Arg Leu Ser Cys Ala Ala Ser Gly Phe Thr Phe Ser Thr His
            20                  25                  30

Gly Met Asp Trp Phe Arg Gln Ala Pro Gly Lys Asp Leu Glu Trp Val
        35                  40                  45

Ser Ala Ile Gln Ser Gly Gly Ser Trp Thr Ser Tyr Ala Ser Ser Val
    50                  55                  60

Lys Gly Arg Phe Thr Ile Ser Arg Asp Asn Ala Lys Asn Thr Leu Tyr
65                  70                  75                  80

Leu Glu Met Ser Ser Leu Arg Ala Glu Asp Thr Ala Val Tyr Trp Cys
                85                  90                  95

Gln Asn Arg Val Thr Arg Gly Gln Gly Thr Leu Val Thr Val
            100                 105                 110

<210> SEQ ID NO 72
<211> LENGTH: 110
<212> TYPE: PRT
<213> ORGANISM: Artificial Sequence
<220> FEATURE:
<223> OTHER INFORMATION: chemically synthesized

<400> SEQUENCE: 72

Glu Val Gln Leu Leu Glu Ser Gly Gly Gly Glu Val Gln Pro Gly Gly
1               5                   10                  15

Ser Leu Arg Leu Ser Cys Ala Ala Ser Gly Phe Thr Phe Ser Thr His
            20                  25                  30

Gly Met Asp Trp Phe Arg Gln Ala Pro Gly Lys Asp Leu Glu Trp Val
```

```
                35                  40                  45
Ser Ala Ile Gln Ser Gly Gly Ser Trp Thr Ser Tyr Ala Ser Ser Val
     50                  55                  60

Lys Gly Arg Phe Thr Ile Ser Arg Asp Asn Ala Lys Asn Thr Leu Tyr
 65                  70                  75                  80

Leu Gln Met Ser Ser Leu Arg Pro Glu Asp Thr Ala Val Tyr Trp Cys
                 85                  90                  95

Gln Asn Arg Val Thr Arg Gly Gln Gly Thr Leu Val Thr Val
            100                 105                 110

<210> SEQ ID NO 73
<211> LENGTH: 110
<212> TYPE: PRT
<213> ORGANISM: Artificial Sequence
<220> FEATURE:
<223> OTHER INFORMATION: chemically synthesized

<400> SEQUENCE: 73

Glu Val Gln Leu Leu Glu Ser Gly Gly Gly Glu Val Gln Pro Gly Gly
 1               5                  10                  15

Ser Leu Arg Leu Ser Cys Ala Ala Ser Gly Phe Thr Phe Ser Thr His
             20                  25                  30

Gly Met Asp Trp Phe Arg Gln Ala Pro Gly Lys Asp Leu Glu Trp Val
         35                  40                  45

Ser Ala Ile Gln Ser Gly Gly Ser Trp Thr Ser Tyr Ala Ser Ser Val
     50                  55                  60

Lys Gly Arg Phe Thr Ile Ser Arg Asp Asn Ala Lys Asn Thr Leu Tyr
 65                  70                  75                  80

Leu Gln Met Gln Gln Leu Arg Ala Glu Asp Thr Ala Val Tyr Trp Cys
                 85                  90                  95

Gln Asn Arg Val Thr Arg Gly Gln Gly Thr Leu Val Thr Val
            100                 105                 110

<210> SEQ ID NO 74
<211> LENGTH: 110
<212> TYPE: PRT
<213> ORGANISM: Artificial Sequence
<220> FEATURE:
<223> OTHER INFORMATION: chemically synthesized

<400> SEQUENCE: 74

Glu Val Gln Leu Leu Glu Ser Gly Gly Gly Glu Val Gln Pro Gly Gly
 1               5                  10                  15

Ser Leu Arg Leu Ser Cys Ala Ala Ser Gly Phe Thr Phe Ser Thr His
             20                  25                  30

Gly Met Asp Trp Phe Arg Gln Ala Pro Gly Lys Asp Leu Glu Trp Val
         35                  40                  45

Ser Ala Ile Gln Ser Gly Gly Ser Trp Thr Ser Tyr Ala Ser Ser Val
     50                  55                  60

Lys Gly Arg Phe Thr Ile Ser Arg Asp Asn Ala Lys Asn Thr Leu Tyr
 65                  70                  75                  80

Leu Gln Met Gln Asn Leu Arg Ala Glu Asp Thr Ala Val Tyr Trp Cys
                 85                  90                  95

Gln Asn Arg Val Thr Arg Gly Gln Gly Thr Leu Val Thr Val
            100                 105                 110

<210> SEQ ID NO 75
<211> LENGTH: 110
```

```
<212> TYPE: PRT
<213> ORGANISM: Artificial Sequence
<220> FEATURE:
<223> OTHER INFORMATION: chemically synthesized

<400> SEQUENCE: 75

Glu Val Gln Leu Leu Glu Ser Gly Gly Gly Glu Val Gln Pro Gly Gly
1               5                   10                  15

Ser Leu Arg Leu Ser Cys Ala Ala Ser Gly Phe Thr Phe Ser Thr His
            20                  25                  30

Gly Met Asp Trp Phe Arg Gln Ala Pro Gly Lys Asp Leu Glu Trp Val
        35                  40                  45

Ser Ala Ile Gln Ser Gly Gly Ser Trp Thr Ser Tyr Ala Ser Ser Val
    50                  55                  60

Lys Gly Arg Phe Thr Ile Ser Arg Asp Asn Ala Lys Asn Thr Leu Tyr
65                  70                  75                  80

Leu Gln Met Asp Asn Leu Arg Ala Glu Asp Thr Ala Val Tyr Trp Cys
                85                  90                  95

Gln Asn Arg Val Thr Arg Gly Gln Gly Thr Leu Val Thr Val
            100                 105                 110

<210> SEQ ID NO 76
<211> LENGTH: 110
<212> TYPE: PRT
<213> ORGANISM: Artificial Sequence
<220> FEATURE:
<223> OTHER INFORMATION: chemically synthesized

<400> SEQUENCE: 76

Glu Val Gln Leu Leu Glu Ser Gly Gly Gly Glu Val Gln Pro Gly Gly
1               5                   10                  15

Ser Leu Arg Leu Ser Cys Ala Ala Ser Gly Phe Thr Phe Ser Thr His
            20                  25                  30

Gly Met Asp Trp Phe Arg Gln Ala Pro Gly Lys Asp Leu Glu Trp Val
        35                  40                  45

Ser Ala Ile Gln Ser Gly Gly Ser Trp Thr Ser Tyr Ala Ser Ser Val
    50                  55                  60

Lys Gly Arg Phe Thr Ile Ser Arg Asp Asn Ala Lys Asn Thr Leu Tyr
65                  70                  75                  80

Leu Gln Met Asn Asp Leu Arg Ala Glu Asp Thr Ala Val Tyr Trp Cys
                85                  90                  95

Gln Asn Arg Val Thr Arg Gly Gln Gly Thr Leu Val Thr Val
            100                 105                 110

<210> SEQ ID NO 77
<211> LENGTH: 110
<212> TYPE: PRT
<213> ORGANISM: Artificial Sequence
<220> FEATURE:
<223> OTHER INFORMATION: chemically synthesized

<400> SEQUENCE: 77

Glu Val Gln Leu Leu Glu Ser Gly Gly Gly Glu Val Gln Pro Gly Gly
1               5                   10                  15

Ser Leu Arg Leu Ser Cys Ala Ala Ser Gly Phe Thr Phe Ser Thr His
            20                  25                  30

Gly Met Asp Trp Phe Arg Gln Ala Pro Gly Lys Asp Leu Glu Trp Val
        35                  40                  45

Ser Ala Ile Gln Ser Gly Gly Ser Trp Thr Ser Tyr Ala Ser Ser Val
    50                  55                  60
```

```
                50            55                 60
Lys Gly Arg Phe Thr Ile Ser Arg Asp Asn Ala Lys Asn Thr Leu Tyr
 65                  70                  75                  80

Leu Gln Met Asp Asp Leu Arg Ala Glu Asp Thr Ala Val Tyr Trp Cys
                 85                  90                  95

Gln Asn Arg Val Thr Arg Gly Gln Gly Thr Leu Val Thr Val
                100                 105                 110

<210> SEQ ID NO 78
<211> LENGTH: 110
<212> TYPE: PRT
<213> ORGANISM: Artificial Sequence
<220> FEATURE:
<223> OTHER INFORMATION: chemically synthesized

<400> SEQUENCE: 78

Glu Val Gln Leu Leu Glu Ser Gly Gly Glu Val Gln Pro Gly Gly
 1               5                  10                  15

Ser Leu Arg Leu Ser Cys Ala Ala Ser Gly Phe Thr Phe Ser Thr His
             20                  25                  30

Gly Met Asp Trp Phe Arg Gln Ala Pro Gly Lys Asp Leu Glu Trp Val
         35                  40                  45

Ser Ala Ile Gln Ser Gly Gly Ser Trp Thr Ser Tyr Ala Ser Ser Val
     50                  55                  60

Lys Gly Arg Phe Thr Ile Ser Arg Asp Asn Ala Lys Asn Thr Leu Tyr
 65                  70                  75                  80

Leu Gln Met Gln Asp Leu Arg Ala Glu Asp Thr Ala Val Tyr Trp Cys
                 85                  90                  95

Gln Asn Arg Val Thr Arg Gly Gln Gly Thr Leu Val Thr Val
                100                 105                 110

<210> SEQ ID NO 79
<211> LENGTH: 110
<212> TYPE: PRT
<213> ORGANISM: Artificial Sequence
<220> FEATURE:
<223> OTHER INFORMATION: chemically synthesized

<400> SEQUENCE: 79

Glu Val Gln Leu Leu Glu Ser Gly Gly Gly Val Gln Pro Gly Gly
 1               5                  10                  15

Ser Leu Arg Leu Ser Cys Ala Ala Ser Gly Phe Thr Phe Ser Thr His
             20                  25                  30

Gly Met Asp Trp Phe Arg Gln Ala Pro Gly Lys Asp Leu Glu Trp Val
         35                  40                  45

Ser Ala Ile Gln Ser Gly Gly Ser Trp Thr Ser Tyr Ala Ser Ser Val
     50                  55                  60

Lys Gly Arg Phe Thr Ile Ser Arg Asp Asn Ala Lys Asn Thr Leu Tyr
 65                  70                  75                  80

Leu Gln Met Asn Gln Leu Arg Ala Glu Asp Thr Ala Val Tyr Trp Cys
                 85                  90                  95

Gln Asn Arg Val Thr Arg Gly Gln Gly Thr Leu Val Thr Val
                100                 105                 110

<210> SEQ ID NO 80
<211> LENGTH: 110
<212> TYPE: PRT
<213> ORGANISM: Artificial Sequence
<220> FEATURE:
```

<223> OTHER INFORMATION: chemically synthesized

<400> SEQUENCE: 80

```
Glu Val Gln Leu Leu Glu Ser Gly Gly Gly Glu Val Gln Pro Gly Gly
1               5                   10                  15

Ser Leu Arg Leu Ser Cys Ala Ala Ser Gly Phe Thr Phe Ser Thr His
            20                  25                  30

Gly Met Asp Trp Phe Arg Gln Ala Pro Gly Lys Asp Leu Glu Trp Val
        35                  40                  45

Ser Ala Ile Gln Ser Gly Gly Ser Trp Thr Ser Tyr Ala Ser Ser Val
    50                  55                  60

Lys Gly Arg Phe Thr Ile Ser Arg Asp Asn Ala Lys Asn Thr Leu Tyr
65                  70                  75                  80

Leu Gln Met Ser Asn Leu Arg Ala Glu Asp Thr Ala Val Tyr Trp Cys
                85                  90                  95

Gln Asn Arg Val Thr Arg Gly Gln Gly Thr Leu Val Thr Val
            100                 105                 110
```

<210> SEQ ID NO 81
<211> LENGTH: 494
<212> TYPE: PRT
<213> ORGANISM: Artificial Sequence
<220> FEATURE:
<223> OTHER INFORMATION: chemically synthesized

<400> SEQUENCE: 81

```
Met Lys Trp Val Thr Phe Ile Ser Leu Leu Phe Leu Phe Ser Ser Ala
1               5                   10                  15

Tyr Ser Glu Val Gln Leu Leu Glu Ser Gly Gly Gly Glu Val Gln Pro
            20                  25                  30

Gly Gly Ser Leu Arg Leu Ser Cys Ala Ala Ser Gly Ser Val Phe Ser
        35                  40                  45

Ile Asp Ala Met Ser Trp Phe Arg Gln Ala Pro Gly Lys Gly Leu Glu
    50                  55                  60

Leu Val Ser Ala Ile Thr Gly Arg Thr Thr Tyr Tyr Ala Glu Ser
65                  70                  75                  80

Val Lys Gly Arg Phe Thr Ile Ser Arg Asp Asn Ala Lys Asn Thr Leu
                85                  90                  95

Tyr Leu Gln Met Ser Ser Leu Arg Ala Glu Asp Thr Ala Val Tyr Tyr
            100                 105                 110

Cys Asn Ala Val Val Ser Thr Gly Trp Gly Arg Asn Ala Asp Asp Tyr
        115                 120                 125

Trp Gly Gln Gly Thr Leu Val Thr Val Lys Pro Gly Gly Ser Gly Gly
    130                 135                 140

Ser Glu Val Gln Leu Leu Glu Ser Gly Gly Gly Glu Val Gln Pro Gly
145                 150                 155                 160

Gly Ser Leu Arg Leu Ser Cys Ala Ala Ser Gly Ser Val Phe Ser Ile
                165                 170                 175

Asp Ala Met Ser Trp Phe Arg Gln Ala Pro Gly Lys Gly Leu Glu Leu
            180                 185                 190

Val Ser Ala Ile Thr Gly Arg Thr Thr Tyr Tyr Ala Glu Ser Val
        195                 200                 205

Lys Gly Arg Phe Thr Ile Ser Arg Asp Asn Ala Lys Asn Thr Leu Tyr
    210                 215                 220

Leu Gln Met Ser Ser Leu Arg Ala Glu Asp Thr Ala Val Tyr Tyr Cys
225                 230                 235                 240
```

Asn Ala Val Val Ser Thr Gly Trp Gly Arg Asn Ala Asp Asp Tyr Trp
                245                 250                 255

Gly Gln Gly Thr Leu Val Thr Val Lys Pro Gly Gly Gly Asp Lys
                260                 265                 270

Thr His Thr Cys Pro Pro Cys Pro Ala Pro Gly Gly Pro Ser Val Phe
                275                 280                 285

Leu Phe Pro Pro Lys Pro Lys Asp Thr Leu Met Ile Ser Arg Thr Pro
290                 295                 300

Glu Val Thr Cys Val Val Val Asp Val Ser His Glu Asp Pro Glu Val
305                 310                 315                 320

Lys Phe Asn Trp Tyr Val Asp Gly Val Glu Val His Asn Ala Lys Thr
                325                 330                 335

Lys Pro Arg Glu Glu Gln Tyr Asn Ser Thr Tyr Arg Val Val Ser Val
                340                 345                 350

Leu Thr Val Leu His Gln Asp Trp Leu Asn Gly Lys Glu Tyr Lys Cys
                355                 360                 365

Lys Val Ser Asn Lys Ala Leu Pro Ala Pro Ile Glu Lys Thr Ile Ser
                370                 375                 380

Lys Ala Lys Gly Gln Pro Arg Glu Pro Gln Val Tyr Thr Leu Pro Pro
385                 390                 395                 400

Ser Arg Asp Glu Leu Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
                420                 425                 430

Gln Pro Glu Asn Asn Tyr Lys Thr Thr Pro Pro Val Leu Asp Ser Asp
                435                 440                 445

Gly Ser Phe Phe Leu Tyr Ser Lys Leu Thr Val Asp Lys Ser Arg Trp
                450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly Lys
                485                 490

<210> SEQ ID NO 82
<211> LENGTH: 494
<212> TYPE: PRT
<213> ORGANISM: Artificial Sequence
<220> FEATURE:
<223> OTHER INFORMATION: chemically synthesized

<400> SEQUENCE: 82

Met Lys Trp Val Thr Phe Ile Ser Leu Leu Phe Leu Phe Ser Ser Ala
1               5                   10                  15

Tyr Ser Glu Val Gln Leu Leu Glu Ser Gly Gly Gly Leu Val Gln Pro
                20                  25                  30

Gly Gly Ser Leu Arg Leu Ser Cys Ala Ala Ser Gly Ser Val Phe Ser
                35                  40                  45

Ile Asp Ala Met Ser Trp Phe Arg Gln Ala Pro Gly Lys Gly Leu Glu
                50                  55                  60

Leu Val Cys Ala Ile Thr Gly Gly Arg Thr Thr Tyr Tyr Ala Glu Ser
65                  70                  75                  80

Val Lys Gly Arg Phe Thr Cys Ser Arg Asp Asn Ala Lys Asn Thr Leu
                85                  90                  95

Tyr Leu Gln Met Ser Ser Leu Arg Ala Glu Asp Thr Ala Val Tyr Tyr
                100                 105                 110

```
Cys Asn Ala Val Val Ser Thr Gly Trp Gly Arg Asn Ala Asp Asp Tyr
            115                 120                 125

Trp Gly Gln Gly Thr Leu Val Thr Val Lys Pro Gly Ser Gly Gly
130                 135                 140

Ser Glu Val Gln Leu Leu Glu Ser Gly Gly Glu Val Gln Pro Gly
145                 150                 155                 160

Gly Ser Leu Arg Leu Ser Cys Ala Ala Ser Gly Ser Val Phe Ser Ile
                165                 170                 175

Asp Ala Met Ser Trp Phe Arg Gln Ala Pro Gly Lys Gly Leu Glu Leu
            180                 185                 190

Val Cys Ala Ile Thr Gly Gly Arg Thr Thr Tyr Tyr Ala Glu Ser Val
            195                 200                 205

Lys Gly Arg Phe Thr Cys Ser Arg Asp Asn Ala Lys Asn Thr Leu Tyr
            210                 215                 220

Leu Gln Met Ser Ser Leu Arg Ala Glu Asp Thr Ala Val Tyr Tyr Cys
225                 230                 235                 240

Asn Ala Val Val Ser Thr Gly Trp Gly Arg Asn Ala Asp Asp Tyr Trp
                245                 250                 255

Gly Gln Gly Thr Leu Val Thr Val Lys Pro Gly Gly Gly Asp Lys
            260                 265                 270

Thr His Thr Cys Pro Pro Cys Pro Ala Pro Gly Gly Pro Ser Val Phe
            275                 280                 285

Leu Phe Pro Pro Lys Pro Lys Asp Thr Leu Met Ile Ser Arg Thr Pro
            290                 295                 300

Glu Val Thr Cys Val Val Val Asp Val Ser His Glu Asp Pro Glu Val
305                 310                 315                 320

Lys Phe Asn Trp Tyr Val Asp Gly Val Glu Val His Asn Ala Lys Thr
                325                 330                 335

Lys Pro Arg Glu Glu Gln Tyr Asn Ser Thr Tyr Arg Val Val Ser Val
            340                 345                 350

Leu Thr Val Leu His Gln Asp Trp Leu Asn Gly Lys Glu Tyr Lys Cys
            355                 360                 365

Lys Val Ser Asn Lys Ala Leu Pro Ala Pro Ile Glu Lys Thr Ile Ser
            370                 375                 380

Lys Ala Lys Gly Gln Pro Arg Glu Pro Gln Val Tyr Thr Leu Pro Pro
385                 390                 395                 400

Ser Arg Asp Glu Leu Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Val Leu Asp Ser Asp
            435                 440                 445

Gly Ser Phe Phe Leu Tyr Ser Lys Leu Thr Val Asp Lys Ser Arg Trp
450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly Lys
                485                 490

<210> SEQ ID NO 83
<211> LENGTH: 497
<212> TYPE: PRT
<213> ORGANISM: Artificial Sequence
<220> FEATURE:
```

<223> OTHER INFORMATION: chemically synthesized

<400> SEQUENCE: 83

```
Met Lys Trp Val Thr Phe Ile Ser Leu Leu Phe Leu Phe Ser Ser Ala
1               5                   10                  15
Tyr Ser Glu Val Gln Leu Leu Glu Ser Gly Gly Gly Val Gln Pro
            20                  25                  30
Gly Gly Ser Leu Arg Leu Ser Cys Ala Ala Ser Gly Ser Val Phe Ser
            35                  40                  45
Ile Asp Ala Met Ser Trp Phe Arg Gln Ala Pro Gly Lys Gly Leu Glu
    50                  55                  60
Leu Val Ser Ala Ile Thr Gly Gly Arg Thr Thr Tyr Tyr Ala Glu Ser
65                  70                  75                  80
Val Lys Gly Arg Phe Thr Ile Ser Arg Asp Asn Ala Lys Asn Thr Leu
                85                  90                  95
Tyr Leu Gln Met Ser Ser Leu Arg Ala Glu Asp Thr Ala Val Tyr Tyr
            100                 105                 110
Cys Asn Ala Val Val Ser Thr Gly Trp Gly Arg Asn Ala Asp Asp Tyr
            115                 120                 125
Trp Gly Gln Gly Thr Leu Val Thr Val Lys Pro Gly Gly Ser Gly Gly
    130                 135                 140
Ser Glu Val Gln Leu Leu Glu Ser Gly Gly Gly Glu Val Gln Pro Gly
145                 150                 155                 160
Gly Ser Leu Arg Leu Ser Cys Ala Ala Ser Gly Ser Val Phe Ser Ile
                165                 170                 175
Asp Ala Met Ser Trp Phe Arg Gln Ala Pro Gly Lys Gly Leu Glu Leu
            180                 185                 190
Val Ser Ala Ile Thr Gly Gly Arg Thr Thr Tyr Tyr Ala Glu Ser Val
            195                 200                 205
Lys Gly Arg Phe Thr Ile Ser Arg Asp Asn Ala Lys Asn Thr Leu Tyr
    210                 215                 220
Leu Gln Met Ser Ser Leu Arg Ala Glu Asp Thr Ala Val Tyr Tyr Cys
225                 230                 235                 240
Asn Ala Val Val Ser Thr Gly Trp Gly Arg Asn Ala Asp Asp Tyr Trp
                245                 250                 255
Gly Gln Gly Thr Leu Val Thr Val Lys Pro Gly Gly Gly Gly Asp Lys
            260                 265                 270
Thr His Thr Cys Pro Pro Cys Pro Ala Pro Glu Leu Leu Gly Gly Pro
            275                 280                 285
Ser Val Phe Leu Phe Pro Pro Lys Pro Lys Asp Thr Leu Met Ile Ser
    290                 295                 300
Arg Thr Pro Glu Val Thr Cys Val Val Val Asp Val Ser His Glu Asp
305                 310                 315                 320
Pro Glu Val Lys Phe Asn Trp Tyr Val Asp Gly Val Glu Val His Asn
                325                 330                 335
Ala Lys Thr Lys Pro Arg Glu Glu Gln Tyr Asn Ser Thr Tyr Arg Val
            340                 345                 350
Val Ser Val Leu Thr Val Leu His Gln Asp Trp Leu Asn Gly Lys Glu
            355                 360                 365
Tyr Lys Cys Lys Val Ser Asn Lys Ala Leu Pro Ala Pro Ile Glu Lys
    370                 375                 380
Thr Ile Ser Lys Ala Lys Gly Gln Pro Arg Glu Pro Gln Val Tyr Thr
385                 390                 395                 400
```

-continued

```
Leu Pro Pro Ser Arg Asp Glu Leu Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Lys Leu Thr Val Asp Lys
    450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys

<210> SEQ ID NO 84
<211> LENGTH: 497
<212> TYPE: PRT
<213> ORGANISM: Artificial Sequence
<220> FEATURE:
<223> OTHER INFORMATION: chemically synthesized

<400> SEQUENCE: 84

Met Lys Trp Val Thr Phe Ile Ser Leu Leu Phe Leu Phe Ser Ser Ala
1               5                   10                  15

Tyr Ser Glu Val Gln Leu Leu Glu Ser Gly Gly Gly Glu Val Gln Pro
                20                  25                  30

Gly Gly Ser Leu Arg Leu Ser Cys Ala Ala Ser Gly Ser Val Phe Ser
            35                  40                  45

Ile Asp Ala Met Ser Trp Phe Arg Gln Ala Pro Gly Lys Gly Leu Glu
        50                  55                  60

Leu Val Cys Ala Ile Thr Gly Gly Arg Thr Thr Tyr Tyr Ala Glu Ser
65                  70                  75                  80

Val Lys Gly Arg Phe Thr Cys Ser Arg Asp Asn Ala Lys Asn Thr Leu
                85                  90                  95

Tyr Leu Gln Met Ser Ser Leu Arg Ala Glu Asp Thr Ala Val Tyr Tyr
                100                 105                 110

Cys Asn Ala Val Val Ser Thr Gly Trp Gly Arg Asn Ala Asp Asp Tyr
            115                 120                 125

Trp Gly Gln Gly Thr Leu Val Thr Val Lys Pro Gly Gly Ser Gly Gly
        130                 135                 140

Ser Glu Val Gln Leu Leu Glu Ser Gly Gly Gly Glu Val Gln Pro Gly
145                 150                 155                 160

Gly Ser Leu Arg Leu Ser Cys Ala Ala Ser Gly Ser Val Phe Ser Ile
                165                 170                 175

Asp Ala Met Ser Trp Phe Arg Gln Ala Pro Gly Lys Gly Leu Glu Leu
                180                 185                 190

Val Cys Ala Ile Thr Gly Gly Arg Thr Thr Tyr Tyr Ala Glu Ser Val
            195                 200                 205

Lys Gly Arg Phe Thr Cys Ser Arg Asp Asn Ala Lys Asn Thr Leu Tyr
        210                 215                 220

Leu Gln Met Ser Ser Leu Arg Ala Glu Asp Thr Ala Val Tyr Tyr Cys
225                 230                 235                 240

Asn Ala Val Val Ser Thr Gly Trp Gly Arg Asn Ala Asp Asp Tyr Trp
                245                 250                 255

Gly Gln Gly Thr Leu Val Thr Val Lys Pro Gly Gly Gly Gly Asp Lys
```

```
                        260                 265                 270
Thr His Thr Cys Pro Pro Cys Pro Ala Pro Glu Leu Leu Gly Gly Pro
            275                 280                 285

Ser Val Phe Leu Phe Pro Pro Lys Pro Lys Asp Thr Leu Met Ile Ser
        290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Ala Leu Pro Ala Pro Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Lys Leu Thr Val Asp Lys
    450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys

<210> SEQ ID NO 85
<211> LENGTH: 494
<212> TYPE: PRT
<213> ORGANISM: Artificial Sequence
<220> FEATURE:
<223> OTHER INFORMATION: chemically synthesized

<400> SEQUENCE: 85

Met Lys Trp Val Thr Phe Ile Ser Leu Leu Phe Leu Phe Ser Ser Ala
1               5                   10                  15

Tyr Ser Glu Val Gln Leu Leu Glu Ser Gly Gly Gly Val Gln Pro
            20                  25                  30

Gly Gly Ser Leu Arg Leu Ser Cys Ala Ala Ser Gly Ser Val Phe Ser
        35                  40                  45

Ile Asp Ser Met Ser Trp Phe Arg Gln Ala Pro Gly Lys Gly Leu Glu
    50                  55                  60

Leu Val Ser Leu Ile Thr Gly Gly Arg Thr Thr Tyr Tyr Ala Glu Ser
65                  70                  75                  80

Val Lys Gly Arg Phe Thr Ile Ser Arg Asp Asn Ala Lys Asn Thr Leu
                85                  90                  95

Tyr Leu Gln Met Ser Ser Leu Arg Ala Glu Asp Thr Ala Val Tyr Tyr
            100                 105                 110

Cys Asn Ala Val Val Ser Thr Gly Trp Gly Arg Asn Ala Asp Asp Tyr
        115                 120                 125
```

```
Trp Gly Gln Gly Thr Leu Val Thr Val Lys Pro Gly Ser Gly Gly
            130                 135                 140
Ser Glu Val Gln Leu Leu Glu Ser Gly Gly Gly Glu Val Gln Pro Gly
145                 150                 155                 160
Gly Ser Leu Arg Leu Ser Cys Ala Ala Ser Gly Ser Val Phe Ser Ile
                165                 170                 175
Asp Ser Met Ser Trp Phe Arg Gln Ala Pro Gly Lys Gly Leu Glu Leu
            180                 185                 190
Val Ser Leu Ile Thr Gly Gly Arg Thr Thr Tyr Tyr Ala Glu Ser Val
            195                 200                 205
Lys Gly Arg Phe Thr Ile Ser Arg Asp Asn Ala Lys Asn Thr Leu Tyr
210                 215                 220
Leu Gln Met Ser Ser Leu Arg Ala Glu Asp Thr Ala Val Tyr Tyr Cys
225                 230                 235                 240
Asn Ala Val Val Ser Thr Gly Trp Gly Arg Asn Ala Asp Asp Tyr Trp
                245                 250                 255
Gly Gln Gly Thr Leu Val Thr Val Lys Pro Gly Gly Gly Gly Asp Lys
            260                 265                 270
Thr His Thr Cys Pro Pro Cys Pro Ala Pro Gly Gly Pro Ser Val Phe
            275                 280                 285
Leu Phe Pro Pro Lys Pro Lys Asp Thr Leu Met Ile Ser Arg Thr Pro
290                 295                 300
Glu Val Thr Cys Val Val Val Asp Val Ser His Glu Asp Pro Glu Val
305                 310                 315                 320
Lys Phe Asn Trp Tyr Val Asp Gly Val Glu Val His Asn Ala Lys Thr
                325                 330                 335
Lys Pro Arg Glu Glu Gln Tyr Asn Ser Thr Tyr Arg Val Val Ser Val
            340                 345                 350
Leu Thr Val Leu His Gln Asp Trp Leu Asn Gly Lys Glu Tyr Lys Cys
            355                 360                 365
Lys Val Ser Asn Lys Ala Leu Pro Ala Pro Ile Glu Lys Thr Ile Ser
370                 375                 380
Lys Ala Lys Gly Gln Pro Arg Glu Pro Gln Val Tyr Thr Leu Pro Pro
385                 390                 395                 400
Ser Arg Asp Glu Leu Thr Lys Asn Gln Val Ser Leu Thr Cys Leu Val
                405                 410                 415
Lys Gly Phe Tyr Pro Ser Asp Ile Ala Val Glu Trp Glu Ser Asn Gly
            420                 425                 430
Gln Pro Glu Asn Asn Tyr Lys Thr Thr Pro Pro Val Leu Asp Ser Asp
            435                 440                 445
Gly Ser Phe Phe Leu Tyr Ser Lys Leu Thr Val Asp Lys Ser Arg Trp
450                 455                 460
Gln Gln Gly Asn Val Phe Ser Cys Ser Val Met His Glu Ala Leu His
465                 470                 475                 480
Asn His Tyr Thr Gln Lys Ser Leu Ser Leu Ser Pro Gly Lys
                485                 490

<210> SEQ ID NO 86
<211> LENGTH: 494
<212> TYPE: PRT
<213> ORGANISM: Artificial Sequence
<220> FEATURE:
<223> OTHER INFORMATION: chemically synthesized

<400> SEQUENCE: 86
```

-continued

```
Met Lys Trp Val Thr Phe Ile Ser Leu Leu Phe Leu Phe Ser Ser Ala
1               5                   10                  15

Tyr Ser Glu Val Gln Leu Leu Glu Ser Gly Gly Glu Val Gln Pro
            20                  25                  30

Gly Gly Ser Leu Arg Leu Ser Cys Ala Ala Ser Gly Ser Val Phe Ser
                35                  40                  45

Ile Asp Ser Met Ser Trp Phe Arg Gln Ala Pro Gly Lys Gly Leu Glu
    50                  55                  60

Leu Val Cys Leu Ile Thr Gly Gly Arg Thr Thr Tyr Tyr Ala Glu Ser
65                  70                  75                  80

Val Lys Gly Arg Phe Thr Cys Ser Arg Asp Asn Ala Lys Asn Thr Leu
                85                  90                  95

Tyr Leu Gln Met Ser Ser Leu Arg Ala Glu Asp Thr Ala Val Tyr Tyr
                100                 105                 110

Cys Asn Ala Val Val Ser Thr Gly Trp Gly Arg Asn Ala Asp Asp Tyr
            115                 120                 125

Trp Gly Gln Gly Thr Leu Val Thr Val Lys Pro Gly Gly Ser Gly Gly
    130                 135                 140

Ser Glu Val Gln Leu Leu Glu Ser Gly Gly Glu Val Gln Pro Gly
145                 150                 155                 160

Gly Ser Leu Arg Leu Ser Cys Ala Ala Ser Gly Ser Val Phe Ser Ile
                165                 170                 175

Asp Ser Met Ser Trp Phe Arg Gln Ala Pro Gly Lys Gly Leu Glu Leu
                180                 185                 190

Val Cys Leu Ile Thr Gly Gly Arg Thr Thr Tyr Tyr Ala Glu Ser Val
            195                 200                 205

Lys Gly Arg Phe Thr Cys Ser Arg Asp Asn Ala Lys Asn Thr Leu Tyr
            210                 215                 220

Leu Gln Met Ser Ser Leu Arg Ala Glu Asp Thr Ala Val Tyr Tyr Cys
225                 230                 235                 240

Asn Ala Val Val Ser Thr Gly Trp Gly Arg Asn Ala Asp Asp Tyr Trp
                245                 250                 255

Gly Gln Gly Thr Leu Val Thr Val Lys Pro Gly Gly Gly Gly Asp Lys
                260                 265                 270

Thr His Thr Cys Pro Pro Cys Pro Ala Pro Gly Gly Pro Ser Val Phe
            275                 280                 285

Leu Phe Pro Pro Lys Pro Lys Asp Thr Leu Met Ile Ser Arg Thr Pro
    290                 295                 300

Glu Val Thr Cys Val Val Val Asp Val Ser His Glu Asp Pro Glu Val
305                 310                 315                 320

Lys Phe Asn Trp Tyr Val Asp Gly Val Glu Val His Asn Ala Lys Thr
                325                 330                 335

Lys Pro Arg Glu Glu Gln Tyr Asn Ser Thr Tyr Arg Val Val Ser Val
            340                 345                 350

Leu Thr Val Leu His Gln Asp Trp Leu Asn Gly Lys Glu Tyr Lys Cys
                355                 360                 365

Lys Val Ser Asn Lys Ala Leu Pro Ala Pro Ile Glu Lys Thr Ile Ser
    370                 375                 380

Lys Ala Lys Gly Gln Pro Arg Glu Pro Gln Val Tyr Thr Leu Pro Pro
385                 390                 395                 400

Ser Arg Asp Glu Leu Thr Lys Asn Gln Val Ser Leu Thr Cys Leu Val
                405                 410                 415
```

```
Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Val Leu Asp Ser Asp
        435                 440                 445

Gly Ser Phe Phe Leu Tyr Ser Lys Leu Thr Val Asp Lys Ser Arg Trp
    450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly Lys
                485                 490
```

<210> SEQ ID NO 87
<211> LENGTH: 497
<212> TYPE: PRT
<213> ORGANISM: Artificial Sequence
<220> FEATURE:
<223> OTHER INFORMATION: chemically synthesized

<400> SEQUENCE: 87

```
Met Lys Trp Val Thr Phe Ile Ser Leu Leu Phe Leu Phe Ser Ser Ala
1               5                   10                  15

Tyr Ser Glu Val Gln Leu Leu Glu Ser Gly Gly Gly Glu Val Gln Pro
            20                  25                  30

Gly Gly Ser Leu Arg Leu Ser Cys Ala Ala Ser Gly Ser Val Phe Ser
        35                  40                  45

Ile Asp Ser Met Ser Trp Phe Arg Gln Ala Pro Gly Lys Gly Leu Glu
    50                  55                  60

Leu Val Ser Leu Ile Thr Gly Gly Arg Thr Thr Tyr Tyr Ala Glu Ser
65                  70                  75                  80

Val Lys Gly Arg Phe Thr Ile Ser Arg Asp Asn Ala Lys Asn Thr Leu
                85                  90                  95

Tyr Leu Gln Met Ser Ser Leu Arg Ala Glu Asp Thr Ala Val Tyr Tyr
            100                 105                 110

Cys Asn Ala Val Val Ser Thr Gly Trp Gly Arg Asn Ala Asp Asp Tyr
        115                 120                 125

Trp Gly Gln Gly Thr Leu Val Thr Val Lys Pro Gly Gly Ser Gly Gly
    130                 135                 140

Ser Glu Val Gln Leu Leu Glu Ser Gly Gly Gly Glu Val Gln Pro Gly
145                 150                 155                 160

Gly Ser Leu Arg Leu Ser Cys Ala Ala Ser Gly Ser Val Phe Ser Ile
                165                 170                 175

Asp Ser Met Ser Trp Phe Arg Gln Ala Pro Gly Lys Gly Leu Glu Leu
            180                 185                 190

Val Ser Leu Ile Thr Gly Gly Arg Thr Thr Tyr Tyr Ala Glu Ser Val
        195                 200                 205

Lys Gly Arg Phe Thr Ile Ser Arg Asp Asn Ala Lys Asn Thr Leu Tyr
    210                 215                 220

Leu Gln Met Ser Ser Leu Arg Ala Glu Asp Thr Ala Val Tyr Tyr Cys
225                 230                 235                 240

Asn Ala Val Val Ser Thr Gly Trp Gly Arg Asn Ala Asp Asp Tyr Trp
                245                 250                 255

Gly Gln Gly Thr Leu Val Thr Val Lys Pro Gly Gly Gly Gly Asp Lys
            260                 265                 270

Thr His Thr Cys Pro Pro Cys Pro Ala Pro Glu Leu Leu Gly Gly Pro
        275                 280                 285
```

```
Ser Val Phe Leu Phe Pro Pro Lys Pro Lys Asp Thr Leu Met Ile Ser
    290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Ala Leu Pro Ala Pro Ile Glu Lys
370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Lys Leu Thr Val Asp Lys
450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys

<210> SEQ ID NO 88
<211> LENGTH: 497
<212> TYPE: PRT
<213> ORGANISM: Artificial Sequence
<220> FEATURE:
<223> OTHER INFORMATION: chemically synthesized

<400> SEQUENCE: 88

Met Lys Trp Val Thr Phe Ile Ser Leu Leu Phe Leu Phe Ser Ser Ala
1               5                   10                  15

Tyr Ser Glu Val Gln Leu Leu Glu Ser Gly Gly Gly Leu Val Gln Pro
            20                  25                  30

Gly Gly Ser Leu Arg Leu Ser Cys Ala Ala Ser Gly Ser Val Phe Ser
        35                  40                  45

Ile Asp Ser Met Ser Trp Phe Arg Gln Ala Pro Gly Lys Gly Leu Glu
    50                  55                  60

Leu Val Cys Leu Ile Thr Gly Gly Arg Thr Thr Tyr Tyr Ala Glu Ser
65                  70                  75                  80

Val Lys Gly Arg Phe Thr Cys Ser Arg Asp Asn Ala Lys Asn Thr Leu
                85                  90                  95

Tyr Leu Gln Met Ser Ser Leu Arg Ala Glu Asp Thr Ala Val Tyr Tyr
            100                 105                 110

Cys Asn Ala Val Val Ser Thr Gly Trp Gly Arg Asn Ala Asp Asp Tyr
        115                 120                 125

Trp Gly Gln Gly Thr Leu Val Thr Val Lys Pro Gly Gly Ser Gly Gly
    130                 135                 140

Ser Glu Val Gln Leu Leu Glu Ser Gly Gly Gly Glu Val Gln Pro Gly
```

```
            145                 150                 155                 160
        Gly Ser Leu Arg Leu Ser Cys Ala Ala Ser Gly Ser Val Phe Ser Ile
                        165                 170                 175

Asp Ser Met Ser Trp Phe Arg Gln Ala Pro Gly Lys Gly Leu Glu Leu
                        180                 185                 190

Val Cys Leu Ile Thr Gly Gly Arg Thr Thr Tyr Tyr Ala Glu Ser Val
                        195                 200                 205

Lys Gly Arg Phe Thr Cys Ser Arg Asp Asn Ala Lys Asn Thr Leu Tyr
                        210                 215                 220

Leu Gln Met Ser Ser Leu Arg Ala Glu Asp Thr Ala Val Tyr Tyr Cys
        225                 230                 235                 240

Asn Ala Val Val Ser Thr Gly Trp Gly Arg Asn Ala Asp Asp Tyr Trp
                            245                 250                 255

Gly Gln Gly Thr Leu Val Thr Val Lys Pro Gly Gly Gly Gly Asp Lys
                        260                 265                 270

Thr His Thr Cys Pro Pro Cys Pro Ala Pro Glu Leu Leu Gly Gly Pro
                        275                 280                 285

Ser Val Phe Leu Phe Pro Pro Lys Pro Lys Asp Thr Leu Met Ile Ser
                290                 295                 300

Arg Thr Pro Glu Val Thr Cys Val Val Val Asp Val Ser His Glu Asp
        305                 310                 315                 320

Pro Glu Val Lys Phe Asn Trp Tyr Val Asp Gly Val Glu Val His Asn
                        325                 330                 335

Ala Lys Thr Lys Pro Arg Glu Glu Gln Tyr Asn Ser Thr Tyr Arg Val
                        340                 345                 350

Val Ser Val Leu Thr Val Leu His Gln Asp Trp Leu Asn Gly Lys Glu
                        355                 360                 365

Tyr Lys Cys Lys Val Ser Asn Lys Ala Leu Pro Ala Pro Ile Glu Lys
                        370                 375                 380

Thr Ile Ser Lys Ala Lys Gly Gln Pro Arg Glu Pro Gln Val Tyr Thr
        385                 390                 395                 400

Leu Pro Pro Ser Arg Asp Glu Leu Thr Lys Asn Gln Val Ser Leu Thr
                        405                 410                 415

Cys Leu Val Lys Gly Phe Tyr Pro Ser Asp Ile Ala Val Glu Trp Glu
                        420                 425                 430

Ser Asn Gly Gln Pro Glu Asn Asn Tyr Lys Thr Thr Pro Pro Val Leu
                        435                 440                 445

Asp Ser Asp Gly Ser Phe Phe Leu Tyr Ser Lys Leu Thr Val Asp Lys
                        450                 455                 460

Ser Arg Trp Gln Gln Gly Asn Val Phe Ser Cys Ser Val Met His Glu
        465                 470                 475                 480

Ala Leu His Asn His Tyr Thr Gln Lys Ser Leu Ser Leu Ser Pro Gly
                        485                 490                 495

Lys

<210> SEQ ID NO 89
<211> LENGTH: 494
<212> TYPE: PRT
<213> ORGANISM: Artificial Sequence
<220> FEATURE:
<223> OTHER INFORMATION: chemically synthesized

<400> SEQUENCE: 89

Met Lys Trp Val Thr Phe Ile Ser Leu Leu Phe Leu Phe Ser Ser Ala
        1               5                   10                  15
```

```
Tyr Ser Glu Val Gln Leu Leu Glu Ser Gly Gly Gly Glu Val Gln Pro
             20                  25                  30

Gly Gly Ser Leu Arg Leu Ser Cys Ala Ala Ser Gly Ser Val Phe Ser
         35                  40                  45

Ile Asp Ala Met Ser Trp Phe Arg Gln Ala Pro Gly Lys Gly Leu Glu
 50                  55                  60

Leu Val Ser Leu Ile Thr Gly Gly Arg Thr Thr Tyr Tyr Ala Glu Ser
 65                  70                  75                  80

Val Lys Gly Arg Phe Thr Ile Ser Arg Asp Asn Ala Lys Asn Thr Leu
                 85                  90                  95

Tyr Leu Gln Met Ser Ser Leu Arg Ala Glu Asp Thr Ala Val Tyr Tyr
            100                 105                 110

Cys Asn Ala Val Val Ser Thr Gly Trp Gly Arg Asn Ala Asp Asp Tyr
            115                 120                 125

Trp Gly Gln Gly Thr Leu Val Thr Val Lys Pro Gly Gly Ser Gly Gly
130                 135                 140

Ser Glu Val Gln Leu Leu Glu Ser Gly Gly Gly Glu Val Gln Pro Gly
145                 150                 155                 160

Gly Ser Leu Arg Leu Ser Cys Ala Ala Ser Gly Ser Val Phe Ser Ile
            165                 170                 175

Asp Ala Met Ser Trp Phe Arg Gln Ala Pro Gly Lys Gly Leu Glu Leu
            180                 185                 190

Val Ser Leu Ile Thr Gly Gly Arg Thr Thr Tyr Tyr Ala Glu Ser Val
            195                 200                 205

Lys Gly Arg Phe Thr Ile Ser Arg Asp Asn Ala Lys Asn Thr Leu Tyr
            210                 215                 220

Leu Gln Met Ser Ser Leu Arg Ala Glu Asp Thr Ala Val Tyr Tyr Cys
225                 230                 235                 240

Asn Ala Val Val Ser Thr Gly Trp Gly Arg Asn Ala Asp Asp Tyr Trp
                245                 250                 255

Gly Gln Gly Thr Leu Val Thr Val Lys Pro Gly Gly Gly Gly Asp Lys
            260                 265                 270

Thr His Thr Cys Pro Pro Cys Pro Ala Pro Gly Gly Pro Ser Val Phe
            275                 280                 285

Leu Phe Pro Pro Lys Pro Lys Asp Thr Leu Met Ile Ser Arg Thr Pro
290                 295                 300

Glu Val Thr Cys Val Val Val Asp Val Ser His Glu Asp Pro Glu Val
305                 310                 315                 320

Lys Phe Asn Trp Tyr Val Asp Gly Val Glu Val His Asn Ala Lys Thr
                325                 330                 335

Lys Pro Arg Glu Glu Gln Tyr Asn Ser Thr Tyr Arg Val Val Ser Val
            340                 345                 350

Leu Thr Val Leu His Gln Asp Trp Leu Asn Gly Lys Glu Tyr Lys Cys
            355                 360                 365

Lys Val Ser Asn Lys Ala Leu Pro Ala Pro Ile Glu Lys Thr Ile Ser
            370                 375                 380

Lys Ala Lys Gly Gln Pro Arg Glu Pro Gln Val Tyr Thr Leu Pro Pro
385                 390                 395                 400

Ser Arg Asp Glu Leu Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
            420                 425                 430
```

```
Gln Pro Glu Asn Asn Tyr Lys Thr Thr Pro Pro Val Leu Asp Ser Asp
            435                 440                 445

Gly Ser Phe Phe Leu Tyr Ser Lys Leu Thr Val Asp Lys Ser Arg Trp
450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly Lys
                485                 490

<210> SEQ ID NO 90
<211> LENGTH: 494
<212> TYPE: PRT
<213> ORGANISM: Artificial Sequence
<220> FEATURE:
<223> OTHER INFORMATION: chemically synthesized

<400> SEQUENCE: 90

Met Lys Trp Val Thr Phe Ile Ser Leu Leu Phe Leu Phe Ser Ser Ala
1               5                   10                  15

Tyr Ser Glu Val Gln Leu Leu Glu Ser Gly Gly Gly Glu Val Gln Pro
            20                  25                  30

Gly Gly Ser Leu Arg Leu Ser Cys Ala Ala Ser Gly Ser Val Phe Ser
        35                  40                  45

Ile Asp Ala Met Ser Trp Phe Arg Gln Ala Pro Gly Lys Gly Leu Glu
    50                  55                  60

Leu Val Cys Leu Ile Thr Gly Gly Arg Thr Thr Tyr Tyr Ala Glu Ser
65                  70                  75                  80

Val Lys Gly Arg Phe Thr Cys Ser Arg Asp Asn Ala Lys Asn Thr Leu
                85                  90                  95

Tyr Leu Gln Met Ser Ser Leu Arg Ala Glu Asp Thr Ala Val Tyr Tyr
            100                 105                 110

Cys Asn Ala Val Val Ser Thr Gly Trp Gly Arg Asn Ala Asp Asp Tyr
        115                 120                 125

Trp Gly Gln Gly Thr Leu Val Thr Val Lys Pro Gly Gly Ser Gly Gly
    130                 135                 140

Ser Glu Val Gln Leu Leu Glu Ser Gly Gly Gly Glu Val Gln Pro Gly
145                 150                 155                 160

Gly Ser Leu Arg Leu Ser Cys Ala Ala Ser Gly Ser Val Phe Ser Ile
                165                 170                 175

Asp Ala Met Ser Trp Phe Arg Gln Ala Pro Gly Lys Gly Leu Glu Leu
            180                 185                 190

Val Cys Leu Ile Thr Gly Gly Arg Thr Thr Tyr Tyr Ala Glu Ser Val
        195                 200                 205

Lys Gly Arg Phe Thr Cys Ser Arg Asp Asn Ala Lys Asn Thr Leu Tyr
    210                 215                 220

Leu Gln Met Ser Ser Leu Arg Ala Glu Asp Thr Ala Val Tyr Tyr Cys
225                 230                 235                 240

Asn Ala Val Val Ser Thr Gly Trp Gly Arg Asn Ala Asp Asp Tyr Trp
                245                 250                 255

Gly Gln Gly Thr Leu Val Thr Val Lys Pro Gly Gly Gly Gly Asp Lys
            260                 265                 270

Thr His Thr Cys Pro Pro Cys Pro Ala Pro Gly Gly Pro Ser Val Phe
        275                 280                 285

Leu Phe Pro Pro Lys Pro Lys Asp Thr Leu Met Ile Ser Arg Thr Pro
    290                 295                 300
```

Glu Val Thr Cys Val Val Asp Val Ser His Glu Asp Pro Glu Val
305                 310                 315                 320

Lys Phe Asn Trp Tyr Val Asp Gly Val Glu Val His Asn Ala Lys Thr
                325                 330                 335

Lys Pro Arg Glu Glu Gln Tyr Asn Ser Thr Tyr Arg Val Val Ser Val
                340                 345                 350

Leu Thr Val Leu His Gln Asp Trp Leu Asn Gly Lys Glu Tyr Lys Cys
                355                 360                 365

Lys Val Ser Asn Lys Ala Leu Pro Ala Pro Ile Glu Lys Thr Ile Ser
                370                 375                 380

Lys Ala Lys Gly Gln Pro Arg Glu Pro Gln Val Tyr Thr Leu Pro Pro
385                 390                 395                 400

Ser Arg Asp Glu Leu Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
                420                 425                 430

Gln Pro Glu Asn Asn Tyr Lys Thr Thr Pro Pro Val Leu Asp Ser Asp
                435                 440                 445

Gly Ser Phe Phe Leu Tyr Ser Lys Leu Thr Val Asp Lys Ser Arg Trp
450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly Lys
                485                 490

<210> SEQ ID NO 91
<211> LENGTH: 497
<212> TYPE: PRT
<213> ORGANISM: Artificial Sequence
<220> FEATURE:
<223> OTHER INFORMATION: chemically synthesized

<400> SEQUENCE: 91

Met Lys Trp Val Thr Phe Ile Ser Leu Leu Phe Leu Phe Ser Ser Ala
1               5                   10                  15

Tyr Ser Glu Val Gln Leu Leu Glu Ser Gly Gly Gly Glu Val Gln Pro
                20                  25                  30

Gly Gly Ser Leu Arg Leu Ser Cys Ala Ala Ser Gly Ser Val Phe Ser
                35                  40                  45

Ile Asp Ala Met Ser Trp Phe Arg Gln Ala Pro Gly Lys Gly Leu Glu
50                  55                  60

Leu Val Ser Leu Ile Thr Gly Gly Arg Thr Thr Tyr Tyr Ala Glu Ser
65                  70                  75                  80

Val Lys Gly Arg Phe Thr Ile Ser Arg Asp Asn Ala Lys Asn Thr Leu
                85                  90                  95

Tyr Leu Gln Met Ser Ser Leu Arg Ala Glu Asp Thr Ala Val Tyr Tyr
                100                 105                 110

Cys Asn Ala Val Val Ser Thr Gly Trp Gly Arg Asn Ala Asp Asp Tyr
                115                 120                 125

Trp Gly Gln Gly Thr Leu Val Thr Val Lys Pro Gly Gly Ser Gly Gly
130                 135                 140

Ser Glu Val Gln Leu Leu Glu Ser Gly Gly Gly Glu Val Gln Pro Gly
145                 150                 155                 160

Gly Ser Leu Arg Leu Ser Cys Ala Ala Ser Gly Ser Val Phe Ser Ile
                165                 170                 175

Asp Ala Met Ser Trp Phe Arg Gln Ala Pro Gly Lys Gly Leu Glu Leu
            180                 185                 190

Val Ser Leu Ile Thr Gly Gly Arg Thr Thr Tyr Tyr Ala Glu Ser Val
        195                 200                 205

Lys Gly Arg Phe Thr Ile Ser Arg Asp Asn Ala Lys Asn Thr Leu Tyr
    210                 215                 220

Leu Gln Met Ser Ser Leu Arg Ala Glu Asp Thr Ala Val Tyr Tyr Cys
225                 230                 235                 240

Asn Ala Val Val Ser Thr Gly Trp Gly Arg Asn Ala Asp Asp Tyr Trp
                245                 250                 255

Gly Gln Gly Thr Leu Val Thr Val Lys Pro Gly Gly Gly Gly Asp Lys
            260                 265                 270

Thr His Thr Cys Pro Pro Cys Pro Ala Pro Glu Leu Leu Gly Gly Pro
        275                 280                 285

Ser Val Phe Leu Phe Pro Pro Lys Pro Lys Asp Thr Leu Met Ile Ser
    290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Ala Leu Pro Ala Pro Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Lys Leu Thr Val Asp Lys
    450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys

<210> SEQ ID NO 92
<211> LENGTH: 497
<212> TYPE: PRT
<213> ORGANISM: Artificial Sequence
<220> FEATURE:
<223> OTHER INFORMATION: chemically synthesized

<400> SEQUENCE: 92

Met Lys Trp Val Thr Phe Ile Ser Leu Leu Phe Leu Phe Ser Ser Ala
1               5                   10                  15

Tyr Ser Glu Val Gln Leu Leu Glu Ser Gly Gly Gly Glu Val Gln Pro
            20                  25                  30

Gly Gly Ser Leu Arg Leu Ser Cys Ala Ala Ser Gly Ser Val Phe Ser

```
                35                  40                  45
Ile Asp Ala Met Ser Trp Phe Arg Gln Ala Pro Gly Lys Gly Leu Glu
 50                  55                  60

Leu Val Cys Leu Ile Thr Gly Gly Arg Thr Thr Tyr Tyr Ala Glu Ser
 65                  70                  75                  80

Val Lys Gly Arg Phe Thr Cys Ser Arg Asp Asn Ala Lys Asn Thr Leu
                 85                  90                  95

Tyr Leu Gln Met Ser Ser Leu Arg Ala Glu Asp Thr Ala Val Tyr Tyr
                100                 105                 110

Cys Asn Ala Val Val Ser Thr Gly Trp Gly Arg Asn Ala Asp Asp Tyr
                115                 120                 125

Trp Gly Gln Gly Thr Leu Val Thr Val Lys Pro Gly Gly Ser Gly Gly
            130                 135                 140

Ser Glu Val Gln Leu Leu Glu Ser Gly Gly Glu Val Gln Pro Gly Gly
145                 150                 155                 160

Gly Ser Leu Arg Leu Ser Cys Ala Ala Ser Gly Ser Val Phe Ser Ile
                165                 170                 175

Asp Ala Met Ser Trp Phe Arg Gln Ala Pro Gly Lys Gly Leu Glu Leu
                180                 185                 190

Val Cys Leu Ile Thr Gly Gly Arg Thr Thr Tyr Tyr Ala Glu Ser Val
                195                 200                 205

Lys Gly Arg Phe Thr Cys Ser Arg Asp Asn Ala Lys Asn Thr Leu Tyr
                210                 215                 220

Leu Gln Met Ser Ser Leu Arg Ala Glu Asp Thr Ala Val Tyr Tyr Cys
225                 230                 235                 240

Asn Ala Val Val Ser Thr Gly Trp Gly Arg Asn Ala Asp Asp Tyr Trp
                245                 250                 255

Gly Gln Gly Thr Leu Val Thr Val Lys Pro Gly Gly Gly Gly Asp Lys
                260                 265                 270

Thr His Thr Cys Pro Pro Cys Pro Ala Pro Glu Leu Leu Gly Gly Pro
            275                 280                 285

Ser Val Phe Leu Phe Pro Pro Lys Pro Lys Asp Thr Leu Met Ile Ser
290                 295                 300

Arg Thr Pro Glu Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
                340                 345                 350

Val Ser Val Leu Thr Val Leu His Gln Asp Trp Leu Asn Gly Lys Glu
                355                 360                 365

Tyr Lys Cys Lys Val Ser Asn Lys Ala Leu Pro Ala Pro Ile Glu Lys
            370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
                405                 410                 415

Cys Leu Val Lys Gly Phe Tyr Pro Ser Asp Ile Ala Val Glu Trp Glu
                420                 425                 430

Ser Asn Gly Gln Pro Glu Asn Asn Tyr Lys Thr Thr Pro Pro Val Leu
            435                 440                 445

Asp Ser Asp Gly Ser Phe Phe Leu Tyr Ser Lys Leu Thr Val Asp Lys
450                 455                 460
```

```
Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys

<210> SEQ ID NO 93
<211> LENGTH: 479
<212> TYPE: PRT
<213> ORGANISM: Artificial Sequence
<220> FEATURE:
<223> OTHER INFORMATION: chemically synthesized

<400> SEQUENCE: 93

Glu Val Gln Leu Leu Glu Ser Gly Gly Gly Glu Val Gln Pro Gly Gly
1               5                   10                  15

Ser Leu Arg Leu Ser Cys Ala Ala Ser Gly Ser Val Phe Ser Ile Asp
            20                  25                  30

Ala Met Gly Trp Tyr Arg Gln Ala Pro Gly Lys Gln Arg Glu Leu Val
        35                  40                  45

Ala Val Leu Ser Gly Ile Ser Ser Ala Lys Tyr Ala Ala Ser Ala Pro
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Tyr
                85                  90                  95

Ala Asp Val Ser Thr Gly Trp Gly Arg Asp Ala His Gly Tyr Trp Gly
            100                 105                 110

Gln Gly Thr Leu Val Thr Val Lys Pro Gly Gly Ser Gly Gly Ser Glu
        115                 120                 125

Val Gln Leu Leu Glu Ser Gly Gly Gly Glu Val Gln Pro Gly Gly Ser
    130                 135                 140

Leu Arg Leu Ser Cys Ala Ala Ser Gly Ser Val Phe Ser Ile Asp Ala
145                 150                 155                 160

Met Gly Trp Tyr Arg Gln Ala Pro Gly Lys Gln Arg Glu Leu Val Ala
                165                 170                 175

Val Leu Ser Gly Ile Ser Ser Ala Lys Tyr Ala Ala Ser Ala Pro Gly
            180                 185                 190

Arg Phe Thr Ile Ser Arg Asp Asn Ala Lys Asn Thr Val Tyr Leu Gln
        195                 200                 205

Met Ser Ser Leu Arg Ala Glu Asp Thr Ala Val Tyr Tyr Cys Tyr Ala
    210                 215                 220

Asp Val Ser Thr Gly Trp Gly Arg Asp Ala His Gly Tyr Trp Gly Gln
225                 230                 235                 240

Gly Thr Leu Val Thr Val Lys Pro Gly Gly Gly Gly Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320
```

```
Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys
465                 470                 475

<210> SEQ ID NO 94
<211> LENGTH: 621
<212> TYPE: PRT
<213> ORGANISM: Artificial Sequence
<220> FEATURE:
<223> OTHER INFORMATION: chemically synthesized

<400> SEQUENCE: 94

Met Lys Trp Val Thr Phe Ile Ser Leu Leu Phe Leu Phe Ser Ser Ala
1               5                   10                  15

Tyr Ser Glu Val Gln Leu Leu Glu Ser Gly Gly Gly Glu Val Gln Pro
            20                  25                  30

Gly Gly Ser Leu Arg Leu Ser Cys Ala Ala Ser Gly Ser Val Phe Ser
        35                  40                  45

Ile Asp Ala Met Ser Trp Phe Arg Gln Ala Pro Gly Lys Gly Leu Glu
    50                  55                  60

Leu Val Ser Ala Ile Thr Gly Gly Arg Thr Thr Tyr Tyr Ala Glu Ser
65                  70                  75                  80

Val Lys Gly Arg Phe Thr Ile Ser Arg Asp Asn Ala Lys Asn Thr Leu
                85                  90                  95

Tyr Leu Gln Met Ser Ser Leu Arg Ala Glu Asp Thr Ala Val Tyr Tyr
            100                 105                 110

Cys Asn Ala Val Val Ser Thr Gly Trp Gly Arg Asn Ala Asp Asp Tyr
        115                 120                 125

Trp Gly Gln Gly Thr Leu Val Thr Val Lys Pro Gly Gly Ser Gly Gly
    130                 135                 140

Ser Glu Val Gln Leu Leu Glu Ser Gly Gly Gly Glu Val Gln Pro Gly
145                 150                 155                 160

Gly Ser Leu Arg Leu Ser Cys Ala Ala Ser Gly Ser Val Phe Ser Ile
                165                 170                 175

Asp Ala Met Ser Trp Phe Arg Gln Ala Pro Gly Lys Gly Leu Glu Leu
            180                 185                 190

Val Ser Ala Ile Thr Gly Gly Arg Thr Thr Tyr Tyr Ala Glu Ser Val
        195                 200                 205
```

```
Lys Gly Arg Phe Thr Ile Ser Arg Asp Asn Ala Lys Asn Thr Leu Tyr
210                 215                 220

Leu Gln Met Ser Ser Leu Arg Ala Glu Asp Thr Ala Val Tyr Tyr Cys
225                 230                 235                 240

Asn Ala Val Val Ser Thr Gly Trp Gly Arg Asn Ala Asp Asp Tyr Trp
            245                 250                 255

Gly Gln Gly Thr Leu Val Thr Val Lys Pro Gly Gly Ser Gly Gly Ser
            260                 265                 270

Glu Val Gln Leu Leu Glu Ser Gly Gly Gly Val Gln Pro Gly Gly
                275                 280                 285

Ser Leu Arg Leu Ser Cys Ala Ala Ser Gly Ser Val Phe Ser Ile Asp
290                 295                 300

Ala Met Ser Trp Phe Arg Gln Ala Pro Gly Lys Gly Leu Glu Leu Val
305                 310                 315                 320

Ser Ala Ile Thr Gly Arg Thr Thr Tyr Tyr Ala Glu Ser Val Lys
                325                 330                 335

Gly Arg Phe Thr Ile Ser Arg Asp Asn Ala Lys Asn Thr Leu Tyr Leu
            340                 345                 350

Gln Met Ser Ser Leu Arg Ala Glu Asp Thr Ala Val Tyr Tyr Cys Asn
            355                 360                 365

Ala Val Val Ser Thr Gly Trp Gly Arg Asn Ala Asp Asp Tyr Trp Gly
    370                 375                 380

Gln Gly Thr Leu Val Thr Val Lys Pro Gly Gly Gly Asp Lys Thr
385                 390                 395                 400

His Thr Cys Pro Pro Cys Pro Ala Pro Gly Gly Pro Ser Val Phe Leu
                405                 410                 415

Phe Pro Pro Lys Pro Lys Asp Thr Leu Met Ile Ser Arg Thr Pro Glu
            420                 425                 430

Val Thr Cys Val Val Val Asp Val Ser His Glu Asp Pro Glu Val Lys
        435                 440                 445

Phe Asn Trp Tyr Val Asp Gly Val Glu Val His Asn Ala Lys Thr Lys
    450                 455                 460

Pro Arg Glu Glu Gln Tyr Asn Ser Thr Tyr Arg Val Val Ser Val Leu
465                 470                 475                 480

Thr Val Leu His Gln Asp Trp Leu Asn Gly Lys Glu Tyr Lys Cys Lys
            485                 490                 495

Val Ser Asn Lys Ala Leu Pro Ala Pro Ile Glu Lys Thr Ile Ser Lys
            500                 505                 510

Ala Lys Gly Gln Pro Arg Glu Pro Gln Val Tyr Thr Leu Pro Pro Ser
        515                 520                 525

Arg Asp Glu Leu Thr Lys Asn Gln Val Ser Leu Thr Cys Leu Val Lys
530                 535                 540

Gly Phe Tyr Pro Ser Asp Ile Ala Val Glu Trp Glu Ser Asn Gly Gln
545                 550                 555                 560

Pro Glu Asn Asn Tyr Lys Thr Thr Pro Val Leu Asp Ser Asp Gly
            565                 570                 575

Ser Phe Phe Leu Tyr Ser Lys Leu Thr Val Asp Lys Ser Arg Trp Gln
            580                 585                 590

Gln Gly Asn Val Phe Ser Cys Ser Val Met His Glu Ala Leu His Asn
        595                 600                 605

His Tyr Thr Gln Lys Ser Leu Ser Leu Ser Pro Gly Lys
610                 615                 620
```

<210> SEQ ID NO 95
<211> LENGTH: 621
<212> TYPE: PRT
<213> ORGANISM: Artificial Sequence
<220> FEATURE:
<223> OTHER INFORMATION: chemically synthesized

<400> SEQUENCE: 95

```
Met Lys Trp Val Thr Phe Ile Ser Leu Leu Phe Leu Phe Ser Ser Ala
1               5                   10                  15

Tyr Ser Glu Val Gln Leu Leu Glu Ser Gly Gly Gly Glu Val Gln Pro
            20                  25                  30

Gly Gly Ser Leu Arg Leu Ser Cys Ala Ala Ser Gly Ser Val Phe Ser
        35                  40                  45

Ile Asp Ala Met Ser Trp Phe Arg Gln Ala Pro Gly Lys Gly Leu Glu
    50                  55                  60

Leu Val Cys Ala Ile Thr Gly Gly Arg Thr Thr Tyr Tyr Ala Glu Ser
65                  70                  75                  80

Val Lys Gly Arg Phe Thr Cys Ser Arg Asp Asn Ala Lys Asn Thr Leu
                85                  90                  95

Tyr Leu Gln Met Ser Ser Leu Arg Ala Glu Asp Thr Ala Val Tyr Tyr
            100                 105                 110

Cys Asn Ala Val Val Ser Thr Gly Trp Gly Arg Asn Ala Asp Asp Tyr
        115                 120                 125

Trp Gly Gln Gly Thr Leu Val Thr Val Lys Pro Gly Gly Ser Gly Gly
    130                 135                 140

Ser Glu Val Gln Leu Leu Glu Ser Gly Gly Gly Glu Val Gln Pro Gly
145                 150                 155                 160

Gly Ser Leu Arg Leu Ser Cys Ala Ala Ser Gly Ser Val Phe Ser Ile
                165                 170                 175

Asp Ala Met Ser Trp Phe Arg Gln Ala Pro Gly Lys Gly Leu Glu Leu
            180                 185                 190

Val Cys Ala Ile Thr Gly Gly Arg Thr Thr Tyr Tyr Ala Glu Ser Val
        195                 200                 205

Lys Gly Arg Phe Thr Cys Ser Arg Asp Asn Ala Lys Asn Thr Leu Tyr
    210                 215                 220

Leu Gln Met Ser Ser Leu Arg Ala Glu Asp Thr Ala Val Tyr Tyr Cys
225                 230                 235                 240

Asn Ala Val Val Ser Thr Gly Trp Gly Arg Asn Ala Asp Asp Tyr Trp
                245                 250                 255

Gly Gln Gly Thr Leu Val Thr Val Lys Pro Gly Gly Ser Gly Gly Ser
            260                 265                 270

Glu Val Gln Leu Leu Glu Ser Gly Gly Gly Glu Val Gln Pro Gly Gly
        275                 280                 285

Ser Leu Arg Leu Ser Cys Ala Ala Ser Gly Ser Val Phe Ser Ile Asp
    290                 295                 300

Ala Met Ser Trp Phe Arg Gln Ala Pro Gly Lys Gly Leu Glu Leu Val
305                 310                 315                 320

Cys Ala Ile Thr Gly Gly Arg Thr Thr Tyr Tyr Ala Glu Ser Val Lys
                325                 330                 335

Gly Arg Phe Thr Cys Ser Arg Asp Asn Ala Lys Asn Thr Leu Tyr Leu
            340                 345                 350

Gln Met Ser Ser Leu Arg Ala Glu Asp Thr Ala Val Tyr Tyr Cys Asn
        355                 360                 365

Ala Val Val Ser Thr Gly Trp Gly Arg Asn Ala Asp Asp Tyr Trp Gly
```

```
                    370                 375                 380
Gln Gly Thr Leu Val Thr Val Lys Pro Gly Gly Gly Asp Lys Thr
385                 390                 395                 400

His Thr Cys Pro Pro Cys Pro Ala Pro Gly Gly Pro Ser Val Phe Leu
                405                 410                 415

Phe Pro Pro Lys Pro Lys Asp Thr Leu Met Ile Ser Arg Thr Pro Glu
                420                 425                 430

Val Thr Cys Val Val Val Asp Val Ser His Glu Asp Pro Glu Val Lys
                435                 440                 445

Phe Asn Trp Tyr Val Asp Gly Val Glu Val His Asn Ala Lys Thr Lys
            450                 455                 460

Pro Arg Glu Glu Gln Tyr Asn Ser Thr Tyr Arg Val Val Ser Val Leu
465                 470                 475                 480

Thr Val Leu His Gln Asp Trp Leu Asn Gly Lys Glu Tyr Lys Cys Lys
                485                 490                 495

Val Ser Asn Lys Ala Leu Pro Ala Pro Ile Glu Lys Thr Ile Ser Lys
                500                 505                 510

Ala Lys Gly Gln Pro Arg Glu Pro Gln Val Tyr Thr Leu Pro Pro Ser
            515                 520                 525

Arg Asp Glu Leu Thr Lys Asn Gln Val Ser Leu Thr Cys Leu Val Lys
530                 535                 540

Gly Phe Tyr Pro Ser Asp Ile Ala Val Glu Trp Glu Ser Asn Gly Gln
545                 550                 555                 560

Pro Glu Asn Asn Tyr Lys Thr Thr Pro Pro Val Leu Asp Ser Asp Gly
                565                 570                 575

Ser Phe Phe Leu Tyr Ser Lys Leu Thr Val Asp Lys Ser Arg Trp Gln
                580                 585                 590

Gln Gly Asn Val Phe Ser Cys Ser Val Met His Glu Ala Leu His Asn
            595                 600                 605

His Tyr Thr Gln Lys Ser Leu Ser Leu Ser Pro Gly Lys
            610                 615                 620

<210> SEQ ID NO 96
<211> LENGTH: 624
<212> TYPE: PRT
<213> ORGANISM: Artificial Sequence
<220> FEATURE:
<223> OTHER INFORMATION: chemically synthesized

<400> SEQUENCE: 96

Met Lys Trp Val Thr Phe Ile Ser Leu Leu Phe Leu Phe Ser Ser Ala
1               5                   10                  15

Tyr Ser Glu Val Gln Leu Leu Glu Ser Gly Gly Gly Glu Val Gln Pro
                20                  25                  30

Gly Gly Ser Leu Arg Leu Ser Cys Ala Ala Ser Gly Ser Val Phe Ser
            35                  40                  45

Ile Asp Ala Met Ser Trp Phe Arg Gln Ala Pro Gly Lys Gly Leu Glu
        50                  55                  60

Leu Val Ser Ala Ile Thr Gly Gly Arg Thr Thr Tyr Tyr Ala Glu Ser
65                  70                  75                  80

Val Lys Gly Arg Phe Thr Ile Ser Arg Asp Asn Ala Lys Asn Thr Leu
                85                  90                  95

Tyr Leu Gln Met Ser Ser Leu Arg Ala Glu Asp Thr Ala Val Tyr Tyr
                100                 105                 110

Cys Asn Ala Val Val Ser Thr Gly Trp Gly Arg Asn Ala Asp Asp Tyr
```

-continued

```
            115                 120                 125
Trp Gly Gln Gly Thr Leu Val Thr Val Lys Pro Gly Gly Ser Gly Gly
130                 135                 140
Ser Glu Val Gln Leu Leu Glu Ser Gly Gly Gly Val Gln Pro Gly
145                 150                 155                 160
Gly Ser Leu Arg Leu Ser Cys Ala Ala Ser Gly Ser Val Phe Ser Ile
                165                 170                 175
Asp Ala Met Ser Trp Phe Arg Gln Ala Pro Gly Lys Gly Leu Glu Leu
            180                 185                 190
Val Ser Ala Ile Thr Gly Gly Arg Thr Thr Tyr Tyr Ala Glu Ser Val
        195                 200                 205
Lys Gly Arg Phe Thr Ile Ser Arg Asp Asn Ala Lys Asn Thr Leu Tyr
    210                 215                 220
Leu Gln Met Ser Ser Leu Arg Ala Glu Asp Thr Ala Val Tyr Tyr Cys
225                 230                 235                 240
Asn Ala Val Val Ser Thr Gly Trp Gly Arg Asn Ala Asp Asp Tyr Trp
                245                 250                 255
Gly Gln Gly Thr Leu Val Thr Val Lys Pro Gly Gly Ser Gly Gly Ser
            260                 265                 270
Glu Val Gln Leu Leu Glu Ser Gly Gly Gly Val Gln Pro Gly Gly
        275                 280                 285
Ser Leu Arg Leu Ser Cys Ala Ala Ser Gly Ser Val Phe Ser Ile Asp
    290                 295                 300
Ala Met Ser Trp Phe Arg Gln Ala Pro Gly Lys Gly Leu Glu Leu Val
305                 310                 315                 320
Ser Ala Ile Thr Gly Gly Arg Thr Thr Tyr Tyr Ala Glu Ser Val Lys
                325                 330                 335
Gly Arg Phe Thr Ile Ser Arg Asp Asn Ala Lys Asn Thr Leu Tyr Leu
            340                 345                 350
Gln Met Ser Ser Leu Arg Ala Glu Asp Thr Ala Val Tyr Tyr Cys Asn
        355                 360                 365
Ala Val Val Ser Thr Gly Trp Gly Arg Asn Ala Asp Asp Tyr Trp Gly
    370                 375                 380
Gln Gly Thr Leu Val Thr Val Lys Pro Gly Gly Gly Gly Asp Lys Thr
385                 390                 395                 400
His Thr Cys Pro Pro Cys Pro Ala Pro Glu Leu Leu Gly Gly Pro Ser
                405                 410                 415
Val Phe Leu Phe Pro Lys Pro Lys Asp Thr Leu Met Ile Ser Arg
            420                 425                 430
Thr Pro Glu Val Thr Cys Val Val Asp Val Ser His Glu Asp Pro
        435                 440                 445
Glu Val Lys Phe Asn Trp Tyr Val Asp Gly Val Glu Val His Asn Ala
    450                 455                 460
Lys Thr Lys Pro Arg Glu Glu Gln Tyr Asn Ser Thr Tyr Arg Val Val
465                 470                 475                 480
Ser Val Leu Thr Val Leu His Gln Asp Trp Leu Asn Gly Lys Glu Tyr
                485                 490                 495
Lys Cys Lys Val Ser Asn Lys Ala Leu Pro Ala Pro Ile Glu Lys Thr
            500                 505                 510
Ile Ser Lys Ala Lys Gly Gln Pro Arg Glu Pro Gln Val Tyr Thr Leu
        515                 520                 525
Pro Pro Ser Arg Asp Glu Leu Thr Lys Asn Gln Val Ser Leu Thr Cys
    530                 535                 540
```

-continued

```
Leu Val Lys Gly Phe Tyr Pro Ser Asp Ile Ala Val Glu Trp Glu Ser
545                 550                 555                 560

Asn Gly Gln Pro Glu Asn Asn Tyr Lys Thr Thr Pro Pro Val Leu Asp
            565                 570                 575

Ser Asp Gly Ser Phe Phe Leu Tyr Ser Lys Leu Thr Val Asp Lys Ser
        580                 585                 590

Arg Trp Gln Gln Gly Asn Val Phe Ser Cys Ser Val Met His Glu Ala
            595                 600                 605

Leu His Asn His Tyr Thr Gln Lys Ser Leu Ser Leu Ser Pro Gly Lys
        610                 615                 620

<210> SEQ ID NO 97
<211> LENGTH: 624
<212> TYPE: PRT
<213> ORGANISM: Artificial Sequence
<220> FEATURE:
<223> OTHER INFORMATION: chemically synthesized

<400> SEQUENCE: 97

Met Lys Trp Val Thr Phe Ile Ser Leu Leu Phe Leu Phe Ser Ser Ala
1               5                   10                  15

Tyr Ser Glu Val Gln Leu Leu Glu Ser Gly Gly Gly Glu Val Gln Pro
            20                  25                  30

Gly Gly Ser Leu Arg Leu Ser Cys Ala Ala Ser Gly Ser Val Phe Ser
        35                  40                  45

Ile Asp Ala Met Ser Trp Phe Arg Gln Ala Pro Gly Lys Gly Leu Glu
    50                  55                  60

Leu Val Cys Ala Ile Thr Gly Gly Arg Thr Thr Tyr Tyr Ala Glu Ser
65                  70                  75                  80

Val Lys Gly Arg Phe Thr Cys Ser Arg Asp Asn Ala Lys Asn Thr Leu
                85                  90                  95

Tyr Leu Gln Met Ser Ser Leu Arg Ala Glu Asp Thr Ala Val Tyr Tyr
            100                 105                 110

Cys Asn Ala Val Val Ser Thr Gly Trp Gly Arg Asn Ala Asp Asp Tyr
        115                 120                 125

Trp Gly Gln Gly Thr Leu Val Thr Val Lys Pro Gly Gly Ser Gly Gly
    130                 135                 140

Ser Glu Val Gln Leu Leu Glu Ser Gly Gly Gly Glu Val Gln Pro Gly
145                 150                 155                 160

Gly Ser Leu Arg Leu Ser Cys Ala Ala Ser Gly Ser Val Phe Ser Ile
                165                 170                 175

Asp Ala Met Ser Trp Phe Arg Gln Ala Pro Gly Lys Gly Leu Glu Leu
            180                 185                 190

Val Cys Ala Ile Thr Gly Gly Arg Thr Thr Tyr Tyr Ala Glu Ser Val
        195                 200                 205

Lys Gly Arg Phe Thr Cys Ser Arg Asp Asn Ala Lys Asn Thr Leu Tyr
    210                 215                 220

Leu Gln Met Ser Ser Leu Arg Ala Glu Asp Thr Ala Val Tyr Tyr Cys
225                 230                 235                 240

Asn Ala Val Val Ser Thr Gly Trp Gly Arg Asn Ala Asp Asp Tyr Trp
                245                 250                 255

Gly Gln Gly Thr Leu Val Thr Val Lys Pro Gly Gly Ser Gly Gly Ser
            260                 265                 270

Glu Val Gln Leu Leu Glu Ser Gly Gly Gly Glu Val Gln Pro Gly Gly
        275                 280                 285
```

Ser Leu Arg Leu Ser Cys Ala Ala Ser Gly Ser Val Phe Ser Ile Asp
    290                 295                 300

Ala Met Ser Trp Phe Arg Gln Ala Pro Gly Lys Gly Leu Glu Leu Val
305                 310                 315                 320

Cys Ala Ile Thr Gly Gly Arg Thr Thr Tyr Tyr Ala Glu Ser Val Lys
                325                 330                 335

Gly Arg Phe Thr Cys Ser Arg Asp Asn Ala Lys Asn Thr Leu Tyr Leu
                340                 345                 350

Gln Met Ser Ser Leu Arg Ala Glu Asp Thr Ala Val Tyr Tyr Cys Asn
            355                 360                 365

Ala Val Val Ser Thr Gly Trp Gly Arg Asn Ala Asp Asp Tyr Trp Gly
        370                 375                 380

Gln Gly Thr Leu Val Thr Val Lys Pro Gly Gly Gly Asp Lys Thr
385                 390                 395                 400

His Thr Cys Pro Pro Cys Pro Ala Pro Glu Leu Leu Gly Gly Pro Ser
                405                 410                 415

Val Phe Leu Phe Pro Pro Lys Pro Lys Asp Thr Leu Met Ile Ser Arg
                420                 425                 430

Thr Pro Glu Val Thr Cys Val Val Val Asp Val Ser His Glu Asp Pro
            435                 440                 445

Glu Val Lys Phe Asn Trp Tyr Val Asp Gly Val Glu Val His Asn Ala
        450                 455                 460

Lys Thr Lys Pro Arg Glu Glu Gln Tyr Asn Ser Thr Tyr Arg Val Val
465                 470                 475                 480

Ser Val Leu Thr Val Leu His Gln Asp Trp Leu Asn Gly Lys Glu Tyr
                485                 490                 495

Lys Cys Lys Val Ser Asn Lys Ala Leu Pro Ala Pro Ile Glu Lys Thr
                500                 505                 510

Ile Ser Lys Ala Lys Gly Gln Pro Arg Glu Pro Gln Val Tyr Thr Leu
            515                 520                 525

Pro Pro Ser Arg Asp Glu Leu Thr Lys Asn Gln Val Ser Leu Thr Cys
        530                 535                 540

Leu Val Lys Gly Phe Tyr Pro Ser Asp Ile Ala Val Glu Trp Glu Ser
545                 550                 555                 560

Asn Gly Gln Pro Glu Asn Asn Tyr Lys Thr Thr Pro Pro Val Leu Asp
                565                 570                 575

Ser Asp Gly Ser Phe Phe Leu Tyr Ser Lys Leu Thr Val Asp Lys Ser
                580                 585                 590

Arg Trp Gln Gln Gly Asn Val Phe Ser Cys Ser Val Met His Glu Ala
            595                 600                 605

Leu His Asn His Tyr Thr Gln Lys Ser Leu Ser Leu Ser Pro Gly Lys
        610                 615                 620

<210> SEQ ID NO 98
<211> LENGTH: 621
<212> TYPE: PRT
<213> ORGANISM: Artificial Sequence
<220> FEATURE:
<223> OTHER INFORMATION: chemically synthesized

<400> SEQUENCE: 98

Met Lys Trp Val Thr Phe Ile Ser Leu Leu Phe Leu Phe Ser Ser Ala
1               5                   10                  15

Tyr Ser Glu Val Gln Leu Leu Glu Ser Gly Gly Gly Glu Val Gln Pro
            20                  25                  30

```
Gly Gly Ser Leu Arg Leu Ser Cys Ala Ala Ser Gly Ser Val Phe Ser
            35                  40                  45
Ile Asp Ser Met Ser Trp Phe Arg Gln Ala Pro Gly Lys Gly Leu Glu
 50                  55                  60
Leu Val Ser Leu Ile Thr Gly Gly Arg Thr Thr Tyr Tyr Ala Glu Ser
 65                  70                  75                  80
Val Lys Gly Arg Phe Thr Ile Ser Arg Asp Asn Ala Lys Asn Thr Leu
                 85                  90                  95
Tyr Leu Gln Met Ser Ser Leu Arg Ala Glu Asp Thr Ala Val Tyr Tyr
                100                 105                 110
Cys Asn Ala Val Val Ser Thr Gly Trp Gly Arg Asn Ala Asp Asp Tyr
                115                 120                 125
Trp Gly Gln Gly Thr Leu Val Thr Val Lys Pro Gly Gly Ser Gly Gly
            130                 135                 140
Ser Glu Val Gln Leu Leu Glu Ser Gly Gly Gly Glu Val Gln Pro Gly
145                 150                 155                 160
Gly Ser Leu Arg Leu Ser Cys Ala Ala Ser Gly Ser Val Phe Ser Ile
                165                 170                 175
Asp Ser Met Ser Trp Phe Arg Gln Ala Pro Gly Lys Gly Leu Glu Leu
            180                 185                 190
Val Ser Leu Ile Thr Gly Gly Arg Thr Thr Tyr Tyr Ala Glu Ser Val
            195                 200                 205
Lys Gly Arg Phe Thr Ile Ser Arg Asp Asn Ala Lys Asn Thr Leu Tyr
        210                 215                 220
Leu Gln Met Ser Ser Leu Arg Ala Glu Asp Thr Ala Val Tyr Tyr Cys
225                 230                 235                 240
Asn Ala Val Val Ser Thr Gly Trp Gly Arg Asn Ala Asp Asp Tyr Trp
                245                 250                 255
Gly Gln Gly Thr Leu Val Thr Val Lys Pro Gly Gly Ser Gly Gly Ser
            260                 265                 270
Glu Val Gln Leu Leu Glu Ser Gly Gly Gly Glu Val Gln Pro Gly Gly
        275                 280                 285
Ser Leu Arg Leu Ser Cys Ala Ala Ser Gly Ser Val Phe Ser Ile Asp
        290                 295                 300
Ser Met Ser Trp Phe Arg Gln Ala Pro Gly Lys Gly Leu Glu Leu Val
305                 310                 315                 320
Ser Leu Ile Thr Gly Gly Arg Thr Thr Tyr Tyr Ala Glu Ser Val Lys
                325                 330                 335
Gly Arg Phe Thr Ile Ser Arg Asp Asn Ala Lys Asn Thr Leu Tyr Leu
                340                 345                 350
Gln Met Ser Ser Leu Arg Ala Glu Asp Thr Ala Val Tyr Tyr Cys Asn
            355                 360                 365
Ala Val Val Ser Thr Gly Trp Gly Arg Asn Ala Asp Asp Tyr Trp Gly
        370                 375                 380
Gln Gly Thr Leu Val Thr Val Lys Pro Gly Gly Gly Gly Asp Lys Thr
385                 390                 395                 400
His Thr Cys Pro Pro Cys Pro Ala Pro Gly Gly Pro Ser Val Phe Leu
                405                 410                 415
Phe Pro Pro Lys Pro Lys Asp Thr Leu Met Ile Ser Arg Thr Pro Glu
                420                 425                 430
Val Thr Cys Val Val Val Asp Val Ser His Glu Asp Pro Glu Val Lys
            435                 440                 445
```

```
Phe Asn Trp Tyr Val Asp Gly Val Glu Val His Asn Ala Lys Thr Lys
    450                 455                 460

Pro Arg Glu Glu Gln Tyr Asn Ser Thr Tyr Arg Val Val Ser Val Leu
465                 470                 475                 480

Thr Val Leu His Gln Asp Trp Leu Asn Gly Lys Glu Tyr Lys Cys Lys
                485                 490                 495

Val Ser Asn Lys Ala Leu Pro Ala Pro Ile Glu Lys Thr Ile Ser Lys
            500                 505                 510

Ala Lys Gly Gln Pro Arg Glu Pro Gln Val Tyr Thr Leu Pro Pro Ser
        515                 520                 525

Arg Asp Glu Leu Thr Lys Asn Gln Val Ser Leu Thr Cys Leu Val Lys
530                 535                 540

Gly Phe Tyr Pro Ser Asp Ile Ala Val Glu Trp Glu Ser Asn Gly Gln
545                 550                 555                 560

Pro Glu Asn Asn Tyr Lys Thr Thr Pro Pro Val Leu Asp Ser Asp Gly
                565                 570                 575

Ser Phe Phe Leu Tyr Ser Lys Leu Thr Val Asp Lys Ser Arg Trp Gln
            580                 585                 590

Gln Gly Asn Val Phe Ser Cys Ser Val Met His Glu Ala Leu His Asn
        595                 600                 605

His Tyr Thr Gln Lys Ser Leu Ser Leu Ser Pro Gly Lys
610                 615                 620

<210> SEQ ID NO 99
<211> LENGTH: 621
<212> TYPE: PRT
<213> ORGANISM: Artificial Sequence
<220> FEATURE:
<223> OTHER INFORMATION: chemically synthesized

<400> SEQUENCE: 99

Met Lys Trp Val Thr Phe Ile Ser Leu Leu Phe Leu Phe Ser Ser Ala
1               5                   10                  15

Tyr Ser Glu Val Gln Leu Leu Glu Ser Gly Gly Gly Glu Val Gln Pro
                20                  25                  30

Gly Gly Ser Leu Arg Leu Ser Cys Ala Ala Ser Gly Ser Val Phe Ser
            35                  40                  45

Ile Asp Ser Met Ser Trp Phe Arg Gln Ala Pro Gly Lys Gly Leu Glu
50                  55                  60

Leu Val Cys Leu Ile Thr Gly Gly Arg Thr Thr Tyr Tyr Ala Glu Ser
65                  70                  75                  80

Val Lys Gly Arg Phe Thr Cys Ser Arg Asp Asn Ala Lys Asn Thr Leu
                85                  90                  95

Tyr Leu Gln Met Ser Ser Leu Arg Ala Glu Asp Thr Ala Val Tyr Tyr
            100                 105                 110

Cys Asn Ala Val Val Ser Thr Gly Trp Gly Arg Asn Ala Asp Asp Tyr
        115                 120                 125

Trp Gly Gln Gly Thr Leu Val Thr Val Lys Pro Gly Gly Ser Gly Gly
    130                 135                 140

Ser Glu Val Gln Leu Leu Glu Ser Gly Gly Gly Glu Val Gln Pro Gly
145                 150                 155                 160

Gly Ser Leu Arg Leu Ser Cys Ala Ala Ser Gly Ser Val Phe Ser Ile
                165                 170                 175

Asp Ser Met Ser Trp Phe Arg Gln Ala Pro Gly Lys Gly Leu Glu Leu
            180                 185                 190
```

```
Val Cys Leu Ile Thr Gly Gly Arg Thr Thr Tyr Tyr Ala Glu Ser Val
            195                 200                 205

Lys Gly Arg Phe Thr Cys Ser Arg Asp Asn Ala Lys Asn Thr Leu Tyr
        210                 215                 220

Leu Gln Met Ser Ser Leu Arg Ala Glu Asp Thr Ala Val Tyr Tyr Cys
225                 230                 235                 240

Asn Ala Val Val Ser Thr Gly Trp Gly Arg Asn Ala Asp Asp Tyr Trp
                245                 250                 255

Gly Gln Gly Thr Leu Val Thr Val Lys Pro Gly Gly Ser Gly Gly Ser
            260                 265                 270

Glu Val Gln Leu Leu Glu Ser Gly Gly Glu Val Gln Pro Gly Gly
        275                 280                 285

Ser Leu Arg Leu Ser Cys Ala Ala Ser Gly Ser Val Phe Ser Ile Asp
    290                 295                 300

Ser Met Ser Trp Phe Arg Gln Ala Pro Gly Lys Gly Leu Glu Leu Val
305                 310                 315                 320

Cys Leu Ile Thr Gly Gly Arg Thr Thr Tyr Tyr Ala Glu Ser Val Lys
                325                 330                 335

Gly Arg Phe Thr Cys Ser Arg Asp Asn Ala Lys Asn Thr Leu Tyr Leu
            340                 345                 350

Gln Met Ser Ser Leu Arg Ala Glu Asp Thr Ala Val Tyr Tyr Cys Asn
        355                 360                 365

Ala Val Val Ser Thr Gly Trp Gly Arg Asn Ala Asp Asp Tyr Trp Gly
    370                 375                 380

Gln Gly Thr Leu Val Thr Val Lys Pro Gly Gly Gly Asp Lys Thr
385                 390                 395                 400

His Thr Cys Pro Pro Cys Pro Ala Pro Gly Gly Pro Ser Val Phe Leu
                405                 410                 415

Phe Pro Pro Lys Pro Lys Asp Thr Leu Met Ile Ser Arg Thr Pro Glu
            420                 425                 430

Val Thr Cys Val Val Val Asp Val Ser His Glu Asp Pro Glu Val Lys
        435                 440                 445

Phe Asn Trp Tyr Val Asp Gly Val Glu Val His Asn Ala Lys Thr Lys
450                 455                 460

Pro Arg Glu Glu Gln Tyr Asn Ser Thr Tyr Arg Val Val Ser Val Leu
465                 470                 475                 480

Thr Val Leu His Gln Asp Trp Leu Asn Gly Lys Glu Tyr Lys Cys Lys
                485                 490                 495

Val Ser Asn Lys Ala Leu Pro Ala Pro Ile Glu Lys Thr Ile Ser Lys
            500                 505                 510

Ala Lys Gly Gln Pro Arg Glu Pro Gln Val Tyr Thr Leu Pro Pro Ser
        515                 520                 525

Arg Asp Glu Leu Thr Lys Asn Gln Val Ser Leu Thr Cys Leu Val Lys
    530                 535                 540

Gly Phe Tyr Pro Ser Asp Ile Ala Val Glu Trp Glu Ser Asn Gly Gln
545                 550                 555                 560

Pro Glu Asn Asn Tyr Lys Thr Thr Pro Pro Val Leu Asp Ser Asp Gly
                565                 570                 575

Ser Phe Phe Leu Tyr Ser Lys Leu Thr Val Asp Lys Ser Arg Trp Gln
            580                 585                 590

Gln Gly Asn Val Phe Ser Cys Ser Val Met His Glu Ala Leu His Asn
        595                 600                 605

His Tyr Thr Gln Lys Ser Leu Ser Leu Ser Pro Gly Lys
```

<210> SEQ ID NO 100
<211> LENGTH: 624
<212> TYPE: PRT
<213> ORGANISM: Artificial Sequence
<220> FEATURE:
<223> OTHER INFORMATION: chemically synthesized

<400> SEQUENCE: 100

```
Met Lys Trp Val Thr Phe Ile Ser Leu Leu Phe Leu Phe Ser Ser Ala
1               5                   10                  15

Tyr Ser Glu Val Gln Leu Leu Glu Ser Gly Gly Gly Glu Val Gln Pro
            20                  25                  30

Gly Gly Ser Leu Arg Leu Ser Cys Ala Ala Ser Gly Ser Val Phe Ser
        35                  40                  45

Ile Asp Ser Met Ser Trp Phe Arg Gln Ala Pro Gly Lys Gly Leu Glu
    50                  55                  60

Leu Val Ser Leu Ile Thr Gly Gly Arg Thr Thr Tyr Tyr Ala Glu Ser
65                  70                  75                  80

Val Lys Gly Arg Phe Thr Ile Ser Arg Asp Asn Ala Lys Asn Thr Leu
                85                  90                  95

Tyr Leu Gln Met Ser Ser Leu Arg Ala Glu Asp Thr Ala Val Tyr Tyr
            100                 105                 110

Cys Asn Ala Val Val Ser Thr Gly Trp Gly Arg Asn Ala Asp Asp Tyr
        115                 120                 125

Trp Gly Gln Gly Thr Leu Val Thr Val Lys Pro Gly Gly Ser Gly Gly
    130                 135                 140

Ser Glu Val Gln Leu Leu Glu Ser Gly Gly Gly Glu Val Gln Pro Gly
145                 150                 155                 160

Gly Ser Leu Arg Leu Ser Cys Ala Ala Ser Gly Ser Val Phe Ser Ile
                165                 170                 175

Asp Ser Met Ser Trp Phe Arg Gln Ala Pro Gly Lys Gly Leu Glu Leu
            180                 185                 190

Val Ser Leu Ile Thr Gly Gly Arg Thr Thr Tyr Tyr Ala Glu Ser Val
        195                 200                 205

Lys Gly Arg Phe Thr Ile Ser Arg Asp Asn Ala Lys Asn Thr Leu Tyr
    210                 215                 220

Leu Gln Met Ser Ser Leu Arg Ala Glu Asp Thr Ala Val Tyr Tyr Cys
225                 230                 235                 240

Asn Ala Val Val Ser Thr Gly Trp Gly Arg Asn Ala Asp Asp Tyr Trp
                245                 250                 255

Gly Gln Gly Thr Leu Val Thr Val Lys Pro Gly Gly Ser Gly Gly Ser
            260                 265                 270

Glu Val Gln Leu Leu Glu Ser Gly Gly Gly Glu Val Gln Pro Gly Gly
        275                 280                 285

Ser Leu Arg Leu Ser Cys Ala Ala Ser Gly Ser Val Phe Ser Ile Asp
    290                 295                 300

Ser Met Ser Trp Phe Arg Gln Ala Pro Gly Lys Gly Leu Glu Leu Val
305                 310                 315                 320

Ser Leu Ile Thr Gly Gly Arg Thr Thr Tyr Tyr Ala Glu Ser Val Lys
                325                 330                 335

Gly Arg Phe Thr Ile Ser Arg Asp Asn Ala Lys Asn Thr Leu Tyr Leu
            340                 345                 350

Gln Met Ser Ser Leu Arg Ala Glu Asp Thr Ala Val Tyr Tyr Cys Asn
```

```
            355                 360                 365
Ala Val Val Ser Thr Gly Trp Gly Arg Asn Ala Asp Asp Tyr Trp Gly
    370                 375                 380

Gln Gly Thr Leu Val Thr Val Lys Pro Gly Gly Gly Asp Lys Thr
385                 390                 395                 400

His Thr Cys Pro Pro Cys Pro Ala Pro Glu Leu Leu Gly Gly Pro Ser
            405                 410                 415

Val Phe Leu Phe Pro Pro Lys Pro Lys Asp Thr Leu Met Ile Ser Arg
            420                 425                 430

Thr Pro Glu Val Thr Cys Val Val Asp Val Ser His Glu Asp Pro
                435                 440                 445

Glu Val Lys Phe Asn Trp Tyr Val Asp Gly Val Glu Val His Asn Ala
            450                 455                 460

Lys Thr Lys Pro Arg Glu Glu Gln Tyr Asn Ser Thr Tyr Arg Val Val
465                 470                 475                 480

Ser Val Leu Thr Val Leu His Gln Asp Trp Leu Asn Gly Lys Glu Tyr
                485                 490                 495

Lys Cys Lys Val Ser Asn Lys Ala Leu Pro Ala Pro Ile Glu Lys Thr
                500                 505                 510

Ile Ser Lys Ala Lys Gly Gln Pro Arg Glu Pro Gln Val Tyr Thr Leu
                515                 520                 525

Pro Pro Ser Arg Asp Glu Leu Thr Lys Asn Gln Val Ser Leu Thr Cys
                530                 535                 540

Leu Val Lys Gly Phe Tyr Pro Ser Asp Ile Ala Val Glu Trp Glu Ser
545                 550                 555                 560

Asn Gly Gln Pro Glu Asn Asn Tyr Lys Thr Thr Pro Pro Val Leu Asp
                565                 570                 575

Ser Asp Gly Ser Phe Phe Leu Tyr Ser Lys Leu Thr Val Asp Lys Ser
                580                 585                 590

Arg Trp Gln Gln Gly Asn Val Phe Ser Cys Ser Val Met His Glu Ala
                595                 600                 605

Leu His Asn His Tyr Thr Gln Lys Ser Leu Ser Leu Ser Pro Gly Lys
            610                 615                 620

<210> SEQ ID NO 101
<211> LENGTH: 624
<212> TYPE: PRT
<213> ORGANISM: Artificial Sequence
<220> FEATURE:
<223> OTHER INFORMATION: chemically synthesized

<400> SEQUENCE: 101

Met Lys Trp Val Thr Phe Ile Ser Leu Leu Phe Leu Phe Ser Ser Ala
1               5                   10                  15

Tyr Ser Glu Val Gln Leu Leu Glu Ser Gly Gly Gly Glu Val Gln Pro
                20                  25                  30

Gly Gly Ser Leu Arg Leu Ser Cys Ala Ala Ser Gly Ser Val Phe Ser
            35                  40                  45

Ile Asp Ser Met Ser Trp Phe Arg Gln Ala Pro Gly Lys Gly Leu Glu
        50                  55                  60

Leu Val Cys Leu Ile Thr Gly Gly Arg Thr Thr Tyr Tyr Ala Glu Ser
65                  70                  75                  80

Val Lys Gly Arg Phe Thr Cys Ser Arg Asp Asn Ala Lys Asn Thr Leu
                85                  90                  95

Tyr Leu Gln Met Ser Ser Leu Arg Ala Glu Asp Thr Ala Val Tyr Tyr
```

-continued

```
                100              105              110
Cys Asn Ala Val Val Ser Thr Gly Trp Gly Arg Asn Ala Asp Asp Tyr
            115                 120                 125

Trp Gly Gln Gly Thr Leu Val Thr Val Lys Pro Gly Gly Ser Gly Gly
130                 135                 140

Ser Glu Val Gln Leu Leu Glu Ser Gly Gly Gly Glu Val Gln Pro Gly
145                 150                 155                 160

Gly Ser Leu Arg Leu Ser Cys Ala Ala Ser Gly Ser Val Phe Ser Ile
                165                 170                 175

Asp Ser Met Ser Trp Phe Arg Gln Ala Pro Gly Lys Gly Leu Glu Leu
            180                 185                 190

Val Cys Leu Ile Thr Gly Gly Arg Thr Thr Tyr Tyr Ala Glu Ser Val
            195                 200                 205

Lys Gly Arg Phe Thr Cys Ser Arg Asp Asn Ala Lys Asn Thr Leu Tyr
            210                 215                 220

Leu Gln Met Ser Ser Leu Arg Ala Glu Asp Thr Ala Val Tyr Tyr Cys
225                 230                 235                 240

Asn Ala Val Val Ser Thr Gly Trp Gly Arg Asn Ala Asp Asp Tyr Trp
                245                 250                 255

Gly Gln Gly Thr Leu Val Thr Val Lys Pro Gly Gly Ser Gly Gly Ser
            260                 265                 270

Glu Val Gln Leu Leu Glu Ser Gly Gly Gly Glu Val Gln Pro Gly Gly
            275                 280                 285

Ser Leu Arg Leu Ser Cys Ala Ala Ser Gly Ser Val Phe Ser Ile Asp
        290                 295                 300

Ser Met Ser Trp Phe Arg Gln Ala Pro Gly Lys Gly Leu Glu Leu Val
305                 310                 315                 320

Cys Leu Ile Thr Gly Gly Arg Thr Thr Tyr Tyr Ala Glu Ser Val Lys
                325                 330                 335

Gly Arg Phe Thr Cys Ser Arg Asp Asn Ala Lys Asn Thr Leu Tyr Leu
            340                 345                 350

Gln Met Ser Ser Leu Arg Ala Glu Asp Thr Ala Val Tyr Tyr Cys Asn
            355                 360                 365

Ala Val Val Ser Thr Gly Trp Gly Arg Asn Ala Asp Asp Tyr Trp Gly
        370                 375                 380

Gln Gly Thr Leu Val Thr Val Lys Pro Gly Gly Gly Gly Asp Lys Thr
385                 390                 395                 400

His Thr Cys Pro Pro Cys Pro Ala Pro Glu Leu Leu Gly Gly Pro Ser
                405                 410                 415

Val Phe Leu Phe Pro Pro Lys Pro Lys Asp Thr Leu Met Ile Ser Arg
            420                 425                 430

Thr Pro Glu Val Thr Cys Val Val Asp Val Ser His Glu Asp Pro
            435                 440                 445

Glu Val Lys Phe Asn Trp Tyr Val Asp Gly Val Glu Val His Asn Ala
        450                 455                 460

Lys Thr Lys Pro Arg Glu Glu Gln Tyr Asn Ser Thr Tyr Arg Val Val
465                 470                 475                 480

Ser Val Leu Thr Val Leu His Gln Asp Trp Leu Asn Gly Lys Glu Tyr
                485                 490                 495

Lys Cys Lys Val Ser Asn Lys Ala Leu Pro Ala Pro Ile Glu Lys Thr
            500                 505                 510

Ile Ser Lys Ala Lys Gly Gln Pro Arg Glu Pro Gln Val Tyr Thr Leu
            515                 520                 525
```

```
Pro Pro Ser Arg Asp Glu Leu Thr Lys Asn Gln Val Ser Leu Thr Cys
    530                 535                 540
Leu Val Lys Gly Phe Tyr Pro Ser Asp Ile Ala Val Glu Trp Glu Ser
545                 550                 555                 560
Asn Gly Gln Pro Glu Asn Asn Tyr Lys Thr Thr Pro Pro Val Leu Asp
                565                 570                 575
Ser Asp Gly Ser Phe Phe Leu Tyr Ser Lys Leu Thr Val Asp Lys Ser
                580                 585                 590
Arg Trp Gln Gln Gly Asn Val Phe Ser Cys Ser Val Met His Glu Ala
                595                 600                 605
Leu His Asn His Tyr Thr Gln Lys Ser Leu Ser Leu Ser Pro Gly Lys
                610                 615                 620

<210> SEQ ID NO 102
<211> LENGTH: 621
<212> TYPE: PRT
<213> ORGANISM: Artificial Sequence
<220> FEATURE:
<223> OTHER INFORMATION: chemically synthesized

<400> SEQUENCE: 102

Met Lys Trp Val Thr Phe Ile Ser Leu Leu Phe Leu Phe Ser Ser Ala
1               5                   10                  15
Tyr Ser Glu Val Gln Leu Leu Glu Ser Gly Gly Gly Glu Val Gln Pro
                20                  25                  30
Gly Gly Ser Leu Arg Leu Ser Cys Ala Ala Ser Gly Ser Val Phe Ser
            35                  40                  45
Ile Asp Ala Met Ser Trp Phe Arg Gln Ala Pro Gly Lys Gly Leu Glu
    50                  55                  60
Leu Val Ser Leu Ile Thr Gly Gly Arg Thr Thr Tyr Tyr Ala Glu Ser
65                  70                  75                  80
Val Lys Gly Arg Phe Thr Ile Ser Arg Asp Asn Ala Lys Asn Thr Leu
                85                  90                  95
Tyr Leu Gln Met Ser Ser Leu Arg Ala Glu Asp Thr Ala Val Tyr Tyr
                100                 105                 110
Cys Asn Ala Val Val Ser Thr Gly Trp Gly Arg Asn Ala Asp Asp Tyr
            115                 120                 125
Trp Gly Gln Gly Thr Leu Val Thr Val Lys Pro Gly Gly Ser Gly Gly
    130                 135                 140
Ser Glu Val Gln Leu Leu Glu Ser Gly Gly Gly Glu Val Gln Pro Gly
145                 150                 155                 160
Gly Ser Leu Arg Leu Ser Cys Ala Ala Ser Gly Ser Val Phe Ser Ile
                165                 170                 175
Asp Ala Met Ser Trp Phe Arg Gln Ala Pro Gly Lys Gly Leu Glu Leu
                180                 185                 190
Val Ser Leu Ile Thr Gly Gly Arg Thr Thr Tyr Tyr Ala Glu Ser Val
            195                 200                 205
Lys Gly Arg Phe Thr Ile Ser Arg Asp Asn Ala Lys Asn Thr Leu Tyr
    210                 215                 220
Leu Gln Met Ser Ser Leu Arg Ala Glu Asp Thr Ala Val Tyr Tyr Cys
225                 230                 235                 240
Asn Ala Val Val Ser Thr Gly Trp Gly Arg Asn Ala Asp Asp Tyr Trp
                245                 250                 255
Gly Gln Gly Thr Leu Val Thr Val Lys Pro Gly Gly Ser Gly Gly Ser
                260                 265                 270
```

Glu Val Gln Leu Leu Glu Ser Gly Gly Gly Val Gln Pro Gly Gly
            275                 280                 285

Ser Leu Arg Leu Ser Cys Ala Ala Ser Gly Ser Val Phe Ser Ile Asp
290                 295                 300

Ala Met Ser Trp Phe Arg Gln Ala Pro Gly Lys Gly Leu Glu Leu Val
305                 310                 315                 320

Ser Leu Ile Thr Gly Gly Arg Thr Thr Tyr Tyr Ala Glu Ser Val Lys
                325                 330                 335

Gly Arg Phe Thr Ile Ser Arg Asp Asn Ala Lys Asn Thr Leu Tyr Leu
            340                 345                 350

Gln Met Ser Ser Leu Arg Ala Glu Asp Thr Ala Val Tyr Tyr Cys Asn
                355                 360                 365

Ala Val Val Ser Thr Gly Trp Gly Arg Asn Ala Asp Asp Tyr Trp Gly
370                 375                 380

Gln Gly Thr Leu Val Thr Val Lys Pro Gly Gly Gly Asp Lys Thr
385                 390                 395                 400

His Thr Cys Pro Pro Cys Pro Ala Pro Gly Gly Pro Ser Val Phe Leu
            405                 410                 415

Phe Pro Pro Lys Pro Lys Asp Thr Leu Met Ile Ser Arg Thr Pro Glu
            420                 425                 430

Val Thr Cys Val Val Val Asp Val Ser His Glu Asp Pro Glu Val Lys
            435                 440                 445

Phe Asn Trp Tyr Val Asp Gly Val Glu Val His Asn Ala Lys Thr Lys
450                 455                 460

Pro Arg Glu Glu Gln Tyr Asn Ser Thr Tyr Arg Val Val Ser Val Leu
465                 470                 475                 480

Thr Val Leu His Gln Asp Trp Leu Asn Gly Lys Glu Tyr Lys Cys Lys
                485                 490                 495

Val Ser Asn Lys Ala Leu Pro Ala Pro Ile Glu Lys Thr Ile Ser Lys
            500                 505                 510

Ala Lys Gly Gln Pro Arg Glu Pro Gln Val Tyr Thr Leu Pro Pro Ser
            515                 520                 525

Arg Asp Glu Leu Thr Lys Asn Gln Val Ser Leu Thr Cys Leu Val Lys
530                 535                 540

Gly Phe Tyr Pro Ser Asp Ile Ala Val Glu Trp Glu Ser Asn Gly Gln
545                 550                 555                 560

Pro Glu Asn Asn Tyr Lys Thr Thr Pro Pro Val Leu Asp Ser Asp Gly
                565                 570                 575

Ser Phe Phe Leu Tyr Ser Lys Leu Thr Val Asp Lys Ser Arg Trp Gln
            580                 585                 590

Gln Gly Asn Val Phe Ser Cys Ser Val Met His Glu Ala Leu His Asn
            595                 600                 605

His Tyr Thr Gln Lys Ser Leu Ser Leu Ser Pro Gly Lys
            610                 615                 620

<210> SEQ ID NO 103
<211> LENGTH: 621
<212> TYPE: PRT
<213> ORGANISM: Artificial Sequence
<220> FEATURE:
<223> OTHER INFORMATION: chemically synthesized

<400> SEQUENCE: 103

Met Lys Trp Val Thr Phe Ile Ser Leu Leu Phe Leu Phe Ser Ser Ala
1               5                   10                  15

```
Tyr Ser Glu Val Gln Leu Leu Glu Ser Gly Gly Gly Glu Val Gln Pro
            20                  25                  30

Gly Gly Ser Leu Arg Leu Ser Cys Ala Ala Ser Gly Ser Val Phe Ser
        35                  40                  45

Ile Asp Ala Met Ser Trp Phe Arg Gln Ala Pro Gly Lys Gly Leu Glu
50                  55                  60

Leu Val Cys Leu Ile Thr Gly Gly Arg Thr Thr Tyr Tyr Ala Glu Ser
65                  70                  75                  80

Val Lys Gly Arg Phe Thr Cys Ser Arg Asp Asn Ala Lys Asn Thr Leu
                85                  90                  95

Tyr Leu Gln Met Ser Ser Leu Arg Ala Glu Asp Thr Ala Val Tyr Tyr
            100                 105                 110

Cys Asn Ala Val Val Ser Thr Gly Trp Gly Arg Asn Ala Asp Asp Tyr
                115                 120                 125

Trp Gly Gln Gly Thr Leu Val Thr Val Lys Pro Gly Gly Ser Gly Gly
        130                 135                 140

Ser Glu Val Gln Leu Leu Glu Ser Gly Gly Gly Glu Val Gln Pro Gly
145                 150                 155                 160

Gly Ser Leu Arg Leu Ser Cys Ala Ala Ser Gly Ser Val Phe Ser Ile
                165                 170                 175

Asp Ala Met Ser Trp Phe Arg Gln Ala Pro Gly Lys Gly Leu Glu Leu
            180                 185                 190

Val Cys Leu Ile Thr Gly Gly Arg Thr Thr Tyr Tyr Ala Glu Ser Val
                195                 200                 205

Lys Gly Arg Phe Thr Cys Ser Arg Asp Asn Ala Lys Asn Thr Leu Tyr
        210                 215                 220

Leu Gln Met Ser Ser Leu Arg Ala Glu Asp Thr Ala Val Tyr Tyr Cys
225                 230                 235                 240

Asn Ala Val Val Ser Thr Gly Trp Gly Arg Asn Ala Asp Asp Tyr Trp
                245                 250                 255

Gly Gln Gly Thr Leu Val Thr Val Lys Pro Gly Gly Ser Gly Gly Ser
            260                 265                 270

Glu Val Gln Leu Leu Glu Ser Gly Gly Gly Glu Val Gln Pro Gly Gly
                275                 280                 285

Ser Leu Arg Leu Ser Cys Ala Ala Ser Gly Ser Val Phe Ser Ile Asp
        290                 295                 300

Ala Met Ser Trp Phe Arg Gln Ala Pro Gly Lys Gly Leu Glu Leu Val
305                 310                 315                 320

Cys Leu Ile Thr Gly Gly Arg Thr Thr Tyr Tyr Ala Glu Ser Val Lys
                325                 330                 335

Gly Arg Phe Thr Cys Ser Arg Asp Asn Ala Lys Asn Thr Leu Tyr Leu
            340                 345                 350

Gln Met Ser Ser Leu Arg Ala Glu Asp Thr Ala Val Tyr Tyr Cys Asn
                355                 360                 365

Ala Val Val Ser Thr Gly Trp Gly Arg Asn Ala Asp Asp Tyr Trp Gly
        370                 375                 380

Gln Gly Thr Leu Val Thr Val Lys Pro Gly Gly Gly Gly Asp Lys Thr
385                 390                 395                 400

His Thr Cys Pro Pro Cys Pro Ala Pro Gly Gly Pro Ser Val Phe Leu
                405                 410                 415

Phe Pro Pro Lys Pro Lys Asp Thr Leu Met Ile Ser Arg Thr Pro Glu
            420                 425                 430
```

```
Val Thr Cys Val Val Asp Val Ser His Glu Asp Pro Glu Val Lys
        435                 440                 445

Phe Asn Trp Tyr Val Asp Gly Val Glu Val His Asn Ala Lys Thr Lys
450                 455                 460

Pro Arg Glu Glu Gln Tyr Asn Ser Thr Tyr Arg Val Val Ser Val Leu
465                 470                 475                 480

Thr Val Leu His Gln Asp Trp Leu Asn Gly Lys Glu Tyr Lys Cys Lys
                485                 490                 495

Val Ser Asn Lys Ala Leu Pro Ala Pro Ile Glu Lys Thr Ile Ser Lys
            500                 505                 510

Ala Lys Gly Gln Pro Arg Glu Pro Gln Val Tyr Thr Leu Pro Pro Ser
        515                 520                 525

Arg Asp Glu Leu Thr Lys Asn Gln Val Ser Leu Thr Cys Leu Val Lys
    530                 535                 540

Gly Phe Tyr Pro Ser Asp Ile Ala Val Glu Trp Glu Ser Asn Gly Gln
545                 550                 555                 560

Pro Glu Asn Asn Tyr Lys Thr Thr Pro Pro Val Leu Asp Ser Asp Gly
                565                 570                 575

Ser Phe Phe Leu Tyr Ser Lys Leu Thr Val Asp Lys Ser Arg Trp Gln
            580                 585                 590

Gln Gly Asn Val Phe Ser Cys Ser Val Met His Glu Ala Leu His Asn
        595                 600                 605

His Tyr Thr Gln Lys Ser Leu Ser Leu Ser Pro Gly Lys
    610                 615                 620
```

<210> SEQ ID NO 104
<211> LENGTH: 624
<212> TYPE: PRT
<213> ORGANISM: Artificial Sequence
<220> FEATURE:
<223> OTHER INFORMATION: chemically synthesized
<400> SEQUENCE: 104

```
Met Lys Trp Val Thr Phe Ile Ser Leu Leu Phe Leu Phe Ser Ser Ala
1               5                   10                  15

Tyr Ser Glu Val Gln Leu Leu Glu Ser Gly Gly Gly Glu Val Gln Pro
            20                  25                  30

Gly Gly Ser Leu Arg Leu Ser Cys Ala Ala Ser Gly Ser Val Phe Ser
        35                  40                  45

Ile Asp Ala Met Ser Trp Phe Arg Gln Ala Pro Gly Lys Gly Leu Glu
    50                  55                  60

Leu Val Ser Leu Ile Thr Gly Gly Arg Thr Thr Tyr Tyr Ala Glu Ser
65                  70                  75                  80

Val Lys Gly Arg Phe Thr Ile Ser Arg Asp Asn Ala Lys Asn Thr Leu
                85                  90                  95

Tyr Leu Gln Met Ser Ser Leu Arg Ala Glu Asp Thr Ala Val Tyr Tyr
            100                 105                 110

Cys Asn Ala Val Val Ser Thr Gly Trp Gly Arg Asn Ala Asp Asp Tyr
        115                 120                 125

Trp Gly Gln Gly Thr Leu Val Thr Val Lys Pro Gly Gly Ser Gly Gly
    130                 135                 140

Ser Glu Val Gln Leu Leu Glu Ser Gly Gly Gly Glu Val Gln Pro Gly
145                 150                 155                 160

Gly Ser Leu Arg Leu Ser Cys Ala Ala Ser Gly Ser Val Phe Ser Ile
                165                 170                 175
```

-continued

Asp Ala Met Ser Trp Phe Arg Gln Ala Pro Gly Lys Gly Leu Glu Leu
            180                 185                 190

Val Ser Leu Ile Thr Gly Gly Arg Thr Thr Tyr Tyr Ala Glu Ser Val
        195                 200                 205

Lys Gly Arg Phe Thr Ile Ser Arg Asp Asn Ala Lys Asn Thr Leu Tyr
    210                 215                 220

Leu Gln Met Ser Ser Leu Arg Ala Glu Asp Thr Ala Val Tyr Tyr Cys
225                 230                 235                 240

Asn Ala Val Val Ser Thr Gly Trp Gly Arg Asn Ala Asp Asp Tyr Trp
                245                 250                 255

Gly Gln Gly Thr Leu Val Thr Val Lys Pro Gly Gly Ser Gly Gly Ser
            260                 265                 270

Glu Val Gln Leu Leu Glu Ser Gly Gly Glu Val Gln Pro Gly Gly
        275                 280                 285

Ser Leu Arg Leu Ser Cys Ala Ala Ser Gly Ser Val Phe Ser Ile Asp
    290                 295                 300

Ala Met Ser Trp Phe Arg Gln Ala Pro Gly Lys Gly Leu Glu Leu Val
305                 310                 315                 320

Ser Leu Ile Thr Gly Gly Arg Thr Thr Tyr Tyr Ala Glu Ser Val Lys
                325                 330                 335

Gly Arg Phe Thr Ile Ser Arg Asp Asn Ala Lys Asn Thr Leu Tyr Leu
            340                 345                 350

Gln Met Ser Ser Leu Arg Ala Glu Asp Thr Ala Val Tyr Tyr Cys Asn
        355                 360                 365

Ala Val Val Ser Thr Gly Trp Gly Arg Asn Ala Asp Asp Tyr Trp Gly
    370                 375                 380

Gln Gly Thr Leu Val Thr Val Lys Pro Gly Gly Gly Asp Lys Thr
385                 390                 395                 400

His Thr Cys Pro Pro Cys Pro Ala Pro Glu Leu Leu Gly Gly Pro Ser
                405                 410                 415

Val Phe Leu Phe Pro Pro Lys Pro Lys Asp Thr Leu Met Ile Ser Arg
            420                 425                 430

Thr Pro Glu Val Thr Cys Val Val Val Asp Val Ser His Glu Asp Pro
        435                 440                 445

Glu Val Lys Phe Asn Trp Tyr Val Asp Gly Val Glu Val His Asn Ala
    450                 455                 460

Lys Thr Lys Pro Arg Glu Glu Gln Tyr Asn Ser Thr Tyr Arg Val Val
465                 470                 475                 480

Ser Val Leu Thr Val Leu His Gln Asp Trp Leu Asn Gly Lys Glu Tyr
                485                 490                 495

Lys Cys Lys Val Ser Asn Lys Ala Leu Pro Ala Pro Ile Glu Lys Thr
            500                 505                 510

Ile Ser Lys Ala Lys Gly Gln Pro Arg Glu Pro Gln Val Tyr Thr Leu
        515                 520                 525

Pro Pro Ser Arg Asp Glu Leu Thr Lys Asn Gln Val Ser Leu Thr Cys
    530                 535                 540

Leu Val Lys Gly Phe Tyr Pro Ser Asp Ile Ala Val Glu Trp Glu Ser
545                 550                 555                 560

Asn Gly Gln Pro Glu Asn Asn Tyr Lys Thr Thr Pro Pro Val Leu Asp
                565                 570                 575

Ser Asp Gly Ser Phe Phe Leu Tyr Ser Lys Leu Thr Val Asp Lys Ser
            580                 585                 590

Arg Trp Gln Gln Gly Asn Val Phe Ser Cys Ser Val Met His Glu Ala

Leu His Asn His Tyr Thr Gln Lys Ser Leu Ser Leu Ser Pro Gly Lys
610                         615                 620

<210> SEQ ID NO 105
<211> LENGTH: 624
<212> TYPE: PRT
<213> ORGANISM: Artificial Sequence
<220> FEATURE:
<223> OTHER INFORMATION: chemically synthesized

<400> SEQUENCE: 105

Met Lys Trp Val Thr Phe Ile Ser Leu Leu Phe Leu Phe Ser Ser Ala
1               5                   10                  15

Tyr Ser Glu Val Gln Leu Leu Glu Ser Gly Gly Gly Glu Val Gln Pro
            20                  25                  30

Gly Gly Ser Leu Arg Leu Ser Cys Ala Ala Ser Gly Ser Val Phe Ser
        35                  40                  45

Ile Asp Ala Met Ser Trp Phe Arg Gln Ala Pro Gly Lys Gly Leu Glu
50                  55                  60

Leu Val Cys Leu Ile Thr Gly Gly Arg Thr Thr Tyr Tyr Ala Glu Ser
65                  70                  75                  80

Val Lys Gly Arg Phe Thr Cys Ser Arg Asp Asn Ala Lys Asn Thr Leu
                85                  90                  95

Tyr Leu Gln Met Ser Ser Leu Arg Ala Glu Asp Thr Ala Val Tyr Tyr
            100                 105                 110

Cys Asn Ala Val Val Ser Thr Gly Trp Gly Arg Asn Ala Asp Asp Tyr
        115                 120                 125

Trp Gly Gln Gly Thr Leu Val Thr Val Lys Pro Gly Gly Ser Gly Gly
130                 135                 140

Ser Glu Val Gln Leu Leu Glu Ser Gly Gly Gly Glu Val Gln Pro Gly
145                 150                 155                 160

Gly Ser Leu Arg Leu Ser Cys Ala Ala Ser Gly Ser Val Phe Ser Ile
                165                 170                 175

Asp Ala Met Ser Trp Phe Arg Gln Ala Pro Gly Lys Gly Leu Glu Leu
            180                 185                 190

Val Cys Leu Ile Thr Gly Gly Arg Thr Thr Tyr Tyr Ala Glu Ser Val
        195                 200                 205

Lys Gly Arg Phe Thr Cys Ser Arg Asp Asn Ala Lys Asn Thr Leu Tyr
210                 215                 220

Leu Gln Met Ser Ser Leu Arg Ala Glu Asp Thr Ala Val Tyr Tyr Cys
225                 230                 235                 240

Asn Ala Val Val Ser Thr Gly Trp Gly Arg Asn Ala Asp Asp Tyr Trp
                245                 250                 255

Gly Gln Gly Thr Leu Val Thr Val Lys Pro Gly Gly Ser Gly Gly Ser
            260                 265                 270

Glu Val Gln Leu Leu Glu Ser Gly Gly Gly Glu Val Gln Pro Gly Gly
        275                 280                 285

Ser Leu Arg Leu Ser Cys Ala Ala Ser Gly Ser Val Phe Ser Ile Asp
290                 295                 300

Ala Met Ser Trp Phe Arg Gln Ala Pro Gly Lys Gly Leu Glu Leu Val
305                 310                 315                 320

Cys Leu Ile Thr Gly Gly Arg Thr Thr Tyr Tyr Ala Glu Ser Val Lys
                325                 330                 335

Gly Arg Phe Thr Cys Ser Arg Asp Asn Ala Lys Asn Thr Leu Tyr Leu

```
                    340                 345                 350
        Gln Met Ser Ser Leu Arg Ala Glu Asp Thr Ala Val Tyr Tyr Cys Asn
                355                 360                 365

Ala Val Val Ser Thr Gly Trp Gly Arg Asn Ala Asp Asp Tyr Trp Gly
            370                 375                 380

Gln Gly Thr Leu Val Thr Val Lys Pro Gly Gly Gly Asp Lys Thr
        385                 390                 395                 400

His Thr Cys Pro Pro Cys Pro Ala Pro Glu Leu Leu Gly Gly Pro Ser
                        405                 410                 415

Val Phe Leu Phe Pro Pro Lys Pro Lys Asp Thr Leu Met Ile Ser Arg
                    420                 425                 430

Thr Pro Glu Val Thr Cys Val Val Asp Val Ser His Glu Asp Pro
                435                 440                 445

Glu Val Lys Phe Asn Trp Tyr Val Asp Gly Val Glu Val His Asn Ala
            450                 455                 460

Lys Thr Lys Pro Arg Glu Glu Gln Tyr Asn Ser Thr Tyr Arg Val Val
        465                 470                 475                 480

Ser Val Leu Thr Val Leu His Gln Asp Trp Leu Asn Gly Lys Glu Tyr
                        485                 490                 495

Lys Cys Lys Val Ser Asn Lys Ala Leu Pro Ala Pro Ile Glu Lys Thr
                    500                 505                 510

Ile Ser Lys Ala Lys Gly Gln Pro Arg Glu Pro Gln Val Tyr Thr Leu
                515                 520                 525

Pro Pro Ser Arg Asp Glu Leu Thr Lys Asn Gln Val Ser Leu Thr Cys
            530                 535                 540

Leu Val Lys Gly Phe Tyr Pro Ser Asp Ile Ala Val Glu Trp Glu Ser
        545                 550                 555                 560

Asn Gly Gln Pro Glu Asn Asn Tyr Lys Thr Thr Pro Pro Val Leu Asp
                        565                 570                 575

Ser Asp Gly Ser Phe Phe Leu Tyr Ser Lys Leu Thr Val Asp Lys Ser
                    580                 585                 590

Arg Trp Gln Gln Gly Asn Val Phe Ser Cys Ser Val Met His Glu Ala
                595                 600                 605

Leu His Asn His Tyr Thr Gln Lys Ser Leu Ser Leu Ser Pro Gly Lys
            610                 615                 620

<210> SEQ ID NO 106
<211> LENGTH: 9
<212> TYPE: PRT
<213> ORGANISM: Artificial Sequence
<220> FEATURE:
<223> OTHER INFORMATION: chemically synthesized

<400> SEQUENCE: 106

Gly Ser Val Phe Ser Ile Asp Ala Met
1               5

<210> SEQ ID NO 107
<211> LENGTH: 8
<212> TYPE: PRT
<213> ORGANISM: Artificial Sequence
<220> FEATURE:
<223> OTHER INFORMATION: chemically synthesized

<400> SEQUENCE: 107

Val Met Ser Ser Gly Ser Pro Lys
1               5
```

<210> SEQ ID NO 108
<211> LENGTH: 16
<212> TYPE: PRT
<213> ORGANISM: Artificial Sequence
<220> FEATURE:
<223> OTHER INFORMATION: chemically synthesized

<400> SEQUENCE: 108

Tyr Ala Asp Val Ala Thr Gly Trp Gly Arg Asp Ala Ser Ala Tyr Trp
1               5                   10                  15

<210> SEQ ID NO 109
<211> LENGTH: 10
<212> TYPE: PRT
<213> ORGANISM: Artificial Sequence
<220> FEATURE:
<223> OTHER INFORMATION: chemically synthesized

<400> SEQUENCE: 109

Ala Gly Ser Thr Phe Ser Val Asn Ser Met
1               5                   10

<210> SEQ ID NO 110
<211> LENGTH: 8
<212> TYPE: PRT
<213> ORGANISM: Artificial Sequence
<220> FEATURE:
<223> OTHER INFORMATION: chemically synthesized

<400> SEQUENCE: 110

Phe Thr Gly Gly Ser Thr Met Asn
1               5

<210> SEQ ID NO 111
<211> LENGTH: 16
<212> TYPE: PRT
<213> ORGANISM: Artificial Sequence
<220> FEATURE:
<223> OTHER INFORMATION: chemically synthesized

<400> SEQUENCE: 111

Asn Ala Glu Val Asn Glu Gly Trp Asn Ala Asp Tyr His Asp Tyr Trp
1               5                   10                  15

<210> SEQ ID NO 112
<211> LENGTH: 10
<212> TYPE: PRT
<213> ORGANISM: Artificial Sequence
<220> FEATURE:
<223> OTHER INFORMATION: chemically synthesized

<400> SEQUENCE: 112

Ser Gly Ser Ile Phe Ser Ile Asn His Met
1               5                   10

<210> SEQ ID NO 113
<211> LENGTH: 9
<212> TYPE: PRT
<213> ORGANISM: Artificial Sequence
<220> FEATURE:
<223> OTHER INFORMATION: chemically synthesized

<400> SEQUENCE: 113

His Ile Thr Gly Gly Ala Ser Thr Lys
1               5

```
<210> SEQ ID NO 114
<211> LENGTH: 16
<212> TYPE: PRT
<213> ORGANISM: Artificial Sequence
<220> FEATURE:
<223> OTHER INFORMATION: chemically synthesized

<400> SEQUENCE: 114

Asn Ala Glu Val Asn Glu Gly Trp Asn Ala Asp Tyr Tyr Asp Val Trp
1               5                   10                  15

<210> SEQ ID NO 115
<211> LENGTH: 9
<212> TYPE: PRT
<213> ORGANISM: Artificial Sequence
<220> FEATURE:
<223> OTHER INFORMATION: chemically synthesized

<400> SEQUENCE: 115

Val Leu Asn Gly Ile Ser Ser Ala Lys
1               5

<210> SEQ ID NO 116
<211> LENGTH: 16
<212> TYPE: PRT
<213> ORGANISM: Artificial Sequence
<220> FEATURE:
<223> OTHER INFORMATION: chemically synthesized

<400> SEQUENCE: 116

Tyr Ala Asp Val Ser Thr Gly Trp Gly Arg Asp Ala His Gly Tyr Trp
1               5                   10                  15

<210> SEQ ID NO 117
<211> LENGTH: 10
<212> TYPE: PRT
<213> ORGANISM: Artificial Sequence
<220> FEATURE:
<223> OTHER INFORMATION: chemically synthesized

<400> SEQUENCE: 117

Ser Gly Asn Ile Phe Ser Ile Asp Ala Met
1               5                   10

<210> SEQ ID NO 118
<211> LENGTH: 5
<212> TYPE: PRT
<213> ORGANISM: Artificial Sequence
<220> FEATURE:
<223> OTHER INFORMATION: chemically synthesized

<400> SEQUENCE: 118

Gln Ile Pro Gly Gly
1               5

<210> SEQ ID NO 119
<211> LENGTH: 16
<212> TYPE: PRT
<213> ORGANISM: Artificial Sequence
<220> FEATURE:
<223> OTHER INFORMATION: chemically synthesized

<400> SEQUENCE: 119

Asn Ile Val Ala Ser Thr Ser Trp Gly Ser Pro Ser Lys Val Tyr Trp
1               5                   10                  15

<210> SEQ ID NO 120
```

```
<211> LENGTH: 10
<212> TYPE: PRT
<213> ORGANISM: Artificial Sequence
<220> FEATURE:
<223> OTHER INFORMATION: chemically synthesized

<400> SEQUENCE: 120

Ser Gly Ser Val Phe Ser Ile Asp Ser Met
1               5                   10

<210> SEQ ID NO 121
<211> LENGTH: 9
<212> TYPE: PRT
<213> ORGANISM: Artificial Sequence
<220> FEATURE:
<223> OTHER INFORMATION: chemically synthesized

<400> SEQUENCE: 121

Leu Ile Thr Gly Gly Arg Thr Thr Thr
1               5

<210> SEQ ID NO 122
<211> LENGTH: 16
<212> TYPE: PRT
<213> ORGANISM: Artificial Sequence
<220> FEATURE:
<223> OTHER INFORMATION: chemically synthesized

<400> SEQUENCE: 122

Asn Ala Val Val Ser Thr Gly Trp Gly Arg Asn Ala Asp Asp Tyr Trp
1               5                   10                  15

<210> SEQ ID NO 123
<211> LENGTH: 8
<212> TYPE: PRT
<213> ORGANISM: Artificial Sequence
<220> FEATURE:
<223> OTHER INFORMATION: chemically synthesized

<400> SEQUENCE: 123

Val Ile Asp Gly Val Ser Pro Asn
1               5

<210> SEQ ID NO 124
<211> LENGTH: 16
<212> TYPE: PRT
<213> ORGANISM: Artificial Sequence
<220> FEATURE:
<223> OTHER INFORMATION: chemically synthesized

<400> SEQUENCE: 124

Asn Ala Ala Val Ser Thr Gly Trp Gly Arg Asn Ala Asp Asp Tyr Trp
1               5                   10                  15

<210> SEQ ID NO 125
<211> LENGTH: 10
<212> TYPE: PRT
<213> ORGANISM: Artificial Sequence
<220> FEATURE:
<223> OTHER INFORMATION: chemically synthesized

<400> SEQUENCE: 125

Ser Gly Ser Val Phe Ser Ile Asp Ser Val
1               5                   10

<210> SEQ ID NO 126
<211> LENGTH: 16
```

```
<212> TYPE: PRT
<213> ORGANISM: Artificial Sequence
<220> FEATURE:
<223> OTHER INFORMATION: chemically synthesized

<400> SEQUENCE: 126

Asn Ala Ala Leu Ser Thr Gly Trp Gly Arg Asp Ala Ser Ala Tyr Trp
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: chemically synthesized

<400> SEQUENCE: 127

Ala Glu Val Asn Glu Gly Trp Asn Ala Asp Tyr Tyr Asp Val Trp
1               5                   10                  15

<210> SEQ ID NO 128
<211> LENGTH: 8
<212> TYPE: PRT
<213> ORGANISM: Artificial Sequence
<220> FEATURE:
<223> OTHER INFORMATION: chemically synthesized

<400> SEQUENCE: 128

Ile Thr Ser Gly Gly Ser Pro Asn
1               5

<210> SEQ ID NO 129
<211> LENGTH: 15
<212> TYPE: PRT
<213> ORGANISM: Artificial Sequence
<220> FEATURE:
<223> OTHER INFORMATION: chemically synthesized

<400> SEQUENCE: 129

Ala Gly Glu Leu Arg Asp Asp Ser Asn Gly Tyr Leu His Tyr Trp
1               5                   10                  15

<210> SEQ ID NO 130
<211> LENGTH: 9
<212> TYPE: PRT
<213> ORGANISM: Artificial Sequence
<220> FEATURE:
<223> OTHER INFORMATION: chemically synthesized

<400> SEQUENCE: 130

His Ile Thr Gly Gly Arg Thr Thr Thr
1               5

<210> SEQ ID NO 131
<211> LENGTH: 10
<212> TYPE: PRT
<213> ORGANISM: Artificial Sequence
<220> FEATURE:
<223> OTHER INFORMATION: chemically synthesized

<400> SEQUENCE: 131

Ser Gly Ser Ile Phe Ser Ile Asp Asp Met
1               5                   10

<210> SEQ ID NO 132
<211> LENGTH: 8
<212> TYPE: PRT
```

```
<213> ORGANISM: Artificial Sequence
<220> FEATURE:
<223> OTHER INFORMATION: chemically synthesized

<400> SEQUENCE: 132

Val His Ser Gly Ser Ser Thr Asn
1               5

<210> SEQ ID NO 133
<211> LENGTH: 16
<212> TYPE: PRT
<213> ORGANISM: Artificial Sequence
<220> FEATURE:
<223> OTHER INFORMATION: chemically synthesized

<400> SEQUENCE: 133

Tyr Ala Ala Ile Ser Ser Gly Trp Gly Arg Asp Ala Glu Asp Tyr Trp
1               5                   10                  15

<210> SEQ ID NO 134
<211> LENGTH: 8
<212> TYPE: PRT
<213> ORGANISM: Artificial Sequence
<220> FEATURE:
<223> OTHER INFORMATION: chemically synthesized

<400> SEQUENCE: 134

Ile Thr Gly Gly Arg Thr Thr Thr
1               5

<210> SEQ ID NO 135
<211> LENGTH: 16
<212> TYPE: PRT
<213> ORGANISM: Artificial Sequence
<220> FEATURE:
<223> OTHER INFORMATION: chemically synthesized

<400> SEQUENCE: 135

Asn Ala Ala Val Ser Thr Gly Trp Gly Arg Ser Ala Asp Asp Tyr Trp
1               5                   10                  15

<210> SEQ ID NO 136
<211> LENGTH: 8
<212> TYPE: PRT
<213> ORGANISM: Artificial Sequence
<220> FEATURE:
<223> OTHER INFORMATION: chemically synthesized

<400> SEQUENCE: 136

Ile Thr Gly Gly Arg Thr Thr Tyr
1               5

<210> SEQ ID NO 137
<211> LENGTH: 9
<212> TYPE: PRT
<213> ORGANISM: Artificial Sequence
<220> FEATURE:
<223> OTHER INFORMATION: chemically synthesized

<400> SEQUENCE: 137

Ala Ile Thr Gly Gly Arg Thr Thr Tyr
1               5

<210> SEQ ID NO 138
<211> LENGTH: 10
<212> TYPE: PRT
<213> ORGANISM: Artificial Sequence
```

```
<220> FEATURE:
<223> OTHER INFORMATION: chemically synthesized

<400> SEQUENCE: 138

Ser Gly Ser Val Phe Ser Ile Asp Ala Met
1               5                   10

<210> SEQ ID NO 139
<211> LENGTH: 8
<212> TYPE: PRT
<213> ORGANISM: Artificial Sequence
<220> FEATURE:
<223> OTHER INFORMATION: chemically synthesized

<400> SEQUENCE: 139

Leu Ser Gly Ile Ser Ser Ala Thr
1               5

<210> SEQ ID NO 140
<211> LENGTH: 15
<212> TYPE: PRT
<213> ORGANISM: Artificial Sequence
<220> FEATURE:
<223> OTHER INFORMATION: chemically synthesized

<400> SEQUENCE: 140

Ala Asp Val Ser Thr Gly Trp Gly Arg Asp Ala His Gly Tyr Trp
1               5                   10                  15

<210> SEQ ID NO 141
<211> LENGTH: 8
<212> TYPE: PRT
<213> ORGANISM: Artificial Sequence
<220> FEATURE:
<223> OTHER INFORMATION: chemically synthesized

<400> SEQUENCE: 141

Leu Ser Gly Ile Ser Ser Ala Lys
1               5

<210> SEQ ID NO 142
<211> LENGTH: 15
<212> TYPE: PRT
<213> ORGANISM: Artificial Sequence
<220> FEATURE:
<223> OTHER INFORMATION: chemically synthesized

<400> SEQUENCE: 142

Ala Asp Val Ser Thr Gly Trp Gly Arg Asp Ala His Gly Tyr Trp
1               5                   10                  15

<210> SEQ ID NO 143
<211> LENGTH: 10
<212> TYPE: PRT
<213> ORGANISM: Artificial Sequence
<220> FEATURE:
<223> OTHER INFORMATION: chemically synthesized

<400> SEQUENCE: 143

Ser Gly Phe Thr Phe Ser Thr His Gly Met
1               5                   10

<210> SEQ ID NO 144
<211> LENGTH: 10
<212> TYPE: PRT
<213> ORGANISM: Artificial Sequence
<220> FEATURE:
```

```
<223> OTHER INFORMATION: chemically synthesized

<400> SEQUENCE: 144

Ala Ile Asn Asn Gly Gly Ser Trp Thr Ser
1               5                   10

<210> SEQ ID NO 145
<211> LENGTH: 7
<212> TYPE: PRT
<213> ORGANISM: Artificial Sequence
<220> FEATURE:
<223> OTHER INFORMATION: chemically synthesized

<400> SEQUENCE: 145

Cys Gln Asn Arg Val Thr Arg
1               5

<210> SEQ ID NO 146
<211> LENGTH: 6
<212> TYPE: PRT
<213> ORGANISM: Artificial Sequence
<220> FEATURE:
<223> OTHER INFORMATION: chemically synthesized

<400> SEQUENCE: 146

Gln Asn Arg Val Thr Arg
1               5

<210> SEQ ID NO 147
<211> LENGTH: 9
<212> TYPE: PRT
<213> ORGANISM: Artificial Sequence
<220> FEATURE:
<223> OTHER INFORMATION: chemically synthesized

<400> SEQUENCE: 147

Ile Asn Gln Gly Gly Ser Trp Thr Ser
1               5

<210> SEQ ID NO 148
<211> LENGTH: 10
<212> TYPE: PRT
<213> ORGANISM: Artificial Sequence
<220> FEATURE:
<223> OTHER INFORMATION: chemically synthesized

<400> SEQUENCE: 148

Ser Arg Ser Ile Ala Ser Ile Asn Val Met
1               5                   10

<210> SEQ ID NO 149
<211> LENGTH: 10
<212> TYPE: PRT
<213> ORGANISM: Artificial Sequence
<220> FEATURE:
<223> OTHER INFORMATION: chemically synthesized

<400> SEQUENCE: 149

Ser Gly Ser Ile Phe Ser Ile Asp Ala Met
1               5                   10

<210> SEQ ID NO 150
<211> LENGTH: 16
<212> TYPE: PRT
<213> ORGANISM: Artificial Sequence
<220> FEATURE:
<223> OTHER INFORMATION: chemically synthesized
```

```
<400> SEQUENCE: 150

Asn Ala Asp Val Ser Thr Gly Trp Gly Arg Pro Ala Asp His Tyr Trp
1               5                   10                  15
```